US011840704B2

(12) United States Patent
Kirn et al.

(10) Patent No.: US 11,840,704 B2
(45) Date of Patent: *Dec. 12, 2023

(54) ADENO-ASSOCIATED VIRUS VARIANT CAPSIDS AND METHODS OF USE THEREOF

(71) Applicant: 4D MOLECULAR THERAPEUTICS INC., Emeryville, CA (US)

(72) Inventors: David H. Kirn, Emeryville, CA (US); Melissa Kotterman, Emeryville, CA (US); David Schaffer, Emeryville, CA (US)

(73) Assignee: 4D Molecular Therapeutics Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/069,701

(22) Filed: Dec. 21, 2022

(65) Prior Publication Data

US 2023/0279435 A1    Sep. 7, 2023

Related U.S. Application Data

(63) Continuation of application No. 17/718,870, filed on Apr. 12, 2022, now Pat. No. 11,613,766, which is a continuation of application No. 17/400,041, filed on Aug. 11, 2021, which is a continuation of application No. 16/648,195, filed as application No. PCT/US2018/051812 on Sep. 19, 2018, now Pat. No. 11,118,192.

(60) Provisional application No. 62/560,901, filed on Sep. 20, 2017.

(51) Int. Cl.
| | |
|---|---|
| *C12N 15/86* | (2006.01) |
| *C07K 14/005* | (2006.01) |
| *C12N 15/864* | (2006.01) |
| *A61P 21/00* | (2006.01) |
| *A61K 38/47* | (2006.01) |
| *C12N 7/00* | (2006.01) |
| *A61K 38/17* | (2006.01) |
| *A61K 38/44* | (2006.01) |
| *C12N 9/10* | (2006.01) |
| *A61K 9/00* | (2006.01) |
| *A61K 48/00* | (2006.01) |

(52) U.S. Cl.
CPC .......... *C12N 15/86* (2013.01); *A61K 38/1719* (2013.01); *A61K 38/44* (2013.01); *A61K 38/47* (2013.01); *A61P 21/00* (2018.01); *C07K 14/005* (2013.01); *C12N 7/00* (2013.01); *C12N 9/1051* (2013.01); *C12N 15/8645* (2013.01); *C12Y 116/03001* (2013.01); *C12Y 204/01001* (2013.01); *C12Y 302/0102* (2013.01); *C12Y 302/01022* (2013.01); *A61K 9/0019* (2013.01); *A61K 48/00* (2013.01); *C12N 2750/14121* (2013.01); *C12N 2750/14122* (2013.01); *C12N 2750/14133* (2013.01); *C12N 2750/14143* (2013.01); *C12N 2750/14145* (2013.01); *C12N 2750/14171* (2013.01)

(58) Field of Classification Search
None
See application file for complete search history.

(56) References Cited

U.S. PATENT DOCUMENTS

| | | | | |
|---|---|---|---|---|
| 11,118,192 B2 * | 9/2021 | Kirn | ................. | A61P 21/00 |
| 11,554,180 B2 * | 1/2023 | Schaffer | ............. | A61K 48/0075 |
| 11,565,000 B2 * | 1/2023 | Schaffer | ................. | C12N 15/86 |
| 11,565,001 B2 * | 1/2023 | Schaffer | ............... | A61K 9/0048 |
| 11,613,766 B2 * | 3/2023 | Kirn | ................. | A61K 38/1719 |
| | | | | 424/93.2 |

* cited by examiner

*Primary Examiner* — Robert M Kelly
(74) *Attorney, Agent, or Firm* — Much Shelist, P.C.; Christopher M. Cabral

(57) ABSTRACT

Provided herein are variant adeno-associated virus (AAV) capsid proteins having one or more modifications in amino acid sequence relative to a parental AAV capsid protein, which, when present in an AAV virion, confer increased infectivity of one or more types of muscle cells as compared to the infectivity of the muscle cells by an AAV virion comprising the unmodified parental AAV capsid protein. Also provided are recombinant AAV virions and pharmaceutical compositions thereof comprising a variant AAV capsid protein as described herein, methods of making these rAAV capsid proteins and virions, and methods for using these rAAV capsid proteins and virions in research and in clinical practice, for example in, e.g., the delivery of nucleic acid sequences to one or more muscle cells for the treatment of muscle disorders and diseases.

20 Claims, 28 Drawing Sheets

Specification includes a Sequence Listing.

FIGURE 5A

```
        1              10              20              30              40
AAV1    M A A D G Y L P D W L E D N L S E G I R E W W D L K P G A P K P K A N Q Q K Q D D G
AAV2    M A A D G Y L P D W L E D T L S E G I R Q W W K L K P G P P P P K P A E R H K D D S
AAV3A   M A A D G Y L P D W L E D N L S E G I R E W W A L K P G V P Q P K A N Q Q H Q D N R
AAV3B   M A A D G Y L P D W L E D N L S E G I R E W W A L K P G V P Q P K A N Q Q H Q D N R
AAV4    M - T D G Y L P D W L E D N L S E G V R E W W A L Q P G A P K P K A N Q Q H Q D N A
AAV5    M S F V D H P P D W L E E - V G E G L R E F L G L E A G P P K P K P N Q Q H Q D Q A
AAV6    M A A D G Y L P D W L E D N L S E G I R E W W D L K P G A P K P K A N Q Q K Q D D G
AAV7    M A A D G Y L P D W L E D N L S E G I R E W W D L K P G A P K P K A N Q Q K Q D N G
AAV8    M A A D G Y L P D W L E D N L S E G I R E W W A L K P G A P K P K A N Q Q K Q D D G
AAV9    M A A D G Y L P D W L E D N L S E G I R E W W A L K P G A P Q P K A N Q Q H Q D N A
AAV10   M A A D G Y L P D W L E D N L S E G I R E W W D L K P G A P K P K A N Q Q K Q D D G
                50              60              70              80
AAV1    R G L V L P G Y K Y L G P F N G L D K G E P V N A A D A A A L E H D K A Y D Q Q L K
AAV2    R G L V L P G Y K Y L G P F N G L D K G E P V N E A D A A A L E H D K A Y D R Q L D
AAV3A   R G L V L P G Y K Y L G P G N G L D K G E P V N E A D A A A L E H D K A Y D Q Q L K
AAV3B   R G L V L P G Y K Y L G P G N G L D K G E P V N E A D A A A L E H D K A Y D Q Q L K
AAV4    R G L V L P G Y K Y L G P G N G L D K G E P V N A A D A A A L E H D K A Y D Q Q L K
AAV5    R G L V L P G Y N Y L G P G N G L D R G E P V N R A D E V A R E H D I S Y N E Q L E
AAV6    R G L V L P G Y K Y L G P F N G L D K G E P V N A A D A A A L E H D K A Y D Q Q L K
AAV7    R G L V L P G Y K Y L G P F N G L D K G E P V N A A D A A A L E H D K A Y D Q Q L K
AAV8    R G L V L P G Y K Y L G P F N G L D K G E P V N A A D A A A L E H D K A Y D Q Q L Q
AAV9    R G L V L P G Y K Y L G P G N G L D K G E P V N A A D A A A L E H D K A Y D Q Q L K
AAV10   R G L V L P G Y K Y L G P F N G L D K G E P V N A A D A A A L E H D K A Y D Q Q L K
                90              100             110             120
AAV1    A G D N P Y L R Y N H A D A E F Q E R L Q E D T S F G G N L G R A V F Q A K K R V L
AAV2    S G D N P Y L K Y N H A D A E F Q E R L K E D T S F G G N L G R A V F Q A K K R V L
AAV3A   A G D N P Y L K Y N H A D A E F Q E R L Q E D T S F G G N L G R A V F Q A K K R I L
AAV3B   A G D N P Y L K Y N H A D A E F Q E R L Q E D T S F G G N L G R A V F Q A K K R I L
AAV4    A G D N P Y L K Y N H A D A E F Q Q R L Q G D T S F G G N L G R A V F Q A K K R V L
AAV5    A G D N P Y L K Y N H A D A E F Q E K L A D D T S F G G N L G K A V F Q A K K R V L
AAV6    A G D N P Y L R Y N H A D A E F Q E R L Q E D T S F G G N L G R A V F Q A K K R V L
AAV7    A G D N P Y L R Y N H A D A E F Q E R L Q E D T S F G G N L G R A V F Q A K K R V L
AAV8    A G D N P Y L R Y N H A D A E F Q E R L Q E D T S F G G N L G R A V F Q A K K R V L
AAV9    A G D N P Y L K Y N H A D A E F Q E R L K E D T S F G G N L G R A V F Q A K K R L L
AAV10   A G D N P Y L R Y N H A D A E F Q E R L Q E D T S F G G N L G R A V F Q A K K R V L
                130             140             150             160
AAV1    E P L G L V E E G A K T A P G K K R P V E Q S P Q - E P D S S S G I G K T G Q Q P A
AAV2    E P L G L V E E P V K T A P G K K R P V E H S P V - E P D S S S G T G K A G Q Q P A
AAV3A   E P L G L V E E A A K T A P G K K G A V D Q S P Q - E P D S S S G V G K S G K Q P A
AAV3B   E P L G L V E E A A K T A P G K K R P V D Q S P Q - E P D S S S G V G K S G K Q P A
AAV4    E P L G L V E Q A G E T A P G K K R P L I E S P Q - Q P D S S T G I G K K G Q Q P A
AAV5    E P F G L V E E G A K T A P T G K R I D D H F P K R K K A R T - - - - E E D S K P S
AAV6    E P F G L V E E G A K T A P G K K R P V E Q S P Q - E P D S S S G I G K T G Q Q P A
AAV7    E P L G L V E E G A K T A P A K K R P V E P S P Q R S P D S S T G I G K K G Q Q P A
AAV8    E P L G L V E E G A K T A P G K K R P V E P S P Q R S P D S S T G I G K K G Q Q P A
AAV9    E P L G L V E E A A K T A P G K K R P V E Q S P Q - E P D S S A G I G K S G A Q P A
AAV10   E P L G L V E E A A K T A P G K K R P V E P S P Q R S P D S S T G I G K K G Q Q P A
```

FIGURE 5B

```
          170         180         190         200         210
AAV1   KRRLNFGQTGDSESVPDQPLGEPPATP-AAVGPTTMASGG
AAV2   RKRLNFGQTGDADSVPDQPLGQPPAAP-SGLGTNTMATGSG
AAV3A  RKRLNFGQTGDSESVPDQPLGEPPAAP-TSLGSNTMASGGG
AAV3B  RKRLNFGQTGDSESVPDQPLGEPPAAP-TSLGSNTMASGGG
AAV4   KKKLVFE---DETGAGDGPPEGSTSGA--MSDDSEMRAAAGG
AAV5   T--------SSDAEAGPSGSQQLQIPAQPASSLGADTMSAGGG
AAV6   KKRLNFGQTGDSESVPDQPLGEPPATP-AAVGPTTMASGGG
AAV7   RKRLNFGQTGDSESVPDQPLGEPPAAP-SSVGSGTVAAGGG
AAV8   RKRLNFGQTGDSESVPDQPLGEPPAAP-SGVGPNTMAAGGG
AAV9   KKRLNFGQTGDTESVPDQPIGEPPAAP-SGVGSLTMASGGG
AAV10  KKRLNFGQTGESESVPDQPIGEPPAGP-SGLGSGTMAAGGG 220         230         240         250
AAV1   APMADNNEGADGVGNASGNWHCDSTWLGDRVITTSTRTWALP
AAV2   APMADNNEGADGVGNSSGNWHCDSTWMGDRVITTSTRTWALP
AAV3A  APMADNNEGADGVGNSSGNWHCDSQWLGDRVITTSTRTWALP
AAV3B  APMADNNEGADGVGNSSGNWHCDSQWLGDRVITTSTRTWALP
AAV4   AAV-EGGQGADGVGNASGDWHCDSTWSEGHVTTTSTRTWVLP
AAV5   GPLGDNNQGADGVGNASGDWHCDSTWMGDRVVTKSTRTWVLP
AAV6   APMADNNEGADGVGNASGNWHCDSTWLGDRVITTSTRTWALP
AAV7   APMADNNEGADGVGNASGNWHCDSTWLGDRVITTSTRTWALP
AAV8   APMADNNEGADGVGSSSGNWHCDSTWLGDRVITTSTRTWALP
AAV9   APVADNNEGADGVGSSSGNWHCDSQWLGDRVITTSTRTWALP
AAV10  APMADNNEGADGVGSSSGNWHCDSTWLGDRVITTSTRTWALP 260         270         280         290
AAV1   TYNNHLYKQISSA-STGASNDNHYFGYSTPWGYFDFNRFHCH
AAV2   TYNNHLYKQISSQ--SGASNDNHYFGYSTPWGYFDFNRFHCH
AAV3A  TYNNHLYKQISSQ--SGASNDNHYFGYSTPWGYFDFNRFHCH
AAV3B  TYNNHLYKQISSQ--SGASNDNHYFGYSTPWGYFDFNRFHCH
AAV4   TYNNHLYKRLGE-----SLQSNTYNGFSTPWGYFDFNRFHCH
AAV5   SYNNHQYREIKSGSVDG-SNANAYFGYSTPWGYFDFNRFHSH
AAV6   TYNNHLYKQISSA-STGASNDNHYFGYSTPWGYFDFNRFHCH
AAV7   TYNNHLYKQISSE-TAGSTNDNTYFGYSTPWGYFDFNRFHCH
AAV8   TYNNHLYKQISNGTSGGATNDNTYFGYSTPWGYFDFNRFHCH
AAV9   TYNNHLYKQISNSTSGGSSNDNAYFGYSTPWGYFDFNRFHCH
AAV10  TYNNHLYKQISNGTSGGSTNDNTYFGYSTPWGYFDFNRFHCH 300         310         320         330
AAV1   FSPRDWQRLINNNWGFRPKRLNFKLFNIQVKEVTTNDGVTTI
AAV2   FSPRDWQRLINNNWGFRPKRLNFKLFNIQVKEVTQNDGTTTI
AAV3A  FSPRDWQRLINNNWGFRPKKLSFKLFNIQVRGVTQNDGTTTI
AAV3B  FSPRDWQRLINNNWGFRPKKLSFKLFNIQVKEVTQNDGTTTI
AAV4   FSPRDWQRLINNNWGMRPKAMRVKIFNIQVKEVTTSNGETTV
AAV5   WSPRDWQRLINNYWGFRPRSLRVKIFNIQVKEVTVQDSTTTI
AAV6   FSPRDWQRLINNNWGFRPKRLNFKLFNIQVKEVTTNDGVTTI
AAV7   FSPRDWQRLINNNWGFRPKKLRFKLFNIQVKEVTTNDGVTTI
AAV8   FSPRDWQRLINNNWGFRPKRLSFKLFNIQVKEVTQNEGTKTI
AAV9   FSPRDWQRLINNNWGFRPKRLNFKLFNIQVKEVTDNNGVKTI
AAV10  FSPRDWQRLINNNWGFRPKRLSFKLFNIQVKEVTQNEGTKTI
```

FIGURE 5C

```
            340         350         360         370
AAV1    ANNLTSTVQVFSDSEYQLPYVLGSAHQGCLPPFPADVFMIPQ
AAV2    ANNLTSTVQVFTDSEYQLPYVLGSAHQGCLPPFPADVFMVPQ
AAV3A   ANNLTSTVQVFTDSEYQLPYVLGSAHQGCLPPFPADVFMVPQ
AAV3B   ANNLTSTVQVFTDSEYQLPYVLGSAHQGCLPPFPADVFMVPQ
AAV4    ANNLTSTVQIFADSSYELPYVMDAGQEGSLPPFNDVFMVPQ
AAV5    ANNLTSTVQVFTDDDYQLPYVVGNTEGCLPAFPPQVFTLPQ
AAV6    ANNLTSTVQVFSDSEYQLPYVLGSAHQGCLPPFPADVFMIPQ
AAV7    ANNLTSTIQVFSDSEYQLPYVLGSAHQGCLPPFPADVFMIPQ
AAV8    ANNLTSTIQVFTDSEYQLPYVLGSAHQGCLPPFPADVFMIPQ
AAV9    ANNLTSTVQVFTDSDYQLPYVLGSAHEGCLPPFPADVFMIPQ
AAV10   ANNLTSTIQVFTDSEYQLPYVLGSAHQGCLPPFPADVFMIPQ 380         390         400         410         420
AAV1    YGYLTLN--NGS-QAVGRSSFYCLEYFPSQMLRTGNNFTFSY
AAV2    YGYLTLN--NGS-QAVGRSSFYCLEYFPSQMLRTGNNFTFSY
AAV3A   YGYLTLN--NGS-QAVGRSSFYCLEYFPSQMLRTGNNFQFSY
AAV3B   YGYLTLN--NGS-QAVGRSSFYCLEYFPSQMLRTGNNFQFSY
AAV4    YGYCGLVTGNTSQQQTDRNAFYCLEYFPSQMLRTGNNFEITY
AAV5    YGYATLNRDNTE-NPTERSSFFCLEYFPSKMLRTGNNFEFTY
AAV6    YGYLTLN--NGS-QAVGRSSFYCLEYFPSQMLRTGNNFTFSY
AAV7    YGYLTLN--NGS-QSVGRSSFYCLEYFPSQMLRTGNNFEFSY
AAV8    YGYLTLN--NGS-QAVGRSSFYCLEYFPSQMLRTGNNFQFTY
AAV9    YGYLTLN--DGS-QAVGRSSFYCLEYFPSQMLRTGNNFQFSY
AAV10   YGYLTLN--NGS-QAVGRSSFYCLEYFPSQMLRTGNNFEFSY 430         440         450         460
AAV1    TFEEVPFHSSYAHSQSLDRLMNPLIDQYLYYLNRTQNQ-SGS
AAV2    TFEDVPFHSSYAHSQSLDRLMNPLIDQYLYYLSRT-NTPSGT
AAV3A   TFEDVPFHSSYAHSQSLDRLMNPLIDQYLYYLNRTQGTTSGT
AAV3B   TFEDVPFHSSYAHSQSLDRLMNPLIDQYLYYLNRTQGTTSGT
AAV4    SFEKVPFHSMYAHSQSLDRLMNPLIDQYLWGLQSTTTGTTLN
AAV5    NFEEVPFHSSFAPSQNLFKLANPLVDQYLYRFVSTNNTGG--
AAV6    TFEDVPFHSSYAHSQSLDRLMNPLIDQYLYYLNRTQNQ-SGS
AAV7    SFEDVPFHSSYAHSQSLDRLMNPLIDQYLYYLARTQSNPGGT
AAV8    TFEDVPFHSSYAHSQSLDRLMNPLIDQYLYYLSRTQTT-GGT
AAV9    EFENVPFHSSYAHSQSLDRLMNPLIDQYLYYLSKTIN--GSG
AAV10   TFEDVPFHSSYAHSQSLDRLMNPLIDQYLYYLSRTQST-GGT 470         480         490         500
AAV1    AQNKDLLFSRGSPAGMSVQPKNWLPGPCYRQQRVSKTKTDN-
AAV2    TTQSRLQFSQAGASDIRDQSRNWLPGPCYRQQRVSKTSADN-
AAV3A   TNQSRLLFSQAGPQSMSLQARNWLPGPCYRQQRLSKTANDN-
AAV3B   TNQSRLLFSQAGPQSMSLQARNWLPGPCYRQQRLSKTANDN-
AAV4    AGTATTNFTKLRPTNFSNFKKNWLPGPSIKQQGFSKTANQNY
AAV5    ------VQFNKNLAGRYANTYKNWFPGPMGRTQGWNLGSGVNR
AAV6    AQNKDLLFSRGSPAGMSVQPKNWLPGPCYRQQRVSKTKTDN-
AAV7    AGNRELQFYQGGPSTMAEQAKNWLPGPCFRQQRVSKTLDQN-
AAV8    ANTQTLGFSQGGPNTMANQAKNWLPGPCYRQQRVSTTTGQN-
AAV9    QNQQTLKFSVAGPSNMAVQGRNYIPGPSYRQQRVSTTVTQN-
AAV10   QGTQQLLFSQAGPANMSAQAKNWLPGPCYRQQRVSTTLSQN-
```

FIGURE 5D

```
             510         520         530         540
AAV1    -----NNSNFTWTGASKYNLGRESIINPGTAMASHKDDEDKF
AAV2    -----NNSEYSWTGATKYHLNGRDSLVNPGPAMASHKDDEEKF
AAV3A   -----NNSNFPWTAASKYHLNGRDSLVNPGPAMASHKDDEEKF
AAV3B   -----NNSNFPWTAASKYHLNGRDSLVNPGPAMASHKDDEEKF
AAV4    KIPATGSDSLIKYETHSTLDGRWSALTPGPPMATAGPADSKF
AAV5    ------ASVSAFATTNRMELEGASYQVPPQPNGMTNNLQGSNT
AAV6    -----NNSNFTWTGASKYNLNGRESIINPGTAMASHKDDKDKF
AAV7    -----NNSNFAWTGATKYNLNGRNSLVNPGVAMATHKDDEDRF
AAV8    -----NNSNFAWTAGTKYHLNGRNSLANPGIAMATHKDDEERF
AAV9    -----NNSEFAWPGASSWALNGRNSLMNPGPAMASHKEGEDRF
AAV10   -----NNSNFAWTGATKYHLNGRDSLVNPGVAMATHKDDEERF 550         560         570         580
AAV1    FPMSGVMIF-GKESAGASNTAL---DNVMITDEEEIKATNPVA
AAV2    FPQSGVLIF-GKQGSEKTNVDI---EKVMITDEEEIRTTNPVA
AAV3A   FPMHGNLIF-GKEGTTASNAEL---DNVMITDEEEIRTTNPVA
AAV3B   FPMHGNLIF-GKEGTTASNAEL---DNVMITDEEEIRTTNPVA
AAV4    --SNSQLIFAGPKQNGNTATVP---GTLIFTSEEELAATNATD
AAV5    YALENTMIFNSQPANPGTTATYLEGNMLITSESETQPVNRVA
AAV6    FPMSGVMIF-GKESAGASNTAL---DNVMITDEEEIKATNPVA
AAV7    FPSSGVLIF-GKTGATNKTTL----ENVLMTNEEEIRPTNPVA
AAV8    FPSNGILIF-GKQNAARDNADY--SDVMLTSEEEIKTTNPVA
AAV9    FPLSGSLIF-GKQGTGRDNVDA---DKVMITNEEEIKTTNPVA
AAV10   FPSSGVLMF-GKQGAGRDNVDY--SSVMLTSEEEIKTTNPVA 590         600         610         620         630
AAV1    TERFGTVAVNFQSSSTDPATGDVHAMGALPGMVWQDRDVYLQ
AAV2    TEQYGSVSTNLQRGNRQAATADVNTQGVLPGMVWQDRDVYLQ
AAV3A   TEQYGTVANNLQSSNTAPTTGTVNHQGALPGMVWQDRDVYLQ
AAV3B   TEQYGTVANNLQSSNTAPTTRTVNDQGALPGMVWQDRDVYLQ
AAV4    TDMWGNLPGGDQSNSNLPTVDRLTALGAVPGMVWQNRDIYYQ
AAV5    YNVGGQMATNNQSSTTAPATGTYNLQEIVPGSVWMERDVYLQ
AAV6    TERFGTVAVNLQSSSTDPATGDVHVMGALPGMVWQDRDVYLQ
AAV7    TEEYGIVSSNLQAANTAAQTQVVNNQGALPGMVWQNRDVYLQ
AAV8    TEEYGIVADNLQQQNTAPQIGTVNSQGALPGMVWQNRDVYLQ
AAV9    TESYGQVATNHQSAQAQAQTGWVQNQGILPGMVWQDRDVYLQ
AAV10   TEQYGVVADNLQQANTGPIVGNVSQGALPGMVWQNRDVYLQ 640         650         660         670
AAV1    GPIWAKIPHTDGHFHPSPLMGGFGLKHPPPQILIKNTPVPAN
AAV2    GPIWAKIPHTDGHFHPSPLMGGFGLKHPPPQILIKNTPVPAN
AAV3A   GPIWAKIPHTDGHFHPSPLMGGFGLKHPPPQIMIKNTPVPAN
AAV3B   GPIWAKIPHTDGHFHPSPLMGGFGLKHPPPQIMIKNTPVPAN
AAV4    GPIWAKIPHTDGHFHPSPLIGGFGLKHPPPQIFIKNTPVPAN
AAV5    GPIWAKIPETGAHFHPSPAMGGFGLKHPPPMLIKNTPVPGN
AAV6    GPIWAKIPHTDGHFHPSPLMGGFGLKHPPPQILIKNTPVPAN
AAV7    GPIWAKIPHTDGNFHPSPLMGGFGLKHPPPQILIKNTPVPAN
AAV8    GPIWAKIPHTDGNFHPSPLMGGFGLKHPPPQILIKNTPVPAD
AAV9    GPIWAKIPHTDGNFHPSPLMGGFMKHPPPQILIKNTPVPAD
AAV10   GPIWAKIPHTDGNFHPSPLMGGFGLKHPPPQILIKNTPVPAD
```

FIGURE 5E

```
              680            690            700            710
AAV1   PPAEFSATKFASFITQYSTGQVSVEIEWELQKENSKRWNPEV
AAV2   PSTTFSAAKFASFITQYSTGQVSVEIEWELQKENSKRWNPEI
AAV3A  PPTTFSPAKFASFITQYSTGQVSVEIEWELQKENSKRWNPEI
AAV3B  PPTTFSPAKFASFITQYSTGQVSVEIEWELQKENSKRWNPEI
AAV4   PATTFSSTPVNSFITQYSTGQVSVQIDWEIQKERSKRWNPEV
AAV5   -ITSFSDVPVSSFITQYSTGQVTVEMEWELKKENSKRWNPEI
AAV6   PPAEFSATKFASFITQYSTGQVSVEIEWELQKENSKRWNPEV
AAV7   PPEVFTPAKFASFITQYSTGQVSVEIEWELQKENSKRWNPEI
AAV8   PPTTFNQSKLNSFITQYSTGQVSVEIEWELQKENSKRWNPEI
AAV9   PPTAFNKDKLNSFITQYSTGQVSVEIEWELQKENSKRWNPEI
AAV10  PPTTFSQAKLASFITQYSTGQVSVEIEWELQKENSKRWNPEI
              720            730            740            750 752
AAV1   QYTSNYAKSANVDFTVDNNGLYTEPRPIGTRYLTRPL*
AAV2   QYTSNYNKSVNVDFTVDTNGVYSEPRPIGTRYLTRNL*
AAV3A  QYTSNYNKSVNVDFTVDTNGVYSEPRPIGTRYLTRNL*
AAV3B  QYTSNYNKSVNVDFTVDTNGVYSEPRPIGTRYLTRNL*
AAV4   QFTSNYGQQNSLLWAPDAAGKYTEPRAIGTRYLTHHL*
AAV5   QYTNNYNDPQFVDFAPDSTGEYRTTRPIGTRYLTRPL*
AAV6   QYTSNYAKSANVDFTVDNNGLYTEPRPIGTRYLTRPL*
AAV7   QYTSNFEKQTGVDFAVDSQGVYSEPRPIGTRYLTRNL*
AAV8   QYTSNYYKSTSVDFAVNTEGVYSEPRPIGTRYLTRNL*
AAV9   QYTSNYYKSNNVEFAVNTEGVYSEPRPIGTRYLTRNL*
AAV10  QYTSNYYKSTNVDFAVNTEGTYSEPRPIGTRYLTRNL*
```

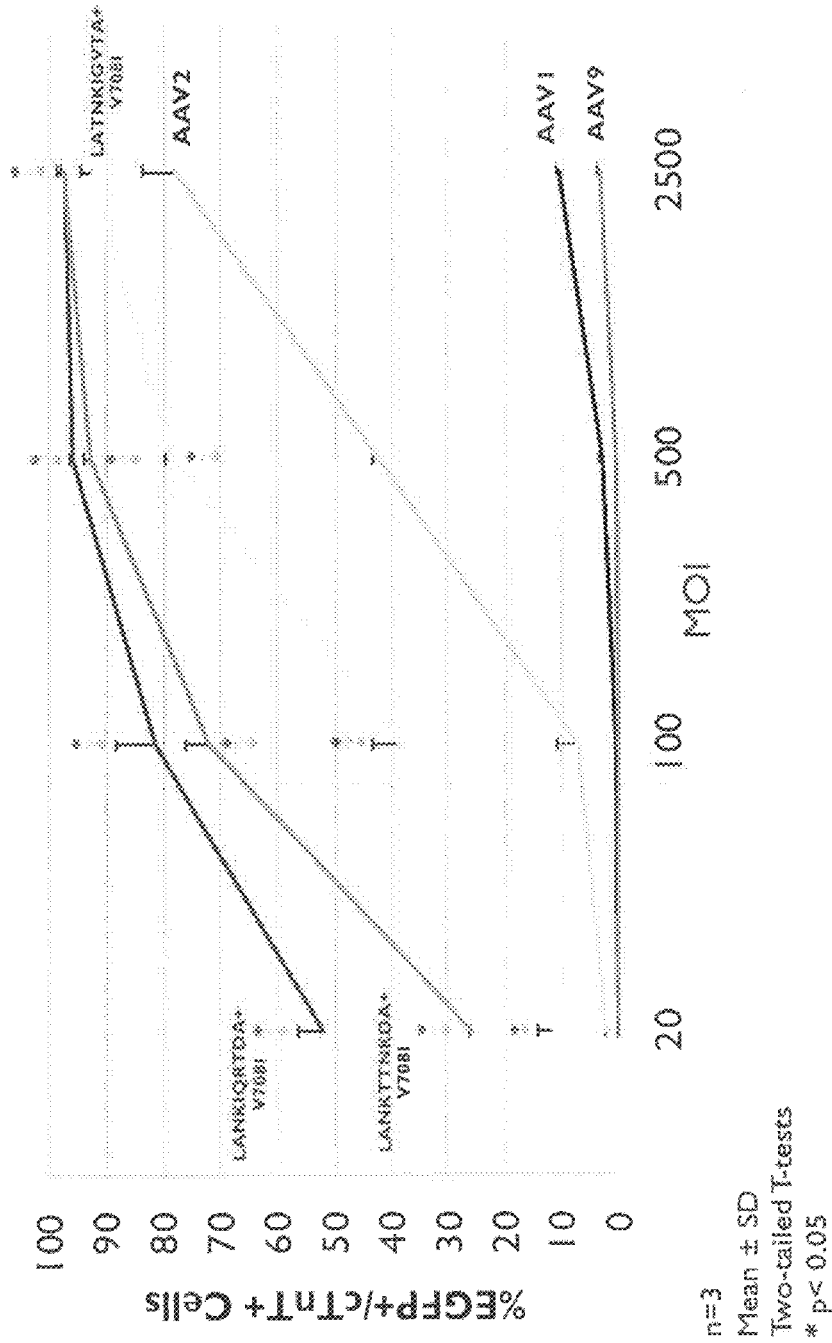

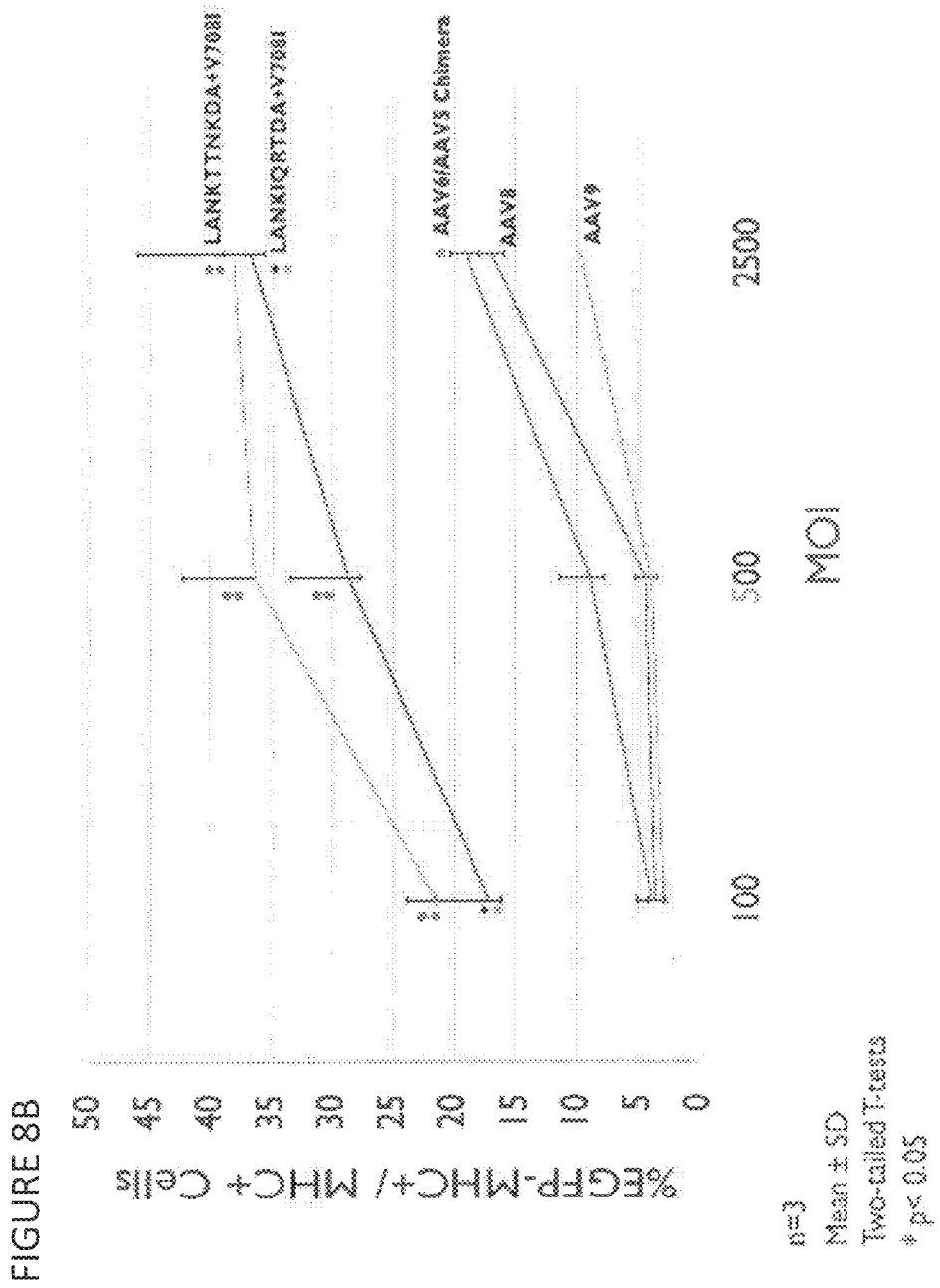

ADENO-ASSOCIATED VIRUS VARIANT CAPSIDS AND METHODS OF USE THEREOF

CROSS-REFERENCE TO RELATED APPLICATIONS

This application is a continuation of U.S. patent application Ser. No. 17/718,870, filed Apr. 12, 2022, which is a continuation of U.S. patent application Ser. No. 17/400,041, filed Aug. 11, 2021, which is a continuation of U.S. patent application Ser. No. 16/648,195 filed Mar. 17, 2020 (now U.S. Pat. No. 11,118,192 issued Sep. 14, 2021), which is a 35 U.S.C. 371 national stage of International Application Number PCT/US2018/051812 filed Sep. 19, 2018, which claims the benefit of U.S. Provisional Patent Application Ser. No. 62/560,901, filed Sep. 20, 2017, the full disclosure of each of which are incorporated herein by reference.

SEQUENCE LISTING SUBMISSION VIA EFS-WEB

A computer readable XML file, entitled "090400-5009-US-03-Sequence-Listing" created on or about Dec. 20, 2022, with a file size of about 128,000 bytes, contains the sequence listing for this application and is hereby incorporated by reference in its entirety.

FIELD OF THE INVENTION

The invention disclosed herein relates generally to the field of adeno-associated virus (AAV) virions comprising variant capsid proteins and the generation of such variant capsids using directed evolution techniques.

BACKGROUND OF THE DISCLOSURE

Muscle is associated with a variety of severe genetic disorders. Muscle is the target tissue in gene therapy for many muscular dystrophy diseases and also can be exploited as a biofactory to produce secretory factors to treat systemic disease. Delivering therapeutic genes to muscle tissue in human is arguably the most urgent unmet need in treating muscle-related diseases.

One approach to accomplish muscle-directed gene delivery is gene-based adeno-associated virus (AAV)-mediated therapy, in which a recombinant adeno associated virus (rAAV) is used to deliver a gene to one or more muscle cells, for example to replace a missing gene, to correct a dominant defective gene, or to provide a template for continuous protein therapy. While AAV-based clinical gene therapy has been increasingly successful, it is still fraught with shortcomings with regard to viral vector properties, including, for example, targeting the desired cells of the muscle with high efficiency. Accordingly, there is a need in the art for new AAV variants with superior transduction capabilities that will provide for more effective gene-based delivery to the cells of the muscle for the treatment of disease. There is a need in the art for such AAV variants which exhibit an enhanced muscle transduction profile—in some instances broadly, in other instances preferentially to certain muscle cell types—as compared to wild-type AAVs and AAV variants as known in the art.

Naturally occurring AAV is a single stranded DNA virus that contains three open reading frames, rep, cap, and aap. The first gene, rep, encodes four proteins necessary for genome replication (Rep78, Rep68, Rep52, and Rep40), the second, cap, expresses three structural proteins (VP1-3) that assemble to form the viral capsid, and the third expresses the assembly activating protein (AAP) that is essential for capsid assembly. AAV is dependent upon the presence of a helper virus, such as an adenovirus or herpesvirus, for active replication. In the absence of a helper virus, AAV establishes a latent state in which its genome is maintained episomally or integrated into the host chromosome in the AAVS1 locus.

In vitro and in vivo directed evolution techniques may be used to select for AAV variants that offer an improvement over current AAV-based gene delivery vectors. Such directed evolution techniques are known in the art and described, e.g., in PCT publication WO 2014/194132 and Kotterman & Schaffer (Nature Review Genetics, AOP, published online 20 May 2014; doi: 10.1038/nrg3742), both of which are incorporated herein in their entirety by reference. Directed evolution is a capsid engineering approach that emulates natural evolution through iterative rounds of genetic diversification and selection processes, thereby enabling the accumulation of beneficial mutations that progressively improve the function of a biomolecule such as an AAV-based virion. In this approach, wild-type AAV cap genes are diversified to create large genetic libraries that are packaged to generate libraries of viral particles, and selective pressure is applied to isolate unique variants with superior phenotypes that can overcome gene delivery barriers.

AAV variants have been disclosed in, for example, U.S. Pat. Nos. 9,193,956; 9,186,419; 8,632,764; 8,663,624; 8,927,514; 8,628,966; 8,263,396; 8,734,809; 8,889,641; 8,632,764; 8,691,948; 8,299,295; 8,802,440; 8,445,267; 8,906,307; 8,574,583; 8,067,015; 7,588,772; 7,867,484; 8,163,543; 8,283,151; 8,999,678; 7,892,809; 7,906,111; 7,259,151; 7,629,322; 7,220,577; 8,802,080; 7,198,951; 8,318,480; 8,962,332; 7,790,449; 7,282,199; 8,906,675; 8,524,446; 7,712,893; 6,491,907; 8,637,255; 7,186,522; 7,105,345; 6,759,237; 6,984,517; 6,962,815; 7,749,492; 7,259,151; and 6,156,303; United States Publication Numbers 2013/0295614; 2015/0065562; 2014/0364338; 2013/0323226; 2014/0359799; 2013/0059732; 2014/0037585; 2014/0056854; 2013/0296409; 2014/0335054 2013/0195801; 2012/0070899; 2011/0275529; 2011/0171262; 2009/0215879; 2010/0297177; 2010/0203083; 2009/0317417; 2009/0202490; 2012/0220492; 2006/0292117; and 2004/0002159; European Publication Numbers 2692731 A1; 2383346 B1; 2359865 B1; 2359866 B1; 2359867 B1; and 2357010 B1; 1791858 B1; 1668143 B1; 1660678 B1; 1664314 B1; 1496944 B1; 1456383 B1; 2341068 B1; 2338900 B1; 1456419 B1; 1310571 B1; 1456383 B1; 1633772 B1; and 1135468 B1; and International (PCT) Publication Numbers WO 2014/124282; WO 2013/170078; WO 2014/160092; WO 2014/103957; WO 2014/052789; WO 2013/174760; WO 2013/123503; WO 2011/038187; and WO 2008/124015; WO 2003/054197; however, none of these references disclose the embodiments and/or features and/or composition of matter structures of the AAV variants disclosed herein.

All documents and references cited herein and in the referenced patent documents, are hereby incorporated herein by reference.

SUMMARY OF THE INVENTION

Provided herein are variant adeno-associated virus (AAV) capsid proteins having one or more modifications in amino acid sequence relative to a parental AAV capsid protein, which, when present in an AAV virion, confer increased infectivity of one or more types of muscle cells as compared to the infectivity of the muscle cells by an AAV virion comprising an unmodified parental AAV capsid protein. Also provided are recombinant AAV virions and pharmaceutical compositions thereof comprising a variant AAV capsid protein as described herein, methods of making variant rAAV capsid proteins and virions, and methods for using these rAAV capsid proteins and virions in research and in clinical practice, for example in the delivery of nucleic acid sequences to one or more muscle cells for the treatment of disorders and diseases.

In some aspects of the disclosure, variant adeno-associated virus (AAV) capsid proteins are provided, these variant AAV capsid proteins having one or more modifications in amino acid sequence relative to a parental AAV capsid, which, when present in an AAV virion, confer increased infectivity of one or more types of muscle cells (e.g. skeletal muscle cells and/or cardiac muscle cells) as compared to the infectivity of the muscle cells by an AAV virion comprising a parental AAV capsid protein that does not comprise the amino acid sequence modification. In related aspects of the disclosure, the variant AAV capsid proteins, when present in an AAV virion also confer enhanced resistance to neutralization by anti-AAV antibodies.

In some aspects of the disclosure, recombinant AAV (rAAV) virions are provided, these rAAV virions comprising a variant capsid protein as described herein, wherein the rAAV virions exhibit increased infectivity of one or more types of muscle cells (e.g. skeletal muscle cells and/or cardiac muscle cells) relative to the infectivity of the muscle cell by an AAV virion comprising a corresponding unmodified parental AAV capsid protein. In some embodiments, the rAAV virion exhibits increased infectivity of all muscle cells relative to the AAV virion comprising the parental AAV capsid protein. In other embodiments, the rAAV virion exhibits increased infectivity of certain muscle cell types but not others relative of the AAV virion comprising the parental AAV capsid protein. Put another way, the rAAV virion exhibits increased infectivity that is preferential for certain muscle cell types but not others, e.g. the rAAV demonstrates a preferentially increased infectivity of one or more cell types selected from skeletal muscle fibroblasts, skeletal muscle satellite cells, cardiac fibroblasts, cardiac progenitor cells, smooth muscle cells and/or diaphragm muscle cells, but does not demonstrate increased infectivity of all cell types.

In some embodiments, the rAAV virion comprises a heterologous nucleic acid. In some such embodiments, the heterologous nucleic acid encodes an RNA that encodes a polypeptide. In other such embodiments, the heterologous nucleic acid sequence encodes an RNA that does not encode a polypeptide, e.g. the heterologous nucleic acid sequence is an RNA interference agent, a guide RNA for a nuclease, etc.

Also provided herein are pharmaceutical compositions comprising the subject infectious rAAV virions and a pharmaceutically acceptable carrier.

Also provided is the use of an rAAV virion comprising a variant capsid protein as herein described in a method of delivering a heterologous nucleic acid to a target cell (such as a cardiomyocyte) by contacting the target cell with the rAAV virion. In some embodiments, the target cell is in vivo, such as in the heart of an individual in need of treatment for a cardiovascular disorder. In other embodiments, the target cell is in vitro.

Also provided are methods of treating and/or preventing a disease (e.g. a cardiac or skeletal muscle disorder) by administering to a subject in need of such treatment an effective amount of rAAV virions comprising a variant capsid protein as herein described or a pharmaceutical composition comprising an effective amount of the rAAV virions.

Also provided is an isolated nucleic acid comprising a sequence encoding a variant AAV capsid protein as described herein and a host cell comprising the isolated nucleic acid. In yet other embodiments, the isolated nucleic acid and/or isolated host cell comprises the rAAV.

In some aspects, the variant AAV capsid protein comprises an insertion of from about 5 amino acids to about 20 amino acids (a "heterologous peptide", or "peptide insertion") in the GH-loop of the capsid protein, relative to a corresponding parental AAV capsid protein, wherein the variant capsid protein, when present in an AAV virion, confers increased infectivity of a muscle cell compared to the infectivity of a muscle cell by an AAV virion comprising the corresponding parental AAV capsid protein. In some embodiments, the peptide comprises or consists essentially of a sequence selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTINKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42). In some preferred embodiments, the peptide comprises or consists essentially of a sequence selected from the group consisting of NKIQRTD (SEQ ID NO:13), NKTTNKD (SEQ ID NO:14), TNKIGVT (SEQ ID NO:15), LANKIQRTDA (SEQ ID NO:27), LANKTTNKDA (SEQ ID NO:28), LATNKIGVTA (SEQ ID NO:29) and LATNKIGVTS (SEQ ID NO:37).

In some aspects, the variant AAV capsid protein comprises one or more amino acid substitutions relative to a corresponding parental AAV capsid protein, wherein the variant capsid protein, when present in an AAV virion, confers increased infectivity of a muscle cell compared to the infectivity of a muscle cell by an AAV virion comprising the corresponding parental AAV capsid protein.

In some embodiments, a variant AAV capsid protein is disclosed comprising a P363L substitution relative to AAV2 and optionally further comprising an E347K and/or V708I substitution relative to AAV2.

In related aspects, the variant AAV capsid protein comprises a peptide insertion and one or more amino acid substitutions relative to a corresponding parental AAV capsid protein, wherein the variant capsid protein, when present in an AAV virion, confers increased infectivity of a muscle cell compared to the infectivity of a muscle cell by an AAV virion comprising the corresponding parental AAV capsid protein. In several embodiments, a variant AAV capsid protein is provided comprising a peptide insertion and a V708I substitution relative to AAV2, wherein the peptide insertion is optionally selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42), preferably from the group consisting of NKIQRTD (SEQ ID NO:13), NKTTNKD (SEQ ID NO:14), TNKIGVT (SEQ ID NO:15), LANKIQRTDA (SEQ ID NO:27), LANKTTNKDA (SEQ ID NO:28), LATNKIGVTA (SEQ ID NO:29) and LATNKIGVTS (SEQ ID NO:37). In several embodiments, a variant AAV capsid protein is provided comprising a peptide insertion and a P363L substitution relative to AAV2, wherein the peptide insertion is optionally selected from the group consisting of GNLTKGN (SEQ ID NO:16), LAGNLTKGNA (SEQ ID NO:30), QADTTKN (SEQ ID NO:23) and LAQADTTKNA (SEQ ID NO:39).

In some embodiments, a variant AAV capsid protein is disclosed comprising the heterologous peptide LANKIQRTDA (SEQ ID NO:27) and a V708I substitution relative to AAV2 and optionally further comprising an A593E and/or S109T and/or T330A and/or R588M substitution relative to AAV2. In other embodiments, a variant AAV capsid protein is disclosed comprising the heterologous peptide LANKIQRTDA (SEQ ID NO:27) and an A35P substitution relative to AAV2. In other embodiments, a variant AAV capsid protein is disclosed comprising the heterologous peptide LANKIQRTDA (SEQ ID NO:27) and amino acid substitutions N312K, N449D, N551S, I698V, and L735Q relative to AAV2 and optionally further comprising a V708I substitution relative to AAV2.

In some embodiments, a variant AAV capsid protein is disclosed comprising the heterologous peptide LANKTTNKDA (SEQ ID NO:28) and a V708I substitution relative to AAV2 and optionally further comprising an S109T and/or W694C and/or W606C substitution relative to AAV2. In other embodiments, a variant AAV capsid protein is disclosed comprising the heterologous peptide LANKTTNKDA (SEQ ID NO:28) and an I698V substitution relative to AAV2. In other embodiments, a variant AAV capsid protein is disclosed comprising the heterologous peptide LANKTTNKDA (SEQ ID NO:28) and amino acid substitutions N312K, N449D, N551S, I698V, and L735Q relative to AAV2 and optionally further comprising a V708I substitution relative to AAV2.

In some embodiments, a variant AAV capsid protein is disclosed comprising the heterologous peptide LATNKIGVTA (SEQ ID NO:29) and a V708I substitution relative to AAV2 and optionally further comprising an N449K and/or G222S substitution relative to AAV2. In other embodiments, a variant AAV capsid protein is disclosed comprising the heterologous peptide LATNKIGVTA (SEQ ID NO:29) and amino acid substitutions N312K, N449D, N551S, I698V, and L735Q relative to AAV2 and optionally further comprising a V708I substitution relative to AAV2.

In some embodiments, a variant AAV capsid protein is disclosed comprising a heterologous peptide as described herein and a P363L substitution relative to AAV2.

Also disclosed herein are methods for manufacture and/or delivery of an rAAV comprising a variant AAV capsid as disclosed herein. In addition, provided herein are kits comprising an rAAV comprising a variant AAV capsid as disclosed herein and for use in methods described herein.

In other embodiments, the AAV virion comprising the variant capsid protein in the preceding paragraphs may incorporate any of the preceding or subsequently disclosed embodiments. Indeed, it is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the invention and are disclosed herein just as if each and every combination was individually and explicitly disclosed. In addition, all sub-combinations of the various embodiments and elements thereof are also specifically embraced by the invention and are disclosed herein just as if each and every such sub-combination was individually and explicitly disclosed herein.

The Summary of the Invention is not intended to define the claims nor is it intended to limit the scope of the invention in any manner.

Other features and advantages of the invention disclosed herein will be apparent from the following Figures, Detailed Description, and the Claims.

BRIEF DESCRIPTION OF THE FIGURES

FIG. 3A provides Round 4 sequencing analysis for the selective pressure of intravenous delivery to cardiac tissue. FIG. 3B provides Round 2 sequencing analysis for the selective pressure of intravenous delivery in the presence of neutralizing antibodies to cardiac tissue. FIG. 3C provides Round 3 sequencing analysis for the selective pressure of intravenous delivery to skeletal muscle tissue. FIG. 3A shows 57.40% LANKIQRTDA (SEQ ID N:27) Motif, 16.96% LANKTTNKDA (SEQ ID NO:28) Motif, 7.32% A593E Motif, 7.32% Other, 4.88% V708I Motif and 4.88% LASNTVKAIA (SEQ ID NO:32) Motif. FIG. 3B shows 21.14% Other, 20.33% LAQADTTKNA (SEQ ID NO:39) Motif, 15.45% LANKTTNKDA (SEQ ID NO:28) Motif, 15.45% LAASNITKAA (SEQ ID NO:33) Motif, 15.45% AAV6/AAV5 Chimera Motif and 12.20% LANTVKLSTA (SEQ ID NO:31) Motif. FIG. 3C shows 43.21% A593E Motif, 41.98% P363L Motif and 14.81% Other.

FIG. 4B is a representative three-dimensional model of the AAV6/AAV5 chimera containing V229I, A490T, and A581T substitutions (corresponding to the amino acid sequence set forth as SEQ ID NO:62). FIG. 4C is a representative three-dimensional model of AAV2 containing a P363L substitution.

FIG. 5 provides an alignment of wild-type AAV SEQ ID NOS:1-11 showing amino acid locations between and across the wild-type (naturally occurring) serotypes AAV1, AAV2, AAV3A, AAV3B, and AAV4-10.

FIGS. 6A-6E provide data on the transduction of human cardiomyocytes in vitro by recombinant AAV virus comprising the novel AAV variant LANKIQRTDA+V708I (SEQ ID NO:43) capsid, the novel AAV variant LANKTTNKDA+V708I (SEQ ID NO:48) capsid, and the novel LATNKIGVTA+V708I (SEQ ID NO:46) variant capsid, each expressing a GFP transgene under the control of the CAG promoter. FIG. 6A: Cells that were differentiated into cardiomyocytes from a human pluripotent stem cell line were infected with novel AAV variant LANKIQRTDA+V708I (SEQ ID N:43).CAG.GFP, novel AAV variant LANKTTNKDA+V708I (SEQ ID NO:48).CAG.GFP, novel AAV variant LATNKIGVTA+V708I (SEQ ID NO:46).CAG.GFP or wild type controls AAV1.CAG.GFP, AAV2.CAG.GFP, and AAV9.CAG.GFP at MOIs of 20, 100, 500, and 2500. Immunofluorescence imaging of the cell cultures 6 days after infection at all MOIs demonstrate that the novel AAV variant capsids transduce cardiomyocytes better than wild type AAV1, AAV2, or AAV9 capsids. FIG. 6B: Quantification of the percent of GFP-positive cardiomyocytes in each culture by flow cytometry reveals that the novel AAV variant capsids provide for a significant, dose-dependent improvement in the number of cells transduced over wild type AAV1, AAV2, or AAV9 capsids. * p<0.05 FIGS. 6C-6D: Quantification of the amount of GFP in each culture by Western blot reveals that the novel AAV variants provide for significant improvement in expression of the transgene over wild type AAV1, AAV2, or AAV9 capsids. NT=not transduced. FIG. 6E: Cells that were differentiated into cardiomyocytes from a human pluripotent stem cell line were infected with novel AAV variant LANKIQRTDA+V708I (SEQ ID NO:43).CAG.GFP, novel AAV variant LANKTTNKDA+V708I (SEQ ID NO:48).CAG.GFP, novel AAV variant LATNKIGVTA+V708I (SEQ ID NO:46).CAG.GFP or wild type controls AAV1.CAG.GFP, AAV2.CAG.GFP, and AAV9.CAG.GFP. Immunofluorescence imaging of the cell cultures on days 1, 2, 3, and 5 after infection at an MOI of 500 demonstrate that the novel AAV variant capsids transduce cardiomyocytes better and begin expressing the GFP transgene earlier than wild type AAV1, AAV2, or AAV9 capsids.

FIG. 7A: Cells that were differentiated into cardiomyocytes from a human pluripotent stem cell line were infected with novel AAV variant AAV6/AAV5 chimera capsid or wild type controls AAV11.CAG.GFP, AAV8.CAG.GFP, and AAV9.CAG.GFP at MOIs of 100, 500, and 2500. Immunofluorescence imaging of the cell cultures 6 days after infection at all MOIs demonstrate that the novel AAV variant capsid transduces cardiomyocytes better than wild type AAV1, AAV8, or AAV9 capsids. FIG. 7B: Quantification of the percent of GFP-positive cardiomyocytes in each culture by flow cytometry reveals that the novel AAV variant capsid provides for a significant, dose-dependent improvement in the number of cells transduced over wild type AAV1, AAV8, or AAV9 capsids. * p<0.05 FIGS. 7C-7D: Quantification of the amount of GFP in each culture by Western blot reveals that the novel AAV variant provides for significant improvement in expression of the transgene over wild type AAV1, AAV8, or AAV9 capsids, vehicle=not transduced. FIG. 7E: Cells that were differentiated into cardiomyocytes from a human pluripotent stem cell line were infected with novel AAV variant AAV6/AAV5 chimera capsid or wild type control AAV8.CAG.GFP. Immunofluorescence imaging of the cell cultures on days 3, 4, 5, and 6 after infection at an MOI of 2500 demonstrate that the novel AAV variant capsids transduce cardiomyocytes better and begin expressing the GFP transgene earlier than the wild type AAV8 capsid.

FIGS. 8A-C provide data on the transduction of human skeletal myofibers in vitro by recombinant AAV virus comprising the novel AAV variant LANKIQRTDA+V708I (SEQ ID NO:43) capsid, the novel AAV variant LANKTTNKDA+V708I (SEQ ID NO:48) capsid, and the novel AAV variant AAV6/AAV5 chimera capsid, each expressing a GFP transgene under the control of the CAG promoter. FIG. 8A: Cells that were differentiated into skeletal myofibers from human primary myoblasts were infected with novel AAV variant LANKIQRTDA+V708I (SEQ ID NO:43).CAG.GFP, novel AAV variant LANKTTNKDA+V708I (SEQ ID NO:48).CAG.GFP, novel AAV variant AAV6/AAV5 chimera.CAG.GFP or wild type controls AAV8.CAG.GFP and AAV9.CAG.GFP at MOIs of 100, 500, and 2500. Immunofluorescence imaging of the cell cultures 7 days after infection at all MOIs demonstrate that the novel AAV variant capsids transduce skeletal myofibers better than wild type AAV8 or AAV9 capsids. FIG. 8B: Quantification of the percent of GFP-positive skeletal myofibers in each culture by flow cytometry reveals that the novel AAV variant capsids provide for a significant, dose-dependent improvement in the number of cells transduced over wild type AAV8 or AAV9 capsids. * p<0.05 FIG. 8C: Cells that were differentiated into skeletal myofibers from human primary myoblasts were infected with novel AAV variant LANKIQRTDA+V708I (SEQ ID NO:43).CAG.GFP, novel AAV variant AAV6/AAV5 chimera.CAG.GFP or wild type controls AAV8.CAG.GFP and AAV9.CAG.GFP. Immunofluorescence imaging of the cell cultures on days 2-7 after infection at an MOI of 2500 demonstrate that the novel AAV variant capsids transduce skeletal myofibers better and begin expressing the GFP transgene earlier than wild type AAV8 or AAV9 capsids.

FIG. 9A: Cells that were differentiated into muscle progenitor cells from a human pluripotent stem cell line were infected with novel AAV variant LANKIQRTDA+ V708I (SEQ ID NO:43).CAG.GFP, novel AAV variant LANKTITNKDA+V708I (SEQ ID NO:48).CAG.GFP, novel AAV variant AAV6/AAV5 chimera.CAG.GFP or wild type control AAV9.CAG.GFP at an MOI of 500. Immunofluorescence imaging of the cell cultures 6 days after infection at all MOIs demonstrate that the novel AAV variant capsids transduce muscle progenitor cells better than wild type AAV9. FIG. 9B: Quantification of the percent of GFP-positive muscle progenitor cells in each culture by flow cytometry reveals that the novel AAV variant capsids provide for a significant improvement in the number of cells transduced over wild type AAV9. * p<0.05.

FIG. 10A: Fold increase in transduction of human cardiomyocytes by the novel AAV capsid variants compared to wild type AAV8 and AAV9, the serotypes most widely used in clinical applications for muscle diseases. FIG. 10B: Fold increase in transduction of human skeletal myofibers by the novel AAV capsid variants compared to wild type AAV8 and AAV9.

FIG. 11B: Luciferase activity in heart, diaphragm, and quadriceps 56 days post-administration demonstrate that the novel AAV variant LANKIQRTDA+V708I (SEQ ID NO:43) capsid can transduce mouse cardiac and skeletal muscle in vivo.

FIG. 12A: Representative images of haemotoxylin and eosin (H&E) and anti-GFP antibody staining of cross-sections of the proximal biopsy site at 2×, 4×, and 20× magnification demonstrate that the novel AAV variant LANKIQRTDA+ V708I (SEQ ID NO:43) capsid can transduce primate skeletal muscle cells in vivo. FIG. 12B: Representative images of haemotoxylin and eosin (H&E) and anti-GFP antibody staining of longitudinal sections of the distal biopsy site at 2×, 4×, and 20× magnification demonstrate that the novel AAV variant LANKIQRTDA+V708I (SEQ ID NO:43) capsid can transduce primate skeletal muscle cells in vivo.

DETAILED DESCRIPTION

Figure 1:
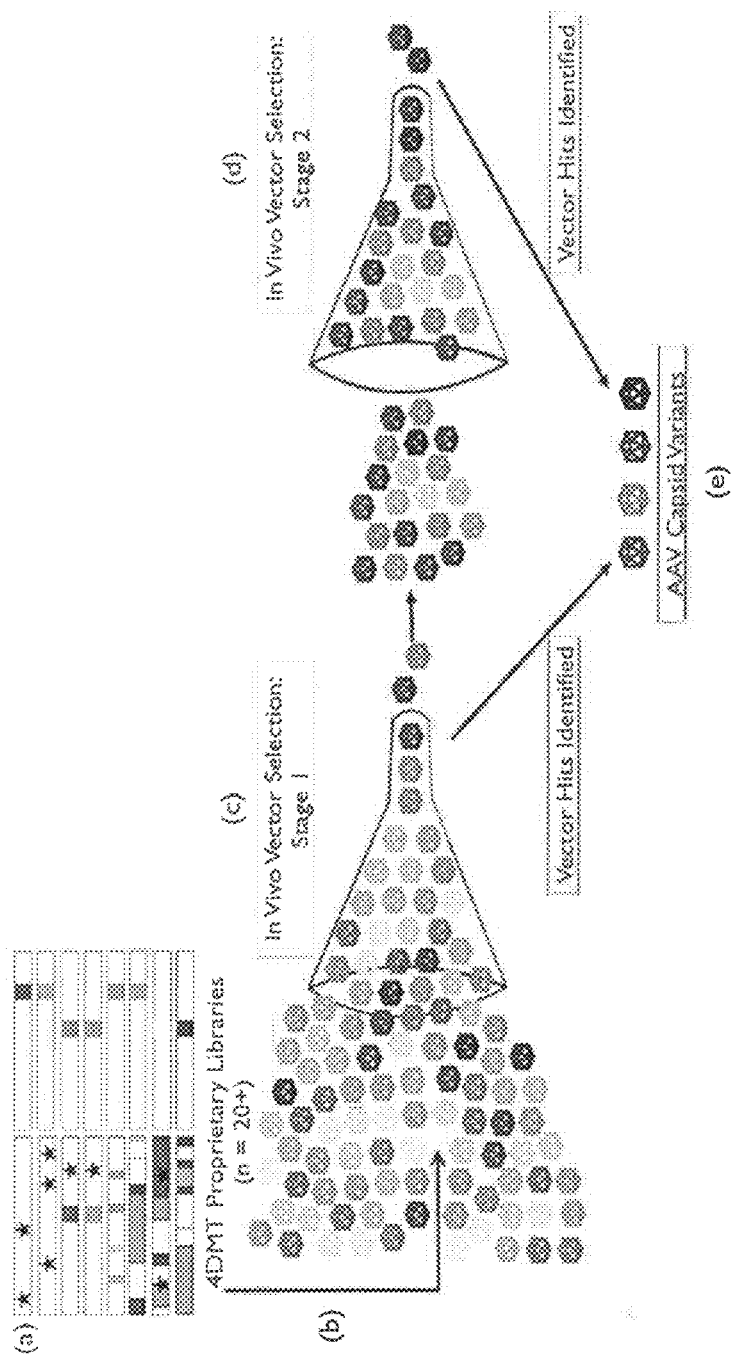
FIG. 1 depicts embodiments of a directed evolution methodology. Step (a) depicts the generation of a viral capsid library comprising combinations of DNA mutation techniques and cap genes. Step (b) depicts the packaging of the viruses such that each viral particle is composed of a mutant capsid surrounding the cap gene encoding that capsid and purified. The capsid library is then placed under selective pressure in vitro or in vivo. In this aspect of the directed evolution technology, tissues or cellular material of interest are harvested for isolation of AAV variants that have successfully infected that target, and the successful viruses are recovered. Step (c) depicts the Stage 1 enrichment of successful clones through repeated selection. Step (d) depicts the Stage 2 enrichment of selected cap genes which undergo re-diversification and further selection steps to iteratively increase viral fitness. Step (e) depicts the variants, identified as hits during Vector Selection Stages 1 and 2, which will be manufactured as recombinant AAV vectors and characterized for the level of transduction of various cell types and tissue targets. By the nature of the AAV directed evolution process, variants that are disclosed herein have already demonstrated the ability to transduce muscle cells and deliver a genome (the genome encoding the variant cap gene) during the selection process.

Before the present methods and compositions are described, it is to be understood that this invention is not limited to a particular method or composition described and as such may vary. It is also to be understood that the terminology used herein is for the purpose of describing particular embodiments only, and is not intended to be limiting, since the scope of the present invention will be limited only by the appended claims.

The invention disclosed herein is illustrated in the figures and description. However, while particular embodiments are illustrated in the figures, there is no intention to limit the invention to the specific embodiment or embodiments illustrated and/or disclosed. Rather, the invention disclosed herein is intended to cover all modifications, alternative constructions, and equivalents falling within the spirit and scope of the invention. As such, the figures are intended to be illustrative and not restrictive.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It is noted that as used herein and in the appended claims, the singular forms "a," "an," and "the" include plural referents unless the context clearly dictates otherwise. Thus, for example, reference to "a recombinant AAV virion" includes a plurality of such virions and reference to "the muscle cell" includes reference to one or more muscle cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Adeno-associated virus is a nonpathogenic parvovirus composed of a 4.7 kb single-stranded DNA genome within a non-enveloped, icosahedral capsid. The genome contains three open reading frames (ORF) flanked by inverted terminal repeats (ITR) that function as the viral origin of replication and packaging signal. The rep ORF encodes four nonstructural proteins that play roles in viral replication, transcriptional regulation, site-specific integration, and virion assembly. The cap ORF encodes three structural proteins (VP 1-3) that assemble to form a 60-mer viral capsid. Finally, an ORF present as an alternate reading frame within the cap gene produces the assembly-activating protein (AAP), a viral protein that localizes AAV capsid proteins to the nucleolus and functions in the capsid assembly process.

There are several naturally occurring ("wild-type") serotypes and over 100 known variants of AAV, each of which differs in amino acid sequence, particularly within the hypervariable regions of the capsid proteins, and thus in their gene delivery properties. No AAV has been associated with any human disease, making recombinant AAV attractive for clinical applications.

For the purposes of the disclosure herein, the terminology "AAV" is an abbreviation for adeno-associated virus, including, without limitation, the virus itself and derivatives thereof. Except where otherwise indicated, the terminology refers to all subtypes or serotypes and both replication-competent and recombinant forms. The term "AAV" includes, without limitation, AAV type 1 (AAV-1 or AAV1), AAV type 2 (AAV-2 or AAV2), AAV type 3A (AAV-3A or AAV3A), AAV type 3B (AAV-3B or AAV3B), AAV type 4 (AAV-4 or AAV4), AAV type 5 (AAV-5 or AAV5), AAV type 6 (AAV-6 or AAV6), AAV type 7 (AAV-7 or AAV7), AAV type 8 (AAV-8 or AAV8), AAV type 9 (AAV-9 or AAV9), AAV type 10 (AAV-10 or AAV10 or AAVrh10), avian AAV, bovine AAV, canine AAV, caprine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers NC_002077.1 (AAV1), AF063497.1 (AAV1), NC_001401.2 (AAV2), AF043303.1 (AAV2), J01901.1 (AAV2), U48704.1 (AAV3A), NC_001729.1 (AAV3A), AF028705.1 (AAV3B), NC_001829.1 (AAV4), U89790.1 (AAV4), NC_006152.1 (AA5), AF085716.1 (AAV-5), AF028704.1 (AAV6), NC_006260.1 (AAV7), AF513851.1 (AAV7), AF513852.1 (AAV8) NC_006261.1 (AAV-8), AY530579.1 (AAV9), AAT46337 (AAV10) and AA088208 (AAVrh10); the disclosures of which are incorporated by reference herein for teaching AAV nucleic acid and amino acid sequences. See also, e.g., Srivistava et al. (1983) J. Virology 45:555; Chiorini et al. (1998) J. Virology 71:6823; Chiorini et al. (1999) J. Virology 73: 1309; Bantel-Schaal et al. (1999) J. Virology 73:939; Xiao et al. (1999) J. Virology 73:3994; Muramatsu et al. (1996) Virology 221:208; Shade et. al. (1986) J. Virol. 58:921; Gao et al. (2002) Proc. Nat. Acad. Sci. USA 99: 11854; Moris et al. (2004) Virology 33:375-383; international patent publications WO 00/28061, WO 99/61601, WO 98/11244; and U.S. Pat. No. 6,156,303.

The sequences of naturally existing cap (capsid) proteins associated with AAV serotypes are known in the art and include those disclosed herein as AAV1 (SEQ ID NO:1), AAV2 (SEQ ID NO:2), AAV3A (SEQ ID NO:3), AAV3B (SEQ ID NO:4), AAV4 (SEQ ID NO:5), AAV5 (SEQ ID NO:6), AAV6 (SEQ ID NO:7), AAV7 (SEQ ID NO:8), AAV8 (SEQ ID NO:9), AAV9 (SEQ ID NO:10), AAV10 (SEQ ID NO:11), and AAVrh10 (SEQ ID NO:12). The terms "variant AAV capsid protein" or "AAV variant' refer to an AAV capsid protein comprising an amino acid sequence that includes at least one modification or substitution (including deletion, insertion, point mutation, etc.) relative to a naturally existing or "wild-type" AAV capsid protein sequences, e.g. as set forth in SEQ ID NO:1-12 herein. A variant AAV capsid protein may have about 80% identity or more to the amino acid sequence of a wild type capsid protein, for example, 85% identity or more, 90% identity or more, or 95% identity or more to the amino acid sequence of the wild type capsid protein, for example, 98% or 99% identity to the wild type capsid protein. A variant AAV capsid protein may not be a wild type capsid protein.

For the purposes of the disclosure herein, "AAV virion" or "AAV viral particle" refers to a viral particle composed of at least one AAV capsid protein and an encapsidated AAV polynucleotide.

For the purposes of the disclosure herein, the terminology "rAAV" is an abbreviation that refers to recombinant adeno-associated virus. "Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

The term "rAAV vector" encompasses rAAV virions (i.e., rAAV viral particles) (e.g., an infectious rAAV virion), which by definition include an rAAV polynucleotide; and also encompasses polynucleotides encoding rAAV (e.g., a single stranded polynucleotide encoding rAAV (ss-rAAV); a double stranded polynucleotide encoding rAAV (ds-rAAV), e.g., plasmids encoding rAAV; and the like).

If an AAV virion comprises a heterologous polynucleotide (i.e. a polynucleotide other than a wild-type AAV genome, e.g., a transgene to be delivered to a target cell, an RNAi agent or CRISPR agent to be delivered to a target cell, etc.), it is typically referred to as a "recombinant AAV (rAAV) virion" or an "rAAV viral particle." In general, the heterologous polynucleotide is flanked by at least one, and generally by two, AAV inverted terminal repeat sequences (ITRs).

The term "packaging" refers to a series of intracellular events that result in the assembly and encapsidation of an AAV particle. AAV "rep" and "cap" genes refer to polynucleotide sequences encoding replication and encapsidation proteins of adeno-associated virus. AAV rep and cap are referred to herein as AAV "packaging genes."

The terminology "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

The terminology "helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans. For example, a plasmid or other expression vector comprising nucleotide sequences encoding one or more adenoviral proteins is transfected into a producer cell along with an rAAV vector.

The terminology "infectious" virus or viral particle is one that comprises a competently assembled viral capsid and is capable of delivering a polynucleotide component into a cell for which the viral species is tropic. The term does not necessarily imply any replication capacity of the virus. Assays for counting infectious viral particles are described elsewhere in this disclosure and in the art. Viral infectivity can be expressed as the ratio of infectious viral particles to total viral particles. Methods of determining the ratio of infectious viral particle to total viral particle are known in the art. See, e.g., Grainger et al. (2005) Mol. Ther. 11: S337 (describing a TCID50 infectious titer assay); and Zolotukhin et al. (1999) Gene Ther. 6:973. See also the Examples.

The term "tropism" as used herein refers to the preferential targeting by a virus (e.g., an AAV) of cells of a particular host species or of particular cell types within a host species. For example, a virus that can infect cells of the heart, lung, liver, and muscle has a broader (i.e., increased) tropism relative to a virus that can infect only lung and muscle cells. Tropism can also include the dependence of a virus on particular types of cell surface molecules of the host. For example, some viruses can infect only cells with surface glycosaminoglycans, while other viruses can infect only cells with sialic acid (such dependencies can be tested using various cells lines deficient in particular classes of molecules as potential host cells for viral infection). In some cases, the tropism of a virus describes the virus's relative preferences. For example, a first virus may be able to infect all cell types but is much more successful in infecting those cells with surface glycosaminoglycans. A second virus can be considered to have a similar (or identical) tropism as the first virus if the second virus also prefers the same characteristics (e.g., the second virus is also more successful in infecting those cells with surface glycosaminoglycans), even if the absolute transduction efficiencies are not similar. For example, the second virus might be more efficient than the first virus at infecting every given cell type tested, but if the relative preferences are similar (or identical), the second virus can still be considered to have a similar (or identical) tropism as the first virus. In some embodiments, the tropism of a virion comprising a subject variant AAV capsid protein is not altered relative to a naturally occurring virion. In some embodiments, the tropism of a virion comprising a subject variant AAV capsid protein is expanded (i.e., broadened) relative to a naturally occurring virion. In some embodiments, the tropism of a virion comprising a subject variant AAV capsid protein is reduced relative to a naturally occurring virion.

The terminology "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per 104 rAAV particles, less than about 1 rcAAV per 10 rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment herein that comprises a polynucleotide encompasses both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

The term "gene" refers to a polynucleotide that performs a function of some kind in the cell. For example, a gene can contain an open reading frame that is capable of encoding a gene product. One example of a gene product is a protein, which is transcribed and translated from the gene. Another example of a gene product is an RNA, e.g. a functional RNA product, e.g., an aptamer, an interfering RNA, a ribosomal RNA (rRNA), a transfer RNA (tRNA), a non-coding RNA (ncRNA), a guide RNA for nucleases, etc., which is transcribed but not translated.

The terminology "gene expression product" or "gene product" is a molecule resulting from expression of a particular gene, as defined above. Gene expression products include, e.g., a polypeptide, an aptamer, an interfering RNA, a messenger RNA (mRNA), an rRNA, a tRNA, a non-coding RNA (ncRNA), and the like.

The term "siRNA agent" ("small interfering" or "short interfering RNA" (or siRNA)) is an RNA duplex of nucleotides that is targeted to a gene of interest (a "target gene"). An "RNA duplex" refers to the structure formed by the complementary pairing between two regions of a RNA molecule, forming a region of double stranded RNA (dsRNA). siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. In some embodiments, siRNA-mediated gene targeting is accomplished through the use of DNA-directed RNA interference (ddRNAi) which is a gene-silencing technique that utilizes DNA constructs to activate an animal cell's endogenous RNA interference (RNAi) pathways. Such DNA constructs are designed to express self-complementary double-stranded RNAs, typically short-hairpin RNAs (shRNA), that once processed bring about silencing of a target gene or genes. Any RNA, including endogenous mRNAs or viral RNAs, can be silenced by designing constructs to express double-stranded RNA complementary to the desired mRNA target. As such, the RNA duplex portion of an siRNA agent can be part of a short hairpin structure referred to as shRNA. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length. In general, the level of expression product (e.g., mRNA, polypeptide, etc.) of a target gene is reduced by an siRNA agent (e.g., an siRNA, an shRNA, etc.) that contains specific double stranded nucleotide sequences that are complementary to at least a 19-25 nucleotide long segment (e.g., a 20-21 nucleotide sequence) of the target gene transcript, including the 5' untranslated (UT) region, the ORF, or the 3' UT region. In some embodiments, short interfering RNAs are about 19-25 nt in length. See, e.g., PCT applications WO 00/44895, WO 99/32619, WO 01/75164, WO 01/92513, WO 01/29058, WO 01/89304, WO 02/16620, and WO 02/29858; and U.S. Patent Publication No. 2004/0023390 for descriptions of siRNA technology. The siRNA and/or shRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

The terminology "antisense RNA" encompasses RNA that is complementary to a gene expression product. For example, an antisense RNA targeted to a specific mRNA is an RNA-based agent (or can be a modified RNA) that is complementary to the mRNA, where hybridization of the antisense RNA to the mRNA alters the expression of the mRNA (e.g., via altering the stability of the RNA, altering the translation of the RNA, etc.). Also included in "antisense RNA" are nucleic acids encoding an antisense RNA.

With regards to "CRISPR/Cas9 agents", the term "CRISPR" encompasses Clustered regularly interspaced short palindromic repeats/CRISPR-associated (Cas) systems that evolved to provide bacteria and archaea with adaptive immunity against viruses and plasmids by using CRISPR RNAs (crRNAs) to guide the silencing of invading nucleic acids. The Cas9 protein (or functional equivalent and/or variant thereof, i.e., Cas9-like protein) naturally contains DNA endonuclease activity that depends on association of the protein with two naturally occurring or synthetic RNA molecules called crRNA and tracrRNA (also called guide RNAs). In some cases, the two molecules are covalently linked to form a single molecule (also called a single guide RNA ("sgRNA")). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence.

If the Cas9 or Cas9-like protein retains its natural enzymatic function, it will cleave target DNA to create a double-strand break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Cas9-like proteins with decreased DNA-cleavage activity (even no DNA-cleaving activity) can still be guided to a target DNA to block RNA polymerase activity. Alternatively, the Cas9 or Cas9-like protein may be modified by fusing a VP64 transcription activation domain to the Cas9 protein and codelivering the fusion protein with a MS2-P65-HSF1 helper protein and a single guide RNA comprising MS2 RNA aptamers at the tetraloop and stem-loop to form a Synergistic Activation Mediator (Cas9-SAM) complex in the cell that activates transcription. Thus enzymatically inactive Cas9-like proteins can be targeted to a specific location in a target DNA by a DNA-targeting RNA in order to block or activate transcription of the target DNA. The term "CRISPR/Cas9 agents" as used herein encompasses all forms of CRISPR/Cas9 as described above or as known in the art.

Detailed information regarding CRISPR agents can be found, for example in (a) Jinek et. al., Science. 2012 Aug. 17; 337(6096):816-21: "A programmable dual-RNA-guided DNA endonuclease in adaptive bacterial immunity"; (b) Qi et al., Cell. 2013 Feb. 28; 152(5): 1173-83: "Repurposing CRISPR as an RNA-guided platform for sequence-specific control of gene expression", and (c) U.S. patent application Ser. No. 13/842,859 and PCT application number PCT/US13/32589; all of which are hereby incorporated by reference in their entirety. Thus, the term "CRISPR agent" as used herein encompasses any agent (or nucleic acid encoding such an agent), comprising naturally occurring and/or synthetic sequences, that can be used in the Cas9-based system (e.g., a Cas9 or Cas9-like protein; any component of a DNA-targeting RNA, e.g., a crRNA-like RNA, a tracrRNA-like RNA, a single guide RNA, etc.; a donor polynucleotide; and the like).

By "Zinc-finger nucleases" (ZFNs) it is meant artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double strand breaks. For more information on the use of ZFNs, see, for example: Asuri et al., Mol. Ther. 2012 February; 20(2):329-38; Bibikova et al. Science. 2003 May 2; 300(5620):764; Wood et al. Science. 2011 Jul. 15; 333(6040):307; Ochiai et al. Genes Cells. 2010 August; 15(8):875-85; Takasu et. al., Insect Biochem Mol Biol. 2010 October; 40(10):759-65; Ekker et al, Zebrafish 2008 Summer; 5(2):121-3; Young et al, Proc Natl Acad Sci USA. 2011 Apr. 26; 108(17):7052-7; Goldberg et al, Cell. 2010 Mar. 5; 140(5):678-91; Geurts et al, Science. 2009 Jul. 24; 325(5939):433; Flisikowska et al, PLoS One. 2011; 6(6):e21045. doi: 10.1371/journal.pone.0021045. Epub 2011 Jun. 13; Hauschild et al, Proc Natl Acad Sci USA. 2011 Jul. 19; 108(29):12013-7; and Yu et al, Cell Res. 2011 November; 21(1 1):1638-40; all of which are herein incorporated by reference for their teachings related to ZFNs. The term "ZFN agent" encompasses a zinc finger nuclease and/or a polynucleotide comprising a nucleotide sequence encoding a zinc finger nuclease.

The terminology "Transcription activator-like effector nuclease" or "TALEN" agents refers to Transcription activator-like effector nucleases (TALENs). TALENs are artificial DNA endonucleases generated by fusing a TAL (Transcription activator-like) effector DNA binding domain to a DNA cleavage domain. TALENs can be quickly engineered to bind practically any desired DNA sequence and when introduced into a cell, TALENs can be used to edit target DNA in the cell (e.g., the cell's genome) by inducing double strand breaks. For more information on the use of TALENs, see, for example: Hockemeyer et al. Nat Biotechnol. 2011 Jul. 7; 29(8):731-4; Wood et al. Science. 2011 Jul. 15; 333(6040):307; Tesson et al. Nat Biotechnol. 2011 Aug. 5; 29(8):695-6; and Huang et. al., Nat Biotechnol. 2011 Aug. 5; 29(8):699-700; all of which are herein incorporated by reference for their teachings related to TALENs. The term "TALEN agent" encompasses a TALEN and/or a polynucleotide comprising a nucleotide sequence encoding a TALEN.

The terminology "control element" or "control sequence" refers to a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters may be ubiquitously acting, i.e. active in many cell types, e.g. CAG or CMV promoters; or tissue or cell specific, e.g. the promoter can be tissue-specific for expression in cardiomyocytes.

The terminology "operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

The terminology "expression vector" encompasses a vector comprising a polynucleotide region which encodes a polypeptide of interest, and is used for effecting the expression of the protein in an intended target cell. An expression vector may also comprise control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

The term "heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid sequence encoding a heterologous gene product is an rAAV that includes a polynucleotide not normally included in a naturally-occurring, wild-type AAV, and the encoded heterologous gene product is a gene product not normally encoded by a naturally-occurring, wild type AAV.

The terminology "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

With regards to cell modification, the terminology "genetically modified" or "transformed" or "transfected" or "transduced" by exogenous DNA (e.g. via a recombinant virus) refers to when such DNA has been introduced inside the cell. The presence of the exogenous DNA results in permanent or transient genetic change. The transforming DNA may or may not be integrated (covalently linked) into the genome of the cell. A "clone" is a population of cells derived from a single cell or common ancestor by mitosis.

A "cell line" is a clone of a primary cell that is capable of stable growth in vitro for many generations.

As used herein, a cell is said to be "stably" altered, transduced, genetically modified, or transformed with a genetic sequence if the sequence is available to perform its function during extended culture of the cell in vitro and/or for an extended period of time in vivo. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

As used herein, an "isolated" plasmid, nucleic acid, vector, virus, virion, host cell, protein, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this disclosure are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease (and/or symptoms caused by the disease) from occurring in a subject which may be predisposed to the disease or at risk of acquiring the disease but has not yet been diagnosed as having it; (b) inhibiting the disease (and/or symptoms caused by the disease), i.e., arresting its development; and (c) relieving the disease (and/or symptoms caused by the disease), i.e., causing regression of the disease (and/or symptoms caused by the disease), i.e., ameliorating the disease and/or one or more symptoms of the disease. For example, the subject compositions and methods may be directed towards the treatment of muscle disease. Nonlimiting methods for assessing muscle diseases and the treatment thereof include measuring therapeutic protein production (e.g. muscle biopsy followed by immunohistochemistry or serum sampling followed by ELISA or enzyme activity assays), measuring symptoms of heart failure (e.g. the New York Heart Association Functional Classification or the Minnesota Living With Heart Failure Questionnaire), functional cardiac status (e.g. the 6-minute walk test or peak maximum oxygen consumption), biomarker analysis (e.g. N-terminal prohormone brain natriuretic peptide), left ventricular function/remodeling (e.g. left ventricular ejection fraction or left ventricular end-systolic volume), muscle strength (e.g. the Medical Research Council Scales Clinical Investigation of Duchenne Dystrophy, hand-held dynamometry, or maximum weight lift), muscle function (e.g. the Vignos Scale, Timed Function Tests, the Hammersmith Motor Ability Score, timed rise from floor, walk tests, Motor Function Measure Scale, North Star Ambulatory Assessment, 9 Hole Peg Test, or Children's Hospital of Philadelphia Infant Test of Neuromuscular Disorders), muscle disease symptoms (e.g. the Neuromuscular Symptoms Score or Clinical Global Impressions), mitochondrial function (e.g. $^{31}P$ magnetic resonance spectroscopy), questionnaire-based assessments of quality of life, patient-reported outcomes, or daily activities.

The terms "individual," "host," "subject," and "patient" are used interchangeably herein, and refer to a mammal, including, but not limited to, humans; non-human primates, including simians; mammalian sport animals (e.g., horses); mammalian farm animals (e.g., sheep, goats, etc.); mammalian pets (dogs, cats, etc.); and rodents (e.g., mice, rats, etc.).

In some embodiments, the individual is a human who has previously been naturally exposed to AAV and as a result harbors anti-AAV antibodies (i.e., AAV neutralizing antibodies). In some embodiments, the individual is a human who has previously been administered an AAV vector (and as a result may harbor anti-AAV antibodies) and needs re-administration of vector for treatment of a different condition or for further treatment of the same condition. Based on positive results in clinical trials involving AAV gene delivery to, for example, liver, muscle, and retina—all tissues affected by neutralizing antibodies against this vehicle—there are many such therapeutic applications/disease targets.

The term "effective amount" as used herein is an amount sufficient to effect beneficial or desired clinical results. An effective amount can be administered in one or more administrations. For purposes of this disclosure, an effective amount of a compound (e.g., an infectious rAAV virion) is an amount that is sufficient to palliate, ameliorate, stabilize, reverse, prevent, slow or delay the progression of (and/or symptoms associated with) a particular disease state (e.g., a muscle disease). Accordingly, an effective amount of an infectious rAAV virion is an amount of the infectious rAAV virion that is able to effectively deliver a heterologous nucleic acid to a target cell (or target cells) of the individual. Effective amounts may be determined preclinically by, e.g., detecting in the cell or tissue the gene product (RNA, protein) that is encoded by the heterologous nucleic acid sequence using techniques that are well understood in the art, e.g. RT-PCR, western blotting, ELISA, fluorescence or other reporter readouts, and the like. Effective amounts may be determined clinically by, e.g. detecting a change in the onset or progression of disease using methods known in the art, e.g. 6-minute walk test, left ventricular ejection fraction, hand-held dynamometry, Vignos Scale and the like as described herein and as known in the art.

The terminology "muscle cell" or "muscle tissue" refers herein to a cell or group of cells derived from muscle of any kind, including, without limitation, skeletal muscle, cardiac muscle, smooth muscle (e.g. from the digestive tract, urinary bladder and blood vessels) and diaphragm muscle. Such muscle cells may be differentiated or undifferentiated such as myoblasts, myocytes, myotubes, cardiomyocytes, and cardiomyoblasts. Since muscle tissue is readily accessible to the circulatory system, a protein produced and secreted by muscle cells and tissue in vivo will logically enter the bloodstream for systemic benefit, thereby providing sustained, therapeutic levels of protein secretion from the muscle.

The terminology "directed evolution" refers to a capsid engineering methodology, in vitro and/or in vivo, which emulates natural evolution through iterative rounds of genetic diversification and selection processes, thereby accumulating beneficial mutations that progressively improve the function of a biomolecule. Directed evolution often involves an in vivo method referred to as "biopanning" for selection of AAV variants from a library which variants possess a more efficient level of infectivity of a cell or tissue type of interest.

DETAILED DESCRIPTION

Adeno-associated viruses (AAVs) are a family of parvoviruses with a 4.7 kb single-stranded DNA genome contained inside a non-enveloped capsid. The viral genome of a naturally occurring AAV has 2 inverted terminal repeats (ITR)—which function as the viral origin of replication and packaging signal—flanking 2 primary open reading frames (ORF): rep (encoding proteins that function in viral replication, transcriptional regulation, site-specific integration, and virion assembly) and cap. The cap ORF codes for 3 structural proteins that assemble to form a 60-mer viral capsid. Many naturally occurring AAV variants and serotypes have been isolated, and none have been associated with human disease.

Recombinant versions of AAV can be used as gene delivery vectors, where a marker or therapeutic gene of interest is inserted between the ITRs in place of rep and cap. These vectors have been shown to transduce both dividing and non-dividing cells in vitro and in vivo and can result in stable transgene expression for years in post-mitotic tissue. See e.g., Knipe D M, Howley P M. *Fields' Virology*. Lippincott Williams & Wilkins, Philadelphia, PA, USA, 2007; Gao G-P, Alvira M R, Wang L, Calcedo R, Johnston J, Wilson J M. Novel adeno-associated viruses from rhesus monkeys as vectors for human gene therapy. *Proc Natl Acad Sci USA* 2002; 99: 11854-9; Atchison R W, Casto B C, Hammon W M. Adenovirus-Associated. Defective Virus Particles. Science 1965; 149: 754-6; Hoggan M D, Blacklow N R, Rowe W P. Studies of small DNA viruses found in various adenovirus preparations: physical, biological, and immunological characteristics. *Proc Natl Acad Sci USA* 1966; 55: 1467-74; Blacklow N R, Hoggan M D, Rowe W P. Isolation of adenovirus-associated viruses from man. *Proc Natl Acad Sci USA* 1967; 58: 1410-5; Bantel-Schaal U, zur Hausen H. Characterization of the DNA of a defective human parvovirus isolated from a genital site. *Virology* 1984; 134: 52-63; Mayor H D, Melnick J L. Small deoxyribonucleic acid-containing viruses (picodnavirus group). *Nature* 1966; 210: 331-2; Mori S, Wang L, Takeuchi T, Kanda T. Two novel adeno-associated viruses from cynomolgus monkey: pseudotyping characterization of capsid protein. *Virology* 2004; 330: 375-83; Flotte T R. Gene therapy progress and prospects: recombinant adeno-associated virus (rAAV) vectors. *Gene Ther* 2004; 11: 805-10.

Recombinant AAV (referred to herein simply as "AAV") has yielded promising results in an increasing number of clinical trials. However, there are impediments to gene delivery that may limit AAV's utility, such as anti-capsid immune responses, low transduction of certain tissues, an inability for targeted delivery to specific cell types and a relatively low carrying capacity. In many situations, there is insufficient mechanistic knowledge to effectively empower rational design with the capacity to improve AAV. As an alternative, directed evolution has emerged as a strategy to create novel AAV variants that meet specific biomedical needs. Directed evolution strategies harness genetic diversification and selection processes to enable the accumulation of beneficial mutations that progressively improve the function of a biomolecule. In this process, wild-type AAV cap genes are diversified by several approaches to create large genetic libraries that are packaged to generate libraries of viral particles, and selective pressure is then applied to isolate novel variants that can overcome gene delivery barriers. Importantly, the mechanistic basis underlying a gene delivery problem does not need to be known for directed evolution of function, which can thus accelerate the development of enhanced vectors.

Typically, the variants disclosed herein were generated through use of an AAV library and/or libraries. Such an AAV library or libraries is/are generated by mutating the cap gene, the gene which encodes the structural proteins of the AAV capsid, by a range of directed evolution techniques known by and readily available to the skilled artisan in the field of viral genome engineering. See e.g., Bartel et al. Am. Soc. Gene Cell Ther. 15$^{th}$ Annu. Meet. 20, S140 (2012); Bowles, D. et al. J. Virol. 77, 423-432 (2003); Gray et al. Mol. Ther. 18, 570-578 (2010); Grimm, D. et al. J. Virol. 82, 5887-5911; Koerber, J. T. et al. Mol. Ther. 16, 1703-1709 (2008); Li W. et al. Mol. Ther. 16, 1252-1260 (2008); Koerber, J. T. et al. Methods Mol. Biol. 434, 161-170 (2008); Koerber, J. T. et al. Hum. Gene Ther. 18, 367-378 (2007); and Koerber, J. T. et al. Mol. Ther. 17, 2088-2095 (2009). Such techniques, without limitation, are as follows: i) Error-prone PCR to introduce random point mutations into the AAV cap open reading frame (ORF) at a predetermined, modifiable rate; ii) In vitro or in vivo viral recombination or "DNA shuffling" to generate random chimeras of AAV cap genes to yield a gene library with multiple AAV serotypes; iii) Random peptide insertions at defined sites of the capsid by ligation of degenerate oligonucleotides in the cap ORF; iv) Defined insertions of peptide-encoding sequences into random locations of the AAV cap ORF using transposon mutagenesis; v) Replacing surface loops of AAV capsids with libraries of peptide sequences bioinformationally designed based on the level of conservation of each amino acid position among natural AAV serotypes and variants to generate "loop-swap" libraries; vi) Random amino acid substitution at positions of degeneracy between AAV serotypes to generate libraries of ancestral variants (Santiago-Ortiz et al., 2015); and a combination of such techniques thereof.

DNA shuffling generates chimeras which combine their parental properties in unique and, often beneficial, ways; however, some may be incapable of packaging which, in effect, reduces the diversity of the library. Concentration of diversity the library into specific region(s) of the capsid is achieved through peptide insertion techniques such as, without limitation, iii-iv) above. Diversity of the library is also concentrated into specific region(s) of the capsid in techniques such as v) above, and such concentration is directed onto multiple hypervariable regions, which lie on surface exposed loops, of the AAV capsid. While many of the techniques generate variant capsids with only a small area of the capsid mutated, these techniques can be paired with additional mutagenesis strategies to modify the full capsid.

Once the AAV library or libraries is/are generated, viruses are then packaged, such that each AAV particle is comprised of a mutant capsid surrounding a cap gene encoding that capsid, and purified. Variants of the library are then subjected to in vitro and/or in vivo selective pressure techniques known by and readily available to the skilled artisan in the field of AAV. See e.g., Maheshri, N. et al. Nature Biotech. 24, 198-204 (2006); Dalkara, D. et al. Sci. Transl. Med. 5, 189ra76 (2013); Lisowski, L. et al. Nature. 506, 382-286 (2013); Yang, L. et al. PNAS. 106, 3946-3951 (2009); Gao, G. et al. Mol. Ther. 13, 77-87 (2006); and Bell, P. et al. Hum. Gene. Ther. 22, 985-997 (2011). For example, without limitation, AAV variants can be selected using i) affinity columns in which elution of different fractions yields variants with altered binding properties; ii) primary cells—isolated from tissue samples or immortal cell lines that mimic the behavior of cells in the human body—which yield AAV variants with increased efficiency and/or tissue specificity; iii) animal models—which mimic a clinical gene therapy environment—which yield AAV variants that have successfully infected target tissue; iv) human xenograft models which yield AAV variants that have infected grafted human cells; and/or a combination of selection techniques thereof.

Once viruses are selected, they may be recovered by known techniques such as, without limitation, adenovirus-mediated replication, PCR amplification, Next Generation sequencing and cloning, and the like. Virus clones are then enriched through repeated rounds of the selection techniques and AAV DNA is isolated to recover selected variant cap genes of interest. Such selected variants can be subjected to further modification or mutation and as such serve as a new starting point for further selection steps to iteratively increase AAV viral fitness. However, in certain instances, successful capsids have been generated without additional mutation.

The AAV variants disclosed herein were generated at least in part through the use of in vivo directed evolution methodology, such as the techniques described above, involving the use of primate cardiac and skeletal muscle screens following intravenous administration. As such, the AAV variant capsids disclosed herein comprise one or more modifications in amino acid sequence that confer more efficient transduction of primate muscle cells than a corresponding parental AAV capsid protein. As used herein, a "corresponding parental AAV capsid protein" refers to an AAV capsid protein of the same wild-type or variant AAV serotype as the subject variant AAV capsid protein but that does not comprise the one or more amino acid sequence modifications of the subject variant AAV capsid protein. In particular embodiments, an AAV comprising a variant AAV capsid protein as herein described has systemic tropism toward cardiac muscle and/or multiple skeletal muscle groups throughout the body following systemic or tissue-targeted administration.

In some embodiments, the subject variant AAV capsid protein comprises a heterologous peptide of from about 5 amino acids to about 20 amino acids inserted by covalent linkage into an AAV capsid protein GH loop, or loop IV, relative to a corresponding parental AAV capsid protein. By the "GH loop," or loop IV, of the AAV capsid protein it is meant the solvent-accessible portion referred to in the art as the GH loop, or loop IV, of AAV capsid protein. For the GH loop/loop IV of AAV capsid, see, e.g., van Vliet et al. (2006) Mol. Ther. 14:809; Padron et al. (2005) J. Virol. 79:5047; and Shen et al. (2007) Mol. Ther. 15:1955. Thus, for example, the insertion site can be within about amino acids 411-650 of an AAV VP1 capsid protein. For example, the insertion site can be within amino acids 571-612 of AAV1 VP1, amino acids 570-611 of AAV2 VP1, within amino acids 571-612 of AAV3A VP1, within amino acids 571-612 of AAV3B VP1, within amino acids 569-610 of AAV4 VP1, within amino acids 560-601 of AAV5 VP1, within amino acids 571 to 612 of AAV6 VP1, within amino acids 572 to 613 of AAV7 VP1, within amino acids 573 to 614 of AAV8 VP1, within amino acids 571 to 612 of AAV9 VP1, or within amino acids 573 to 614 of AAV10 VP 1, or the corresponding amino acids of any variant thereof. Those skilled in the art would know, based on a comparison of the amino acid sequences of capsid proteins of various AAV serotypes, where an insertion site "corresponding to amino acids of AAV2" would be in a capsid protein of any given AAV serotype. See also FIG. 6 for an alignment of wild-type AAV SEQ ID NOS:1-11 which provides amino acid locations between and across the wild-type (naturally-occurring) serotypes AAV1, AAV2, AAV3A, AAV3B, and AAV4-10.

In certain embodiments, the insertion site is a single insertion site between two adjacent amino acids located between amino acids 570-614 of VP1 of any wild-type AAV serotype or AAV variant, e.g., the insertion site is between two adjacent amino acids located in amino acids 570-610, amino acids 580-600, amino acids 570-575, amino acids 575-580, amino acids 580-585, amino acids 585-590, amino acids 590-600, or amino acids 600-614, of VP1 of any AAV serotype or variant. For example, the insertion site can be between amino acids 580 and 581, amino acids 581 and 582, amino acids 583 and 584, amino acids 584 and 585, amino acids 585 and 586, amino acids 586 and 587, amino acids 587 and 588, amino acids 588 and 589, or amino acids 589 and 590. The insertion site can be between amino acids 575 and 576, amino acids 576 and 577, amino acids 577 and 578, amino acids 578 and 579, or amino acids 579 and 580. The insertion site can be between amino acids 590 and 591, amino acids 591 and 592, amino acids 592 and 593, amino acids 593 and 594, amino acids 594 and 595, amino acids 595 and 596, amino acids 596 and 597, amino acids 597 and 598, amino acids 598 and 599, or amino acids 599 and 600. For example, the insertion site can be between amino acids 587 and 588 of AAV2, between amino acids 590 and 591 of AAV1, between amino acids 588 and 589 of AAV3A, between amino acids 588 and 589 of AAV3B, between amino acids 584 and 585 of AAV4, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, or between amino acids 588 and 589 of AAV10.

In some embodiments, a peptide insertion disclosed herein has a length of 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, or 20 amino acids. In another embodiment, a peptide insertion disclosed herein comprises from 1 to 4 spacer amino acids at the amino terminus (N-terminus) and/or at the carboxyl terminus (C-terminus)

of any one of the peptide insertions disclosed herein. Exemplary spacer amino acids include, without limitation, leucine (L), alanine (A), glycine (G), serine (S), threonine (T), and proline (P). In certain embodiments, a peptide insertion comprises 2 spacer amino acids at the N-terminus and 2 spacer amino acids at the C-terminus. In other embodiments, a peptide insertion comprises 2 spacer amino acids at the N-terminus and 1 spacer amino acids at the C-terminus.

The peptide insertions disclosed herein have not been previously described and/or inserted into an AAV capsid. Without wishing to be bound by theory, the presence of any of the disclosed peptide insertions may act to lower the variant capsid's affinity for heparin sulfate which could alter extracellular or intracellular steps within the viral transduction pathway. In addition, the peptide insertion motifs disclosed herein may confer enhanced transduction of muscle cells (e.g. cardiomyocytes) through the addition of a cell surface receptor binding domain.

In some preferred embodiments, the insertion peptide comprises an amino acid sequence of any one of the formulas below.

In some aspects, an insertion peptide can be a peptide of 7 to 10 amino acids in length, of Formula 1a:

$$Y_1Y_2X_1X_2X_3X_4X_5X_6X_7Y_3$$

Where each of $Y_1$-$Y_3$, if present, is independently selected from Ala, Leu, Gly, Ser, Thr, Pro
$X_1$ is selected from Ala, Asn, Thr, Gly, Ser, Ala, Gin, and Asp
$X_2$ is selected from Lys, Asn, Thr, Ser, Ala, and Gin
$X_3$ is selected from Ile, Thr, Lys, Leu, Val, Asn, Asp, and Arg
$X_4$ is selected from Gin, Thr, Ile, Lys, Val, Ser, and Tyr
$X_5$ is selected from Arg, Asn, Gly, Lys, Leu, Thr, Ala, Ser, and Gin
$X_6$ is selected from Thr, Lys, Val, Gly, Ser, Ala, Arg, and Pro
$X_7$ is selected from Asp, Thr, Asn, Ile, Ala, and Ser.

In certain embodiments, the insertion peptide of Formula 1a comprises an amino acid sequence selected from NKIQRTD (SEQ ID NO:13), NKTTNKD (SEQ ID NO:14), TNKIGVT (SEQ ID NO:15), GNLTKGN (SEQ ID NO: 16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25) and ASDSTKA (SEQ ID NO:26). In other embodiments, the insertion peptide of Formula 1a does not comprise an amino acid sequence selected from NKTTNKD (SEQ ID NO:14), QADTTKN (SEQ ID NO:23), TNRTSPD (SEQ ID NO:24) and NQDYTKT (SEQ ID NO:22).

In other aspects, an insertion peptide can be a peptide of 7 to 10 amino a acids in length, of Formula 1b:

$$Y_1Y_2X_1X_2X_3X_4X_5X_6X_7Y_3$$

Where each of $Y_1$-$Y_3$, if present, is independently selected from Ala, Leu, Gly, Ser, Thr, Pro
$X_1$ is selected from Thr and Asn
$X_2$ is selected from Asn and Lys
$X_3$ is selected from Lys, Ile and Thr
$X_4$ is selected from Ile, Gin, and Thr
$X_5$ is selected from Gly, Arg and Asn
$X_6$ is selected from Val, Thr and Lys
$X_7$ is selected from Thr and Asp In certain embodiments, the insertion peptide of Formula 1b comprises an amino acid sequence selected from NKIQRTD (SEQ ID NO:13), NKTTNKD (SEQ ID NO:14) and TNKIGVT (SEQ ID NO:15). In other embodiments, the insertion peptide of Formula 1a does not comprise the amino acid sequence NKTTNKD (SEQ ID NO:14).

In other aspects, an insertion peptide can be a peptide of 7 to 10 amino acids in length, of Formula 1c $$Y_1Y_2X_1X_2X_3X_4X_5X_6X_7Y_3$$

Where each of $Y_1$-$Y_3$, if present, is independently selected from Ala, Leu, Gly, Ser, Thr, Pro
$X_1$ is selected from Thr and Asn
$X_2$ is selected from Asn and Lys
$X_3$ is selected from Lys and Ile
$X_4$ is selected from Ile and Gln
$X_5$ is selected from Gly and Arg
$X_6$ is selected from Val and Thr
$X_7$ is selected from Thr and Asp In certain embodiments, the insertion peptide of Formula 1c comprises an amino acid sequence selected from NKIQRTD (SEQ ID NO:13) and TNKIGVT (SEQ ID NO:15).

In other aspects, an insertion peptide can be a peptide of 7 to 10 amino acids in length, of Formula 1d:

$$Y_1Y_2X_1X_2X_3X_4X_5X_6X_7Y_3$$

Where each of $Y_1$-$Y_3$, if present, is independently selected from Ala, Leu, Gly, Ser, Thr, Pro
$X_1$ is selected from Asn and Thr
$X_2$ is selected from Asn and Lys
$X_3$ is selected from Lys and Thr
$X_4$ is selected from Ile and Thr
$X_5$ is selected from Gly, Lys and Thr
$X_6$ is selected from Lys, Arg and Val
$X_7$ is selected from Asp, Thr and Asn In certain embodiments, the insertion peptide of Formula 1d comprises the amino acid sequence TNKIGVT (SEQ ID NO:15).

In other embodiments, the insertion peptide comprises an amino acid sequence selected from NKIQRTD (SEQ ID NO:13), NKTTNKD (SEQ ID NO:14) and TNKIGVT (SEQ ID NO:15). In related embodiments, the insertion peptide comprises an amino acid sequence selected from NKIQRTD (SEQ ID NO:13) and TNKIGVT (SEQ ID NO:15).

In some embodiments, the insertion peptide comprises an amino acid sequence selected from NKIQRTD (SEQ ID NO:13), NKTTNKD (SEQ ID NO:14), TNKIGVT (SEQ 1D NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25) and ASDSTKA (SEQ ID NO:26).

In other preferred embodiments, the insertion peptide has from 1 to 3 spacer amino acids ($Y_1$-$Y_3$) at the amino and/or carboxyl terminus of an amino acid sequence selected from NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25) and ASDSTKA (SEQ ID NO:26). In certain such embodiments, the insertion peptide is selected from the group consisting of: LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42).

In some embodiments, the subject variant AAV capsid protein does not include any other amino acid sequence modifications other than a peptide insertion of from about 5 amino acids to about 20 amino acids in the GH loop, or loop IV. For example, in some embodiments, the subject variant AAV capsid protein comprises a peptide insertion comprising an amino acid sequence selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42), and the variant AAV capsid does not include any other amino acid substitutions, insertions, or deletions (i.e., the variant AAV capsid protein comprises said insertion and is otherwise identical to the corresponding AAV capsid protein). Put another way, the variant AAV capsid protein comprising said insertion is otherwise identical to the parental AAV capsid protein into which the peptide has been inserted. As another example, the subject variant AAV capsid protein comprises a peptide insertion comprising an amino acid sequence selected from NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ 1D NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42), wherein the peptide insertion is located between amino acids 587 and 588 of the VP1 of the AAV2 capsid; between amino acids 588 and 589 of VP1 of AAV3A, AAV3B, AAV9, or AAV10; between amino acids 589 and 590 of VP1 of AAV7; between amino acids 590 to 591 of VP1 of AAV1, AAV6, or AAV8, between amino acids 584 and 585 of VP1 of AAV4, or between amino acids 575 and 576 of AAV5, wherein the variant AAV capsid protein sequence is otherwise identical to the corresponding parental AAV capsid protein sequence, e.g. any one of SEQ ID NOs:1-12.

In other embodiments, the subject variant AAV capsid protein, in addition to comprising a peptide insertion, e.g. as disclosed herein or as known in the art, in the GH loop, comprises from about 1 to about 100 amino acid substitutions or deletions, e.g. 1 to about 5, from about 2 to about 4, from about 2 to about 5, from about 5 to about 10, from about 10 to about 15, from about 15 to about 20, from about 20 to about 25, from about 25-50, from about 50-100 amino acid substitutions or deletions compared to the parental AAV capsid protein. Thus, in some embodiments, a subject variant capsid protein comprises an amino acid sequence having a sequence identity of 85% or more, 90% or more, 95% or more, or 98% or more, e.g. or 99% identity to the corresponding parental AAV capsid, e.g. a wild type capsid protein as set forth in SEQ ID NOs:1-12.

In a further embodiment, the one or more amino acid substitutions are at amino acid residue(s) 35, 109, 195, 213, 222, 229, 312, 319, 330, 333, 347, 363, 427, 447, 449, 453, 490, 527, 551, 581, 585, 588, 593, 606, 649, 651, 694, 698, 708, and/or 735 of AAV2 VP1 capsid protein as numbered prior to insertion of the peptide, or the corresponding amino acid residue(s) of another AAV capsid protein. In some such embodiments, the one or more amino acid substitutions are selected from the group consisting of A35P, S109T, P195L, D213N, G222S, V229I, N312K, A319T, T330A, A333S, E347K, P363L, A427D, V447F, N449D, N449K, G453R, A490T, K527Q, N551S, A581T, Y585S, R588M, A593E, W606C, K649E, R651H, W694C, I698V, V708I, and L735Q of AAV2 VP1 capsid protein as numbered prior to the insertion of the peptide, or the corresponding amino acid residue(s) of another AAV capsid protein.

In a preferred embodiment, a variant AAV capsid protein is provided comprising a) a peptide insertion in the GH-loop of the capsid protein, wherein the peptide insertion comprises an amino acid sequence selected from NKIQRTD (SEQ ID NO:13), NKTTNKD (SEQ ID NO:14) and TNKIGVT (SEQ ID NO:15), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: A35P, S109T, P195L, D213N, G222S, V229I, N312K, A319T, T330A, A333S, E347K, P363L, A427D, V447F, N449D, N449K, G453R, A490T, K527Q, N551S, A581T, Y585S, R588M, A593E, W606C, K649E, R651H, W694C, I698V, V708I, L735Q and a combination thereof. In some embodiments, the one or more amino acid substitutions are selected from the group consisting of: V708I, V708I+A593E, V708I+S109T, V708I+T330A, A35P, V708I+R588M, V708I+W606C, V708I+W694C, I698V, N312K+N449D+N551S+I698V+L735Q, N312K+N449D+N551S+I698V+V708I+L735Q, V708I+N449K, and V70814G222S. Preferably, the peptide insertion site is located between amino acids 587 and 588 of AAV2 capsid, between amino acids 587 and 588 of AAV2 capsid, between amino acids 588 and 589 of AAV3A, AAV3B, AAV9, or AAV10 capsid, between amino acids 589 and 590 of AAV7 capsid, between amino acids 590 to 591 of AAV1, AAV6, or AAV8 capsid, between amino acids 584 and 585 of AAV4 capsid, or between amino acids 575 and 576 of AAV5 capsid.

In a particularly preferred embodiment, the variant AAV capsid comprises a peptide insertion comprising the amino acid sequence NKIQRTD (SEQ ID NO:13) or comprising, consisting essentially of, or consisting of the amino acid sequence LANKIQRTDA (SEQ ID NO:27) between amino acids 587 and 588 of VP1 of AAV2 or the corresponding amino acids of another AAV capsid, and further comprises a V708I amino acid substitution at residue 708 relative to the amino acid sequence of AAV2 capsid (SEQ ID NO:2) and optionally further comprises an A593E and/or S109T and/or T330A and/or R588M substitution relative to AAV2 or the corresponding substitutions in another AAV parental serotype, wherein the substituted amino acid(s) do not naturally occur at the corresponding position. In another particularly preferred embodiment, the variant AAV capsid comprises a peptide insertion comprising the amino acid sequence NKIQRTD (SEQ ID NO:13) or comprising, consisting essentially of, or consisting of the amino acid sequence LANKIQRTDA (SEQ ID NO:27) between amino acids 587 and 588 of VP1 of AAV2 or the corresponding amino acids of another AAV capsid, and further comprises an A35P amino acid substitution at residue 35 relative to the amino acid sequence of AAV2 capsid (SEQ ID NO:2) or the corresponding substitution in another AAV parental serotype. The variant AAV capsid may have at least about 85%, at least about 90%, at least about 95%, at least about 98%, or at least about 99%, or greater, amino acid sequence identity to the entire length of the amino acid sequence set forth in SEQ ID NO:2 or the corresponding parental AAV capsid. In a particularly preferred embodiment, the variant AAV capsid has an amino acid sequence having at least about 85%, at least about 90%, at least about 95%, at least about 98% sequence identity to or is 100% identical to the following amino acid sequence:

```
                                        (SEQ ID NO: 43)
MAADGYLPDWLEDTLSEGIRQWWKLKPGPPPPKPAERHKDDSRGLVLP

GYKYLGPFNGLDKGEPVNEADAAALEHDKAYDRQLDSGDNPYLKYNHA

DAEFQERLKEDTSFGGNLGRAVFQAKKRVLEPLGLVEEPVKTAPGKKR

PVEHSPVEPDSSSGTGKAGQQPARKRLNFGQTGDADSVPDPQPLGQPP

AAPSGLGTNTMATGSGAPMADNNEGADGVGNSSGNWHCDSTWMGDRVI

TTSTRTWALPTYNNHLYKQISSQSGASNDNHYFGYSTPWGYFDFNRFH

CHFSPRDWQRLINNNWGFRPKRLNFKLFNIQVKEVTQNDGTTTIANNL

TSTVQVFTDSEYQLPYVLGSAHQGCLPPFPADVFMVPQYGYLTLNNGS

QAVGRSSFYCLEYFPSQMLRTGNNFTFSYTFEDVPFHSSYAHSQSLDR

LMNPLIDQYLYYLSRTNTPSGTTTQSRLQFSQAGASDIRDQSRNQLPG

PCYRQQRVSKTSADNNNSEYSWTGATKYHLNGRDSLVNPGPAMASHKD

DEEKFFPQSGVLIFGKQGSEKTNVDIEKVMITDEEEIRTTNPVATEQY

GSVSTNLQRGNLANKIQRTDARQAATADVNTQGVLPGMVWQDRDVYL

QGPIWAKIPHTDGHFHPSPLMGGFGLKHPPPQILIKNTPVPANPSTTF

SAAKFASFITQYSTGQVSVEIEWELQKENSKRWNPEIQYTSNYNKSI

NVDFTVDTNGVYSEPRPIGTRYLTRNL
```

In another particularly preferred embodiment, the variant AAV capsid comprises a peptide insertion comprising the amino acid sequence NKIQRTD (SEQ ID NO:13) or comprising, consisting essentially of, or consisting of the amino acid sequence LANKIQRTDA (SEQ ID NO:27) between amino acids 587 and 588 of AAV2 capsid protein or the corresponding position in the capsid protein of another AAV serotype and comprises an N312K amino acid substitution compared to the amino acid sequence of AAV2 capsid (SEQ ID NO:2) or the corresponding substitution in another AAV parental serotype and optionally further comprises (i) N449D, N551S, I698V and L735Q or (ii) N449D, N551S, I698V, L735Q and V708I amino acid substitutions compared to the amino acid sequence of AAV2 capsid or the corresponding substitutions in another AAV parental serotype. The variant AAV capsid may have at least about 85%, at least about 90%, at least about 95%, at least about 98%, or greater, amino acid sequence identity to the entire length of the amino acid sequence set forth in SEQ ID NO:2. In a particularly preferred embodiment, the variant AAV capsid has an amino acid sequence having at least about 85%, at least about 90%, at least about 95%, at least about 98% sequence identity to or is 100% identical to the following amino acid sequence:

```
                                        (SEQ ID NO: 44)
MAADGYLPDWLEDTLSEGIRQWWKLKPGPPPPKPAERHKDDSRGLVLP

GYKYLGPFNGLDKGEPVNEADAAALEHDKAYDRQLDSGDNPYLKYNHA

DAEFQERLKEDTSFGGNLGRAVFQAKKRVLEPLGLVEEPVKTAPGKKR

PVEHSPVEPDSSSGTGKAGQQPARKRLNFGQTGDADSVPDPQPLGQPP

AAPSGLGTNTMATGSGAPMADNNEGADGVGNSSGNWHCDSTWMGDRVI

TTSTRTWALPTYNNHLYKQISSQSGADNDNHYFGYSTPWGYFDFNRFH

CHFSPRDWQRLINNNWGFRPKRLKFKLFNIQVKEVTQNDGTTTIANN

LTSTVQVFTDSEYQLPYVLGSAHQGCLPPFPADVFMVPQYGYLTLNNG

SQAVGRSSFYCLEYFPSQMLRTGNNFTFSYTFEDVPFHSSYAHSQSLD

RLMNPLIDQYLYYLSRTDTPSGTTTQSRLQFSQAGASDIRDQSRNWL

PGPCYRQQRVSKTSADNNNSEYSWTGATKYHLNGRDSLVNPGPAMASH

KDDEEKFFPQSGVLIFGKQGSEKTSVDIEKVMITDEEEIRTTNPVATE

QYGSVSTNLQRGNLANKIQRTDARQAATADVNTQGVLPGMVWQDRDVY

LQGPIWAKIPHTDGHFHPSPLMGGFGLKHPPPQILIKNTPVPANPSTT

FSAAKFASFITQYSTGQVSVEIEWELQKENSKRWNPEVQYTSNYNKSV

NVDFTVDTNGVYSEPRPIGTRLYTRNQ
```

In another embodiment, a variant AAV capsid protein is provided comprising a) a peptide insertion located between amino acids 588 and 589 of VP1 of AAV3A, AAV3B, AAV9, or AAV10, between amino acids 589 and 590 of AAV7, between amino acids 590 to 591 of AAV1, AAV6 or AAV8, between amino acids 584 and 585 of AAV4 or between amino acids 575 and 576 of AAV5, the peptide insertion comprising an amino acid sequence selected from NKIQRTD (SEQ ID NO:13) and LANKIQRTDA (SEQ ID NO:27), and b) a valine to isoleucine substitution at amino acid 709 of AAV3A or AAV3B, an alanine to isoleucine substitution at position 709 of AAV1 or AAV6, an asparagine to isoleucine substitution at amino acid 707 of AAV4 or amino acid 709 of AAV9 or a threonine to isoleucine substitution at amino acid 710 of AAV7 or amino acid 711 of AAV8 or AAV10 or a glutamine to isoleucine substitution at amino acid 697 of AAV5 and is optionally otherwise identical to any one of SEQ ID NOs: 1 and 3-12. In preferred embodiments, the variant capsid protein comprises a) a peptide insertion comprising the amino acid sequence NKIQRTD (SEQ ID NO:13) or comprising, consisting essentially of, or consisting of the amino acid sequence LANKIQRTDA (SEQ ID NO:27) between amino acids 587 and 588 of AAV2 capsid and b) a valine to isoleucine amino acid substitution at amino acid 708 compared to the amino acid sequence of AAV2, wherein the variant capsid protein comprises from 2 to 5, from 5 to 10, or from 10 to 15 amino acid substitutions.

In yet another embodiment, the variant capsid protein comprises a) a peptide insertion comprising the amino acid sequence NKIQRTD (SEQ ID NO:13) or comprising, consisting essentially of, or consisting of the amino acid sequence LANKIQRTDA (SEQ ID NO:27) between amino acids 587 and 588 of AAV2 capsid and b) a valine to isoleucine amino acid substitution at amino acid 708 compared to the amino acid sequence of AAV2 and is otherwise identical to the amino acid sequence of SEQ ID NO:2.

In yet another embodiment, the variant capsid protein comprises a) a peptide insertion comprising the amino acid sequence NKIQRTD (SEQ ID NO:13) or comprising, consisting essentially of, or consisting of the amino acid sequence LANKIQRTDA (SEQ ID NO:27) between amino acids 587 and 588 of AAV2 capsid and is otherwise identical to the amino acid sequence of SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 45)
MAADGYLPDWLEDTLSEGIRQWWKLKPGPPPPKPAERHKDDSRGLVLP

GYKYLGPFNGLDKGEPVNEADAAALEHDKAYDRQLDSGDNPYLKYNHA

DAEFQERLKEDTSFGGNLGRAVFQAKKRVLEPLGLVEEPVKTAPGKKR

PVEHSPVEPDSSSGTGKAGQQPARKRLNFGQTGDADSVPDPQPLGQPP

AAPSGLGTNTMATGSGAPMADNNEGADGVGNSSGNWHCDSTWMGDRVI

TTSTRTWALPTYNNHLYKQISSQSGASNDNHYFGYSTPWGYFDFNRFH

CHFSPRDWQRLINNNWGFRPKRLNFKLFNIQVKEVTQNDGTTTIANNL

TSTVQVFTDSEYQLPYVLGSAHQGCLPPFPADVFMVPQYGYLTLNNGS

QAVGRSSFYCLEYFPSQMLRTGNNFTFSYTFEDVPFHSSYAHSQSLDR

LMNPLIDQYLYYLSRTNTPSGTTTQSRLQFSQAGASDIRDQSRNWLPG

PCYRQQRVSKTSADNNNSEYSWTGATKYHLNGRDSLVNPGPAMASHKD

DEEKFFPQSGVLIFGKQGSEKTNVDIEKVMITDEEEIRTTNPVATEQY

GSVSTNLQRGNLANKIQRTDARQAATADVNTQGVLPGMVWQDRDVYLQ

GPIWAKIPHTDGHFHPSPLMGGFGLKHPPPQILIKNTPVPANPSTTFS

AAKFASFITQYSTGQVSVEIEWELQKENSKRWNPEIQYTSNYNKSVNV

DFTVDTNGVYSEPRPIGTRYLTRNL

In another particularly preferred embodiment, the variant AAV capsid comprises a peptide insertion comprising the amino acid sequence TNKIGVT (SEQ ID NO:15) or comprising, consisting essentially of, or consisting of the amino acid sequence LATNKIGVTA (SEQ ID NO:29) or LATNKIGVTS (SEQ ID NO:37) between amino acids 587 and 588 of AAV2 capsid or the corresponding position in the capsid protein of another AAV serotype and comprises a V708I amino acid substitution compared to the amino acid sequence of AAV2 or the corresponding substitution in another AAV parental serotype and optionally further comprises an N449K and/or G222S substitution relative to AAV2 or the corresponding substitution in the capsid protein of another AAV parental serotype, wherein the substituted amino acids do not naturally occur at the corresponding position. In another preferred embodiment, the variant AAV capsid comprises a peptide insertion comprising the amino acid sequence TNKIGVT (SEQ ID NO:15) or comprising, consisting essentially of, or consisting of the amino acid sequence LATNKIGVTA (SEQ ID NO:29) or LATNKIGVTS (SEQ ID NO:37) between amino acids 587 and 588 of AAV2 capsid or the corresponding position in the capsid protein of another AAV serotype and comprises N312K, N449D, N551S, I698V and L735Q and optionally V708I amino acid substitutions compared to the amino acid sequence of AAV2 or the corresponding substitution(s) in another AAV parental serotype, wherein the substituted amino acid(s) do not naturally occur at the corresponding position. The variant AAV capsid may have at least about 85%, at least about 90%, at least about 95%, at least about 98%, or greater, amino acid sequence identity to the entire length of the amino acid sequence set forth in SEQ ID NO:2. In a particularly preferred embodiment, the variant AAV capsid has an amino acid sequence having at least about 85%, at least about 90%, at least about 95%, at least about 98% sequence identity to or is 100% identical to the following amino acid sequence:

(SEQ ID NO: 46)
MAADGYLPDWLEDTLSEGIRQWWKLKPGPPPPKPAERHKDDSRGLVLP

GYKYLGPFNGLDKGEPVNEADAAALEHDKAYDRQLDSGDNPYLKYNHA

DAEFQERLKEDTSFGGNLGRAVFQAKKRVLEPLGLVEEPVKTAPGKKR

PVEHSPVEPDSSSGTGKAGQQPARKRLNFGQTGDADSVPDPQPLGQPP

AAPSGLGTNTMATGSGAPMADNNEGADGVGNSSGNWHCDSTWMGDRVI

TTSTRTWALPTYNNHLYKQISSQSGASNDNHYFGYSTPWGYFDFNRFH

CHFSPRDWQRLINNNWGFRPKRLNFKLFNIQVKEVTQNDGTTTIANNL

TSTVQVFTDSEYQLPYVLGASQGCLPPFPADVFMVPQYGYLTLNNGSQ

AVGRSSFYCLEYFPSQMLRTGNNFTFSYTFEDVPFHSSYAHSQSLDRL

MNPLIDQYLYYLSRTNTPSGTTTQSRLQFSQAGASDIRDQSRNWLPGP

CYRQQRVSKTSADNNNSEYSWTGATKYHLNGRDSLVNPGPAMASHKDD

EEKFFPQSGVLIFGKQGSEKTNVDIEKVMITDEEEIRTTNPVATEQYG

SVSTNLQRGNLATNKIGVTARQAATADVNTQGVLPGMVWQDRDVYLQ

GPIWAKIPHTDGHFHPSPLMGGFGLKHPPPQILIKNTPVPANPSTTFS

AAKFASFITQYSTGQVSVEIEWELQKENSKRWNPEIQYTSNYNKS<u>IN</u>

VDFTVDTNGVYSEPRPIGTRYLTRNL

In another embodiment, a variant AAV capsid protein is provided comprising a) a peptide insertion located between amino acids 588 and 589 of VP1 of AAV3A, AAV3B, AAV9, or AAV10, between amino acids 589 and 590 of AAV7, between amino acids 590 to 591 of AAV1, AAV6 or AAV8, between amino acids 584 and 585 of AAV4 or between amino acids 575 and 576 of AAV5, the peptide insertion comprising an amino acid sequence selected from TNKIGVT (SEQ ID NO:15), LATNKIGVTA (SEQ ID NO:29) and LATNKIGVTS (SEQ ID NO:37), and b) a valine to isoleucine substitution at amino acid 709 of AAV3A or AAV3B, an alanine to isoleucine substitution at position 709 of AAV1 or AAV6, an asparagine to isoleucine substitution at amino acid 707 of AAV4 or amino acid 709 of AAV9 or a threonine to isoleucine substitution at amino acid 710 of AAV7 or amino acid 711 of AAV8 or AAV10 or a glutamine to isoleucine substitution at amino acid 697 of AAV5. In preferred embodiments, the variant AAV capsid comprises a peptide insertion comprising the amino acid sequence TNKIGVT (SEQ ID NO:15) or comprising, consisting essentially of, or consisting of the amino acid sequence LATNKIGVTA (SEQ ID NO:29) or LATNKIGVTS (SEQ ID NO:37) between amino acids 587 and 588 of AAV2 capsid and comprises a valine to isoleucine amino acid substitution at amino acid 708 (V708I) compared to the amino acid sequence of AAV2, wherein the variant capsid protein comprises from 2 to 5, from 5 to 10, or from 10 to 15 amino acid substitutions and is preferably at least about 85%, at least about 90%, at least about 95%, at least about 98%, or greater amino acid sequence identity to the entire length of the amino acid sequence set forth in SEQ ID NO:2.

In yet another embodiment, the variant capsid protein comprises a) a peptide insertion comprising the amino acid sequence TNKIGVT (SEQ ID NO:15) or comprising, consisting essentially of, or consisting of the amino acid sequence LATNKIGVTA (SEQ ID NO:29) or LATNKIGVTS (SEQ ID NO:37) between amino acids 587 and 588 of AAV2 capsid and b) a valine to isoleucine amino acid substitution at amino acid 708 compared to the amino acid sequence of AAV2 and is otherwise identical to the amino acid sequence of SEQ ID NO:2.

In yet another embodiment, the variant capsid protein comprises a) a peptide insertion comprising the amino acid sequence TNKIGVT (SEQ ID NO:15) or comprising, consisting essentially of, or consisting of the amino acid sequence LATNKIGVTA (SEQ ID NO:29) or LATNKIGVTS (SEQ ID NO:37) between amino acids 587 and 588 of AAV2 capsid and is otherwise identical to the amino acid sequence of SEQ ID NO:2. In some embodiments, the variant AAV capsid has an amino acid sequence having at least about 85%, at least about 90%, at least about 95%, at least about 98% sequence identity to or is 100% identical to the following amino acid sequence:

```
                                          (SEQ ID NO: 47)
MAADGYLPDWLEDTLSEGIRQWWKLKPGPPPPKPAERHKDDSRGLVLP

GYKYLGPFNGLDKGEPVNEADAAALEHDKAYDRQLDSGDNPYLKYNHA

DAEFQERLKEDTSFGGNLGRAVFQAKKRVLEPLGLVEEPVKTAPGKKR

PVEHSPVEPDSSSGTGKAGQQPARKRLNFGQTGDADSVPDPQPLGQPP

AAPSGLGTNTMATGSGAPMADNNEGADGVGNSSGNWHCDSTWMGDRVI

TTSTRTWALPTYNNHLYKQISSQSGADNDNHYFGYSTPWGYFDFNRFH

CHFSPRDWQRLINNNWGFRPKRLNFKLFNIQVKEVTQNDGTTTIANNL

TSTVQVFTDSEYQLPYVLGSAHQGCLPPFPADVFMVPQYGYLTLNNGS

QAVGRSSFYCLEYFPSQMLRTGNNFTFSYTFEDVPFHSSYAHSQSLDR

LMNPLIDQYLYYLSRTNTPSGTTTQSRLQFSQAGASDIRDQSRNWLPG

PCYRQQRVSKTSADNNNSEYSWTGATKYHLNGRDSLVNPGPAMASHKD

DEEKFFPQSGVLIFGKQGSEKTNVDIEKVMITDEEEIRTTNPVATEQY

GSVSTNLQRGNLATNKIGVTARQAATADVNTQGLVLPGMVWQDRDVY
```

-continued
```
LQGPIWAKIPHTDGHFHPSPLMGGFGLKHPPPQILIKNTPVPANPSTT

FSAAKFASFITQYSTGQVSVEIEWELQKENSKRWNPEIQYTSNYNKSV

NVDFTVDTNGVYSEPRPIGTRYLTRNL
```

In another preferred embodiment, the variant AAV capsid comprises a peptide insertion comprising the amino acid sequence NKTTNKD (SEQ ID NO:14) or LANKTTNKDA (SEQ ID NO:28) between amino acids 587 and 588 of AAV2 capsid and further comprises a V708I amino acid substitution at residue 708 relative to the amino acid sequence of AAV2 capsid (SEQ ID NO:2) or the corresponding substitution in another AAV parental serotype and optionally further comprises an S109T and/or W694C and/or W606C amino acid substitution compared to the amino acid sequence of AAV2 or the corresponding substitution in another AAV parental serotype, wherein the substituted amino acid(s) do not naturally occur at the corresponding position. In another particularly preferred embodiment, the variant AAV capsid comprises a peptide insertion comprising the amino acid sequence NKTTNKD (SEQ ID NO:14) or comprising, consisting essentially of, or consisting of the amino acid sequence LANKTTNKDA (SEQ ID NO:28) between amino acids 587 and 588 of VP1 of AAV2 or the corresponding amino acids of another AAV capsid, and further comprises an I698V amino acid substitution at residue 698 relative to the amino acid sequence of AAV2 capsid (SEQ ID NO:2) or the corresponding residue of another AAV capsid. The variant AAV capsid may have at least about 85%, at least about 90%, at least about 95%, at least about 98%, or greater amino acid sequence identity to the entire length of the amino acid sequence set forth in SEQ ID NO:2 or the corresponding parental AAV capsid. In a particularly preferred embodiment, the variant AAV capsid has an amino acid sequence having at least about 85%, at least about 90%, at least about 95%, at least about 98% sequence identity to or is 100% identical to the following amino acid sequence:

```
                                          (SEQ ID NO: 48)
MAADGYLPDWLEDTLSEGIRQWWKLKPGPPPPKPAERHKDDSRGLVLP

GYKYLGPFNGLDKGEPVNEADAAALEHDKAYDRQLDSGDNPYLKYNHA

DAEFQERLKEDTSFGGNLGRAVFQAKKRVLEPLGLVEEPVKTAPGKKR

PVEHSPVEPDSSSGTGKAGQQPARKRLNFGQTGDADSVPDPQPLGQPP

AAPSGLGTNTMATGSGAPMADNNEGADGVGNSSGNWHCDSTWMGDRVI

TTSTRTWALPTYNNHLYKQISSQSGASNDNHYFGYSTPWGYFDFNRFH

CHFSPRDWQRLINNNWGFRPKRLNFKLFNIQVKEVTQNDGTTTIANNL

TSTVQVFTDSEYQLPYVLGSAHQGCLPPFPADVFMVPQYGYLTLNNGS

QAVGRSSFYCLEYFPSQMLRTGNNFTFSYRFEDVPFHSSYAHSQSLDR

LMNPLIDQYLYYLSRTNTPSGTTTQSRLQFSQAGASDIRDQSRNWLPG

PCYRQQRVSKTSADNNNSEYSWTGATKYHLNGRDSLVNPGPAMASHKD

DEEKFFPQSGVLIFGKQGSEKTNVDIEKVMITDEEEIRTTNPVATEQY

GSVSTNLQRGNLANKTTNKDARQAATADVNTQGVLPGMVWQDPDVYL
```

-continued
QGPIWAKIPHTDGHFHPSPLMGGFGLKHPPPQILIKNTPVPANPSTTF

SAAKFASFITQYSTGQVSVEIEWELQKENSKRWNPEIQYTSNYNKSI

NVDFTVDTNGVYSEPRPIGTRYLTRNL

In another particularly preferred embodiment, the variant AAV capsid comprises a peptide insertion comprising the amino acid sequence NKTTNKD (SEQ ID NO:14) or comprising, consisting essentially of, or consisting of the amino acid sequence LANKTTNKDA (SEQ ID NO:28) between amino acids 587 and 588 of AAV2 capsid protein or the corresponding position in the capsid protein of another AAV serotype and comprises an N312K amino acid substitution compared to the amino acid sequence of AAV2 capsid (SEQ ID NO:2) or the corresponding substitution in another AAV parental serotype and optionally further comprises N449D, N551S, I698V, and L735Q and optionally V708I amino acid substitutions compared to the amino acid sequence of AAV2 capsid or the corresponding substitutions in another AAV parental serotype. The variant AAV capsid may have at least about 85%, at least about 90%, at least about 95%, at least about 98%, or greater, amino acid sequence identity to the entire length of the amino acid sequence set forth in SEQ ID NO:2. In a particularly preferred embodiment, the variant AAV capsid has an amino acid sequence having at least about 85%, at least about 90%, at least about 95%, at least about 98% sequence identity to or is 100% identical to the following amino acid sequence:

(SEQ ID NO: 49)
MAADGYLPDWLEDTLSEGIRQWWKLKPGPPPPKPAERHKDDSRGLVLP

GYKYLGPFNGLDKGEPVNEADAAALEHDKAYDRQLDSGDNPYLKYNHA

DAEFQERLKEDTSFGGNLGRAVFQAKKRVLEPLGLVEEPVKTAPGKKR

PVEHSPVEPDSSSGTGKAGQQPARKRLNFGQTGDADSVPDPQPLGQPP

AAPSGLGTNTMATGSGAPMADNNEGADGVGNSSGNWHCDSTWMGDRVI

TTSTRTWALPTYNNHLYKQISSQSGASNDNHYFGYSTPWGYFDFNRFH

CHFSPRDWQRLINNNWGFRPRKLKFKLFNIQVKEVTQNDGTTTIANN

LTSTVQVFTDSEYQLPYVLGSAHQGCLPPFPADVFMVPQYGYLTLNNG

SQAVGRSSFYCLEYFPSQMLRTGNNFTFSYTFEDVPFHSSYAHSQSLD

RLMNPLIDQYLYYLSRTDTPSGTTTQSRLQFSQAGASDIRDQSRNWLP

GPCYRQQRVSKTSADNNNSEYSWTGATKYHLNGRDSLVNPGPAMASHK

DDEEKFFPQSGVLIFGKQGSEKTSVDIEKVMITDEEEIRTTNPVATEQ

YGSVSTNLQRGNLANKTTNKDARQAATADVNTQGVLPGMVWQDRDVY

LQGPIWAKIPHTDGHFHPSPLMGGFGLKHPPPQILIKNTPVPANPSTT

FSAAKFASFITQYSTGQVSVEIEWELQKENSKRWNPEVQYTSNYNKSV

NVDFTVDTNGVYSEPRIGTRYLTRNQ

In another embodiment, a variant AAV capsid protein is provided comprising a) a peptide insertion located between amino acids 588 and 589 of VP1 of AAV3A, AAV3B, AAV9, or AAV10, between amino acids 589 and 590 of AAV7, between amino acids 590 to 591 of AAV1, AAV6 or AAV8, between amino acids 584 and 585 of AAV4 or between amino acids 575 and 576 of AAV5, the peptide insertion comprising an amino acid sequence selected from NKTTNKD (SEQ ID NO:14) and LANKTTNKDA (SEQ ID NO:28), and b) a valine to isoleucine substitution at amino acid 709 of AAV3A or AAV3B, an alanine to isoleucine substitution at position 709 of AAV1 or AAV6, an asparagine to isoleucine substitution at amino acid 707 of AAV4 or amino acid 709 of AAV9 or a threonine to isoleucine substitution at amino acid 710 of AAV7 or amino acid 711 of AAV8 or AAV10 or a glutamine to isoleucine substitution at amino acid 697 of AAV5 and is optionally otherwise identical to any one of SEQ ID NOs: 1 and 3-12. In preferred embodiments, the variant capsid protein comprises a) a peptide insertion comprising the amino acid sequence NKTTNKD (SEQ ID NO:14) or comprising, consisting essentially of, or consisting of the amino acid sequence LANKTTNKDA (SEQ ID NO:28) between amino acids 587 and 588 of AAV2 capsid and b) a valine to isoleucine amino acid substitution at amino acid 708 compared to the amino acid sequence of AAV2, wherein the variant capsid protein comprises from 2 to 5, from 5 to 10, or from 10 to 15 amino acid substitutions.

In yet another embodiment, the variant capsid protein comprises a) a peptide insertion comprising the amino acid sequence NKTTNKD (SEQ ID NO:14) or comprising, consisting essentially of, or consisting of the amino acid sequence LANKTTNKDA (SEQ ID NO:28) between amino acids 587 and 588 of AAV2 capsid and b) a valine to isoleucine amino acid substitution at amino acid 708 compared to the amino acid sequence of AAV2 and is otherwise identical to the amino acid sequence of SEQ ID NO:2.

In another embodiment, the variant capsid comprises a peptide insertion comprising the amino acid sequence NKTTNKD (SEQ ID NO:14) or comprising, consisting essentially of, or consisting of the amino acid sequence LANKTTNKDA (SEQ ID NO:28) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 50)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSTGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGS

AHQGCLPPFPADVFMVPQYGYLTLNNGSQAVGRSSFYCLEYFPSQMLRTGN

NFTFSYTFEDVPFHSSYAHSQSLDRLMNPLIDQYLYYLSRTNTPSGTTTQS

RLQFSQAGASDIRDQSRNWLPGPCYRQQRVSKTSADNNNSEYSWTGATKYH

LNGRDSLVNPGPAMASHKDDEEKFFPQSGVLIFGKQGSEKTNVDIEKVMIT

DEEEIRTTNPVATEQYGSVSTNLQRGNLANKTTNKDARQAATADVNT

QGVLPGMVWQDRDVYLQGPIWAKIPHTDGHFHPSPLMGGFGLKHPPPQIL

IKNTPVPANPSTTFSAAKFASFITQYSTGQVSVEIEWELQKENSKRWNPE

IQYTSNYNKSVNVDFTVDTNGVYSEPRPIGTRYLTRNL

In other embodiments, a variant AAV capsid protein is provided comprising a) a peptide insertion in the GH-loop of the capsid protein, wherein the peptide insertion comprises an amino acid sequence selected from GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25) and ASDSTKA (SEQ ID NO:26), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: A35P, S109T, P195L, D213N, G222S, V229I, N312K, A319T, T330A, A333S, E347K, P363L, A427D, V447F, N449D, N449K, G453R, A490T, K527Q, N551S, A581T, Y585S, R588M, A593E, W606C, K649E, R651H, W694C, I698V, V708I, L735Q and a combination thereof. In some embodiments, the one or more amino acid substitutions are selected from the group consisting of: V708I, S109T, R651H, A319T, P195L, P363L, I698V, D213N, G453R and a combination thereof. In some preferred embodiments, the one or more amino acid substitutions include at least a V708I and/or P363L amino acid substitution or the corresponding substitution in another AAV parental serotype. Preferably, the peptide insertion site is located between amino acids 587 and 588 of AAV2 capsid or the corresponding position in the capsid protein of another AAV serotype.

In some embodiments, the variant AAV capsid comprises a peptide insertion comprising the amino acid sequence GNLTKGN (SEQ ID NO:16) or comprising, consisting essentially of, or consisting of the amino acid sequence LAGNLTKGNA (SEQ ID NO:30) between amino acids 587 and 588 of VP1 of AAV2 or the corresponding amino acids of another AAV capsid and further comprises one or more of the following amino acid substitutions relative to the amino acid sequence of AAV2 capsid (SEQ ID NO:2) or the corresponding substitution in another AAV parental serotype, wherein the substituted amino acid(s) do not naturally occur at the corresponding positions: V708I, V708I+S109T, R651H, A319T+P195L, P363L, P363L+V708I. In some embodiments, the variant AAV capsid comprises (i) a peptide insertion comprising the amino acid sequence GNLTKGN (SEQ ID NO:16) or comprising, consisting essentially of, or consisting of the amino acid sequence LAGNLTKGNA (SEQ ID NO:30) between amino acids 587 and 588 of VP1 of AAV2 or the corresponding amino acids of another AAV capsid and (ii) a V708I substitution relative to the amino acid sequence of AAV2 capsid (SEQ ID NO:2) or the corresponding residue of another AAV capsid and comprises from 2 to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence GNLTKGN (SEQ ID NO:16) or comprising, consisting essentially of, or consisting of the amino acid sequence LAGNLTKGNA (SEQ ID NO:30) between amino acids 587 and 588 of VP1 of AAV2 or the corresponding amino acids of another AAV capsid and (ii) a P363L substitution relative to the amino acid sequence of AAV2 capsid (SEQ ID NO:2) or the corresponding residue of another AAV capsid and comprises from 2 to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence GNLTKGN (SEQ ID NO:16) or comprising, consisting essentially of, or consisting of the amino acid sequence LAGNLTKGNA (SEQ ID NO:30) between amino acids 587 and 588 of VP1 of AAV2 or the corresponding amino acids of another AAV capsid and (ii) an R651H substitution relative to the amino acid sequence of AAV2 capsid (SEQ ID NO:2) or the corresponding residue of another AAV capsid and comprises from 2 to 5, from 5 to 10, or from 10 to 15 amino acid substitutions or is otherwise identical to the amino acid sequence of SEQ ID NO:2 or the to the corresponding parental AAV capsid protein sequence. In another embodiment, the variant capsid comprises a peptide insertion comprising the amino acid sequence GNLTKGN (SEQ ID NO:16) or comprising, consisting essentially of, or consisting of the amino acid sequence LAGNLTKGNA (SEQ ID NO:30) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 51)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSTGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGS

AHQGCLPPFPADVFMVPQYGYLTLNNGSQAVGRSSFYCLEYFPSQMLRTGN

NFTFSYTFEDVPFHSSYAHSQSLDRLMNPLIDQYLYYLSRTNTPSGTTTQS

RLQFSQAGASDIRDQSRNWLPGPCYRQQRVSKTSADNNNSEYSWTGATKYH

LNGRDSLVNPGPAMASHKDDEEKFFPQSGVLIFGKQGSEKTNVDIEKVMIT

DEEEIRTTNPVATEQYGSVSTNLQRGNLAGNLTKGNARQAATADVNT

QGVLPGMVWQDRDVYLQGPIWAKIPHTDGHFHPSPLMGGFGLKHPPPQIL

IKNTPVPANPSTTFSAAKFASFITQYSTGQVSVEIEWELQKENSKRWNPE

IQYTSNYNKSVNVDFTVDTNGVYSEPRPIGTRYLTRNL

In some embodiments, the variant AAV capsid comprises (i) a peptide insertion comprising the amino acid sequence NTVKLST (SEQ ID NO:17) or comprising, consisting essentially of, or consisting of the amino acid sequence LANTVKLSTA (SEQ ID NO:31) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) the corresponding substitution in another AAV parental serotype, wherein the substituted amino acid(s) do not naturally occur at the corresponding positions, and comprises from 2 to 5, from 5 to 10, or from 10 to 15 amino acid substitutions or is otherwise identical to the amino acid sequence of SEQ ID NO:2 or to the corresponding parental AAV capsid protein sequence. In another embodiment, the variant capsid comprises a peptide insertion comprising the amino acid sequence NTVKLST (SEQ ID NO:17) or comprising, consisting essentially of, or consisting of the amino acid sequence LANTVKLSTA (SEQ ID NO:31) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 52)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSTGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGS

AHQGCLPPFPADVFMVPQYGYLTLNNGSQAVGRSSFYCLEYFPSQMLRTGN

NFTFSYTFEDVPFHSSYAHSQSLDRLMNPLIDQYLYYLSRTNTPSGTTTQS

RLQFSQAGASDIRDQSRNWLPGPCYRQQRVSKTSADNNNSEYSWTGATKYH

LNGRDSLVNPGPAMASHKDDEEKFFPQSGVLIFGKQGSEKTNVDIEKVMIT

DEEEIRTTNPVATEQYGSVSTNLQRGNLANTVKLSTARQAATADVNTQ

GVLPGMVWQDRDVYLQGPIWAKIPHTDGHFHPSPLMGGFGLKHPPPQILIK

NTPVPANPSTTFSAAKFASFITQYSTGQVSVEIEWELQKENSKRWNPEIQY

TSNYNKSVNVDFTVDTNGVYSEPRPIGTRYLTRNL

In some embodiments, the variant AAV capsid comprises (i) a peptide insertion comprising the amino acid sequence SNTVKAI (SEQ ID NO:18) or comprising, consisting essentially of, or consisting of the amino acid sequence LASNTVKAIA (SEQ ID NO:32) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) or the corresponding substitution in another AAV parental serotype, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In another embodiment, the variant capsid comprises a peptide insertion comprising the amino acid sequence SNTVKAI (SEQ ID NO:18) or comprising, consisting essentially of, or consisting of the amino acid sequence LASNTVKAIA (SEQ ID NO:32) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 53)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSTGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGS

AHQGCLPPFPADVFMVPQYGYLTLNNGSQAVGRSSFYCLEYFPSQMLRTGN

NFTFSYTFEDVPFHSSYAHSQSLDRLMNPLIDQYLYYLSRTNTPSGTTTQS

RLQFSQAGASDIRDQSRNWLPGPCYRQQRVSKTSADNNNSEYSWTGATKYH

LNGRDSLVNPGPAMASHKDDEEKFFPQSGVLIFGKQGSEKTNVDIEKVMIT

DEEEIRTTNPVATEQYGSVSTNLQRGNLASNTVKAIARQAATADVNTQ

GVLPGMVWQDRDVYLQGPIWAKIPHTDGHFHPSPLMGGFGLKHPPPQILIK

NTPVPANPSTTFSAAKFASFITQYSTGQVSVEIEWELQKENSKRWNPEIQY

TSNYNKSVNVDFTVDTNGVYSEPRPIGTRYLTRNL

In some embodiments, the variant AAV capsid comprises (i) a peptide insertion comprising the amino acid sequence ASNITKA (SEQ ID NO:19) or comprising, consisting essentially of, or consisting of the amino acid sequence LAASNITKAA (SEQ ID NO:33) between amino acids 587 and 588 of VP1 of AAV2 or the corresponding amino acids of another AAV capsid and (ii) a V708I amino acid substitution relative to the amino acid sequence of AAV2 capsid (SEQ 1D NO:2) or the corresponding substitution in another AAV parental serotype, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In another embodiment, the variant capsid comprises a peptide insertion comprising the amino acid sequence ASNITKA (SEQ ID NO:19) or comprising, consisting essentially of, or consisting of the amino acid sequence LAASNITKAA (SEQ ID NO:33) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 54)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSTGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGS

AHQGCLPPFPADVFMVPQYGYLTLNNGSQAVGRSSFYCLEYFPSQMLRTGN

NFTFSYTFEDVPFHSSYAHSQSLDRLMNPLIDQYLYYLSRTNTPSGTTTQS

RLQFSQAGASDIRDQSRNWLPGPCYRQQRVSKTSADNNNSEYSWTGATKYH

LNGRDSLVNPGPAMASHKDDEEKFFPQSGVLIFGKQGSEKTNVDIEKVMIT

DEEEIRTTNPVATEQYGSVSTNLQRGNLAASNITKAARQAATADVNTQ

GVLPGMVWQDRDVYLQGPIWAKIPHTDGHFHPSPLMGGFGLKHPPPQILIK

NTPVPANPSTTFSAAKFASFITQYSTGQVSVEIEWELQKENSKRWNPEIQY

TSNYNKSVNVDFTVDTNGVYSEPRPIGTRYLTRNL

In some embodiments, the variant AAV capsid comprises (i) a peptide insertion comprising the amino acid sequence DNTVTRS (SEQ ID NO:20) or comprising, consisting essentially of, or consisting of the amino acid sequence LADNTVTRSA (SEQ ID NO:34) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) or the corresponding substitution in another AAV parental serotype, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence DNTVTRS (SEQ ID NO:20) or comprising, consisting essentially of, or consisting of the amino acid sequence LADNTVTRSA (SEQ ID NO:34) between amino acids 587 and 588 of VP1 of AAV2 or the corresponding amino acids of another AAV capsid and (ii) an I698V amino acid substitution relative to the amino acid sequence of AAV2 capsid (SEQ ID NO:2) or the corresponding substitution in another AAV parental serotype, wherein the substituted amino acid does not naturally occur at the corresponding position, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In another embodiment, the variant capsid comprises a peptide insertion comprising the amino acid sequence DNTVTRS (SEQ ID NO:20) or comprising, consisting essentially of, or consisting of the amino acid sequence LADNTVTRSA (SEQ ID NO:34) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 55)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSTGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGS

AHQGCLPPFPADVFMVPQYGYLTLNNGSQAVGRSSFYCLEYFPSQMLRTGN

NFTFSYTFEDVPFHSSYAHSQSLDRLMNPLIDQYLYYLSRTNTPSGTTTQS

RLQFSQAGASDIRDQSRNWLPGPCYRQQRVSKTSADNNNSEYSWTGATKYH

LNGRDSLVNPGPAMASHKDDEEKFFPQSGVLIFGKQGSEKTNVDIEKVMIT

DEEEIRTTNPVATEQYGSVSTNLQRGNLADNTVTRSARQAATADVNT

QGVLPGMVWQDRDVYLQGPIWAKIPHTDGHFHPSPLMGGFGLKHPPPQILI

KNTPVPANPSTTFSAAKFASFITQYSTGQVSVEIEWELQKENSKRWNPEIQ

YTSNYNKSVNVDFTVDTNGVYSEPRPIGTRYLTRNL

In some embodiments, the variant AAV capsid comprises (i) a peptide insertion comprising the amino acid sequence NKISAKD (SEQ ID NO:21) or comprising, consisting essentially of, or consisting of the amino acid sequence LANKISAKDA (SEQ ID NO:35) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) or the corresponding substitution in another AAV parental serotype, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In another embodiment, the variant capsid comprises a peptide insertion comprising the amino acid sequence NKISAKD (SEQ ID NO:21) or comprising, consisting essentially of, or consisting of the amino acid sequence LANKISAKDA (SEQ ID NO:35) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 56)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSTGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGS

AHQGCLPPFPADVFMVPQYGYLTLNNGSQAVGRSSFYCLEYFPSQMLRTGN

NFTFSYTFEDVPFHSSYAHSQSLDRLMNPLIDQYLYYLSRTNTPSGTTTQS

RLQFSQAGASDIRDQSRNWLPGPCYRQQRVSKTSADNNNSEYSWTGATKYH

LNGRDSLVNPGPAMASHKDDEEKFFPQSGVLIFGKQGSEKTNVDIEKVMIT

DEEEIRTTNPVATEQYGSVSTNLQRGNLANKISAKDARQAATADVNTQ

GVLPGMVWQDRDVYLQGPIWAKIPHTDGHFHPSPLMGGFGLKHPPPQILIK

NTPVPANPSTTFSAAKFASFITQYSTGQVSVEIEWELQKENSKRWNPEIQY

TSNYNKSVNVDFTVDTNGVYSEPRPIGTRYLTRNL

In some embodiments, the variant AAV capsid comprises (i) a peptide insertion comprising the amino acid sequence NQDYTKT (SEQ ID NO:22) or comprising, consisting essentially of, or consisting of the amino acid sequence LANQDYTKTA (SEQ ID NO:36) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) or the corresponding substitution in another AAV parental serotype and comprises from 2 to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence NQDYTKT (SEQ ID NO:22) or comprising, consisting essentially of, or consisting of the amino acid sequence LANQDYTKTA (SEQ ID NO:36) between amino acids 587 and 588 of VP1 of AAV2 or the corresponding amino acids of another AAV capsid and (ii) an I698V amino acid substitution relative to the amino acid sequence of AAV2 capsid (SEQ ID NO:2) or the corresponding substitution in another AAV parental serotype (i.e. other than AAV2), wherein the substituted amino acid does not naturally occur at the corresponding position, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In another embodiment, the variant capsid comprises a peptide insertion comprising the amino acid sequence NQDYTKT (SEQ ID NO:22) or comprising, consisting essentially of, or consisting of the amino acid sequence LANQDYTKTA (SEQ ID NO:36) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 57)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSTGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGS

AHQGCLPPFPADVFMVPQYGYLTLNNGSQAVGRSSFYCLEYFPSQMLRTGN

NFTFSYTFEDVPFHSSYAHSQSLDRLMNPLIDQYLYYLSRTNTPSGTTTQS

RLQFSQAGASDIRDQSRNWLPGPCYRQQRVSKTSADNNNSEYSWTGATKYH

LNGRDSLVNPGPAMASHKDDEEKFFPQSGVLIFGKQGSEKTNVDIEKVMIT

DEEEIRTTNPVATEQYGSVSTNLQRGNLANQDYTKTARQAATADVNTQ

GVLPGMVWQDRDVYLQGPIWAKIPHTDGHFHPSPLMGGFGLKHPPPQILIK

NTPVPANPSTTFSAAKFASFITQYSTGQVSVEIEWELQKENSKRWNPEIQY

TSNYNKSVNVDFTVDTNGVYSEPRPIGTRYLTRNL

In some embodiments, the variant AAV capsid comprises a peptide insertion comprising the amino acid sequence QADTTKN (SEQ ID NO:23) or comprising, consisting essentially of, or consisting of the amino acid sequence LAQADTTKNA (SEQ ID NO:39) between amino acids 587 and 588 of VP1 of AAV2 or the corresponding amino acids of another AAV capsid and further comprises one or more of the following amino acid substitutions relative to the amino acid sequence of AAV2 capsid (SEQ ID NO:2) or the corresponding substitutions in another AAV parental serotype, wherein the substituted amino acid(s) do not naturally occur at the corresponding positions: V708I, D213N, P363L, G453R. In some embodiments, the variant AAV capsid comprises (i) a peptide insertion comprising the amino acid sequence QADTTKN (SEQ ID NO:23) or comprising, consisting essentially of, or consisting of the amino acid sequence LAQADTTKNA (SEQ ID NO:39) between amino acids 587 and 588 of VP1 of AAV2 or the corresponding amino acids of another AAV capsid and (ii) a V708I substitution relative to the amino acid sequence of AAV2 capsid (SEQ ID NO:2) or the corresponding substitution in another AAV parental serotype and comprises from 2 to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence QADTTKN (SEQ ID NO:23) or comprising, consisting essentially of, or consisting of the amino acid sequence LAQADTTKNA (SEQ ID NO:39) between amino acids 587 and 588 of VP1 of AAV2 or the corresponding amino acids of another AAV capsid and (ii) a P363L substitution relative to the amino acid sequence of AAV2 capsid (SEQ ID NO:2) or the corresponding residue of another AAV capsid and comprises from 2 to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence QADTTKN (SEQ ID NO:23) or comprising, consisting essentially of, or consisting of the amino acid sequence LAQADTTKNA (SEQ ID NO:39) between amino acids 587 and 588 of VP1 of AAV2 or the corresponding amino acids of another AAV capsid and (ii) a D213N substitution relative to the amino acid sequence of AAV2 capsid (SEQ ID NO:2) or the corresponding substitution in another AAV parental serotype, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence QADTTKN (SEQ ID NO:23) or comprising, consisting essentially of, or consisting of the amino acid sequence LAQADTTKNA (SEQ ID NO:39) between amino acids 587 and 588 of VP1 of AAV2 or the corresponding amino acids of another AAV capsid and (ii) a G453R substitution relative to the amino acid sequence of AAV2 capsid (SEQ ID NO:2) or the corresponding substitution in another AAV parental serotype and comprises from 2 to 5, from 5 to 10, or from 10 to 15 amino acid substitutions or is otherwise identical to the amino acid sequence of SEQ ID NO:2 or to the corresponding parental AAV capsid protein sequence. In another embodiment, the variant capsid comprises a peptide insertion comprising the amino acid sequence QADTTKN (SEQ ID NO:23) or comprising, consisting essentially of, or consisting of the amino acid sequence LAQADTFKNA (SEQ ID NO:39) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 58)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSTGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGS

AHQGCLPPFPADVFMVPQYGYLTLNNGSQAVGRSSFYCLEYFPSQMLRTGN

NFTFSYTFEDVPFHSSYAHSQSLDRLMNPLIDQYLYYLSRTNTPSGTTTQS

RLQFSQAGASDIRDQSRNWLPGPCYRQQRVSKTSADNNNSEYSWTGATKYH

LNGRDSLVNPGPAMASHKDDEEKFFPQSGVLIFGKQGSEKTNVDIEKVMIT

DEEEIRTTNPVATEQYGSVSTNLQRGNLAQADTTKNARQAATADVNT

QGVLPGMVWQDRDVYLQGPIWAKIPHTDGHFHPSPLMGGFGLKHPPPQILI

KNTPVPANPSTTFSAAKFASFITQYSTGQVSVEIEWELQKENSKRWNPEIQ

YTSNYNKSVNVDFTVDTNGVYSEPRPIGTRYLTRNL

In some embodiments, the variant AAV capsid comprises (i) a peptide insertion comprising the amino acid sequence TNRTSPD (SEQ ID NO:24) or comprising, consisting essentially of, or consisting of the amino acid sequence LATNRTSPDA (SEQ ID NO:40) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) or the corresponding the corresponding substitution in another AAV parental serotype and comprises from 2 to 5, from 5 to 10, or from 10 to 15 amino acid substitutions or is otherwise identical to the amino acid sequence of SEQ ID NO:2 or the to the corresponding parental AAV capsid protein sequence. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 59)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSTGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGS

AHQGCLPPFPADVFMVPQYGYLTLNNGSQAVGRSSFYCLEYFPSQMLRTGN

NFTFSYTFEDVPFHSSYAHSQSLDRLMNPLIDQYLYYLSRTNTPSGTTTQS

RLQFSQAGASDIRDQSRNWLPGPCYRQQRVSKTSADNNNSEYSWTGATKYH

-continued
LNGRDSLVNPGPAMASHKDDEEKFFPQSGVLIFGKQGSEKTNVDIEKVMIT

DEEEIRTTNPVATEQYGSVSTNLQRGNLATNRTSPDARQAATADVNTQ

GVLPGMVWQDRDVYLQGPIWAKIPHTDGHFHPSPLMGGFGLKHPPPQILIK

NTPVPANPSTTFSAAKFASFITQYSTGQVSVEIEWELQKENSKRWNPEIQY

TSNYNKSINVDFTVDTNGVYSEPRPIGTRYLTRNL

In some embodiments, the variant AAV capsid comprises a peptide insertion comprising the amino acid sequence SNTTQKT (SEQ ID NO:25) or comprising, consisting essentially of, or consisting of the amino acid sequence LASNTTQKTA (SEQ ID NO:41) between amino acids 587 and 588 of VP1 of AAV2 or the corresponding amino acids of another AAV capsid and is otherwise identical to the amino acid sequence of SEQ ID NO:2 or the to the corresponding parental AAV capsid protein sequence. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 60)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSTGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGS

AHQGCLPPFPADVFMVPQYGYLTLNNGSQAVGRSSFYCLEYFPSQMLRTGN

NFTFSYTFEDVPFHSSYAHSQSLDRLMNPLIDQYLYYLSRTNTPSGTTTQS

RLQFSQAGASDIRDQSRNWLPGPCYRQQRVSKTSADNNNSEYSWTGATKYH

LNGRDSLVNPGPAMASHKDDEEKFFPQSGVLIFGKQGSEKTNVDIEKVMIT

DEEEIRTTNPVATEQYGSVSTNLQRGNLASNTTQKTARQAATADVNTQ

GVLPGMVWQDRDVYLQGPIWAKIPHTDGHFHPSPLMGGFGLKHPPPQILIK

NTPVPANPSTTFSAAKFASFITQYSTGQVSVEIEWELQKENSKRWNPEIQY

TSNYNKSVNVDFTVDTNGVYSEPRPIGTRYLTRNL

In some embodiments, the variant AAV capsid comprises (i) a peptide insertion comprising the amino acid sequence ASDSTKA (SEQ ID NO:26) or comprising, consisting essentially of, or consisting of the amino acid sequence LAASDSTKAA (SEQ ID NO:42) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) the corresponding substitution in another AAV parental serotype, wherein the substituted amino acid(s) do not naturally occur at the corresponding positions, and comprises from 2 to 5, from 5 to 10, or from 10 to 15 amino acid substitutions or is otherwise identical to the amino acid sequence of SEQ ID NO:2 or to the corresponding parental AAV capsid protein sequence. In another embodiment, the variant capsid comprises a peptide insertion comprising the amino acid sequence ASDSTKA (SEQ ID NO:26) or comprising, consisting essentially of, or consisting of the amino acid sequence LAASDSTKAA (SEQ ID NO:42) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 61)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSTGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGS

AHQGCLPPFPADVFMVPQYGYLTLNNGSQAVGRSSFYCLEYFPSQMLRTGN

NFTFSYTFEDVPFHSSYAHSQSLDRLMNPLIDQYLYYLSRTNTPSGTTTQS

RLQFSQAGASDIRDQSRNWLPGPCYRQQRVSKTSADNNNSEYSWTGATKYH

LNGRDSLVNPGPAMASHKDDEEKFFPQSGVLIFGKQGSEKTNVDIEKVMIT

DEEEIRTTNPVATEQYGSVSTNLQRGNLAASDSTKAARQAATADVNTQ

GVLPGMVWQDRDVYLQGPIWAKIPHTDGHFHPSPLMGGFGLKHPPPQILIK

NTPVPANPSTTFSAAKFASFITQYSTGQVSVEIEWELQKENSKRWNPEIQY

TSNYNKSVNVDFTVDTNGVYSEPRPIGTRYLTRNL.

In several aspects, a variant AAV capsid protein is provided comprising one or more amino acid substitutions relative to a corresponding parental AAV capsid protein, wherein the variant capsid protein, when present in an AAV virion, confers increased infectivity of a muscle cell (e.g. a skeletal or cardiac muscle cell) compared to the infectivity of a muscle cell by an AAV virion comprising the corresponding parental AAV capsid protein.

In some embodiments a variant AAV capsid protein comprises an amino acid substitution at amino acid 363 compared to the amino acid sequence of AAV2 capsid (SEQ ID NO:2) or the corresponding position in another AAV parental serotype (i.e. other than AAV2). In some preferred embodiments, the variant capsid protein comprises an amino acid sequence having at least about 85%, at least about 90%, at least about 95%, at least about 98%, or at least about 99%, or greater, amino acid sequence identity to the entire length of the amino acid sequence set forth in SEQ ID NO 2 and comprises an amino acid substitution at amino acid 363 compared to the amino acid sequence of AAV2 capsid (SEQ ID NO:2). In some preferred embodiments, a variant AAV capsid protein comprises a P363L amino acid substitution compared to the amino acid sequence of AAV2 capsid (SEQ ID NO:2), AAV3A capsid (SEQ ID NO:3) or AAV3B capsid (SEQ ID NO:4); or a P364L amino acid substitution compared to the amino acid sequence of AAV1 capsid (SEQ ID NO:1) or AAV6 capsid (SEQ ID NO: 7); or a P354L amino acid substitution compared to the amino acid sequence of AAV4 capsid (SEQ ID NO:5) or AAV5 capsid (SEQ ID NO:6); or a P365L amino acid substitution compared to the amino acid sequence of AAV7 capsid (SEQ ID NO:8) or AAV9 capsid (SEQ ID NO:10); or a P366L amino acid substitution compared to the amino acid sequence of AAV8 capsid (SEQ ID NO:9) or AAV10 capsid (SEQ ID NO:11). In some preferred embodiments, the variant capsid protein comprises a P363L substitution compared to the amino acid sequence of SEQ ID NO:2, or the corresponding substitution compared to any of SEQ ID NOs: 1 and 3-12, and has at least about 85%, at least about 90%, at least about 95%, at least about 98%, or at least about 99%, or greater, amino acid sequence identity to the entire length of an amino acid sequence set forth in SEQ ID NO:2, or any of SEQ ID NOs: 1 and 3-12. In some preferred embodiments, the variant capsid protein comprises an amino acid sequence comprising a P363L amino acid substitution compared to the amino acid sequence set forth in SEQ ID NO:2 and is otherwise identical to the amino acid sequence set forth in SEQ ID NO:2. In related embodiments, the variant capsid protein comprises a P363L amino acid substitution compared to the amino acid sequence of SEQ ID NO:2, or the corresponding substitution in another AAV parental serotype (i.e. other than AAV2) wherein the variant capsid protein comprises from 1 to 5, from 5 to 10, or from 10 to 15 amino acid substitutions compared to the amino acid sequence of an AAV2 capsid protein set forth in SEQ ID NO:2 or compared to the amino acid sequence of a capsid protein in another AAV parental serotype. In another preferred embodiment, the variant capsid comprises a P363L amino acid substitution and further comprises E347K and/or V708I amino acid substitution(s) compared to the amino acid sequence of SEQ ID NO:2 or the corresponding substitutions in a capsid from another AAV parental serotype (i.e. other than AAV2). In another preferred embodiment, the variant capsid comprises a P363L amino acid substitution compared to the amino acid sequence of SEQ ID NO:2 or the corresponding substitution in a capsid from another AAV parent serotype and further comprises a peptide insertion, preferably located between amino acids 587 and 588 of VP1 of AAV2, amino acids 588 and 589 of AAV3A, AAV3B, AAV9, or AAV10, amino acids 589 and 590 of VP1 of AAV7, amino acids 590 to 591 of VP1 of AAV1, AAV6, or AAV8, amino acids 584 and 585 of VP1 of AAV4, or amino acids 575 and 576 of AAV5, wherein the peptide insertion preferably comprises an amino acid sequence selected from NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42), more preferably selected from GNLTKGN (SEQ ID NO:16), LAGNLTKGNA (SEQ ID NO:30), QADTTKN (SEQ ID NO:23) and LAQADTTKNA (SEQ ID NO:39), and optionally comprises from 2 to 5, from 5 to 10, or from 10 to 15 amino acid substitutions or is otherwise identical to the amino acid sequence of SEQ ID NO:2 or the to the corresponding parental AAV capsid protein sequence.

In other embodiments a variant AAV capsid protein comprises an amino acid substitution at amino acid 593 compared to the amino acid sequence of AAV2 capsid (SEQ ID NO:2) or the corresponding position in another AAV parental serotype (i.e. other than AAV2). In some preferred embodiments, the variant capsid protein comprises an amino acid substitution at amino acid 593 compared to the amino acid sequence of AAV2 capsid (SEQ ID NO:2) and has at least about 85%, at least about 90%, at least about 95%, at least about 98%, or at least about 99%, or greater, amino acid sequence identity to the entire length of the amino acid sequence set forth in SEQ ID NO 2 or is otherwise identical to the amino acid sequence set forth in SEQ ID NO: 2. In some embodiments, the variant capsid protein comprises a glycine to glutamate amino acid substitution at amino acid 594 compared to the amino acid sequence of AAV1, AAV3A, AAV6, or AAV9, or at amino acid 583 of AAV5, or at amino acid 596 of AAV8 or AAV10, or an arginine to glutamate amino acid substitution at amino acid 594 of AAV3B, or an aspartate to glutamate amino acid substitution at amino acid 592 of AAV4 or a glutamine to glutamate amino acid substitution at position 595 of AAV7. In other embodiments, the variant capsid protein comprises an A593E amino acid substitution compared to the amino acid sequence of AAV2 and does not comprise one or more of the following amino acid substitutions compared to the amino acid sequence of AAV2: I19V, V369A, K26R, N215D, G355S, V46A and S196P. In related embodiments, the variant capsid protein comprises A593E and V708I amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2 or is otherwise identical to the amino acid sequence set forth in SEQ ID NO:2. In related embodiments, the variant capsid protein comprises A593E and S109T amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2 or is otherwise identical to the amino acid sequence set forth in SEQ ID NO:2. In related embodiments, the variant capsid protein comprises A593E, V708I and S109T amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2 or is otherwise identical to SEQ ID NO:2. In other embodiments, the variant capsid comprises A593E, V708I and N551S amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2 or is otherwise identical to the amino acid sequence set forth in SEQ ID NO:2. In other embodiments, the variant capsid comprises A593E, V708I and K649E amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2 or is otherwise identical to the amino acid sequence set forth in SEQ ID NO:2. In other embodiments, the variant capsid comprises A593E, V708I, S109T and K527Q amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2 or is otherwise identical to the amino acid sequence set forth in SEQ ID NO:2.

In other embodiments a variant AAV capsid protein comprises an amino acid substitution at amino acid 708 compared to the amino acid sequence of AAV2 capsid (SEQ ID NO:2) or the corresponding position in another AAV parental serotype (i.e. other than AAV2) wherein the substituted amino acid does not naturally occur at the corresponding position. Preferably, the rAAV virion does not comprise a proline to serine substitution at amino acid 250 compared to AAV2 or a corresponding amino acid in another AAV parental serotype. In some embodiments, the variant capsid protein comprises an amino acid substitution at amino acid 708 compared to the amino acid sequence of AAV2 capsid (SEQ ID NO:2) and has at least about 85%, at least about 90%, at least about 95%, at least about 98%, or at least about 99%, or greater, amino acid sequence identity to the entire length of the amino acid sequence set forth in SEQ ID NO 2 or is otherwise identical to SEQ ID NO:2. In preferred embodiments, the variant capsid protein comprises a valine to isoleucine (V708I) substitution at amino acid 708 compared to the amino acid sequence of AAV2 capsid and has at least about 85%, at least about 90%, at least about 95%, at least about 98%, or at least about 99%, or greater, amino acid sequence identity to the entire length of the amino acid sequence set forth in SEQ ID NO 2 or is otherwise identical to the amino acid sequence of SEQ ID NO:2, wherein the variant capsid protein does not comprise a P250S amino acid substitution. In some embodiments, the variant capsid protein comprises a valine to isoleucine substitution at amino acid 709 of AAV3A or AAV3B, an alanine to isoleucine substitution at position 709 of AAV1 or AAV6, an asparagine to isoleucine substitution at amino acid 707 of AAV4 or amino acid 709 of AAV9 or a threonine to isoleucine substitution at amino acid 710 of AAV7 or amino acid 711 of AAV8 or AAV10 or a glutamine to isoleucine substitution at amino acid 697 of AAV5. In related embodiments, the variant capsid protein comprises a V708I amino acid substitution compared to the amino acid sequence of AAV2, wherein the variant capsid protein comprises from 2 to 5, from 5 to 10, or from 10 to 15 amino acid substitutions and wherein the variant capsid protein does not comprise a P250S amino acid substitution. In other embodiments, the variant capsid protein comprises a V708I amino acid substitution and also comprises an A333S and/or S721L amino acid substitution compared to the amino acid sequence of AAV2. In other related embodiments, the variant capsid comprises a V708I amino acid substitution and also comprises an A333S and/or S721L amino acid substitution compared to the amino acid sequence of AAV2 and has at least about 85%, at least about 90%, at least about 95%, at least about 98%, or at least about 99%, or greater, amino acid sequence identity to the entire length of the amino acid sequence set forth in SEQ ID NO 2 or is otherwise identical to the amino acid sequence of SEQ ID NO:2.

In other embodiments, a variant AAV capsid protein comprises an amino acid sequence at least 85%, at least 90%, at least 95% or at least 98% identical to a wild-type AAV capsid sequence selected from the group consisting of SEQ ID NOS: 1, 2, 3, 4, 5, 6, 7, 8, 10, 11 and 12 and also comprises i) one or more amino acid substitutions selected from the group consisting of A35P, D213N, A319T+P195L, P363L, P363L+V708I, G453R, R651H, I698V, V708I, V708I+A593, V708I+S109T, V708I+T330A, V708I+R588M, V708I+W694C, V708I+W606C, V708I+N449K, V708I+G222S, N312K+N449D+N551S+I698V+L735Q, N312K+N449D+N551S+I698V+V708I+L735Q, and/or (ii) a peptide insertion selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42). In some embodiments, the variant AAV capsid comprises the specified one or more amino acid substitutions and/or peptide insertions and is otherwise identical to a sequence selected from the group consisting of SEQ ID NOS: 1-12.

In some embodiments, a variant AAV capsid protein is an ancestral capsid protein comprising one or more peptide insertion(s) and/or amino acid substitutions as herein described. By an ancestral capsid protein it is meant an evolutionary ancestor of a capsid protein that is found in nature today, e.g. AAV1, AAV2, AAV3, AAV4, AAV5, AAV6, AAV7, AAV8, AAV9, AAVrh0, AAV11, AAV12, AAV13, which is generated in silico by random amino acid substitution at positions of degeneracy between AAV capsid proteins that are found in nature today.

In other embodiments, a variant AAV capsid protein is a chimera comprising amino acids 130-725 of AAV5 capsid (SEQ ID NO:6) or an amino acid sequence at least 90%, at least 95% or at least 98% identical thereto.

In some aspects, a variant AAV capsid protein is a chimera comprising (i) amino acids 1-129 of AAV6 (SEQ ID NO:7) or an amino acid sequence at least 90%, at least 95% or at least 98% identical thereto and (ii) amino acids 130-725 of AAV5 (SEQ ID NO:6) or an amino acid sequence at least 90%, at least 95% or at least 98% identical thereto and further comprising V229I, A490T and A581T and optionally V447F or Y585S amino acid substitutions relative to the sequence of AAV5 (SEQ ID NO:6). In some embodiments, the variant AAV capsid has an amino acid sequence having at least about 85%, at least about 90%, at least about 95%, at least about 98% sequence identity to or is 100% identical to the following amino acid sequence:

(SEQ ID NO: 62)
MAADGYLPDWLEDNLSEGIREWWDLKPGAPKPKANQQKQDDGRGLVLPGY

KYLGPFNGLDKGEPVNAADAAALEHDKAYDQQLKAGDNPYLRYNHADAEF

QERLQEDTSFGGNLGRAVFQAKKRVLEPFGLVEEGAKTAPTGKRIDDHFP

KRKKARTEEDSKPSTSSDAEAGPSGSQQLQIPAQPASSLGADTMSAGGGG

PLGDNNQGADGVGNASGDWHCDSTWMGDR<u>I</u>VTKSTRTWVLPSYNNHQYRE

IKSGSVDGSNANAYFGYSTPWGYFDFNRFHSHWSPRDWQRLINNYWGFRP

RSLRVKIFNIQVKEVTVQDSTTTIANNLTSTVQVFTDDDYQLPYVVGNGT

EGCLPAFPPQVFTLPQYGYATLNRDNTENPTERSSFFCLEYFPSKMLRTG

NNFEFTYNFEEVPFHSSFAPSQNLFKLANPLVDQYLYRFVSTNNTGGVQF

NKNLAGRYANTYKNWFPGPMGRTQGWNLGSGVNRASVSAF<u>T</u>TTNRMELEG

ASYQVPPQPNGMTNNLQGSNTYALENTMIFNSQPANPGTTATYLEGNMLI

TSESETQPVNRVAYNVGGQMATNNQSSTTAP<u>TT</u>GTYNLQEIVPGSVWMER

DVYLQGPIWAKIPETGAHFHPSPAMGGFGLKHPPPMMLIKNTPVPGNITS

FSDVPVSSFITQYSTGQVTVEMEWELKKENSKRWNPEIQYTNNYNDPQFV

DFAPDSTGEYRTTRPIGTRYLTRPL

In other aspects, a variant AAV capsid protein is a chimera comprising (i) amino acids 1-61 of AAV2 (SEQ ID NO:2) or an amino acid sequence at least 90%, at least 95% or at least 98% identical thereto, (ii) amino acids 62-129 of AAV6 (SEQ ID NO:7) or an amino acid sequence at least 90%, at least 95% or at least 98% identical thereto, and (iii) amino acids 130-725 of AAV5 (SEQ ID NO:6) and further comprising V229I, A490T and A581T amino acid substitutions relative to the sequence of AAV5 (SEQ ID NO:6). In some embodiments, the variant AAV capsid has an amino acid sequence having at least about 85%, at least about 90%, at least about 95%, at least about 98% sequence identity to or is 100% identical to the following amino acid sequence:

(SEQ ID NO: 63)
MAADGYLPDWLEDTLSEGIRQWWKLKPGPPPPKPAERHKDDSRGLVLPGY

KYLGPFNGLDKGEPVNAADAAALEHDKAYDQQLKAGDNPYLRYNHADAEF

QERLQEDTSFGGNLGRAVFQAKKRVLEPFGLVEEGAKTAPTGKRIDDHFP

KRKKARTEEDSKPSTSSDAEAGPSGSQQLQIPAQPASSLGADTMSAGGGG

PLGDNNQGADGVGNASGDWHCDSTWMGDR<u>I</u>VTKSTRTWVLPSYNNHQYRE

IKSGSVDGSNANAYFGYSTPWGYFDFNRFHSHWSPRDWQRLINNYWGFRP

RSLRVKIFNIQVKEVTVQDSTTTIANNLTSTVQVFTDDDYQLPYVVGNGT

EGCLPAFPPQVFTLPQYGYATLNRDNTENPTERSSFFCLEYFPSKMLRTG

NNFEFTYNFEEVPFHSSFAPSQNLFKLANPLVDQYLYRFVSTNNTGGVQF

NKNLAGRYANTYKNWFPGPMGRTQGWNLGSGVNRASVSAF<u>T</u>TTNRMELEG

ASYQVPPQPNGMTNNLQGSNTYALENTMIFNSQPANPGTTATYLEGNMLI

TSESETQPVNRVAYNVGGMATNNQSSTTAP<u>TT</u>GTYNLQEIVPGSVWMERD

VYLQGPIWAKIPETGAHFHPSPAMGGFGLKHPPPMMLIKNTPVPGNITSF

SDVPVSSFITQYSTGQVTVEMEWELKKENSKRWNPEIQYTNNYNDPQFVD

FAPDSTGEYRTTRPIGTRYLTRPL

The AAV variants disclosed herein were generated through the use of in vivo directed evolution involving the use of primate cardiac and skeletal muscle screens following intravenous administration. In some embodiments, the variant capsid proteins disclosed herein, when present in an AAV virion, confer increased transduction of a muscle cell compared to the transduction of the muscle cell by an AAV virion comprising the corresponding parental AAV capsid protein or wild-type AAV. For example, in some embodiments, the variant capsid proteins disclosed herein, when present in an AAV virion, confer more efficient transduction of primate muscle cells than AAV virions comprising the corresponding parental AAV capsid protein or wild-type AAV capsid protein, e.g. the muscle cells take up more AAV virions comprising the subject variant AAV capsid protein than AAV virions comprising the parental AAV capsid protein or wild-type AAV. In some such embodiments, the AAV variant virion or variant rAAV exhibits at least 2-fold, at least 5-fold, at least 10-fold, at least 15-fold, at least 20-fold, at least 25-fold, at least 50-fold, or more than 50-fold, increased transduction of a muscle cell, compared to the transduction of the muscle cell by a wild-type AAV virion or rAAV comprising the corresponding parental AAV capsid protein. In preferred embodiments, the AAV variant virion or variant rAAV exhibits at least 2-fold, at least 5-fold, at least 10-fold, at least 15-fold, at least 20-fold, at least 25-fold, at least 50-fold, at least 100-fold, at least 1000-fold or more than 1000-fold, increased transduction of a muscle cell, compared to the transduction of the muscle cell by a wild-type AAV8 or AAV9 virion. In certain such embodiments, the variant capsid proteins disclosed herein, when present in an AAV virion, confer broader transduction of the primate muscle cells than AAV virions comprising the corresponding parental AAV capsid protein or wild type AAV capsid protein. In other words, the variant AAV virion transduces cell types not transduced by virions comprising the corresponding parental AAV capsid protein, and hence more types of cells in the muscle than the corresponding parental AAV virion. In some embodiments, the AAV variant virion preferentially transduces a muscle cell, e.g., a subject rAAV virion infects a muscle cell with 2-fold, 5-fold, 10-fold, 15-fold, 20-fold, 25-fold, 50-fold, or more than 50-fold, specificity than another muscle cell or a non-muscle cell. In some embodiments, the transduced muscle cell is a cardiac muscle cell (e.g. cardiomyocte, cardiac fibroblast, or a cardiac progenitor cell). In some embodiments, the muscle cell is a skeletal muscle cell (e.g. a myoblast, a myotube or a satellite cell). An increase in transduction of a muscle cell, e.g. increased efficiency of transduction, broader transduction, more preferential transduction, etc. may be readily assessed in vitro or in vivo by any number of methods in the art for measuring gene expression. For example, the AAV may be packaged with a genome comprising an expression cassette comprising a reporter gene, e.g. a fluorescent protein, under the control of a ubiquitous or tissue specific promoter, and the extent of transduction assessed by detecting the fluorescent protein by, e.g., fluorescence microscopy. As another example, the AAV may be packaged with a genome comprising a barcoded nucleic acid sequence, and the extent of transduction assessed by detecting the nucleic acid sequence by, e.g., PCR. As another example, the AAV may be packaged with a genome comprising an expression cassette comprising a therapeutic gene for the treatment of a muscle disease, and the extent of transduction assessed by detecting the treatment of the muscle disease in an afflicted patient that was administered the AAV.

Diseases that can be treated using a variant rAAV vector or virion and/or method disclosed herein include, but are not limited to, monogenic diseases, complex diseases, and traumatic injuries. Examples of monogenic diseases include, but are not limited to, muscular dystrophies such as Duchenne, Becker, congenital (including, but not limited to Bethlem myopathy, Ullrich muscular dystrophy, Fukuyama muscular dystrophy, Integrin-Deficient, merosin-deficient muscular dystrophy, and Walker-Warburgh syndrome), distal (including, but not limited to Gowers-Laing, Miyoshi, and Nonaka), Emery-Dreifuss, facioscapulohumeral, limb girdle, myotonic and muscular dystrophies; myotonia congenita and paramyotonia congenita; myotubular myopathy; centronuclear myopathy; myofibrillary myopathy, desmin related; anemia; Andersen-Tawil syndrome; Nemaline myopathy; Brody disease; lysosomal storage disorders such as alpha-mannosidosis, aspartylglucosaminuria, beta-mannosidosis, cystinosis, Farber disease, fucosidosis, Gaucher disease, galactosialidosis, gangliosidoses (including, but not limited to AB variant, activator deficiency, beta-galactosidase deficiency, Fabry disease, Sandhoff disease, and Schindler disease), glycogen storage disorders (including, but not limited to as Andersen disease, Cori disease, Danon disease, Forbes disease, glucose-6-phosphate defect, Hers disease, lactate dehydrogenase A deficiency, Pompe disease, Tarui disease, and von Gierke disease), infantile free sialic acid storage disease, lysosomal acid lipase deficiency, Krabbe disease, Metachromatic Leukodystrophy, mucopolysaccharidoses (including, but not limited to hyaluronidase deficiency, Hunter syndrome, Hurler syndrome, Hurler-Scheie syndrome, Maroteaux-Lamy syndrome, Morquio syndrome, Sanfilippo syndrome, Scheie syndrome, and Sly syndrome), mucolipidosis (including, but not limited to Sialidosis, I-cell disease, mucolipidin 1 deficiency, and Psuedy-Hurler Polydystrophy), multiple sulfase deficiency, Niemann-Pick disease, neuronal ceroid lipofuscinoses (including, but not limited to Batten-Spielmeyer-Vogt disease, congenital Cathepsin D deficiency, German/Serbian Late Infantile, Jansky-Bielschowsky disease, Kufs disease, late infantile, late infantile variant, Northern Epilepsy, Santavuori-Haltia disease, and Turkish Late Infantile), pyknodysostosis, Salla disease, Saposin B deficiency, Tay-Sach's disease and Wolman disease; metabolic disorders such as adenosine monophosphate deaminase deficiency, alkaptonuria, carnitine deficiency, carnitine palmityl transferase deficiency, Hartnup disorder, homocystinuria, maple syrup urine disease, myophosphorylase deficiency, phosphofuctokinase deficiency, phosphoglycerate kinase deficiency, phosphoglycerate mutase deficiency, phosphorylase deficiency, and Tangier disease; Friedreich's ataxia; ataxia talengiectasia; ataxia with vitamin E deficiency; periodic paralysis, such as Gamstorp disease and hypokalemic periodic paralysis; mitochondrial diseases such as Barth syndrome, Kearns-Sayre syndrome, mitochondrial myopathy, mitochondrial encephalopathy lactic acidosis and stroke-like episodes, myoclonic epilepsy with ragged-red fibers, and Pearson syndrome; familial hypertrophic cardiomyopathies; dilated cardiomyopathies; familial congenital heart diseases, such as familial aortic valve disease and non-compaction of the left ventricle with congenital heart defects; familial arrhythmias, such as Anderson cardiodysrhythmic periodic paralysis, atrial septai defects with AV conduction defects, Brugada syndrome, cardiac conductance defect, catecholaminergic polymorphic ventricular tachycardia, and congenital heart block; familial vascular disorders, such as arterial tortuosity syndrome, cerebral autosomal dominant arteriopathy with sobcortical infacts and leukoenceophalopathy, cerebral recessive dominant arteriopathy with sobcortical infacts and leukoenceophalopathy, familial type aortic aneurysm, Marfan syndrome, Ehlers-Danlos syndrome, Beals congenital contractual arachnodactyly, Loeys-Dietz syndrome, and pseudoxanthoma elasticum; arrhythmogenic right ventricular cardiomyopathy; familial arrhythmogenic right ventricular dysplasia; Naxos disease; left ventricular non-compaction; familial atrial fibrillation; familial ventricular tachycardia; familial Wolff-Parkinson-White syndrome; long QT syndromes; short QT syndrome; sick sinus syndromes; lipoprotein diseases, such as abetalipoproteinemia and lipoprotein lipase deficiency; alpha-1 antitrypsin deficiency; coagulation factor VIII deficiency (hemophilia A) or coagulation factor IX deficiency (hemophilia B); thalassemia; fibrodysplasia ossificans progressive;

laminopathies; Huntington disease; congenital myasthenic syndromes; lutchinson-Gilford Progeria syndrome; Noonan syndrome; congenital fibre type disproportion myopathy; congenital fibrosis of the extraocular muscles; minicore myopathy; rippling muscle disease; Schwartz-Jampel syndrome; tubular aggregate myopathy; and zebra body myopathy Examples of complex diseases include, but are not limited to, heart/cardiovascular disease (e.g. congestive heart failure, myocardial infarction, angina, coronary artery disease, ischaemic heart disease, cardiomyopathy); cancer; diabetes; and infection. Examples of traumatic injuries include, but are not limited to, viral infection of the muscle, muscle laceration; and muscle contusion. In preferred embodiments, a variant rAAV vector or virion and/or method disclosed herein is used to treat Fabry disease, Friedreich's ataxia, Duchenne muscular dystrophy, Becker muscular dystrophy, Pompe disease, myophosphorylase deficiency, facioscapulohumeral muscular dystrophy, limb girdle muscular dystrophy, or myotonic dystrophy.

In another embodiment, a variant capsid disclosed herein comprises a heterologous nucleic acid comprising a nucleotide sequence encoding a gene product such as, without limitation, an interfering RNA, a long non-coding RNA, a short non-coding RNA, an antisense RNA, an aptamer, a polypeptide, a secreted antibody, a single chain antibody, a $V_{HH}$ domain, a soluble receptor, an affibody, a knottin, a DARPin, a centurin, a chaperone, a site-specific nuclease that provides for site-specific knock-down of gene function or a modified site-specific nuclease that provides for gene-specific activation of transcription.

A rAAV variant virion disclosed herein comprises a heterologous nucleic acid comprising a nucleotide sequence encoding a gene product. In some embodiments, the gene product is an antisense RNA, a microRNA (miRNA), a short hairpin RNA (shRNA) or a small interfering RNA (siRNA) or a precursor or mimic thereof. In some embodiments, the gene product is a long non-coding RNA. In some embodiments, the gene product is a short non-coding RNA. In some embodiments, the gene product is an antisense RNA. In some embodiments, the gene product is an aptamer. In some embodiments, the gene product is a polypeptide. In some embodiments, the gene product is a secreted antibody. In some embodiments, the gene product is a single chain antibody. In some embodiments, the gene product is a $V_{HH}$ domain. In some embodiments, the gene product is a soluble receptor. In some embodiments, the gene product is an affibody. In some embodiments, the gene product is a knottin. In some embodiments, the gene product is a DARPin. In some embodiments, the gene product is a centurin. In some embodiments, the gene product is a chaperone. In some embodiments, the gene product is a site-specific nuclease that provide for site-specific knock-down of gene function.

The uses of the gene product include, but are not limited to, enhancing the level of a factor in a cell, enhancing the level of a factor in a neighboring or distant cell through secretion of a factor, decreasing the level of a factor in a cell, or decreasing the level of a factor in a neighboring or distant cell through secretion of a factor. The gene product can be designed to supplement the level of a defective of missing gene product, decrease the level of a defective of missing gene product, introduce a new supporting gene product, supplement the level of a supporting gene product, decrease the level of a hindering gene product, or both decrease the level of a hindering gene product and introduce or supplement the level of a supporting gene product.

Gene products delivered by the subject AAV variants can be used to alter the level of gene products or gene product activity directly or indirectly linked to muscle diseases and trauma. Skeletal, cardiac or smooth muscle transduced with subject AAV variants can also be used as a biofactory to produce and secrete therapeutic proteins for the treatment of diseases in trans in distant organs. Genes whose gene products are directly or indirectly linked to genetic diseases include, e.g., genes encoding any of the following gene products: dystrophin including mini- and micro-dystrophins (DMD; e.g. GenBank Accession Number NP_003997.1; SEQ ID NO:64); titin (TTN); titin cap (TCAP) α-sarcoglycan (SGCA), β-sarcoglycan (SGCB), γ-sarcoglycan (SGCG) or δ-sarcoglycan (SGCD); alpha-1-antitrypsin (A1-AT); myosin heavy chain 6 (MYH6); myosin heavy chain 7 (MYH7); myosin heavy chain 11 (MYH11); myosin light chain 2 (ML2); myosin light chain 3 (ML3); myosin light chain kinase 2 (MYLK2); myosin binding protein C (MYBPC3); desmin (DES); dynamin 2 (DNM2); laminin α2 (LAMA2); lamin A/C (LMNA); lamin B (LMNB); lamin B receptor (LBR); dysferlin (DYSF); emerin (EMD); insulin; blood clotting factors, including but not limited to, factor VIII and factor IX; erythropoietin (EPO); lipoprotein lipase (LPL); sarcoplasmic reticulum $Ca^{2+}$-ATPase (SERCA2A), S100 calcium binding protein A1 (S100A1); myotubularin (MTM); DM1 protein kinase (DMPK; e.g. GenBank Accession Number NG_009784.1; SEQ ID NO:65); glycogen phosphorylase L (PYGL); glycogen phosphorylase, muscle associated (PYGM; e.g. GenBank Accession Number NP_005600.1; SEQ ID NO:66); glycogen synthase 1 (GYS1); glycogen synthase 2 (GYS2); α-galactosidase A (GLA; e.g. GenBank Accession Number NP_000160.1; SEQ ID NO:67); α-N-acetylgalactosaminidase (NAGA); acid α-glucosidase (GAA; e.g. GenBank Accession Number NP_000143.2; SEQ ID NO:68), sphingomyelinase phosphodiesterase 1 (SMPD1); lysosomal acid lipase (LIPA); collagen type I α1 chain (COL1A1); collagen type I α2 chain (COL1A2); collagen type III α1 chain (COL3A1); collagen type V α1 chain (COL5A1); collagen type V α2 chain (COL5A2); collagen type VI α1 chain (COL6A1); collagen type VI α2 chain (COL6A2); collagen type VI α3 chain (COL6A3); procollagen-lysine 2-oxoglutarate 5-dioxygenase (PLODI); lysosomal acid lipase (LIPA); frataxin (FXN; e.g. GenBank Accession Number NP_000135.2; SEQ ID NO:69); myostatin (MSTN); β-N-acetyl hexosaminidase A (HEXA); β-N-acetylhexosaminidase B (HEXB); β-glucocerebrosidase (GBA); adenosine monophosphate deaminase 1 (AMPD1); β-globin (HBB); iduronidase (IDUA); iduronate 2-sulfate (IDS); troponin 1 (TNNI3); troponin T2 (TNNT2); troponin C (TNNC1); tropomyosin 1 (TPM1); tropomyosin 3 (TPM3); N-acetyl-α-glucosaminidase (NAGLU); N-sulfoglucosamine sulfohydrolase (SGSH); heparan-α-glucosaminide N-acetyltransferase (HGSNAT); integrin α 7 (IGTA7); integrin α 9 (IGTA9); glucosamine (N-acetyl)-6-sulfatase (GNS); galactosamine (N-acetyl)-6-sulfatase (GALNS); β-galactosidase (GLBI); β-glucuronidase (GUSB); hyaluronoglucosaminidase 1 (HYAL1); acid ceramidase (ASAHI); galactosylcermidase (GALC); cathepsin A (CTSA); cathepsin D (CTSA); cathepsin K (CTSK); GM2 ganglioside activator (GM2A); arylsulfatase A (ARSA); arylsulfatase B (ARSB); formylglycine-generating enzyme (SUMF1); neuraminidase 1 (NEU1); N-acetylglucosamine-1-phosphate transferase α (GNPTA); N-acetylglucosamine-1-phosphate transferase β (GNPTB); N-acetylglucosamine-1-phosphate transferase γ (GNPTG); mucolipin-1 (MCOLNI); NPC intracellular transporter 1 (NPC1); NPC intracellular transporter 2

(NPC2); ceroid lipofuscinosis 5 (CLN5); ceroid lipofuscinosis 6 (CLN6); ceroid lipofuscinosis 8 (CLN8); palmitoyl protein thioesterase 1 (PPTI); tripeptidyl peptidase 1 (TPP1); battenin (CLN3); DNAJ heat shock protein family 40 member C5 (DNAJC5); major facilitator superfamily domain containing 8 (MFSD8); mannosidase α class 2B member 1 (MAN2B1); mannosidase β (MANBA); aspartylglucosaminidase (AGA); α-L-fucosidase (FUCAI); cystinosin, lysosomal cysteine transporter (CTNS); sialin; solute carrier family 2 member 10 (SLC2A10); solute carrier family 17 member 5 (SLC17A5); solute carrier family 6 member 19 (SLC6A19); solute carrier family 22 member 5 (SLC22A5); solute carrier family 37 member 4 (SLC37A4); lysosomal associated membrane protein 2 (LAMP2); sodium voltage-gated channel a subunit 4 (SCN4A); sodium voltage-gated channel § subunit 4 (SCN4B); sodium voltage-gated channel a subunit 5 (SCN5A); sodium voltage-gated channel a subunit 4 (SCN4A); calcium voltage-gated channel subunit α1c (CACNA1C); calcium voltage-gated channel subunit α1s (CACNA1S); phosphoglycerate kinase 1 (PGK1); phosphoglycerate mutase 2 (PGAM2); amylo-α-1,6-glucosidase, 4-α-glucanotransferase (AGL); potassium voltage-gated channel ISK-related subfamily member 1 (KCNE1); potassium voltage-gated channel ISK-related subfamily member 2 (KCNE2); potassium voltage-gated channel subfamily J member 2 (KCNJ2); potassium voltage-gated channel subfamily J member 5 (KCNJ5); potassium voltage-gated channel subfamily H member 2 (KCNH2); potassium voltage-gated channel KQT-like subfamily member 1 (KCNQ1); hyperpolarization-activated cyclic nucleotide-gated potassium channel 4 (HCN4); chloride voltage-gated channel 1 (CLCN1); carnitine palmitoyltransferase 1A (CPT1A); ryanodine receptor 1 (RYR1); ryanodine receptor 2 (RYR2); bridging integrator 1 (BIN1); LARGE xylosyl- and glucuronyltransferase 1 (LARGE1); docking protein 7 (DOK7); fukutin (FKTN); fukutin related protein (FKRP); selenoprotein N (SELENON); protein O-mannosyltransferase 1 (POMT1); protein O-mannosyltransferase 2 (POMT2); protein O-linked mannose N-acetylglucosaminyltransferase 1 (POMGNT1); protein O-linked mannose N-acetylglucosaminyltransferase 2 (POMGNT2); protein-O-mannose kinase (POMK); isoprenoid synthase domain containing (ISPD); plectin (PLEC); cholinergic receptor nicotinic epsilon subunit (CHRNE); choline O-acetyltransferase (CHAT); choline kinase p (CHKB); collagen like tail subunit of asymmetric acetylcholindsterase (COLQ); receptor associated protein of the synapse (RAPSN); four and a half LIM domains 1 (FHLI); β-1,4-glucuronyltransferase 1 (B4GAT1); β-1,3-N-acetylgalactosaminyltransferase 2 (B3GALNT2); dystroglycan 1 (DAG1); transmembrane protein 5 (TMEM5); transmembrane protein 43 (TMEM43); SECIS binding protein 2 (SECISBP2); glucosamine (UDP-N-acetyl)-2-epimerase/N-acetylmannosamine kinase (GNE); anoctamin 5 (ANO5); structural maintenance of chromosomes flexible hinge domain containing 1 (SMCHD1); lactate dehydrogenase A (LDHA); lactate dehydrogenase B (LHDB); calpain 3 (CAPN3); caveolin 3 (CAV3); tripartite motif containing 32 (TRIM32); CCHC-type zinc finger nucleic acid binding protein (CNBP); nebulin (NEB); actin, α1, skeletal muscle (ACTA1); actin, α1, cardiac muscle (ACTC1); actinin α2 (ACTN2); poly(A)-binding protein nuclear 1 (PABPN1); LEM domain-containing protein 3 (LEMD3); zinc metalloproteinase STE24 (ZMPSTE24); microsomal triglyceride transfer protein (MTTP); cholinergic receptor nicotinic α1 subunit (CHRNA1); cholinergic receptor nicotinic α2 subunit (CHRNA2); cholinergic receptor nicotinic α3 subunit (CHRNA3); cholinergic receptor nicotinic α4 subunit (CHRNA4); cholinergic receptor nicotinic α5 subunit (CHRNA5); cholinergic receptor nicotinic α6 subunit (CHRNA6); cholinergic receptor nicotinic α7 subunit (CHRNA7); cholinergic receptor nicotinic α8 subunit (CHRNA8); cholinergic receptor nicotinic α9 subunit (CHRNA9); cholinergic receptor nicotinic α10 subunit (CHRNAIO); cholinergic receptor nicotinic β1 subunit (CHRNB1); cholinergic receptor nicotinic β2 subunit (CHRNB2); cholinergic receptor nicotinic β3 subunit (CHRNB3); cholinergic receptor nicotinic β4 subunit (CHRNB4); cholinergic receptor nicotinic γ subunit (CHRNG1); cholinergic receptor nicotinic ∂ subunit (CHRND); cholinergic receptor nicotinic ε subunit (CHRNE1); ATP binding cassette subfamily A member 1 (ABCA1); ATP binding cassette subfamily C member 6 (ABCC6); ATP binding cassette subfamily C member 9 (ABCC9); ATP binding cassette subfamily D member 1 (ABCD1); ATPase sarcoplasmic/endoplasmic reticulum Ca2+ transporting 1 (ATP2A1); ATM serine/threonine kinase (ATM); a tocopherol transferase protein (TTPA); kinesin family member 21A (KIF21A); paired-like homeobox 2a (PHOX2A); heparan sulfate proteoglycan 2 (HSPG2); stromal interaction molecule 1 (STIM1); notch 1 (NOTCH1); notch 3 (NOTCH3); dystrobrevin a (DTNA); protein kinase AMP-activated, noncatalytic γ2 (PRKAG2); cysteine- and glycine-rich protein 3 (CSRP3); viniculin (VCL); myozenin 2 (MyoZ2); myopalladin (MYPN); junctophilin 2 (JPH2); phospholamban (PLN); calreticulin 3 (CALR3); nexilin F-actin-binding protein (NEXN); LIM domain binding 3 (LDB3); eyes absent 4 (EYA4); huntingtin (HTT); androgen receptor (AR); protein tyrosine phosphate non-receptor type 11 (PTPN11); junction plakoglobin (JUP); desmoplakin (DSP); plakophilin 2 (PKP2); desmoglein 2 (DSG2); desmocollin 2 (DSC2); catenin α3 (CTNNA3); NK2 homeobox 5 (NKX2-5); A-kinase anchor protein 9 (AKAP9); A-kinase anchor protein 10 (AKAP10); guanine nucleotide-binding protein α-inhibiting activity polypeptide 2 (GNAI2); ankyrin 2 (ANK2); syntrophin α-1 (SNTA1); calmodulin 1 (CALM1); calmodulin 2 (CALM2); HTRA serine peptidase 1 (HTRA1); fibrillin 1 (FBN1); fibrillin 2 (FBN2); xylosyltransferase 1 (XYLT1); xylosyltransferase 2 (XYLT2); tafazzin (TAZ); homogentisate 1,2-dioxygenase (HGD); glucose-6-phosphatase catalytic subunit (G6PC); 1,4-alpha-glucan enzyme 1 (GBE1); phosphofructokinase, muscle (PFKM); phosphorylase kinase regulatory subunit alpha 1 (PHKA1); phosphorylase kinase regulatory subunit alpha 2 (PHKA2); phosphorylase kinase regulatory subunit beta (PHKB); phosphorylase kinase catalytic subunit gamma 2 (PHKG2); phosphoglycerate mutase 2 (PGAM2); cystathionine-beta-synthase (CBS); methylenetetrahydrofolate reductase (MTHFR); 5-methyltetrahydrofolate-homocysteine methyltransferase (MTR); 5-methyltetrahydrofolate-homocysteine methyltransferase reductase (MTRR); methylmalonic aciduria and homocystinuria, cbID type (MMADHC); mitochondrial DNA, including, but not limited to mitochondrially encoded NADH:ubiquinone oxidoreductase core subunit 1 (MT-ND1); mitochondrially encoded NADH:ubiquinone oxidoreductase core subunit 5 (MT-ND5); mitochondrially encoded tRNA glutamic acid (MT-TE); mitochondrially encoded tRNA histadine (MT-TH); mitochondrially encoded tRNA leucine 1 (MT-TL1); mitochondrially encoded tRNA lysine (MT-TK); mitochondrially encoded tRNA serine 1 (MT-TS1); mitochondrially encoded tRNA valine (MT-TV); mitogen-activated protein kinase 1 (MAP2K1); B-Raf proto-oncogene, serine/threonine kinase (BRAF); raf-1 proto-oncogene, serine/threonine kinase (RAF1); growth factors, including, but not limited to insulin growth factor 1 (IGF-1); transforming growth factor β3 (TGFβ3); transforming growth factor β receptor, type I (TGFβR1); transforming growth factor β receptor, type II (TGFβR2), fibroblast growth factor 2 (FGF2), fibroblast growth factor 4 (FGF4), vascular endothelial growth factor A (VEGF-A), vascular endothelial growth factor B (VEGF-B); vascular endothelial growth factor C (VEGF-C), vascular endothelial growth factor D (VEGF-D), vascular endothelial growth factor receptor 1 (VEGFR1), and vascular endothelial growth factor receptor 2 (VEGFR2); interleukins; immunoadhesins; cytokines; and antibodies.

In preferred embodiments, gene products delivered by the subject AAV variants are selected from alpha galactosidase A (GLA), Frataxin (FXN), Dystrophin (DMD), Acid alpha glucosidase (GAA), and Glycogen phosphorylase, muscle (PYGM). In some preferred embodiments, a subject AAV variant comprises a nucleic acid segment comprising a nucleotide sequence encoding (i) a GLA polypeptide comprising or consisting of the amino acid sequence set forth as SEQ ID NO:67, (ii) an FXN polypeptide comprising or consisting of the amino acid sequence set forth as SEQ ID NO:69, (iii) a DMD polypeptide comprising or consisting of a functional fragment (e.g. mini or micro dystrophin, preferably comprising an intact actin-binding domain, at least 4 of the 24 spectrin-like repeats and the dystroglycan-binding domain) of the amino acid sequence set forth as SEQ ID NO:64, (iv) a GAA polypeptide comprising or consisting of the amino acid sequence set forth as SEQ ID NO:68, (v) a PYGM polypeptide comprising or consisting of the amino acid sequence set forth as SEQ ID NO:66, (vi) or (v) an amino acid sequence at least 80%, at least 85%, at least 90% or at least 95% identical to any one of SEQ ID NOs:64 and 66-69.

In another preferred embodiment, a subject AAV variant comprises a transgene encoding an interfering RNA, e.g. an antisense RNA, an miRNA, an shRNA, or an siRNA, that decreases the expression of DMPK. In some aspects, the interfering RNA decreases the expression of DMPK encoded by a nucleic acid having a nucleotide sequence as set forth as SEQ ID NO:65 or a sequence at least 80%, at least 85%, at least 90%, or at least 95% identical to SEQ ID NO:65.

Genes whose gene products induce or promote apoptosis are referred to herein as "pro-apoptotic genes" and the products of those genes (mRNA; protein) are referred to as "pro-apoptotic gene products." Pro-apoptotic targets include, e.g., Bax gene products; Bid gene products; Bak gene products; Bad gene products; Bcl-2; Bcl-X1. Anti-apoptotic gene products include X-linked inhibitor of apoptosis.

Genes whose gene products induce or promote angiogenesis are referred to herein as "pro-angiogenic genes" and the products of those genes (mRNA; protein) are referred to as "pro-angiogenic gene products." Pro-angiogenic targets include. e.g., vascular endothelial growth factor (VEGFa, VEGFb, VEGFc, VEGFd); vascular endothelial growth factor receptor 1 (VEGFR1); vascular endothelial growth factor receptor 2 (VEGFR2); Fms-Related Tyrosine Kinase 1 (Flt1); placenta growth factor (PGF); Platelet-derived growth factor (PDGF); angiopoietins; sonic hedgehog. Genes whose gene products inhibit angiogenesis are referred to herein as "anti-angiogenic genes" and the products of those genes (mRNA; protein) are referred to as "anti-angiogenic gene products." Anti-angiogenic gene products include endostatin; tumstatin; angiostatin; pigment epithelium-derived factor (PEDF), and fusion proteins or antibodies that are specific for pro-angiogenic targets and/or their receptors, e.g. the VEGF-specific antibody Avastin™, etc.

Genes whose gene products function as immune modulators, e.g., complement factors, toll-like receptors, are called "immunomodulatory genes". Exemplary immunomodulatory genes include cytokines, chemokines, and the fusion proteins or antibodies that are specific for them and/or their receptors, e.g. the anti-IL-6 fusion protein Rilonacept™, the Complement Factor H-specific antibody lampamizumab, etc. Genes whose gene products function as muscle protective factors, e.g., insulin growth factor 1 (IGF-1); transforming growth factor β (TGFβ); fibroblast growth factor (FGF).

In some cases, a gene product of interest is a site-specific endonuclease that provide for site-specific knock-down of gene function, e.g., where the endonuclease knocks out an allele associated with a muscle disease. For example, where a dominant allele encodes a defective copy of a gene that, when wild-type, is a muscle structural protein and/or provides for normal muscle function, a site-specific endonuclease can be targeted to the defective allele and knock out the defective allele.

In addition to knocking out a defective allele, a site-specific nuclease can also be used to stimulate homologous recombination with a donor DNA that encodes a functional copy of the protein encoded by the defective allele. Thus, e.g., a subject rAAV virion can be used to deliver both a site-specific endonuclease that knocks out a defective allele, and can be used to deliver a functional copy of the defective allele, resulting in repair of the defective allele, thereby providing for production of a functional muscle protein (e.g., functional lamin A/C, functional fibrillin, functional collagen type VI, etc.). In some embodiments, a rAAV virion disclosed herein comprises a heterologous nucleotide sequence that encodes a site-specific endonuclease: and a heterologous nucleotide sequence that encodes a functional copy of a defective allele, where the functional copy encodes a functional muscle protein. Functional muscle proteins include, e.g., lamin A/C, fibrillin 1, COL6A1, COL6A2, COL6A3, and the like.

Site-specific endonucleases that are suitable for use include, e.g., meganucleases; zinc finger nucleases (ZFNs); transcription activator-like effector nucleases (TALENs); and Clustered regularly interspaced short palindromic repeats/CRISPR-associated (Cas), where such site-specific endonucleases are non-naturally occurring and are modified to target a specific gene. Such site-specific nucleases can be engineered to cut specific locations within a genome, and non-homologous end joining can then repair the break while inserting or deleting several nucleotides. Such site-specific endonucleases (also referred to as "INDELs") then throw the protein out of frame and effectively knock out the gene. See, e.g., U.S. Patent Publication No. 2011/0301073.

In some embodiments of the variant rAAV vector disclosed herein, a nucleotide sequence encoding a gene product of interest is operably linked to a constitutive promoter. Suitable constitutive promoters include e.g. cytomegalovirus promoter (CMV) (Stinski et al. (1985) *Journal of Virology* 55(2): 431-441), CMV early enhancer/chicken β-actin (CBA) promoter/rabbit β-globin intron (CAG) (Miyazaki et al. (1989) *Gene* 79(2): 269-277, CB$^{SB}$ (Jacobson et al. (2006) *Molecular Therapy* 13(6): 1074-1084), human elongation factor 1α promoter (EF1α) (Kim et al. (1990) *Gene* 91(2): 217-223), human phosphoglycerate kinase promoter (PGK) (Singer-Sam et al. (1984) *Gene* 32(3): 409-417, mitochondrial heavy-strand promoter (Loderio et al. (2012)

*PNAS* 109(17): 6513-6518), ubiquitin promoter (Wulff et al. (1990) *FEBS Letters* 261: 101-105). In other embodiments, a nucleotide sequence encoding a gene product of interest is operably linked to an inducible promoter. In some instances, a nucleotide sequence encoding a gene product of interest is operably linked to a tissue-specific or cell type-specific regulatory element. For example, in some instances, a nucleotide sequence encoding a gene product of interest is operably linked to a muscle-specific regulatory element (e.g., a cardiac specific promoter or a skeletal muscle specific promoter), e.g., a regulatory element that confers selective expression of the operably linked gene in a muscle cell. Suitable muscle-specific regulatory elements include, e.g., skeletal muscle α-actin promoter (Muscat and Kedes (1987) *Mol. Cell. Biol.* 7:4089-4099); cardiac muscle α-actin promoter (Minty and Kedes (1986) *Mol. Cell. Biol.* 6:2125-2136); smooth muscle α-actin promoter (Nakano et al. (1991) *Gene* 99:285-289); vascular smooth muscle α-actin promoter (Keogh et al. (1999) *Gene Therapy* 6(4):616-628); muscle creatine kinase promoter (Bartlett et al. (1996) *Cell Transplantation* 5(3):411-419); myosin light chain 1 and myosin light chain 3 promoters (Seidel and Arnold (1989) *J. Biol. Chem.* 264(27):16109-16117); myosin light chain 2v (MLC2v) promoter (Su et al. (2004) *PNAS* 101 (46):16280-16285); myogenic factor 5 (Myf5) promoter (Fujimaki et al. (2004) *Journal of Biological Chemistry* 289(11):7399-7412); myogenic differentiation 1 (Myod1) promoter (Zingg et al. (1994) *Nucleic Acids Research* 22(12):2234-2241); myogenin (Myog) promoter (Salminen et al. (1991) *Journal of Cell Biology* 115(4):905-917); paired box gene 7 (Pax7) promoter (Murmann et al. (2000) *Biol Chem.* 381(4):331-335); paired like homeodomain 3 (Pitx3) promoter (Coulon et al. (2007) *Journal of Biological Chemistry* 282:33192-33200); MHCK7 promoter (Salva et al. (2007) *Mol. Ther.* 15(2):320-329); MCK/SV40 promoter (Takeshita et al. (2007) *International Journal of Molecular Medicine* 19:309-315); C5-12 promoter (Li et al. (1999) *Nature Biotechnology* 17:241-245); double and triple tandem MCK enhancer/promoters (Wang et al. (2008) *Gene Therapy* 15:1489-1499); myosin heavy chain 7 (MYH7) promoter; (Iwaki et al. (2104) *PLoS ONE* 9(4):e88610); myosin heavy chain 6 (MYH6) promoter (Pacak et al. (2008) *Genet. Vaccines Ther.* 6:13); cardiac troponin T (TNNT2) promoter (Farza et al. (1998) *J. Mol. Cell Cardiol.* 30(6):1247-53); α-tropomyosin promoter (Helfman et al. (1986) *Molecular and Cellular Biology* 6(11):3582-3595); cardiac troponin C (TNNC1) promoter (Scheier et al. (1990) *Journal of Biological Chemistry* 34(5):21247-21253); cardiac myosin-binding protein C promoter (Lin et al. (2013) *PLoS ONE* 8(7): e69671); cardiac troponin I (TNNI3) promoter (Bhavsar et al. (1996) *Genomics* 35(1):11-23); the desmin promoter (Li et al. (1991) *Journal of Biological Chemistry* 10(5):6562-6570); sodium-calcium exchanger (NCX1) promoter (Scheller et al. (1997) *Journal of Biological Chemistry* 273(13):7643-7649); atrial natriuretic factor promoter (Durocher et al. (1996) *Molecular and Cellular Biology* 16(9):4648-4655); and SM22α promoter (Kemp et al. (1995) *Biochemical Journal* 310(3):1037-1043.

For the purposes of the invention, the disclosure herein provides an isolated nucleic acid comprising a nucleotide sequence that encodes a variant AAV capsid protein as described above. An isolated nucleic acid can be an AAV vector, e.g., a recombinant AAV vector.

The disclosure herein also provides a method of treating a muscle disease, the method comprising administering to an individual in need thereof an effective amount of a rAAV variant virion comprising a transgene of interest as described above and disclosed herein. One of ordinary skill in the art would be readily able to determine an effective amount of the subject rAAV virion and that the disease had been treated by testing for a change in one or more functional or anatomical parameters, e.g. muscle biopsy followed by immunohistochemistry, serum sampling followed by ELISA or enzyme activity assays, walk test, peak maximum oxygen consumption, biomarker analysis left ventricular ejection fraction, left ventricular end-systolic volume, hand-held dynamometry, maximum weight lit, Timed Function Tests, the Hammersmith Motor Ability Score, timed rise from floor, or 9 Hole Peg Test.

Nonlimiting methods for assessing muscle function and changes thereof include assessing walk test, peak maximum oxygen consumption, biomarker analysis, left ventricular ejection fraction, left ventricular end-systolic volume, Vignos Scale, Timed Function Tests, the Hammersmith Motor Ability Score, timed rise from floor, Motor Function Measure Scale, North Star Ambulatory Assessment, 9 Hole Peg Test, or Children's Hospital of Philadelphia Infant Test of Neuromuscular Disorders.

In some embodiments, an effective amount of the subject rAAV virion results in a decrease in the rate of loss of muscle function, anatomical muscle integrity, or muscle mass, e.g. a 2-fold, 3-fold, 4-fold, or 5-fold or more decrease in the rate of loss and hence progression of disease, for example, a 10-fold decrease or more in the rate of loss and hence progression of disease. In some embodiments, the effective amount of the subject rAAV virion results in a gain in muscle function, gain in muscle strength, gain in muscle mass, and/or an improvement in anatomical muscle integrity or biomarkers, e.g. a 2-fold, 3-fold, 4-fold or 5-fold improvement or more in muscle function, muscle strength, muscle mass, and/or improvement in anatomical muscle integrity or biomarkers, e.g. a 10-fold improvement or more in muscle function, muscle strength, muscle mass and/or improvement in anatomical muscle integrity or biomarkers. As will be readily appreciated by the ordinarily skilled artisan, the dose required to achieve the desired treatment effect will typically be in the range of $1\times10^8$ to about $1\times10^{16}$ recombinant virions, typically referred to by the ordinarily skilled artisan as $1\times10^8$ to about $1\times10^{16}$ "vector genomes" and preferably will be in the range of about $1\times10^{11}$ to about $1\times10^{15}$ recombinant virions.

A subject rAAV virion can be delivered to skeletal muscle by intravascular (intravenous or intra-arterial) administration, intraperitoenal administration, limb perfusion and/or direct intramuscular injection or by any other convenient mode or route of administration that will result in the delivery of the rAAV virion to skeletal muscle. The rAAV virion can be delivered to cardiac muscle by intravascular (intravenous or intra-arterial) administration, direct cardiac injection (into the left atrium, right atrium, right ventricle and/or septum), antegrade or retrograde infusion into the coronary artery (via the left anterior descending or left circumflex coronary arteries), recirculation, intrapericardial injection, transendocardial injection, or by any other convenient mode or route of administration that will result in the delivery of the rAAV virion to cardiac muscle. In a preferred embodiment, a subject rAAV virion is delivered to skeletal and/or cardiac muscle by systemic intravenous administration. When administered via intravenous injection, the subject rAAV virion is able to move through the circulatory system and transduce muscle cells more efficiently, compared to the capability of a wild type AAV virion or an AAV virion comprising the corresponding parental AAV capsid protein.

A variant capsid protein disclosed herein is isolated, e.g., purified. In some embodiments, a variant capsid protein disclosed herein is included in an AAV vector or a recombinant AAV (rAAV) virion. In other embodiments, such AAV variant vectors and/or AAV variant virions are used in an in vivo or ex vivo method of treating a muscle disease in primate cardiac or skeletal muscle.

The disclosure herein further provides host cells such as, without limitation, isolated (genetically modified) host cells comprising a subject nucleic acid. A host cell according to the invention disclosed herein, can be an isolated cell, such as a cell from an in vitro cell culture. Such a host cell is useful for producing a subject rAAV variant virion, as described herein. In one embodiment, such a host cell is stably genetically modified with a nucleic acid. In other embodiments, a host cell is transiently genetically modified with a nucleic acid. Such a nucleic acid is introduced stably or transiently into a host cell, using established techniques, including, but not limited to, electroporation, calcium phosphate precipitation, liposome-mediated transfection, and the like. For stable transformation, a nucleic acid will generally further include a selectable marker, e.g., any of several well-known selectable markers such as neomycin resistance, and the like. Such a host cell is generated by introducing a nucleic acid into any of a variety of cells, e.g., mammalian cells, including, e.g., murine cells, and primate cells (e.g., human cells). Exemplary mammalian cells include, but are not limited to, primary cells and cell lines, where exemplary cell lines include, but are not limited to, HEK293 cells, HEK293T cells, COS cells, HeLa cells, Vero cells, 3T3 mouse fibroblasts, C3H10T1/2 fibroblasts, CHO cells, and the like. Exemplary host cells include, without limitation, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK293) cells (ATCC No. CRL1573), HLHepG2 cells, and the like. A host cell can also be made using a baculovirus to infect insect cells such as Sf9 cells, which produce AAV (see, e.g., U.S. Pat. No. 7,271, 002; U.S. patent application Ser. No. 12/297,958). In some embodiments, a genetically modified host cell includes, in addition to a nucleic acid comprising a nucleotide sequence encoding a variant AAV capsid protein, as described above, a nucleic acid that comprises a nucleotide sequence encoding one or more AAV rep proteins. In other embodiments, a host cell further comprises an rAAV variant vector. An rAAV variant virion can be generated using such host cells. Methods of generating an rAAV virion are described in, e.g., U.S. Patent Publication No. 2005/0053922 and U.S. Patent Publication No. 2009/0202490.

The disclosure herein additionally provides a pharmaceutical composition comprising: a) the rAAV variant virion, as described above and disclosed herein; and b) a pharmaceutically acceptable carrier, diluent, excipient, or buffer. In some embodiments, the pharmaceutically acceptable carrier, diluent, excipient, or buffer is suitable for use in a human or non-human patient. Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, surfactants, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., 3 ed. Amer. Pharmaceutical Assoc. In some aspects of the present invention, the present invention provides a pharmaceutical composition comprising about $1 \times 10^8$ to about $1 \times 10^{16}$ recombinant viruses or $1 \times 10^8$ to about $1 \times 10^{16}$ vector genomes, wherein each said recombinant virus comprises a genome encoding one or more gene products.

Some embodiments of the invention are exemplified in the following items 1 to 54:

1. A variant adeno-associated virus (AAV) capsid protein comprising a peptide insertion in the GH-loop of the capsid protein, wherein the insertion is in AAV2 or a corresponding position in a capsid portion of a wild-type AAV serotype other than AAV2 or an AAV variant, and wherein the peptide insertion is selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:2I1), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42).

2. The variant AAV of item 1, wherein the capsid protein comprises one or more point mutations relative to AAV2 or one or more corresponding point mutations relative to other wild-type AAV serotypes or AAV variants.

3. The variant AAV of item 2, wherein the one or more point mutations is selected from the group consisting of A35P, S109T, P195L, D213N, G222S, V229I, N312K, A319T, T330A, A333S, E347K, P363L, A427D, V447F, N449D, N449K?, G453R, A490T, K527Q, N551S, A581T, Y585S, R588M, A593E, W606C, K649E, R651H, W694C, I698V, V708I, and L735Q, and is preferably selected from the group consisting of V708I, V708I+A593E, V708I+S109T, V708I+T330A, A35P, V708I+R588M, V708I+W606C, V708I+W694C, I698V, N312K+N449D+N551S+I698V+L735Q, N312K+N449D+N551S+I698V+V708I+L735Q, V708I+N449K, and V708I+G222S.

4. The variant AAV of item 1, wherein the peptide insertion is inserted following any of amino acids in positions 570-671 in VP1 of AAV2 or a corresponding position in another wild-type AAV serotype or AAV variant.

5. The variant AAV of item 4, wherein the peptide insertion is inserted following amino acid 587 in VP1 of AAV2 or a corresponding position in another AAV serotype.

6. An infectious recombinant adeno-associated virus (rAAV) virion comprising: (a) a variant AAV capsid protein according to any one of items 1-5, and a heterologous nucleic acid.

7. The rAAV of item 6, wherein the heterologous nucleic acid comprises a nucleotide sequence encoding an RNA interfering agent or a polypeptide.

8. A method of delivering a heterologous nucleic acid to a target cells, comprising contacting a target cell with the rAAV virion of item 7.

9. The method of item 8, wherein the target cell is a cardiac and/or skeletal muscle cell.

10. The method of item 8, wherein the target cell is in vitro.

11. The method of item 8, wherein the target cell is in vivo.

12. An isolated nucleic acid comprising a nucleotide sequence encoding a variant adeno-associated virus (AAV) capsid protein comprising a peptide insertion in the GH-loop of the capsid protein, wherein the insertion is in AAV2 or a corresponding position in a capsid portion of a wild-type AAV serotype other than AAV2 or an AAV variant, and wherein the peptide insertion is selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42).

13. An isolated host cell comprising the nucleic acid of item 12.

14. A variant adeno-associated virus (AAV) capsid protein comprising a peptide insertion relative to a parental AAV capsid protein corresponding to two adjacent amino acids at a position between amino acids 570 and 611 of VP1 of AAV2, wherein the insertion comprises the amino acid sequence $Y_1Y_2X_1X_2X_3X_4X_5X_6X_7Y_3$, and wherein $X_1$ is selected from T and N; $X_2$ is selected from N and K; $X_3$ is selected from K, I and T; $X_4$ is selected from I, Q and T; $X_5$ is selected from G, R and N; $X_6$ is selected from V, T and K; and $X_7$ is selected from T and D.

15. The variant AAV of item 14, wherein the peptide insertion is selected from the group consisting of NKIQRTD (SEQ ID NO:13), NKTTNKD (SEQ ID NO:14) and TNKIGVT (SEQ ID NO:15).

16. The variant AAV of item 15, wherein the peptide insertion is flanked by N-terminus amino acids LA and C-terminus amino acid A.

17. The variant AAV of item 15, wherein the peptide insertion is between amino acids 587 and 588 of VP1 of AAV2 or a corresponding position in another wild-type AAV serotype or AAV variant.

18. An infectious recombinant adeno-associated virus (rAAV) virion comprising: (a) a variant AAV capsid protein according to any one of items 14-17, and a heterologous nucleic acid.

19. The rAAV of item 18, wherein the heterologous nucleic acid comprises an RNA interfering agent or a nucleotide sequence encoding a polypeptide.

20. A method of delivering a heterologous nucleic acid to a target cell, comprising contacting the target cell with the rAAV virion of item 18.

21. The method of item 20, wherein the target cell is a cardiac and/or skeletal cell.

22. The method of item 21, wherein the target cell is in vitro or in vivo.

23. A variant adeno-associated virus (AAV) capsid protein comprising i) an AAV amino acid sequence at least 90% identical to a wild-type AAV selected from the group consisting of SEQ ID NOS: 1-10 and 11; and ii) one or more amino acid substitutions selected from the group consisting of P363L, P363L+V708I, P363L+E347K, V708I+A593E, V708I+A333S, V708I+S721L, V708I+A593E+N551S, V708I+A593E+K649E, V708I+A593E+S109T, V708I+A593E+S109T+K527Q, A593E+SI09T, wherein the one or more substitutions are relative to AAV2 or the one or more corresponding substitutions relative to other AAV serotypes.

24. The variant AAV of item 23, wherein the capsid protein comprises a peptide insertion.

25. The variant AAV of item 24, wherein the peptide insertion is selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42).

26. The variant AAV of item 23, wherein the AAV amino acid sequence is at least 95% identical to the wild-type AAV.

27. The variant AAV of item 23, wherein the AAV amino acid sequence is at least 99% identical to the wild-type AAV.

28. The variant AAV of item 23, wherein the capsid protein is a chimeric capsid protein or is an ancestral capsid protein.
29. An infectious recombinant adeno-associated virus (rAAV) virion comprising: (a) a variant AAV capsid protein according to any one of items 23-28, and a heterologous nucleic acid.
30. The rAAV of item 29, wherein the heterologous nucleic acid comprises a nucleotide sequence encoding an RNA interfering agent or a polypeptide.
31. A method of delivering a heterologous nucleic acid to a target cell, comprising contacting the target cell with the rAAV virion of item 29.
32. The method of item 31, wherein the target cell is a cardiac and/or skeletal muscle cell.
33. The method of item 32, wherein the cardiac cell is selected from the group consisting of cardiomyocytes, cardiomyoblasts, cardiac fibroblasts, and cardiac progenitor cells.
34. The method of item 31, wherein the target cell is in vitro.
35. The method of item 31, wherein the target cell is in vivo.
36. An isolated nucleic acid comprising a nucleotide sequence encoding a variant adeno-associated virus (AAV) capsid protein comprising an amino acid sequence at least 90% identical to a wild-type AAV selected from the group consisting of SEQ ID NO:1-12 or an AAV variant; and ii) one or more amino acid substitutions selected from the group consisting of P363L, P363L+V708I, P363L+E347K, V708I+A593E, V708I+A333S, V708I+S721L, V708I+A593E+N551S, V708I+A593E+K649E, V708I+A593E+S109T, V708I+A593E+S109T+K527Q, A593E+S109T.
37. An isolated host cell comprising the nucleic acid of item 36.
38. A variant adeno-associated virus (AAV) capsid protein comprising a peptide insertion in the GH-loop of the capsid protein and optionally comprising one or more point mutations, wherein the peptide insertion is selected from the group consisting of NKIQRTD (SEQ ID NO:13) and LANKIQRTDA (SEQ ID NO:26).
39. The variant AAV capsid protein according to item 38, comprising a V708I amino acid substitution.
40. The variant AAV capsid protein according to item 39, comprising a V708I+A593E, V708I+S109T, V708I+T330A, V708I+R588M or V708I+N312K+N449D+N551S+I698V+L735Q amino acid substitution.
41. The variant AAV capsid protein according to item 38, comprising an A35P amino acid substitution.
42. The variant AAV capsid protein according to item 38, comprising a N312K+N449D+N551S+I698V+L735Q amino acid substitution.
43. A variant adeno-associated virus (AAV) capsid protein comprising a peptide insertion in the GH-loop of the capsid protein and optionally comprising one or more point mutations, wherein the peptide insertion is selected from the group consisting of NKTTNKD (SEQ ID NO:14) and LANKTTNKDA (SEQ ID NO:28).
44. The variant AAV capsid protein according to item 43, comprising a V708I amino acid substitution.
45. The variant AAV capsid protein according to item 44, comprising a V708I+S109T, V708I+W694C, V708I+W606C, or V708I+N312K+N449D+N551S+I698V+L735Q amino acid substitution.
46. The variant AAV capsid protein according to item 43, comprising an I698V amino acid substitution.
47. The variant AAV capsid protein according to item 46, comprising a N312K+N449D+N551S+I698V+L735Q amino acid substitution.
48. A variant adeno-associated virus (AAV) capsid protein comprising a peptide insertion in the GH-loop of the capsid protein and optionally comprising one or more point mutations, wherein the peptide insertion is selected from the group consisting of TNKIGVT (SEQ ID NO:15), LATNKIGVTA (SEQ ID NO:29) and LATNKIGVTS (SEQ ID NO:37).
49. The variant AAV capsid protein according to item 48, comprising a V708I amino acid substitution.
50. The variant AAV capsid protein according to item 49, comprising a V708I+N449K, V708I+G222S, or V708I+N312K+N449D+N551S+I698V+L735Q amino acid substitution.
51. The variant AAV capsid protein according to item 48, comprising a N312K+N449D+N551S+I698V+L735Q amino acid substitution.
52. A variant adeno-associated virus (AAV) capsid protein comprising the sequence of SEQ ID NO:62 or a sequence at least 90% identical thereto, wherein the variant AAV capsid proteins comprises the following amino acid substitutions relative to AAV5 capsid: V229I+A490T+A581T.
53. The variant AAV capsid protein according to item 52, further comprising a Y585S or V447F amino acid substitution relative to AA5 capsid.
54. A variant adeno-associated virus (AAV) capsid protein comprising the sequence of SEQ ID NO:63 or a sequence at least 90% identical thereto, wherein the variant AAV capsid proteins comprises the following amino acid substitutions relative to AAV5 capsid: V229I+A427D+A490T+A581T.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this

Example 1

Intravenous Injection and Tissue Harvesting. A single male cynomolgus macaque (*Macaca fascicularis*) age 3-10 years old and weighing at least 3 kg was dosed via intravenous injection via the saphenous vein for each round of selection. The animal was anesthetized and 1-5 mL of the library (in the first round, the library consists of variants generated using all mutagenesis techniques described in FIG. 1A; in each subsequent round, the variants isolated from the previous round), in some cases pre-incubated with human IVIG for 30 minutes at 37° C., was administered.

Euthanasia was performed by trained veterinary staff using 100 mg/kg pentobarbital sodium intravenous injection on day 14±3 or 21±3, depending on the selection. The cardiac and/or skeletal muscle tissue from the quadriceps was removed, and DNA was isolated from the tissue. In some cases, the cardiac tissue was divided into several regions: the atrium, ventricular septum, left papillary muscle, right papillary muscle, left ventricle, and right ventricle.

Directed Evolution. The directed evolution process is shown in FIG. 1A-1E. Briefly, a viral capsid library comprising 20+ proprietary combinations of DNA mutation technique and cap genes is created (FIG. 1A). Viruses are then packaged (FIG. 1B)—such that each particle is composed of a mutant capsid surrounding the cap gene encoding that capsid—and purified. The capsid library is placed under selective pressure in vivo. The tissue or cellular material of interest is harvested to isolate AAV variants that have successfully infected that target, and the successful viruses are recovered. Successful clones are enriched through repeated selection (Stage 1—FIG. 1D). Selected cap genes then undergo proprietary re-diversification and are enriched through further selection steps to iteratively increase viral fitness (Stage 2—FIG. 1D). Variants identified during Vector Selection Stages 1 and 2 demonstrate the ability to transduce primate muscle cells (FIG. 1E).

Figure 2:
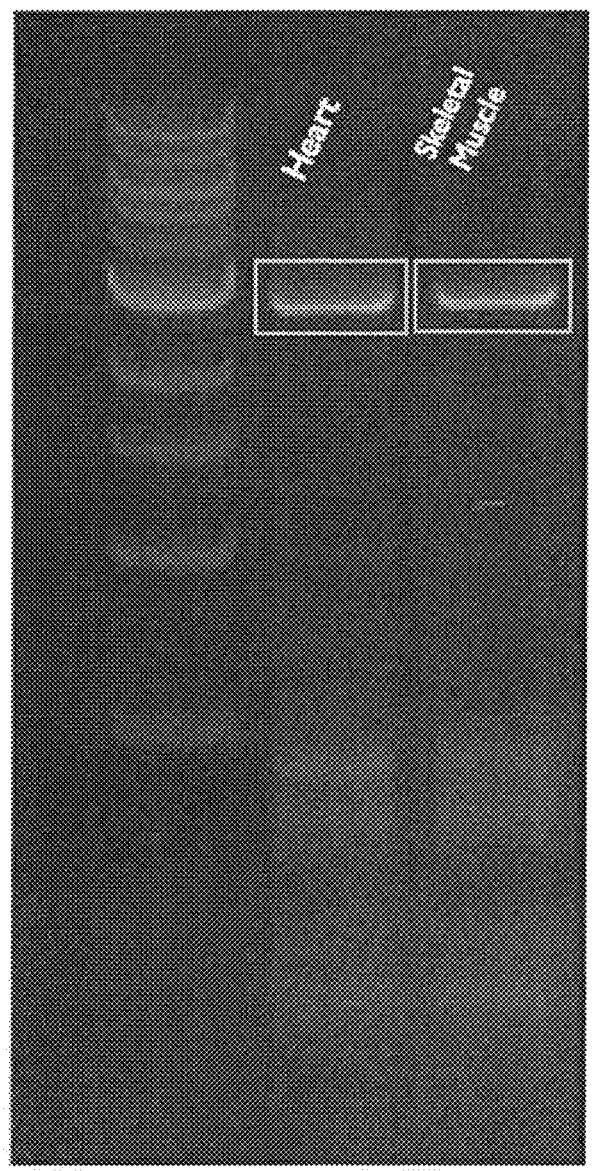
FIG. 2 shows PCR amplification of viral genomes from the heart and skeletal muscle tissues from a representative round of selection. Bands within red boxes represent successful amplification of viral genomes.

Successful Recovery of AAV Capsid Genomes. The capsids recovered from each round of selection were used to package the library injected to initiate the subsequent round of selection. Recovery of capsid genes from tissue represents successful internalization of library vectors into the tissue of interest. Recovery of viral genomes from cardiac and skeletal muscle tissue from a representative round of selection are shown in FIG. 2. Bands within boxes represent successful recovery of viral genomes.

Figure 3A:
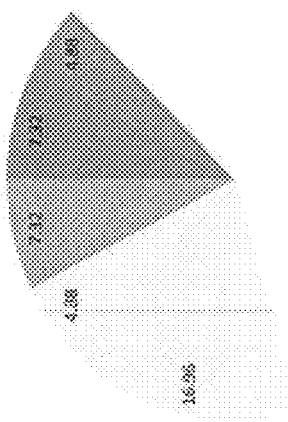
FIGS. 3A-3C show frequency of motifs within sequencing analysis.
Figure 3C:
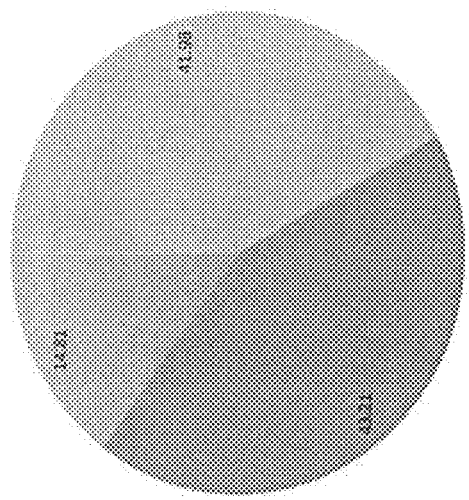
Figure 3B:
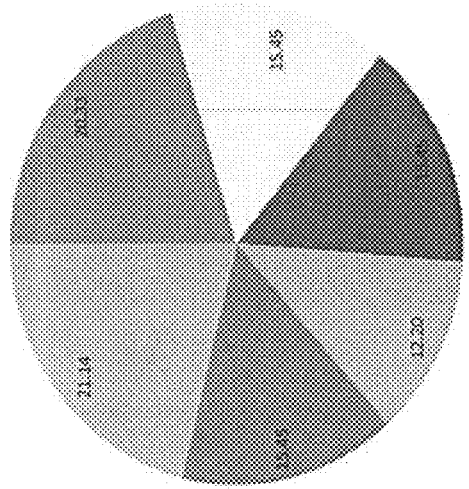
Figure 4B:
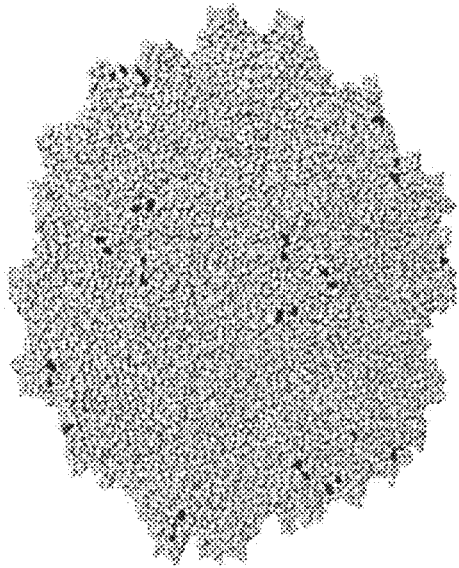
FIGS. 4A-4C FIG. 4A is a representative three-dimensional model of AAV2 containing a random heptamer following amino acid 587 and a V708I substitution.
Figure 4C:
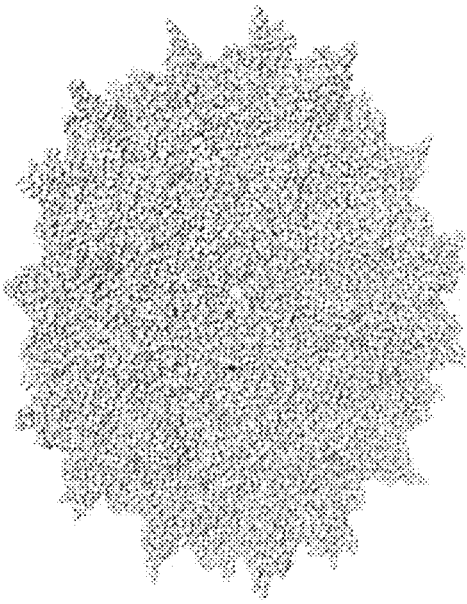
Figure 4A:
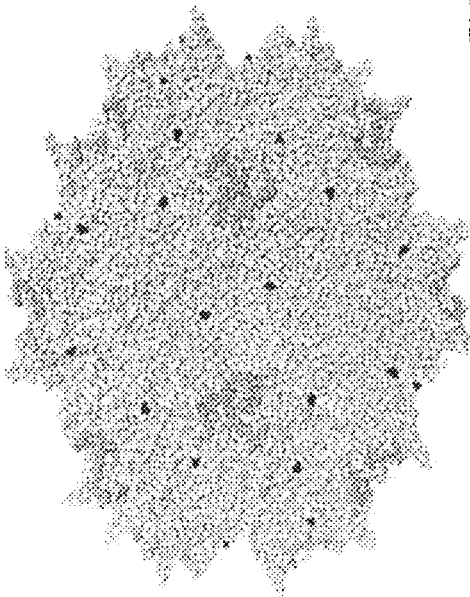

Sequencing Analysis. During rounds 3-4 of selections including the selective pressure of intravenous delivery to cardiac tissue or skeletal muscle tissue and rounds 1-2 of a selection including the selective pressure of intravenous delivery in the presence of neutralizing antibodies to cardiac tissue, sequencing was performed on individual clones within the library to determine the frequency of variants within the population. Variants were evaluated for the presence of motifs within the sequencing data. Variants were grouped into motifs based on the presence of a unifying variation (for example, a specific point mutation or specific peptide insertion sequence in a consistent location within the capsid) that occurred in multiple sequences. Motifs representing at least 5% of the sequenced population in two or more rounds of the selection or at least 10% of the sequenced population in one or more rounds of the selection are represented in FIG. 3A (Round 4 sequencing analysis for the selective pressure of intravenous delivery to cardiac tissue), FIG. 3B (Round 2 sequencing analysis for the selective pressure of intravenous delivery in the presence of neutralizing antibodies to cardiac tissue), and FIG. 3C (provides Round 3 sequencing analysis for the selective pressure of intravenous delivery to skeletal muscle tissue).

Several representative clones that were identified as conferring increased infectivity of cardiac and/or skeletal muscle cells are listed in Table 1 below (each clone contains the identified substitution(s) and/or peptide insertion TABLE 1-continued Amino acid sequence modifications to the AAV VP1 capsid protein that confer increased infectivity of cardiac and/or skeletal muscle cells.

| Insertion | Substitution | Cardiac | Cardiac + NAb | Skeletal Muscle |
|---|---|---|---|---|
| 588~LANKIQRTDA~ (SEQ ID NO: 27) | +V7081 | Round 3: 13 (20.97%)<br>Round 4: 10 (23.26%) | Round 1: 1 (0.70%) | — |
| 588~LANKTTNKDA~ (SEQ ID NO: 28) | None | Round 4: 2 (4.88%) | Round 1: 10 (7.04%)<br>Round 2: 8 (6.50%) | — |
| 588~LANKTTNKDA~ (SEQ ID NO: 28) | +S109T+V708I | Round 4: 1 (2.44%) | — | — |
| 588~LANKTTNKDA~ (SEQ ID NO: 28) | +W694C+V708I | Round 4: 1 (2.44%) | — | — |
| 588~LANKTTNKDA~ (SEQ ID NO: 28) | +I698V | — | Round 1: 1 (0.70%) | — |
| 588~LANKTTNKDA~ (SEQ ID NO: 28) | +W606C+V708I | — | Round 2: 1 (0.81%) | — |
| 588~LANKTTNKDA~ (SEQ ID NO: 28) | +V708I | Round 3: 6 (9.68%)<br>Round 4: 3 (7.32%) | Round 1: 4 (2.82%)<br>Round 2: 10 (8.13%) | — |
| 588~LATNKIGVTA~ (SEQ ID NO: 29) | +V708I | Round 4: 1 (2.44%) | — | — |
| 588~LAQADTTKNA~ (SEQ ID NO: 39) | None | — | Round 1: 23 (16.02%)<br>Round 2: 21 (17.07%) | — |
| 588~LAQADTTKNA~ (SEQ ID NO: 39) | +D213N | — | Round 2: 1 (0.81%) | — |
| 588~LAQADTTKNA~ (SEQ ID NO: 39) | +G453R | — | Round 1: 1 (0.70%) | — |
| 588~LAQADTTKNA~ (SEQ ID NO: 39) | +V708I | Round 4: 1 (2.44%) | Round 1: 3 (2.11%)<br>Round 2: 3 (2.44%) | — |
| 588~LAQADTTKNA~ (SEQ ID NO: 39) | +P363L | — | Round 1: 1 (0.70%) | — |
| 588~LANQDYTKTA~ (SEQ ID NO: 36) | None | — | Round 1: 1 (0.70%) | — |
| 588~LANQDYTKTA~ (SEQ ID NO: 36) | +I698V | — | Round 2: 2 (1.63%) | — |
| 588~LANQDYTKTA~ (SEQ ID NO: 36) | +V708I | — | Round 1: 1 (0.70%) | — |
| 588~LATNRTSPDA~ (SEQ ID NO: 40) | +V708I | — | Round 2: 1 (0.81%) | — |
| 588~LAASDSTKAA~ (SEQ ID NO: 42) | None | — | — | Round 3: 1 (1.23%) |
| 588~LAASDSTKAA~ (SEQ ID NO: 42) | +V708I | Round 3: 2 (3.23%) | — | — |
| 588~LAASNITKAA~ (SEQ ID NO: 33) | None | — | Round 1: 2 (1.41%)<br>Round 2: 3 (6.50%) | — |

TABLE 1-continued

Amino acid sequence modifications to the AAV VP1 capsid protein that confer increased infectivity of cardiac and/or skeletal muscle cells.

| Insertion | Substitution | Cardiac | Cardiac + NAb | Skeletal Muscle |
|---|---|---|---|---|
| 588~LAASNITKAA~ (SEQ ID NO: 33) | +V708I | — | Round 1: 6 (4.23%) Round 2: 11 (8.94%) | — |
| 588~LAGNLTKGNA~ (SEQ ID NO: 30) | None | Round 3: 4 (6.44%) | Round 1: 6 (4.23%) Round 2: 3 (2.44%) | — |
| 588~LAGNLTKGNA~ (SEQ ID NO: 30) | +S109T+V708I | Round 3: 2 (3.23%) | — | — |
| 588~LAGNLTKGNA~ (SEQ ID NO: 30) | +A139T+P195L | — | Round 1: 1 (0.70%) | — |
| 588~LAGNLTKGNA~ (SEQ ID NO: 30) | +P363L+V708I | — | Round 1: 1 (0.70%) | — |
| 588~LAGNLTKGNA~ (SEQ ID NO: 30) | +R651H | — | Round 2: 1 (0.81%) | — |
| 588~LAGNLTKGNA~ (SEQ ID NO: 30) | +V708I | Round 3: 2 (3.23%) | Round 1: 1 (0.70%) Round 2: 2 (1.63%) | — |
| 588~LAGNLTKGNA~ (SEQ ID NO: 30) | +P363L | — | Round 1: 1 (0.70%) | — |
| 588~LADNTVTRSA~ (SEQ ID NO: 34) | None | — | Round 1: 9 (6.34%) Round 2: 6 (4.88%) | — |
| 588~LADNTVTRSA~ (SEQ ID NO: 34) | +I698V | — | Round 2: 1 (0.81%) | — |
| 588~LADNTVTRSA~ (SEQ ID NO: 34) | +V708I | — | Round 1: 1 (0.70%) Round 2: 2 (1.63%) | — |
| 588~LANTVKLSTA~ (SEQ ID NO: 31) | None | — | Round 1: 3 (2.11%) Round 2: 7 (5.69%) | — |
| 588~LANTVKLSTA~ (SEQ ID NO: 31) | +V708I | — | Round 2: 8 (6.50%) | — |
| 588~LASNTVKAIA~ (SEQ ID NO: 32) | None | Round 3: 2 (3.23%) Round 4: 1 (2.44%) | — | — |
| 588~LASNTVKAIA~ (SEQ ID NO: 32) | +V708I | Round 4: 1 (2.44%) | — | — |
| 588~LATNKIGVTS~ (SEQ ID NO: 37) | None | Round 4: 1 (2.44%) | — | — |
| 588~LASNTTQKTA~ (SEQ ID NO: 41) | None | — | — | Round 3: 2 (2.46%) |
| 588~LANKISAKDA~ (SEQ ID NO: 35) | None | — | Round 2: 3 (2.44%) | — |
| 588~LANKISAKDA~ (SEQ ID NO: 35) | +V708I | — | Round 2: 2 (1.63%) | — |
| None | P34A | — | — | Round 4: 2 (10%) |

TABLE 1-continued

Amino acid sequence modifications to the AAV VP1 capsid protein that confer increased infectivity of cardiac and/or skeletal muscle cells.

| Insertion | Substitution | Cardiac | Cardiac + NAb | Skeletal Muscle |
|---|---|---|---|---|
| None | P34S | — | Round 1: 1 (0.70%) | — |
| None | P64S | — | — | Round 4: 1 (5.00%) |
| None | S109+P235S | — | — | Round 4: 1 (5.00%) |
| None | Q120R | — | — | Round 4: 1 (5.00%) |
| None | A193V | — | — | Round 3: 1 (1.23%) |
| None | T277N | — | — | Round 4: 1 (5.00%) |
| None | P351L | — | — | Round 4: 1 (5.00%) |
| None | P363L | — | Round 1: 13 (9.15%) | Round 3: 34 (41.98%) Round 4: 4 (20.00%) |
| None | P363L+E347K | — | — | Round 3: 1 (1.23%) |
| None | P363L+V708I | — | Round 1: 2 (1.41%) | — |
| None | S427T+I698V | — | Round 1: 1 (0.70%) | — |
| None | Q440K | — | — | Round 3: 1 (1.23%) |
| None | Y444F | — | — | Round 4: 1 (5.00%) |
| None | N449D | — | — | Round 4: 1 (5.00%) |
| None | T568N | — | — | Round 3: 1 (1.23%) |
| None | A593E | Round 4: 3 (7.32%) | Round 1: 1 (0.70%) | Round 3: 31 (38.27%) Round 4: 2 (10%) |
| None | S109T+A593E | — | — | Round 3: 2 (2.47%) |
| None | S109T+K527Q+ A593E+V708I | Round 3: 1 (1.61%) | — | — |
| None | S109T+A593E+ V708I | Round 3: 1 (1.61%) | — | — |
| None | A593E+N551S+ V708I | — | — | Round 3: 1 (1.23%) |
| None | A593E+K649E+ V708I | Round 3: 1 (1.61%) | — | — |
| None | A593E+V708I | Round 3: 12 (19.35%) | Round 1: 5 (3.52%) | Round 3: 1 (1.23%) |

TABLE 1-continued

Amino acid sequence modifications to the AAV VP1 capsid protein that confer increased infectivity of cardiac and/or skeletal muscle cells.

| Insertion | Substitution | Cardiac | Cardiac + NAb | Skeletal Muscle |
|---|---|---|---|---|
| None | I698V | — | — | Round 4: 1 (5.00%) |
| None | V708I | Round 3: 6 (9.68%) Round 4: 2 (4.88%) | Round 1: 10 (7.04%) | Round 3: 1 (1.23%) Round 4: 1 (5.00%) |
| None | V708I+A333S | — | — | Round 3: 1 (1.23%) |
| None | V708I+S721L | Round 3: 1 (1.61%) | — | — |
| None | V708I+L735V | — | — | Round 3: 1 (1.23%) |

Substitutions listed in column 2 are based on the amino acid sequence for wild type AAV2, i.e. in the absence of inserted peptide. "Cardiac + NAb" in column 5 indicates that the amino acid sequence modifications should confer increased resistance to neutralization by anti-AAV antibodies in addition to increased infectivity of cardiac muscle cells.

Also identified as capsids conferring increased infectivity of cardiac muscle cell and increased resistance to neutralization by anti-AAV antibodies were the following chimeras:

A chimera with (i) amino acids 1-129 of AAV6 and (ii) amino acids 130-725 of AAV5 and having the following amino acid substitutions relative to AAV5: V229I+A490T+A581T (the sequence of SEQ ID NO:62).

A chimera with (i) amino acids 1-61 of AAV2, (ii) amino acids 62-129 of AAV6, and (iii) amino acids 130-725 of AAV5 and having the following amino acid substitutions relative to AAV5: V229I+A490T+A581T (the sequence of SEQ ID NO:63).

A chimera with (i) amino acids 1-129 of AAV6 and (ii) amino acids 130-725 of AAV5 and having the following amino acid substitutions relative to AAV5: V229I+A490T+A581T+Y585S A chimera with (i) amino acids 1-129 of AAV6 and (ii) amino acids 130-725 of AAV5 and having the following amino acid substitutions relative to AAV5: V229I+A447F+A490T+A581T The AAV variant virions disclosed herein may incorporate reasonable rational design parameters, features, modifications, advantages, and variations that are readily apparent to those skilled in the art in the field of engineering AAV viral vectors.

Example 2

The cell tropism of recombinant AAV virions comprising the novel AAV variants LANKIQRTDA+V708I (SEQ ID NO:43), LANKTTNKDA+V708I (SEQ ID NO:48), and LATNKIGVTA+V708I (SEQ ID NO:46) for cardiomyocytes was assessed in vitro using cardiomyocytes generated from human embryonic stem cells (ESC).

Recombinant AAV virions comprising either an AAV1 capsid, an AAV2 capsid, an AAV9 capsid, the novel variant capsid LANKIQRTDA+V708I (SEQ ID NO:43), the novel variant capsid LANKTTNKDA+V708I (SEQ ID NO:48), or the novel variant capsid LATNKIGVTA+V708I (SEQ ID NO:46) and a genome comprising a green fluorescent protein (EGFP) transgene operably linked to a CAG promoter (AAV1.CAG.EGFP, AAV2.CAG.EGFP, AAV9.CAG.EGFP, LANKIQRTDA+V708I (SEQ ID NO:43).CAG.EGFP, LANKTTNKDA+V708I (SEQ ID NO:48).CAG.EGFP, and LATNKIGVTA+V708I (SEQ ID NO:46).CAG.GFP, respectively) were manufactured using standard methods. Cardiomyocytes were generated from a human embryonic stem cell line, ESI-017, by modulation of Wnt signaling using small molecules. After 14 days of cardiac mesoderm induction, cultures were further enriched for cardiomyocytes by glucose deprivation. After approximately 24 days of differentiation, the majority of cells expressed the cardiac myocyte marker, cardiac Troponin T (cTnT), and a ventricular-specific marker, MLC-2V. The generated cardiomyocytes were evaluated for expression of gap junction protein Connexin 43, membrane potential fluctuation, calcium handling, and contractile function to ensure that the generated cardiomyocytes reached a mature state prior to vector characterization.

Figure 6A:
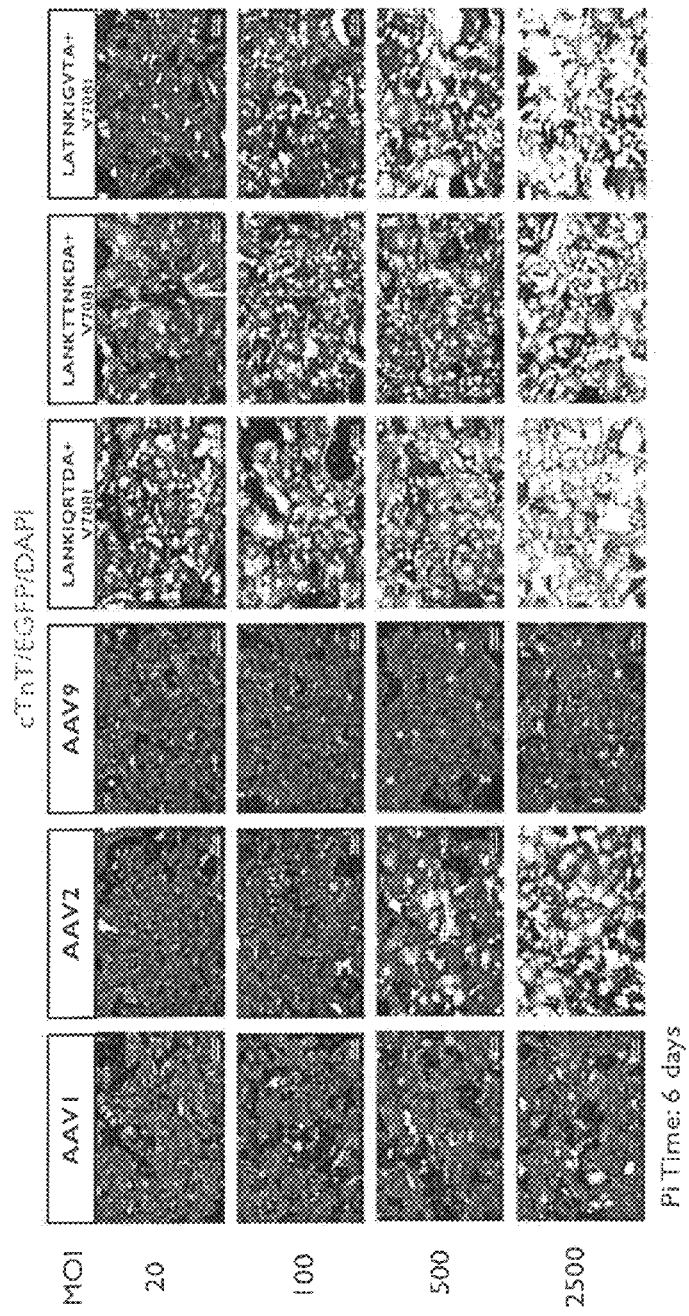
Figure 6C:
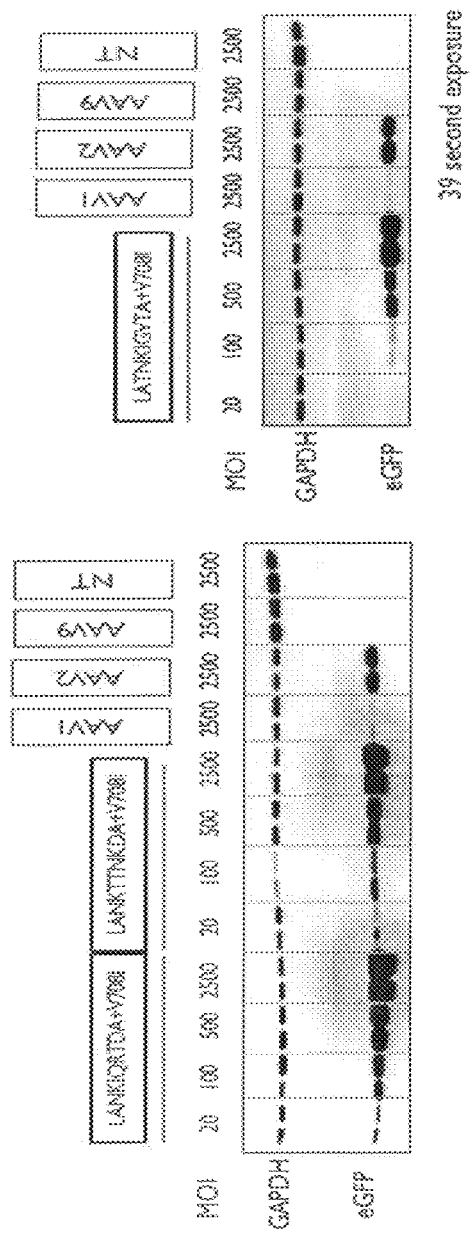
Figure 6D:
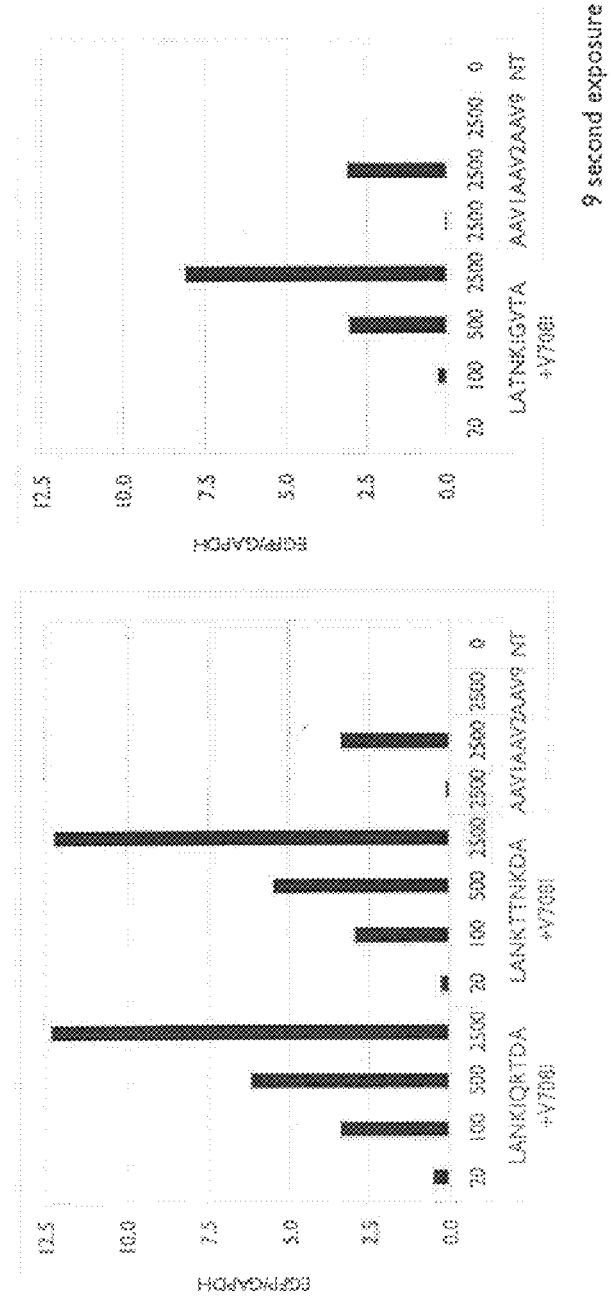
Figure 6E:
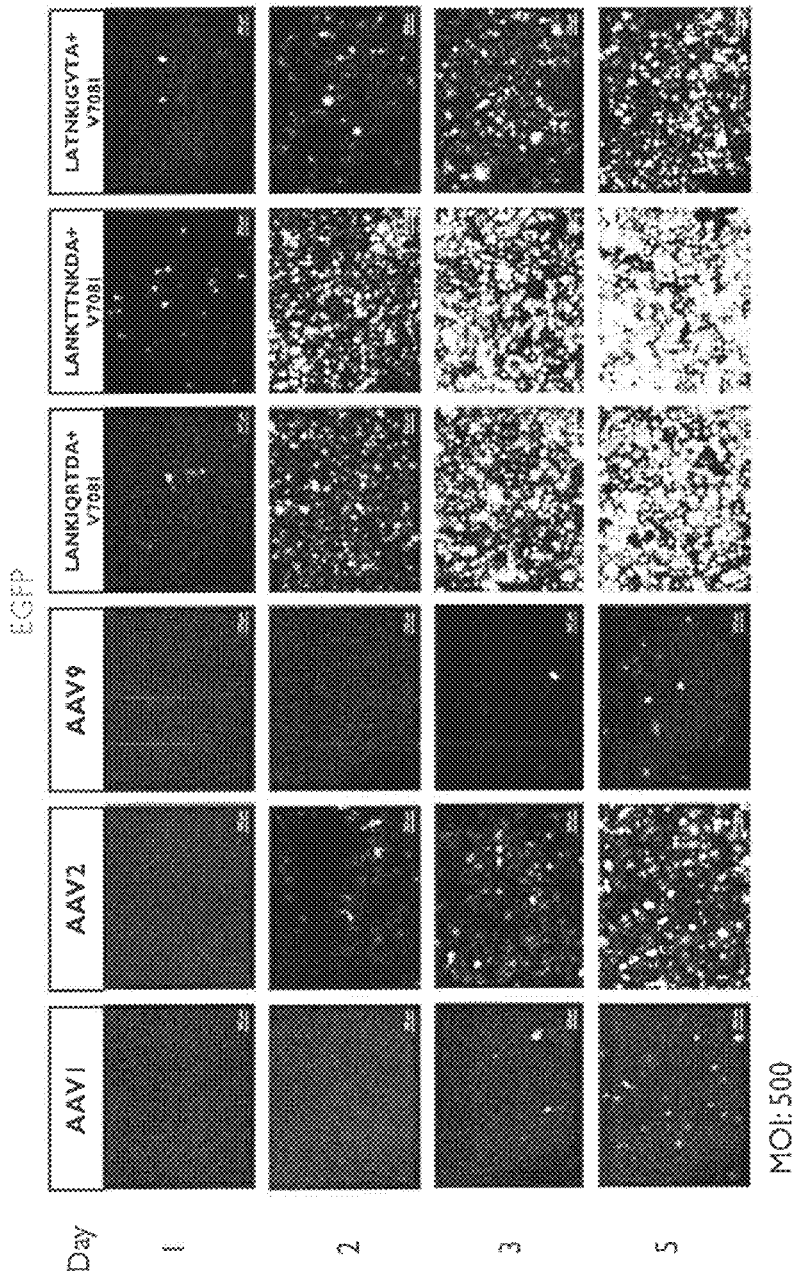
Figure 10A:
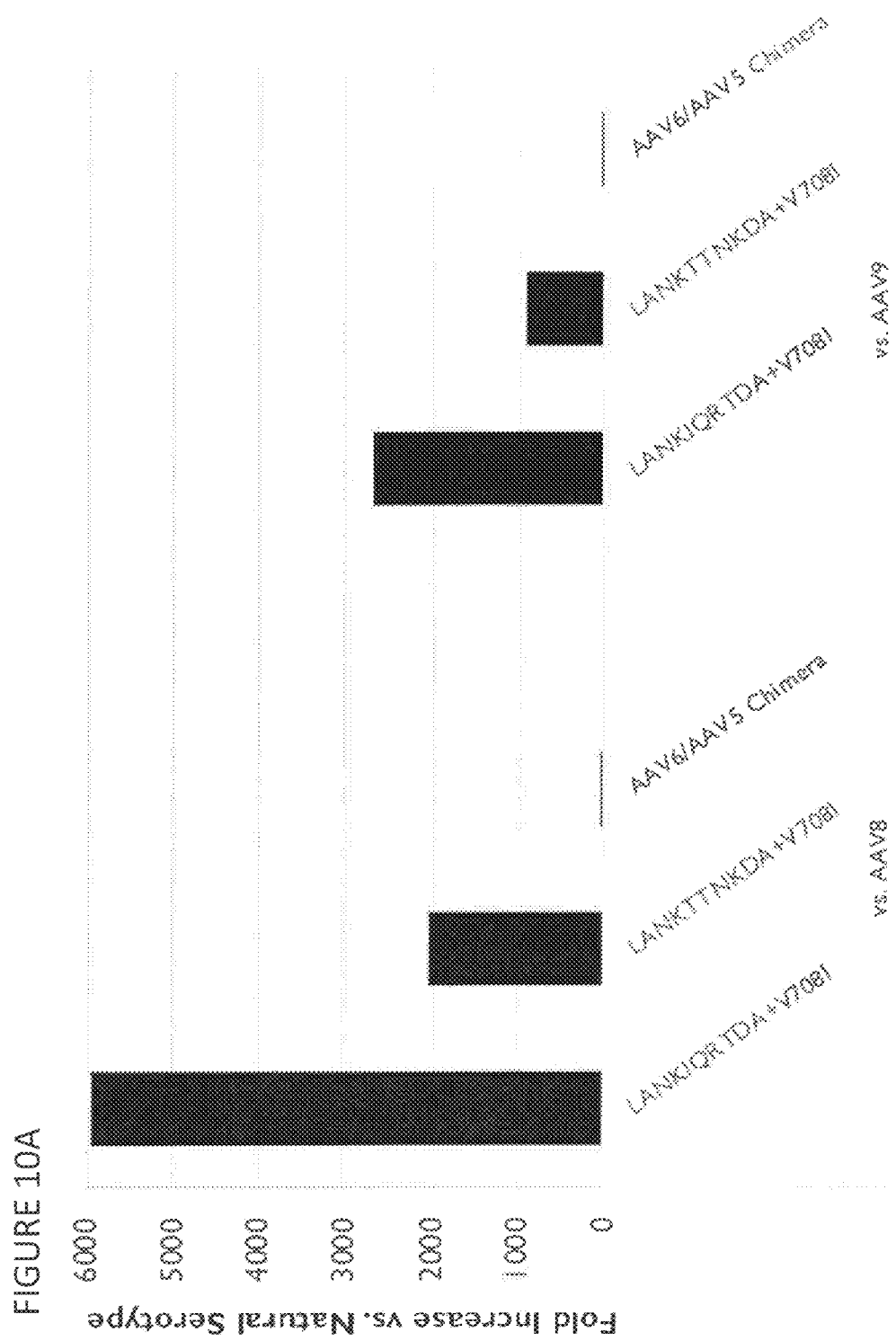
FIGS. 10A-B provide data on the magnitude of improvement of transduction of human cardiomyocytes and human skeletal myofibers in vitro by recombinant AAV virus comprising the novel AAV variant LANKIQRTDA+V708I (SEQ ID NO:43) capsid, the novel AAV variant LANKTTNKDA+ V708I (SEQ ID NO:48) capsid, and the novel AAV variant AAV6/AAV5 chimera capsid, each expressing a GFP transgene under the control of the CAG promoter.

Relative to AAV1, AAV2, and AAV9, the LANKIQRTDA+V708I (SEQ ID NO:43), LANKTTNKDA+V708I (SEQ ID NO:48), and LATNKIGVTA+V708I (SEQ ID NO:46) variants provided for significantly higher transduction efficiency of and transgene expression in human cardiomyocyte cultures six days post-infection as determined by immunofluorescence (FIG. 6A), flow cytometry (FIG. 6B) and Western blot analysis (FIGS. 6C-D). Furthermore, relative to AAV1, AAV2, and AAV9, LANKIQRTDA+V708I (SEQ ID NO:43), LANKTTNKDA+V708I (SEQ ID NO:48), and LATNKIGVTA+V708I (SEQ ID NO:46) provided for faster onset of gene expression in human cardiomyocyte cultures, as determined by immunofluorescence (FIG. 6E). Relative to AAV8 and AAV9, which exhibit cardiac and skeletal muscle cell tropism, the number of infectious units per administered viral genome were multiple orders of magnitude higher for LANKIQRTDA+V708I (SEQ ID NO:43) and LANKTTNKDA+V708I (SEQ ID NO:48) (FIG. 10A). This study illustrates the superior ability of NK1QRTD (SEQ ID NO:13)-, NKTTNKD (SEQ ID NO:14)-, and TNKIGVT (SEQ ID NO:15)-comprising AAV capsid variants to deliver genes to cardiac cells.

Example 3

The cell tropism of recombinant AAV virions comprising the novel AAV variant AAV6/AAV5 chimera for cardiomyocytes was assessed in vitro using cardiomyocytes generated from human embryonic stem cells (ESC).

Recombinant AAV virions comprising either an AAV1 capsid, an AAV8 capsid, an AAV9 capsid, or the novel variant capsid AAV6/AAV5 chimera (of SEQ ID NO:62) and a genome comprising a green fluorescent protein (EGFP) transgene operably linked to a CAG promoter (AAV1.CAG.EGFP, AAV8.CAG.EGFP, AAV9.CAG.EGFP, AAV6/AAV5 chimera.CAG.EGFP, respectively) were manufactured using standard methods. Cardiomyocytes were generated from a human embryonic stem cell line, ESI-017, by modulation of Wnt signaling using small molecules. After 14 days of cardiac mesoderm induction, cultures were further enriched for cardiomyocytes by glucose deprivation. After approximately 24 days of differentiation, the majority of cells expressed the cardiac myocyte marker, cardiac Troponin T (cTnT), and a ventricular-specific marker, MLC-2V. The generated cardiomyocytes were evaluated for expression of gap junction protein Connexin 43, membrane potential fluctuation, calcium handling, and contractile function to ensure that the generated cardiomyocytes reached a mature state prior to vector characterization.

Figure 7A:
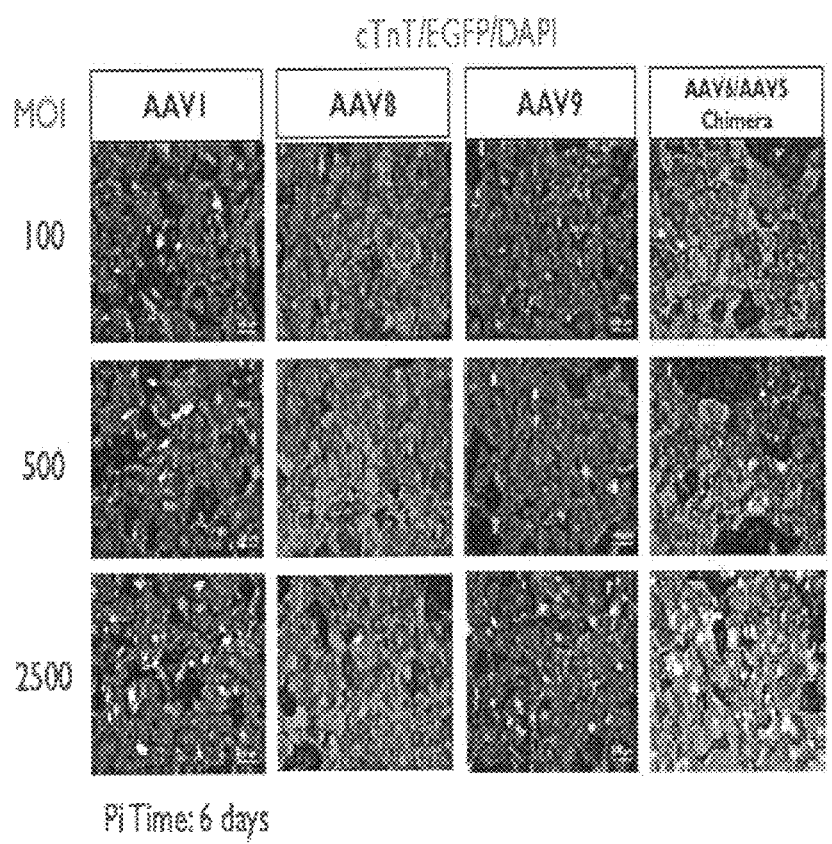
FIGS. 7A-E provide data on the transduction of human cardiomyocytes in vitro by recombinant AAV virus comprising the novel AAV variant AAV6/AAV5 chimera capsid of SEQ 1D NO: 62, expressing a GFP transgene under the control of the CAG promoter.
Figure 7B:
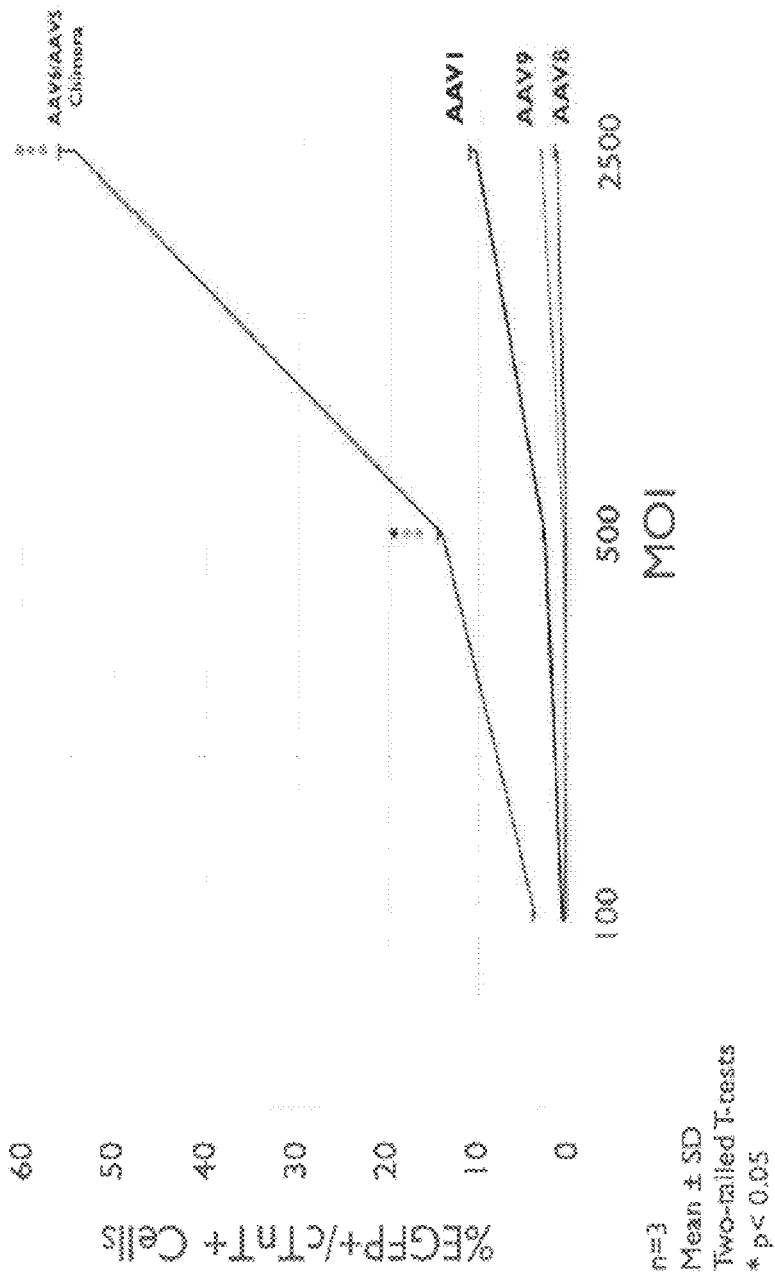
Figure 7C:
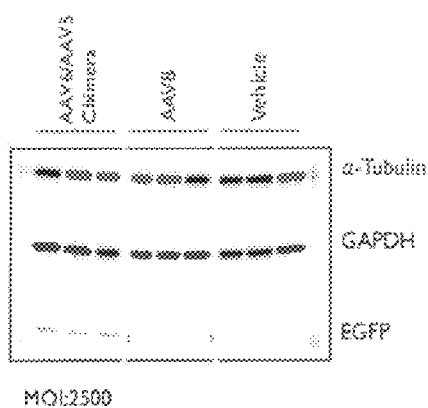
Figure 7D:
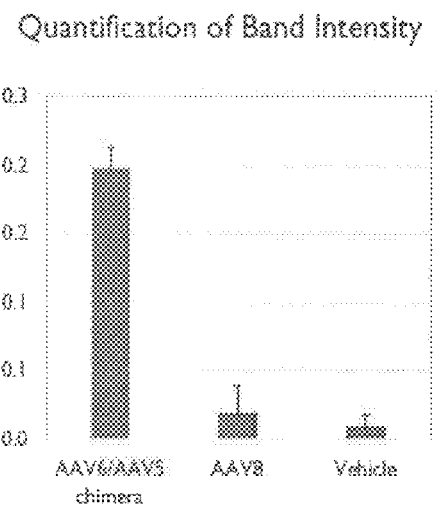
Figure 7E:
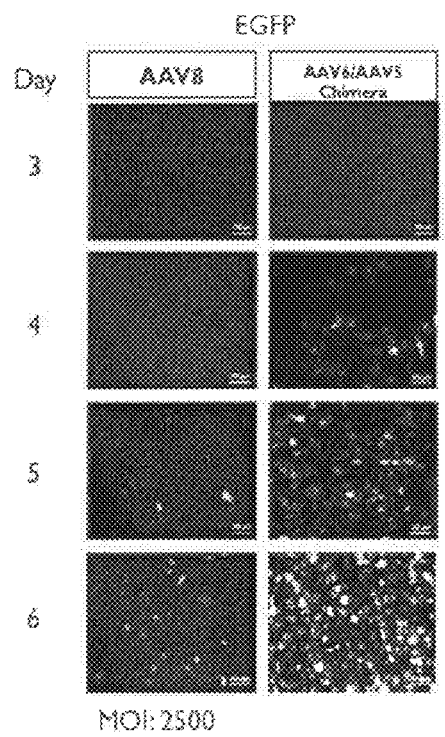

Relative to AAV1, AAV8, and AAV9, the AAV6/AAV5 chimera provided for significantly higher transduction efficiency of and transgene expression in human cardiomyocyte cultures six days post-infection as determined by immunofluorescence (FIG. 7A), flow cytometry (FIG. 7B), and Western blot analysis (FIGS. 7C-D). Furthermore, relative to AAV8, the AAV6/AAV5 chimera provided for faster onset of gene expression in human cardiomyocyte cultures, as determined by immunofluorescence (FIG. 7E). Relative to AAV8 and AAV9, the number of infectious units per administered viral genome were multiple orders of magnitude higher for the AAV6/AAV5 chimera (FIG. 10A). This study illustrates the superior ability of SEQ ID NO:62-comprising AAV capsid variants to deliver genes to cardiac cells.

Example 4

The cell tropism of recombinant AAV virions comprising the novel AAV variants LANKIQRTDA+V708I (SEQ ID NO:43), LANKTTNKDA+V708I (SEQ ID NO:48), and AAV6/AAV5 chimera for skeletal myofibers was assessed in vitro using skeletal myofibers generated from primary human myoblasts.

Recombinant AAV virions comprising either an AAV8 capsid, an AAV9 capsid, the novel variant capsid LANKIQRTDA+V708I (SEQ ID NO:43), the novel variant capsid LANKTTNKDA+V708I (SEQ ID NO:48), or the novel variant capsid AAV6/AAV5 chimera and a genome comprising a green fluorescent protein (EGFP) transgene operably linked to a CAG promoter (AAV8.CAG.EGFP, AAV9.CAG.EGFP, LANKIQRTDA+V708I (SEQ ID NO:43).CAG.EGFP, LANKTTNKDA+V708I (SEQ ID NO:48).CAG.EGFP, and AAV6/AAV5 chimera.CAG.GFP, respectively) were manufactured using standard methods. Skeletal myofibers were generated from primary human skeletal myoblasts obtained from a healthy 51 year old male (Cook Myosites). The myoblasts were differentiated for 30 days to form mature multinucleated skeletal muscle fibers. The generated skeletal myofibers were evaluated for expression of Myosin Heavy Chain (MHC) and Dystrophin to ensure that the majority of the generated skeletal myofibers reached a mature state prior to vector characterization.

Figure 8A:
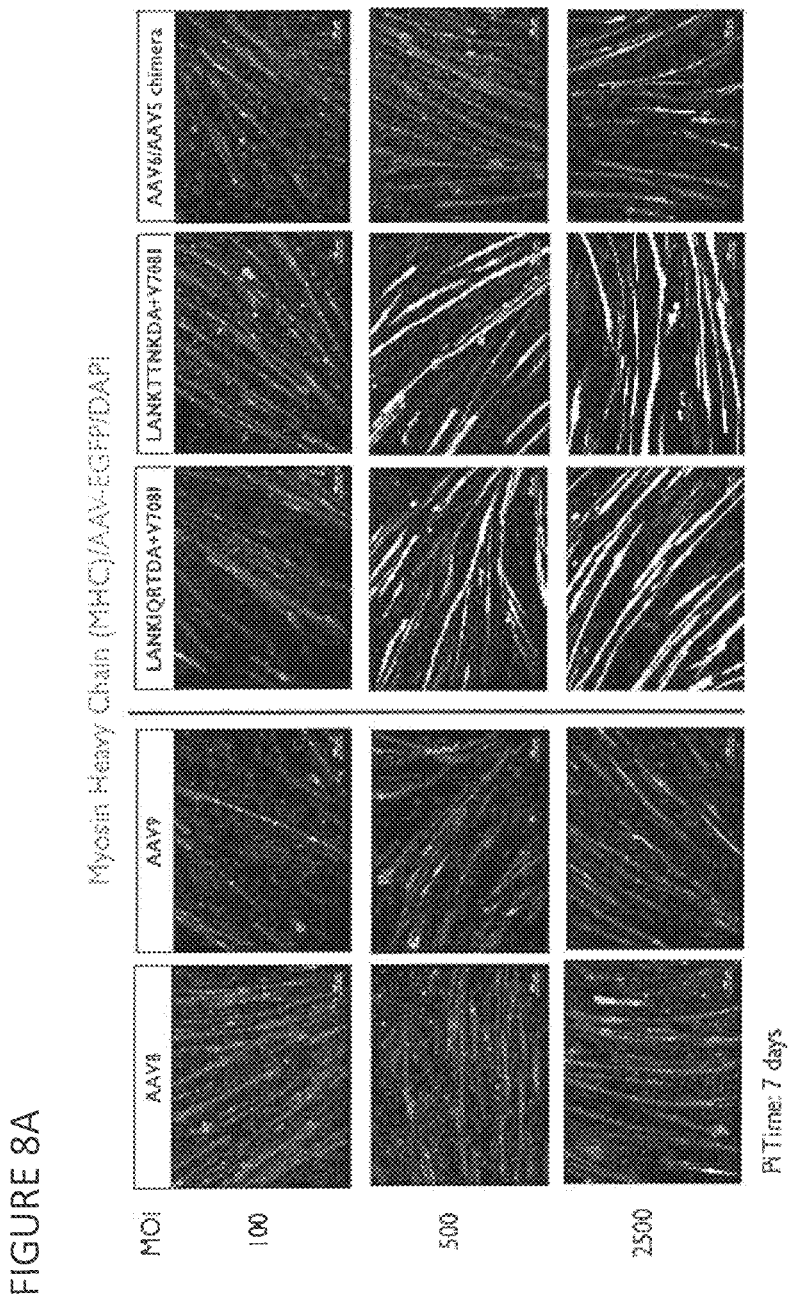
Figure 8C:
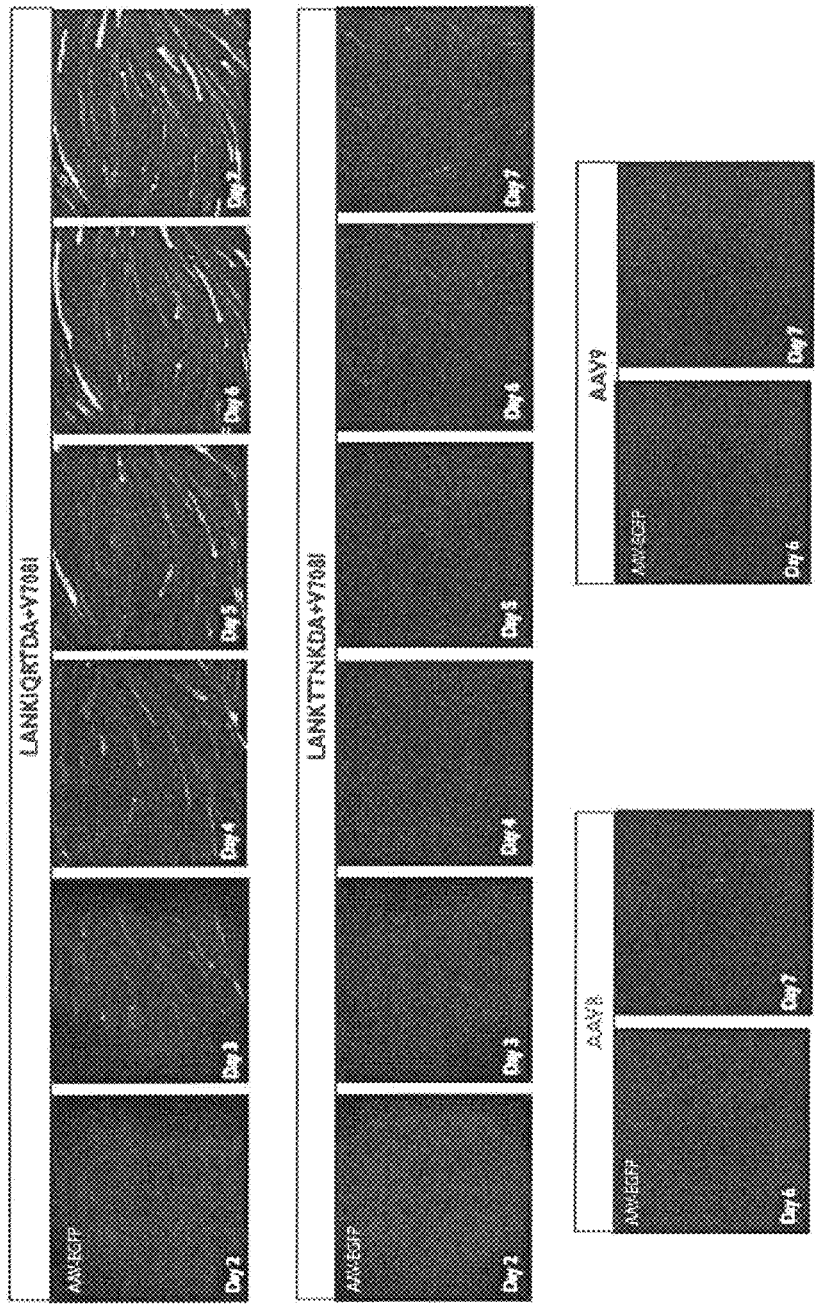
Figure 10B:
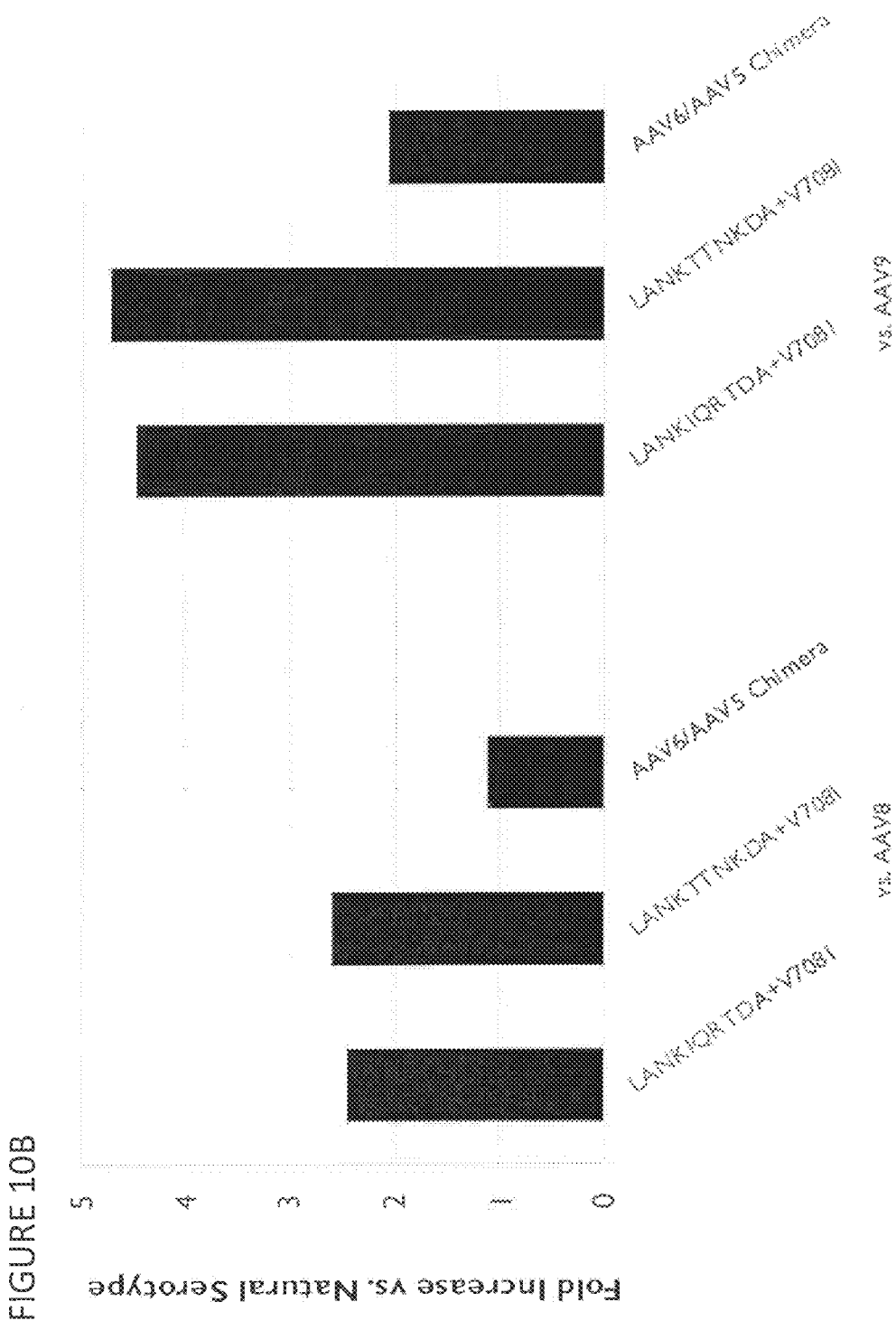

Relative to AAV8 and AAV9, the LANKIQRTDA+V708I (SEQ ID NO:43), LANKTTNKDA+V708I (SEQ ID NO:48), and AAV6/AAV5 chimera provided for significantly higher transduction efficiency of and transgene expression in human skeletal myofiber cultures seven days post-infection as determined by immunofluorescence (FIG. 8A) and flow cytometry (FIG. 8B). Furthermore, relative to AAV8 and AAV9, LANKIQRTDA+V708I (SEQ ID NO:43) and LANKTTNKDA+V708I (SEQ ID NO:48) provided for faster onset of gene expression in human skeletal myofiber cultures, as determined by immunofluorescence (FIG. 8C). Relative to AAV8 and AAV9, the number of infectious units per administered viral genome were multiple fold magnitude higher for LANKIQRTDA+V708I (SEQ ID NO:43), LANKTTNKDA+V708I (SEQ ID NO:48), and the AAV6/5 chimera (FIG. 10B). This study illustrates the superior ability of NKIQRTD (SEQ ID NO:13)-, NKTTNKD (SEQ ID NO:14)-, and SEQ ID NO:62-comprising variants to deliver genes to skeletal myofibers.

Example 5

The cell tropism of recombinant AAV virions comprising the novel AAV variants LANKIQRTDA+V708I (SEQ ID NO:43), LANKTTNKDA+V708I (SEQ ID NO:48), and AAV6/AAV5 chimera for skeletal muscle progenitor cells was assessed in vitro using skeletal muscle progenitor cells generated from fibroblast-derived human induced pluripotent stem cells (FB-iPSC) or human embryonic stem cells (ESC).

Recombinant AAV virions comprising either an AAV9 capsid, the novel variant capsid LANKIQRTDA+V708I (SEQ ID NO:43), the novel variant capsid LANKTTNKDA+V708I (SEQ ID NO:48), or the novel variant capsid AAV6/AAV5 chimera and a genome comprising a green fluorescent protein (EGFP) transgene operably linked to a CAG promoter (AAV8.CAG.EGFP, AAV9.CAG.EGFP, LANKIQRTDA+V708I (SEQ ID NO:43).CAG.EGFP, LANKTTNKDA+V708I (SEQ ID NO:48).CAG.EGFP, and AAV6/AAV5 chimera.CAG.GFP, respectively) were manufactured using standard methods. Skeletal muscle progenitors were generated from a human embryonic stem cell line, ESI-017 (ESI-BIO) following the differentiation strategy described in Shelton et al. Methods, 2016 with minor modifications. After approximately 40 days of differentiation, lineage restriction to skeletal muscle progenitors was confirmed by expression of PAX7, and MyoD in the majority of cells prior to using the cultures for vector characterization.

Figure 9A:
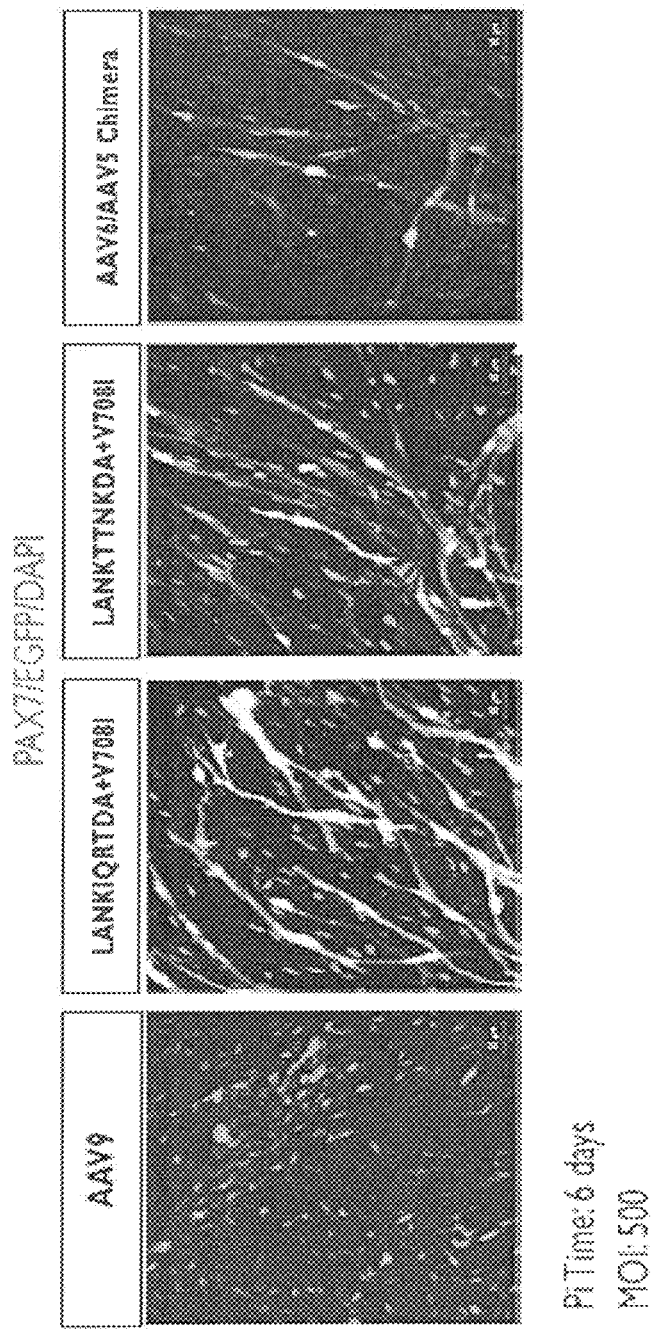
FIGS. 9A-B provide data on the transduction of human muscle progenitor cells in vitro by recombinant AAV virus comprising the novel AAV variant LANKIQRTDA+V708I (SEQ ID NO:43) capsid, the novel AAV variant LANKTTNKDA+V708I (SEQ ID NO:48) capsid, and the novel AAV variant AAV6/AAV5 chimera capsid, each expressing a GFP transgene under the control of the CAG promoter.
Figure 9B:
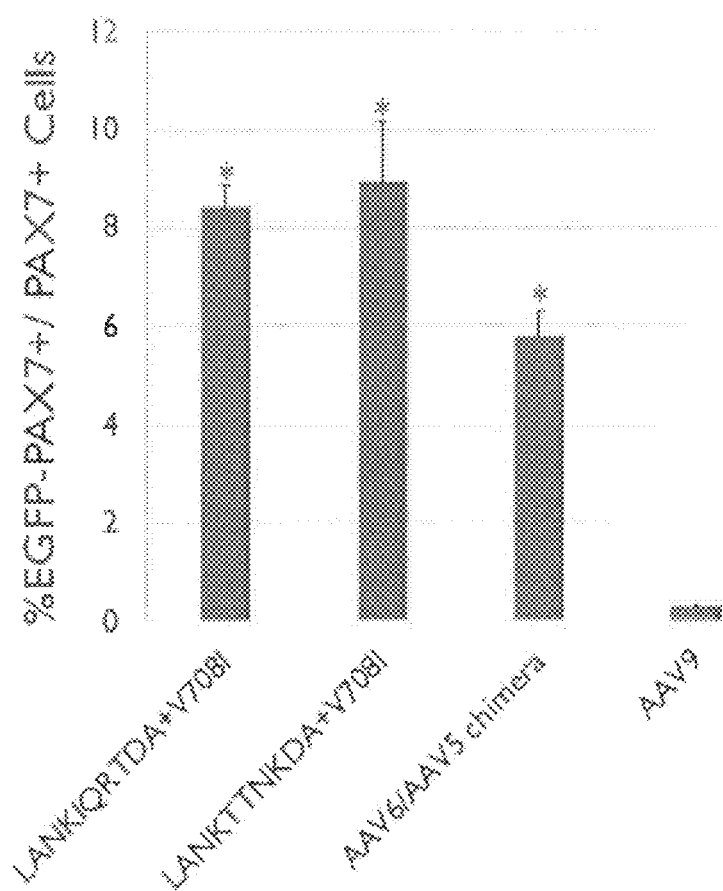

Relative to AAV9, the LANKIQRTDA+V708I (SEQ ID NO:43), LANKTTNKDA+V708I (SEQ ID NO:48), and AAV6/AAV5 chimera provided for significantly higher transduction efficiency of and transgene expression in human skeletal muscle progenitor cultures six days post-infection as determined by immunofluorescence (FIG. 9A) and flow cytometry (FIG. 9B). This study illustrates the superior ability of NKIQRTD (SEQ ID NO:13)-, NKTTNKD (SEQ ID NO:14)-, and SEQ ID NO:62-comprising AAV capsid variants to deliver genes to skeletal muscle progenitors.

Example 6

Directed evolution was employed to discover novel adeno-associated virus (AAV) variants with superior gene delivery to cardiac and skeletal muscle cells following intravenous (IV) administration, a route of administration with significant advantages over other methods of gene delivery to the human heart and skeletal muscle (Example 1). The cell tropism following intramuscular administration of recombinant AAV virions comprising the novel AAV variant comprising a V708I substitution and the peptide LANKIQRTDA (SEQ ID NO:27) inserted between amino acids 587 and 588 (LANKIQRTDA+V708I; SEQ ID NO:43) was assessed in vivo in mice as a representative example of the ability of rAAV virions comprising NKIQRTD (SEQ ID NO:13)-containing AAV capsid variants to transduce muscle cells.

Figure 11A:
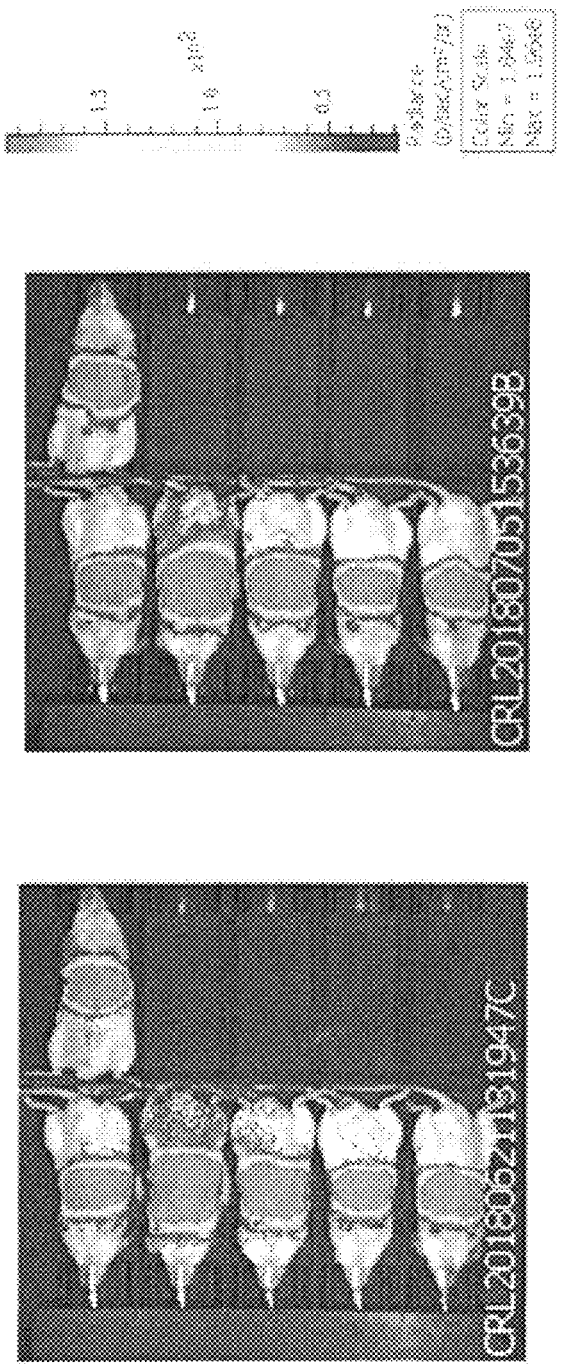
FIGS. 11A-B provide data on the transduction of mouse tissue in vivo by recombinant AAV virus comprising the novel AAV variant LANKIQRTDA+V708I (SEQ ID NO:43) capsid expressing a luciferase transgene under the control of the CAG promoter. The mice were given a single intravenous injection via the tail vein of $2 \times 10^{11}$ viral genomes per animal. Figure h A: In life imaging of luciferase at day 14 (left) and day 28 (right) post-administration demonstrate that the novel AAV variant LANKIQRTDA+ V708I (SEQ ID NO:43) capsid can transduce mouse cells in vivo.
Figure 11B:
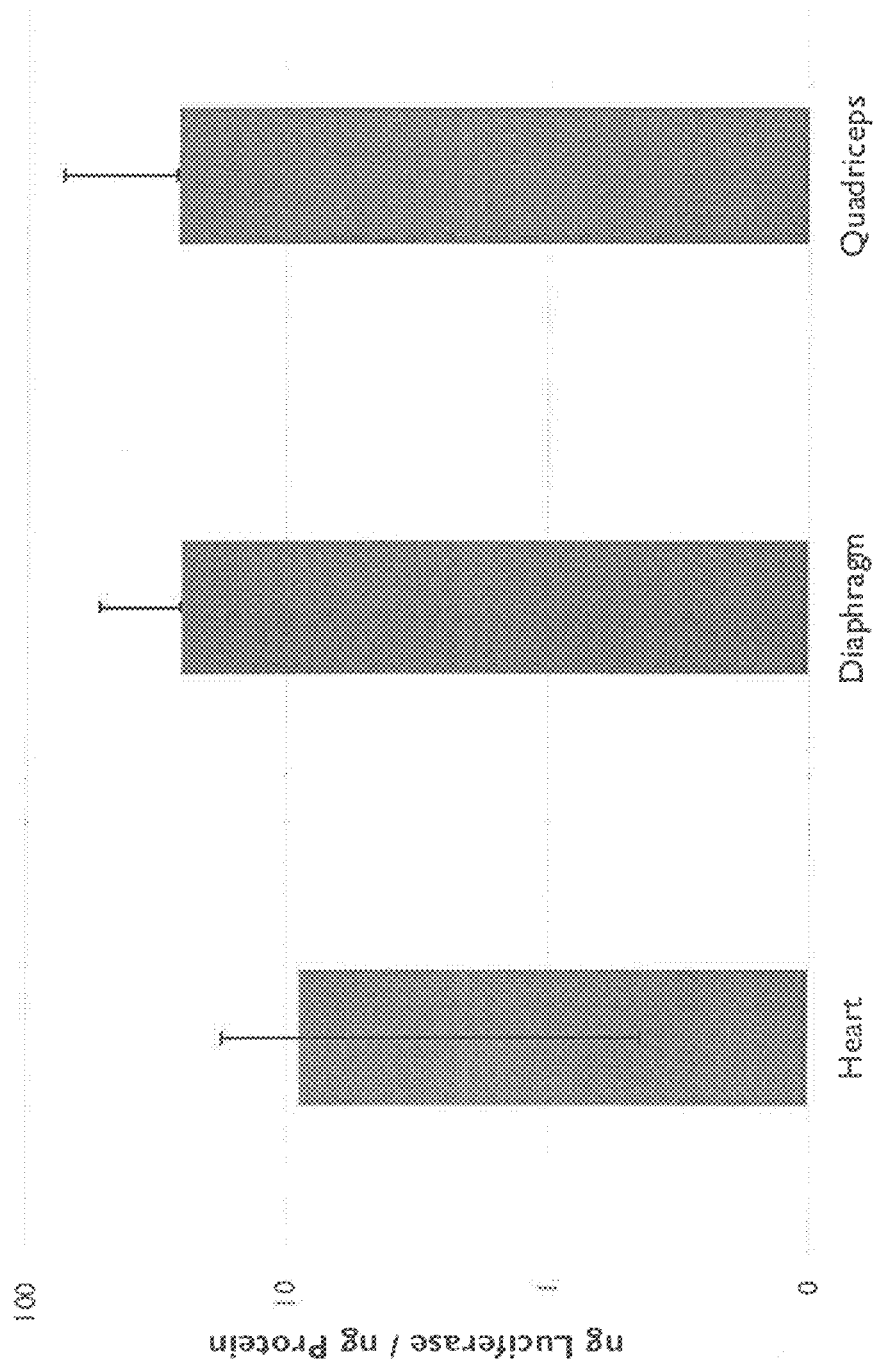

Recombinant AAV virions comprising the novel variant capsid LANKIQRTDA+V708I (SEQ ID NO:43) and a genome comprising a luciferase transgene operably linked to a CAG promoter (LANKIQRTDA+V708I (SEQ ID NO:43).CAG.luciferase) were manufactured using standard methods. B6 Albino (C57BL/6) mice were injected via tail vein intravenous injection with of $2\times10^{12}$ vg, and transduction was assessed in-life by luciferase imaging and post-mortem by tissue luciferase activity. In life imaging of luciferase at day 14 (left) and day 28 (right) post-administration demonstrate that the novel AAV variant LANKIQRTDA+V708I (SEQ ID NO:43) capsid can transduce mouse cells in vivo (FIG. 11A). Luciferase activity in heart, diaphragm, and quadriceps 56 days post-administration demonstrate that the novel AAV variant LANKIQRTDA+V708I (SEQ ID NO:43) capsid can transduce mouse cardiac and skeletal muscle in vivo (FIG. 11B).

This study illustrates gene delivery by the NKIQRTD (SEQ ID NO:13)-comprising variant following one of several clinically acceptable routes of administration. Similar efficacy is achievable with other variants comprising this peptide insertion motif. Likewise, similar efficacy is achievable with other variants disclosed herein that were identified using the same directed evolution approach.

Example 7

Directed evolution was employed to discover novel adeno-associated virus (AAV) variants with superior gene delivery to cardiac and skeletal muscle cells following intravenous (IV) administration, a route of administration with significant advantages over other methods of gene delivery to the human heart and skeletal muscle (Example 1). The cell tropism following intramuscular administration of recombinant AAV virions comprising the novel AAV variant comprising a V708I substitution and the peptide LANKIQRTDA (SEQ ID NO:27) inserted between amino acids 587 and 588 (LANKIQRTDA+V708I; SEQ ID NO:43) was assessed in vivo in non-human primates (NHP) as a representative example of the ability of rAAV variants comprising NKIQRTD (SEQ ID NO:13)-containing AAV capsid variants to transduce muscle cells.

Figure 12A:
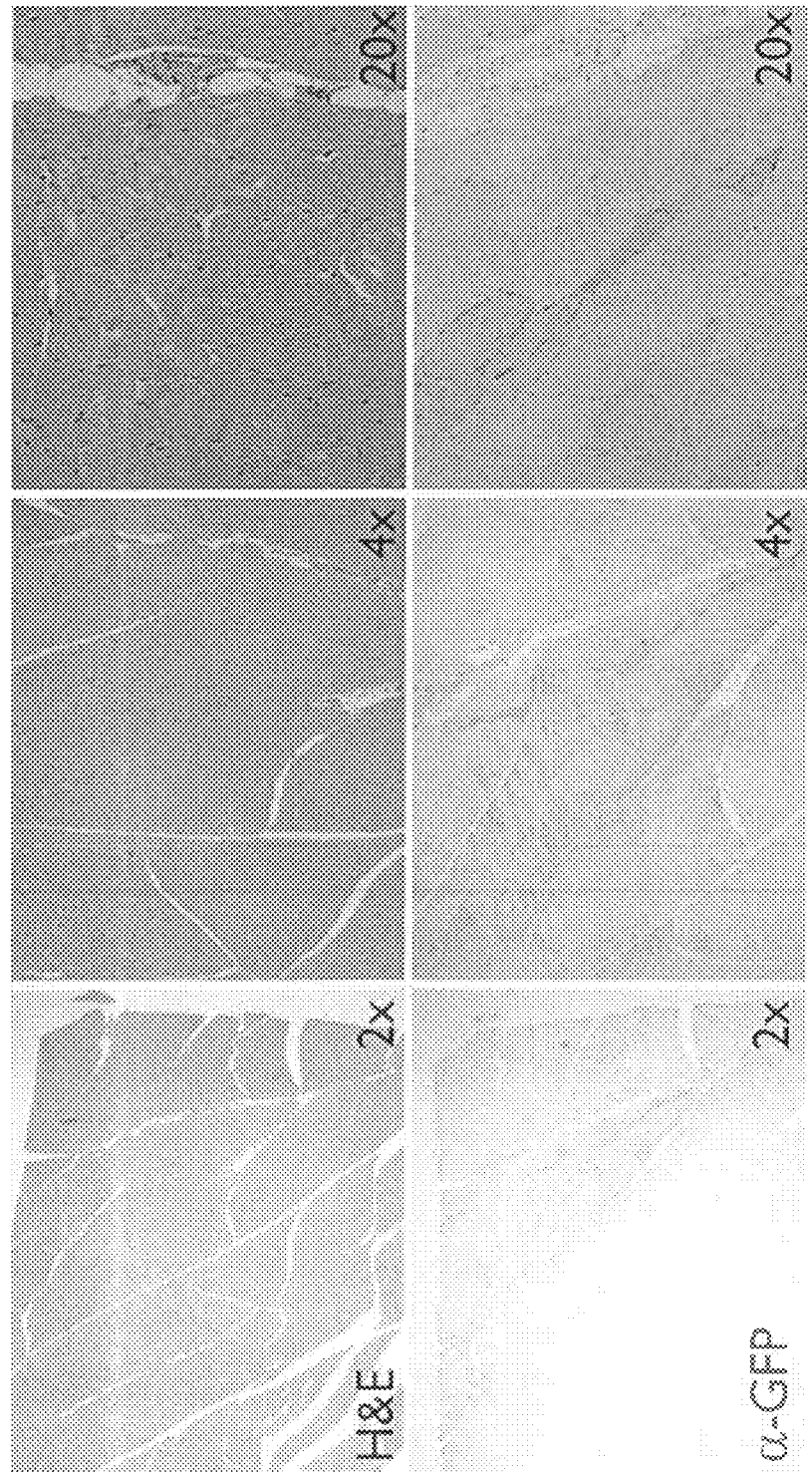
FIGS. 12A-B provide data on the transduction of non-human primate skeletal muscle in vivo by recombinant AAV virus comprising the novel AAV variant LANKIQRTDA+ V708I (SEQ ID NO:43) capsid expressing a GFP transgene under the control of the CAG promoter. The non-human primate was given 3 intramuscular injections of $10^{11}$ viral genomes each into the left vastus lateralis, and the muscle tissue was analyzed 4 weeks post-administration.
Figure 12B:
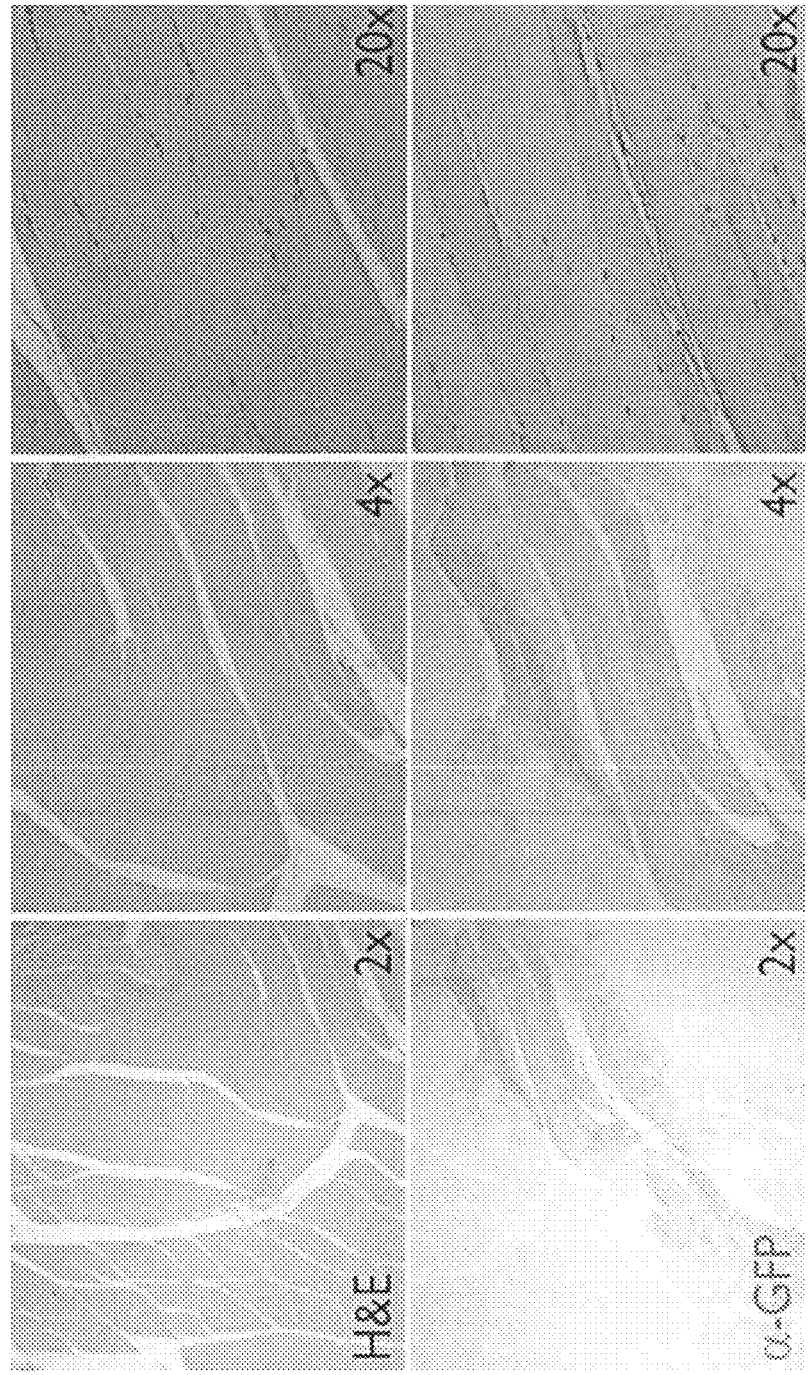

Recombinant AAV virions comprising the novel variant capsid LANKIQRTDA+V708I (SEQ ID NO:43) and a genome comprising a green fluorescent protein (GFP) transgene operably linked to a CAG promoter (LANKIQRTDA+V708I (SEQ ID NO:43).CAG.GFP) were manufactured using standard methods. Cynomolgus macaques were injected via intramuscular injection with three doses of vector into sites in the vastus lateralis of $1\times10^{11}$ vg and the transduction of skeletal muscle cells was assessed post-mortem by immunofluorescence imaging. Representative images of haemotoxylin and eosin (H&E) and anti-GFP antibody staining of cross-sections of the proximal biopsy site at 2×, 4×, and 20× magnification demonstrate that the novel AAV variant LANKIQRTDA+V708I (SEQ ID NO:43) capsid can transduce primate skeletal muscle cells in vivo (FIG. 12A). Representative images of haemotoxylin and eosin (H&E) and anti-GFP antibody staining of longitudinal sections of the distal biopsy site at 2×, 4×, and 20× magnification demonstrate that the novel AAV variant LANKIQRTDA+V708I capsid can transduce primate skeletal muscle cells in vivo (FIG. 12B).

This study illustrates gene delivery by the NKIQRTD (SEQ ID NO:13)-comprising variant following one of several clinically acceptable routes of administration. Similar efficacy is achievable with other variants comprising this peptide insertion motif. Likewise, similar efficacy is achievable with other variants disclosed herein that were identified using the same directed evolution approach.

The preceding merely illustrates the principles of the invention. It will be appreciated that those skilled in the art will be able to devise various arrangements Ill which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A recombinant adeno-associated virus (rAAV) comprising:
   (i) a variant AAV capsid protein comprising a heterologous peptide insertion with a length of 7 to 20 amino acids covalently inserted in the GH-loop of the capsid protein relative to a corresponding parental AAV capsid protein, wherein the peptide insertion comprises the amino acid sequence NKIQRTD (SEQ ID NO: 13) and
   (ii) a heterologous nucleic acid comprising a nucleotide sequence encoding a gene product.

2. The rAAV of claim 1, wherein the insertion peptide has from 1 to 3 spacer amino acids ($Y_1$-$Y_3$) at the amino and/or carboxyl terminus of amino acid sequence NKIQRTD (SEQ ID NO: 13).

3. The rAAV of claim 2, wherein the insertion peptide is LANKIQRTDA (SEQ ID NO: 27).

4. The rAAV of claim 3, wherein the variant capsid protein comprises a V708I amino acid substitution relative to VP1 of AAV2 (SEQ ID NO:2) and wherein the variant capsid protein comprises an amino acid sequence at least 90% identical to the entire length of the amino acid sequence set forth as SEQ ID NO:43.

5. The rAAV of claim 4, wherein the variant capsid protein comprises an amino acid sequence at least 95% identical to the entire length of the amino acid sequence set forth as SEQ ID NO:43.

6. A pharmaceutical composition comprising the rAAV of claim 4 and a pharmaceutically acceptable carrier, wherein the pharmaceutical composition comprises from $1 \times 10^{11}$ to $1 \times 10^{15}$ rAAV virions.

7. The rAAV of claim 1, wherein the insertion site is located between two adjacent amino acids at a position between amino acids 570 and 611 of VP1 of AAV2 (SEQ ID NO:2), or the corresponding position in the capsid protein of another AAV serotype, wherein the insertion site is located within:
   (i) amino acids 571-612 of AAV1 VP1,
   (ii) amino acids 571-612 of AAV3A VP1,
   (iii) amino acids 571-612 of AAV3B VP1,
   (iv) amino acids 569-610 of AAV4 VP1,
   (v) amino acids 560-601 of AAV5 VP1,
   (vi) amino acids 571-612 of AAV6 VP1,
   (vii) amino acids 572-613 of AAV7 VP1,
   (viii) amino acids 573-614 of AAV8 VP1,
   (ix) amino acids 571-612 of AAV9 VP1, or
   (x) amino acids 573-614 of AAV10 VP1.

8. The rAAV of claim 7, wherein the insertion site is located between amino acids corresponding to amino acids 587 and 588 of VP1 of AAV2 (SEQ NO:2) or between amino acids corresponding to amino acids 588 and 589 of VP1 of AAV2 (SEQ ID NO:2) or the corresponding position in the capsid protein of another AAV serotype, wherein the insertion site is located between:
   (i) amino acids 590 and 591 or amino acids 591 and 592 of AAV1 VP1,
   (ii) amino acids 588 and 589 or amino acids 589 and 590 of AAV3A VP1,
   (iii) amino acids 588 and 589 or amino acids 589 and 590 of AAV3B VP1,
   (iv) amino acids 584 and 585 or amino acids 585 and 586 of AAV4 VP1,
   (v) amino acids 575 and 576 or amino acids 576 and 577 of AAV5 VP1,
   (vi) amino acids 590 and 591 or amino acids 591 and 592 of AAV6 VP1,
   (vii) amino acids 589 and 590 or amino acids 590 and 591 of AAV7 VP1,
   (viii) amino acids 590 and 591 or amino acids 591 and 592 of AAV8 VP1,
   (ix) amino acids 588 and 589 or amino acids 589 and 590 of AAV9 VP1, or
   (x) amino acids 588 and 589 or amino acids 589 and 590 of AAV10 VP1.

9. The rAAV of claim 1, wherein the gene product is a protein, a small interfering RNA, an antisense RNA, a microRNA, and/or a short hairpin RNA.

10. The rAAV of claim 9, wherein the gene product is a protein selected from alpha galactosidase A (GLA), frataxin (FXN), dystrophin (DMD) or a functional fragment thereof, acid alpha glucosidase (GAA), and glycogen phosphorylase, muscle (PYGM).

11. The rAAV of claim 10, wherein the gene product is GLA.

12. The rAAV of claim 11, wherein the nucleotide sequence encoding GLA is operably linked to a CAG or CBA promoter.

13. The rAAV of claim 10, wherein the gene product is frataxin.

14. A pharmaceutical composition comprising the rAAV of claim 13 and a pharmaceutically acceptable carrier.

15. The rAAV of claim 10, wherein the gene product is dystrophin or a functional fragment thereof.

16. A pharmaceutical composition comprising the rAAV of claim 15 and a pharmaceutically acceptable carrier, wherein the pharmaceutical composition comprises from $1 \times 10^{11}$ to $1 \times 10^{15}$ rAAV virions.

17. The rAAV of claim 10, wherein the gene product is GAA.

18. The rAAV of claim 10, wherein the gene product is PYGM.

19. A pharmaceutical composition comprising the rAAV of claim 1 and a pharmaceutically acceptable carrier.

20. The pharmaceutical composition of claim 19, comprising from $1 \times 10^{11}$ to $1 \times 10^{15}$ rAAV virions.

* * * * *

SEQUENCE LISTING

```
Sequence total quantity: 69
SEQ ID NO: 1             moltype = AA  length = 736
FEATURE                  Location/Qualifiers
source                   1..736
                         mol_type = protein
                         organism = Adeno-associated virus 1
SEQUENCE: 1
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
```

```
TTSTRTWALP  TYNNHLYKQI  SSASTGASND  NHYFGYSTPW  GYFDFNRFHC  HFSPRDWQRL   300
INNNWGFRPK  RLNFKLFNIQ  VKEVTTNDGV  TTIANNLTST  VQVFSDSEYQ  LPYVLGSAHQ   360
GCLPPFPADV  FMIPQYGYLT  LNNGSQAVGR  SSFYCLEYFP  SQMLRTGNNF  TFSYTFEEVP   420
FHSSYAHSQS  LDRLMNPLID  QYLYYLNRTQ  NQSGSAQNKD  LLFSRGSPAG  MSVQPKNWLP   480
GPCYRQQRVS  KTKTDNNNSN  FTWTGASKYN  LNGRESIINP  GTAMASHKDD  EDKFFPMSGV   540
MIFGKESAGA  SNTALDNVMI  TDEEEIKATN  PVATERFGTV  AVNFQSSSTD  PATGDVHAMG   600
ALPGMVWQDR  DVYLQGPIWA  KIPHTDGHFH  PSPLMGGFGL  KNPPPQILIK  NTPVPANPPA   660
EFSATKFASF  ITQYSTGQVS  VEIEWELQKE  NSKRWNPEVQ  YTSNYAKSAN  VDFTVDNNGL   720
YTEPRPIGTR  YLTRPL                                                      736

SEQ ID NO: 2            moltype = AA  length = 735
FEATURE                 Location/Qualifiers
source                  1..735
                        mol_type = protein
                        organism = adeno-associated virus 2
SEQUENCE: 2
MAADGYLPDW  LEDTLSEGIR  QWWKLKPGPP  PKPAERHKD   DSRGLVLPGY  KYLGPFNGLD    60
KGEPVNEADA  AALEHDKAYD  RQLDSGDNPY  LKYNHADAEF  QERLKEDTSF  GGNLGRAVFQ   120
AKKRVLEPLG  LVEEPVKTAP  GKKRPVEHSP  VEPDSSSGTG  KAGQQPARKR  LNFGQTGDAD   180
SVPDPQPLGQ  PPAAPSGLGT  NTMATGSGAP  MADNNEGADG  VGNSSGNWHC  DSTWMGDRVI   240
TTSTRTWALP  TYNNHLYKQI  SSQSGASNDN  HYFGYSTPWG  YFDFNRFHCH  FSPRDWQRLI   300
NNNWGFRPKR  LNFKLFNIQV  KEVTQNDGTT  TIANNLTSTV  QVFTDSEYQL  PYVLGSAHQG   360
CLPPFPADVF  MVPQYGYLTL  NNGSQAVGRS  SFYCLEYFPS  QMLRTGNNFT  FSYTFEDVPF   420
HSSYAHSQSL  DRLMNPLIDQ  YLYYLSRTNT  PSGTTTQSRL  QFSQAGASDI  RDQSRNWLPG   480
PCYRQRVSK  TSADNNNSEY  SWTGATKYHL  NGRDSLVNPG  PAMASHKDDE  EKFFPQSGVL   540
IFGKQGSEKT  NVDIEKVMIT  DEEEIRTTNP  VATEQYGSVS  TNLQRGNRQA  ATADVNTQGV   600
LPGMVWQDRD  VYLQGPIWAK  IPHTDGHFHP  SPLMGGFGLK  HPPPQILIKN  TPVPANPSTT   660
FSAAKFASFI  TQYSTGQVSV  EIEWELQKEN  SKRWNPEIQY  TSNYNKSVNV  DFTVDTNGVY   720
SEPRPIGTRY  LTRNL                                                       735

SEQ ID NO: 3            moltype = AA  length = 736
FEATURE                 Location/Qualifiers
source                  1..736
                        mol_type = protein
                        organism = Adeno-associated virus 3A
SEQUENCE: 3
MAADGYLPDW  LEDNLSEGIR  EWWALKPGVP  QPKANQQHQD  NRRGLVLPGY  KYLGPGNGLD    60
KGEPVNEADA  AALEHDKAYD  QQLKAGDNPY  LKYNHADAEF  QERLQEDTSF  GGNLGRAVFQ   120
AKKRILEPLG  LVEEAAKTAP  GKKRGAVDQSP  QEPDSSGVG  KSGKQPARKR  LNFGQTGDSE   180
SVPDPQPLGE  PPAAPTSLGS  NTMASGGGAP  MADNNEGADG  VGNSSGNWHC  DSQWLGDRVI   240
TTSTRTWALP  TYNNHLYKQI  SSQSGASNDN  HYFGYSTPWG  YFDFNRFHCH  FSPRDWQRLI   300
NNNWGFRPKK  LSFKLFNIQV  RGVTQNDGTT  TIANNLTSTV  QVFTDSEYQL  PYVLGSAHQG   360
CLPPFPADVF  MVPQYGYLTL  NNGSQAVGRS  SFYCLEYFPS  QMLRTGNNFQ  FSYTFEDVPF   420
HSSYAHSQSL  DRLMNPLIDQ  YLYYLNRTQG  TTSGTTNQSR  LLFSQAGPQS  MSLQARNWLP   480
GPCYRQQRLS  KTANDNNNSN  FPWTAASKYH  LNGRDSLVNP  GPAMASHKDD  EEKFFPMHGN   540
LIFGKEGTTA  SNAELDNVMI  TDEEEIRTTN  PVATEQYGTV  ANNLQSSNTA  PTTGTVNHQG   600
ALPGMVWQDR  DVYLQGPIWA  KIPHTDGHFH  PSPLMGGFGL  KHPPPQIMIK  NTPVPANPPT   660
TFSPAKFASF  ITQYSTGQVS  VEIEWELQKE  NSKRWNPEIQ  YTSNYNKSVN  VDFTVDTNGV   720
YSEPRPIGTR  YLTRNL                                                      736

SEQ ID NO: 4            moltype = AA  length = 736
FEATURE                 Location/Qualifiers
source                  1..736
                        mol_type = protein
                        organism = Adeno-associated virus 3B
SEQUENCE: 4
MAADGYLPDW  LEDNLSEGIR  EWWALKPGVP  QPKANQQHQD  NRRGLVLPGY  KYLGPGNGLD    60
KGEPVNEADA  AALEHDKAYD  QQLKAGDNPY  LKYNHADAEF  QERLQEDTSF  GGNLGRAVFQ   120
AKKRILEPLG  LVEEAAKTAP  GKKRPVDQSP  QEPDSSSGVG  KSGKQPARKR  LNFGQTGDSE   180
SVPDPQPLGE  PPAAPTSLGS  NTMASGGGAP  MADNNEGADG  VGNSSGNWHC  DSQWLGDRVI   240
TTSTRTWALP  TYNNHLYKQI  SSQSGASNDN  HYFGYSTPWG  YFDFNRFHCH  FSPRDWQRLI   300
NNNWGFRPKK  LSFKLFNIQV  KEVTQNDGTT  TIANNLTSTV  QVFTDSEYQL  PYVLGSAHQG   360
CLPPFPADVF  MVPQYGYLTL  NNGSQAVGRS  SFYCLEYFPS  QMLRTGNNFQ  FSYTFEDVPF   420
HSSYAHSQSL  DRLMNPLIDQ  YLYYLNRTQG  TTSGTTNQSR  LLFSQAGPQS  MSLQARNWLP   480
GPCYRQQRLS  KTANDNNNSN  FPWTAASKYH  LNGRDSLVNP  GPAMASHKDD  EEKFFPMHGN   540
LIFGKEGTTA  SNAELDNVMI  TDEEEIRTTN  PVATEQYGTV  ANNLQSSNTA  PTTRTVNDQG   600
ALPGMVWQDR  DVYLQGPIWA  KIPHTDGHFH  PSPLMGGFGL  KHPPPQIMIK  NTPVPANPPT   660
TFSPAKFASF  ITQYSTGQVS  VEIEWELQKE  NSKRWNPEIQ  YTSNYNKSVN  VDFTVDTNGV   720
YSEPRPIGTR  YLTRNL                                                      736

SEQ ID NO: 5            moltype = AA  length = 734
FEATURE                 Location/Qualifiers
source                  1..734
                        mol_type = protein
                        organism = Adeno-associated virus 4
SEQUENCE: 5
MTDGYLPDWL  EDNLSEGVRE  WWALQPGAPK  PKANQQHQDN  ARGLVLPGYK  YLGPGNGLDK    60
GEPVNAADAA  ALEHDKAYDQ  QLKAGDNPYL  KYNHADAEFQ  QRLQGDTSFG  GNLGRAVFQA   120
KKRVLEPLGL  VEQAGETAPG  KKRPLIESPQ  QPDSSTGIGK  GKQPAKKKL  VFEDETGAGD   180
```

```
GPPEGSTSGA MSDDSEMRAA AGGAAVEGGQ GADVGNASG  DWHCDSTWSE GHVTTTSTRT      240
WVLPTYNNHL YKRLGESLQS NTYNGFSTPW GYFDFNRFHC HFSPRDWQRL INNNWGMRPK      300
AMRVKIFNIQ VKEVTTSNGE TTVANNLTST VQIFADSSYE LPYVMDAGQE GSLPPFPNDV      360
FMVPQYGYCG LVTGNTSQQQ TDRNAFYCLE YFPSQMLRTG NNFEITYSFE KVPFHSMYAH      420
SQSLDRLMNP LIDQYLWGLQ STTTGTTLNA GTATTNFTKL RPTNFSNFKK NWLPGPSIKQ      480
QGFSKTANQN YKIPATGSDS LIKYETHSTL DGRWSALTPG PPMATAGPAD SKFSNSQLIF      540
AGPKQNGNTA TVPGTLIFTS EEELAATNAT DTDMWGNLPG GDQSNSNLPT VDRLTALGAV      600
PGMVWQNRDI YYQGPIWAKI PHTDGHFHPS PLIGGFGLKH PPPQIFIKNT PVPANPATTF      660
SSTPVNSFIT QYSTGQVSVQ IDWEIQKERS KRWNPEVQFT SNYGQQNSLL WAPDAAGKYT      720
EPRAIGTRYL THHL                                                       734

SEQ ID NO: 6            moltype = AA  length = 724
FEATURE                 Location/Qualifiers
source                  1..724
                        mol_type = protein
                        organism = Adeno-associated virus 5
SEQUENCE: 6
MSFVDHPPDW LEEVGEGLRE FLGLEAGPPK PKPNQQHQDQ ARGLVLPGYN YLGPGNGLDR       60
GEPVNRADEV AREHDISYNE QLEAGDNPYL KYNHADAEFQ EKLADDTSFG GNLGKAVFQA      120
KKRVLEPFGL VEEGAKTAPT GKRIDDHFPK RKKARTEEDS KPSTSSDAEA GPSGSQQLQI      180
PAQPASSLGA DTMSAGGGGP LGDNNQGADG VGNASGDWHC DSTWMGDRVV TKSTRTWVLP      240
SYNNHQYREI KSGSVDGSNA NAYFGYSTPW GYFDFNRFHC HWSPRDWQRL INNYWGFRPR      300
SLRVKIFNIQ VKEVTVQDST TTIANNLTST VQVFTDDDYQ LPYVVGNGTE GCLPAFPPQV      360
FTLPQYGYAT LNRDNTENPT ERSSFFCLEY FPSKMLRTGN NFEFTYNFEE VPFHSSFAPS      420
QNLFKLANPL VDQYLYRFVS TNNTGGVQFN KNLAGRYANT YKNWFPGPMG RTQGWNLGSG      480
VNRASVSAFA TTNRMELEGA SYQVPPQPNG MTNNLQGSNT YALENTMIFN SQPANPGTTA      540
TYLEGNMLIT SESETQPVNR VAYNVGGQMA TNNQSSTTAP ATGTYNLQEI VPGSVWMERD      600
VYLQGPIWAK IPETGAHFHP SPAMGGFGLK HPPPMMLIKN TPVPGNITSF SDVPVSSFIT      660
QYSTGQVTVE MEWELKKENS KRWNPEIQYT NNYNDPQFVD FAPDSTGEYR TTRPIGTRYL      720
TRPL                                                                  724

SEQ ID NO: 7            moltype = AA  length = 736
FEATURE                 Location/Qualifiers
source                  1..736
                        mol_type = protein
                        organism = Adeno-associated virus 6
SEQUENCE: 7
MAADGYLPDW LEDNLSEGIR EWWDLKPGAP KPKANQQKQD DGRGLVLPGY KYLGPFNGLD       60
KGEPVNAADA AALEHDKAYD QQLKAGDNPY LRYNHADAEF QERLQEDTSF GGNLGRAVFQ      120
AKKRVLEPFG LVEEGAKTAP GKKRPVEQSP QEPDSSSGIG KTGQQPAKKR LNFGQTGDSE      180
SVPDPQPLGE PPATPAAVGP TTMASGGGAP MADNNEGADG VGNASGNWHC DSTWLGDRVI      240
TTSTRTWALP TYNNHLYKQI SSASTGASND NHYFGYSTPW GYFDFNRFHC HFSPRDWQRL      300
INNNWGFRPK RLNFKLFNIQ VKEVTTNDGV TTIANNLTST VQVFSDSEYQ LPYVLGSAHQ      360
GCLPPFPADV FMIPQYGYLT LNNGSQAVGR SSFYCLEYFP SQMLRTGNNF TFSYTFEDVP      420
FHSSYAHSQS LDRLMNPLID QYLYYLNRTQ NQSGSAQNKD LLFSRGSPAG MSVQPKNWLP      480
GPCYRQQRVS KTKTDNNNSN FTWTGASKYN LNGRESIINP GTAMASHKDD KDKFFPMSGV      540
MIFGKESAGA SNTALDNVMI TDEEEIKATN PVATERFGTV AVNLQSSSTD PATGDVHVMG      600
ALPGMVWQDR DVYLQGPIWA KIPHTDGHFH PSPLMGGFGL KHPPPQILIK NTPVPANPPA      660
EFSATKPASF ITQYSTGQVS VEIEWELQKE NSKRWNPEVQ YTSNYAKSAN VDFTVDNNGL      720
YTEPRPIGTR YLTRPL                                                     736

SEQ ID NO: 8            moltype = AA  length = 737
FEATURE                 Location/Qualifiers
source                  1..737
                        mol_type = protein
                        organism = Adeno-associated virus 7
SEQUENCE: 8
MAADGYLPDW LEDNLSEGIR EWWDLKPGAP KPKANQQKQD NGRGLVLPGY KYLGPFNGLD       60
KGEPVNAADA AALEHDKAYD QQLKAGDNPY LRYNHADAEF QERLQEDTSF GGNLGRAVFQ      120
AKKRVLEPLG LVEEGAKTAP AKKRPVEPSP QRSPDSSTGI GKKGQQPARK RLNFGQTGDS      180
ESVPDPQPLG EPPAAPSSVG SGTVAAGGGA PMADNNEGAD GVGNASGNWH CDSTWLGDRV      240
ITTSTRTWAL PTYNNHLYKQ ISSETAGSTN DNTYFGYSTP WGYFDFNRFH CHFSPRDWQR      300
LINNNWGFRP KKLRFKLFNI QVKEVTTNDG VTTIANNLTS TVQVFSDSEY QLPYVLGSAH      360
QGCLPPFPAD VFMIPQYGYL TLNNGSQSVG RSSFYCLEYF PSQMLRTGNN FEFSYSFEDV      420
PFHSSYAHSQ SLDRLMNPLI DQYLYYLART QSNPGGTAGN RELQFYQGGP STMAEQAKNW      480
LPGPCFRQQR VSKTLDQNNN SNFAWTGATK YHLNGRNSLV NPGVAMATHK DDEDRFFPSS      540
GVLIFGKTGA TNKTTLENVL MTNEEEIRPT NPVATEEYGI VSSNLQAANT AAQTQVVNNQ      600
GALPGMVWQN RDVYLQGPIW AKIPHTDGNF HPSPLMGGFG LKHPPPQILI KNTPVPANPP      660
EVFTPAKFAS FITQYSTGQV SVEIEWELQK ENSKRWNPEI QYTSNFEKQT GVDFAVDSQG      720
VYSEPRPIGT RYLTRNL                                                    737

SEQ ID NO: 9            moltype = AA  length = 738
FEATURE                 Location/Qualifiers
source                  1..738
                        mol_type = protein
                        organism = Adeno-associated virus 8
SEQUENCE: 9
MAADGYLPDW LEDNLSEGIR EWWALKPGAP KPKANQQKQD DGRGLVLPGY KYLGPFNGLD       60
KGEPVNAADA AALEHDKAYD QQLQAGDNPY LRYNHADAEF QERLQEDTSF GGNLGRAVFQ      120
```

```
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTTTGQNNN SNFAWTAGTK YHLNGRNSLA NPGIAMATHK DDEERFFPSN    540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                 738

SEQ ID NO: 10             moltype = AA  length = 736
FEATURE                   Location/Qualifiers
source                    1..736
                          mol_type = protein
                          organism = Adeno-associated virus 9
SEQUENCE: 10
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 11             moltype = AA  length = 738
FEATURE                   Location/Qualifiers
source                    1..738
                          mol_type = protein
                          organism = Adeno-associated virus 10
SEQUENCE: 11
MAADGYLPDW LEDNLSEGIR EWWDLKPGAP KPKANQQKQD DGRGLVLPGY KYLGPFNGLD     60
KGEPVNAADA AALEHDKAYD QQLKAGDNPY LRYNHADAEF QERLQEDTSF GGNLGRAVFQ    120
AKKRVLEPLG LVEEAAKTAP GKKRPVEPSP QRSPDSSTGI GKKGQQPAKK RLNFGQTGES    180
ESVPDPQPIG EPPAGPSGLG SGTMAAGGGA PMADNNEGAD GVGSSSGNWH CDSTWLGDRV    240
ITTSTRTWAL PTYNNHLYKQ ISNGTSGGST NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFEFSYTFED    420
VPFHSSYAHS QSLDRLMNPL IDQYLYYLSR TQSTGGTQGT QQLLFSQAGP ANMSAQAKNW    480
LPGPCYRQQR VSTTLSQNNN SNFAWTGATK YHLNGRDSLV NPGVAMATHK DDEERFFPSS    540
GVLMFGKQGA GRDNVDYSSV MLTSEEEIKT TNPVATEQYG VVADNLQQAN TGPIVGNVNS    600
QGALPGMVWQ NRDVYLQGPI WAKIPHTDGN FHPSPLMGGF GLKHPPPQIL IKNTPVPADP    660
PTTFSQAKLA SFITQYSTGQ VSVEIEWELQ KENSKRWNPE IQYTSNYYKS TNVDFAVNTE    720
GTYSEPRPIG TRYLTRNL                                                 738

SEQ ID NO: 12             moltype = AA  length = 738
FEATURE                   Location/Qualifiers
source                    1..738
                          mol_type = protein
                          organism = Adeno-associated virus rh10
SEQUENCE: 12
MAADGYLPDW LEDNLSEGIR EWWALKPGAP KPKANQQKQD DGRGLVLPGY KYLGPFNGLD     60
KGEPVNAADA AALEHDKAYD QQLKAGDNPY LRYNHADAEF QERLQEDTSF GGNLGRAVFQ    120
AKKRVLEPLG LVEEGAKTAP GKKRPVEPSP QRSPDSSTGI GKKGQQPAKK RLNFGQTGDS    180
ESVPDPQPIG EPPAGPSGLG SGTMAAGGGA PMADNNEGAD GVGSSSGNWH CDSTWLGDRV    240
ITTSTRTWAL PTYNNHLYKQ ISNGTSGGST NDNTYFGYST PWGYFDFNRF HCHFSPRDWQ    300
RLINNNWGFR PKSLNFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFEFSYQFED    420
VPFHSSYAHS QSLDRLMNPL IDQYLYYLSR TQSTGGTAGT QQLLFSQAGP NNMSAQAKNW    480
LPGPCYRQQR VSTTLSQNDN SNFAWTGATK YHLNGRDSLV NPGVAMATHK DDEERFFPSS    540
GVLMFGKQGA GKDNVDYSSV MLTSEEEIKT TNPVATEQYG VVADNLQQAN AAPIVGAVNS    600
QGALPGMVWQ NRDVYLQGPI WAKIPHTDGN FHPSPLMGGF GLKHPPPQIL IKNTPVPADP    660
PTTFSQAKLA SFITQYSTGQ VSVEIEWELQ KENSKRWNPE IQYTSNYYKS TNVDFAVNTD    720
GTYSEPRPIG TRYLTRNL                                                 738

SEQ ID NO: 13             moltype = AA  length = 7
FEATURE                   Location/Qualifiers
REGION                    1..7
                          note = heterologous peptide insertion
source                    1..7
                          mol_type = protein
                          organism = synthetic construct
```

```
SEQUENCE: 13
NKIQRTD                                                                    7

SEQ ID NO: 14            moltype = AA  length = 7
FEATURE                  Location/Qualifiers
REGION                   1..7
                         note = heterologous peptide insertion
source                   1..7
                         mol_type = protein
                         organism = synthetic construct
SEQUENCE: 14
NKTTNKD                                                                    7

SEQ ID NO: 15            moltype = AA  length = 7
FEATURE                  Location/Qualifiers
REGION                   1..7
                         note = heterologous peptide insertion
source                   1..7
                         mol_type = protein
                         organism = synthetic construct
SEQUENCE: 15
TNKIGVT                                                                    7

SEQ ID NO: 16            moltype = AA  length = 7
FEATURE                  Location/Qualifiers
REGION                   1..7
                         note = heterologous peptide insertion
source                   1..7
                         mol_type = protein
                         organism = synthetic construct
SEQUENCE: 16
GNLTKGN                                                                    7

SEQ ID NO: 17            moltype = AA  length = 7
FEATURE                  Location/Qualifiers
REGION                   1..7
                         note = heterologous peptide insertion
source                   1..7
                         mol_type = protein
                         organism = synthetic construct
SEQUENCE: 17
NTVKLST                                                                    7

SEQ ID NO: 18            moltype = AA  length = 7
FEATURE                  Location/Qualifiers
REGION                   1..7
                         note = heterologous peptide insertion
source                   1..7
                         mol_type = protein
                         organism = synthetic construct
SEQUENCE: 18
SNTVKAI                                                                    7

SEQ ID NO: 19            moltype = AA  length = 7
FEATURE                  Location/Qualifiers
REGION                   1..7
                         note = heterologous peptide insertion
source                   1..7
                         mol_type = protein
                         organism = synthetic construct
SEQUENCE: 19
ASNITKA                                                                    7

SEQ ID NO: 20            moltype = AA  length = 7
FEATURE                  Location/Qualifiers
REGION                   1..7
                         note = heterologous peptide insertion
source                   1..7
                         mol_type = protein
                         organism = synthetic construct
SEQUENCE: 20
DNTVTRS                                                                    7

SEQ ID NO: 21            moltype = AA  length = 7
FEATURE                  Location/Qualifiers
REGION                   1..7
                         note = heterologous peptide insertion
source                   1..7
                         mol_type = protein
```

```
                            organism = synthetic construct
SEQUENCE: 21
NKISAKD                                                                 7

SEQ ID NO: 22           moltype = AA  length = 7
FEATURE                 Location/Qualifiers
REGION                  1..7
                        note = heterologous peptide insertion
source                  1..7
                        mol_type = protein
                        organism = synthetic construct
SEQUENCE: 22
NQDYTKT                                                                 7

SEQ ID NO: 23           moltype = AA  length = 7
FEATURE                 Location/Qualifiers
REGION                  1..7
                        note = heterologous peptide insertion
source                  1..7
                        mol_type = protein
                        organism = synthetic construct
SEQUENCE: 23
QADTTKN                                                                 7

SEQ ID NO: 24           moltype = AA  length = 7
FEATURE                 Location/Qualifiers
REGION                  1..7
                        note = heterologous peptide insertion
source                  1..7
                        mol_type = protein
                        organism = synthetic construct
SEQUENCE: 24
TNRTSPD                                                                 7

SEQ ID NO: 25           moltype = AA  length = 7
FEATURE                 Location/Qualifiers
REGION                  1..7
                        note = heterologous peptide insertion
source                  1..7
                        mol_type = protein
                        organism = synthetic construct
SEQUENCE: 25
SNTTQKT                                                                 7

SEQ ID NO: 26           moltype = AA  length = 7
FEATURE                 Location/Qualifiers
REGION                  1..7
                        note = heterologous peptide insertion
source                  1..7
                        mol_type = protein
                        organism = synthetic construct
SEQUENCE: 26
ASDSTKA                                                                 7

SEQ ID NO: 27           moltype = AA  length = 10
FEATURE                 Location/Qualifiers
REGION                  1..10
                        note = heterologous peptide insertion
source                  1..10
                        mol_type = protein
                        organism = synthetic construct
SEQUENCE: 27
LANKIQRTDA                                                             10

SEQ ID NO: 28           moltype = AA  length = 10
FEATURE                 Location/Qualifiers
REGION                  1..10
                        note = heterologous peptide insertion
source                  1..10
                        mol_type = protein
                        organism = synthetic construct
SEQUENCE: 28
LANKTTNKDA                                                             10

SEQ ID NO: 29           moltype = AA  length = 10
FEATURE                 Location/Qualifiers
REGION                  1..10
                        note = heterologous peptide insertion
source                  1..10
```

```
                        mol_type = protein
                        organism = synthetic construct
SEQUENCE: 29
LATNKIGVTA                                                                        10

SEQ ID NO: 30           moltype = AA   length = 10
FEATURE                 Location/Qualifiers
REGION                  1..10
                        note = heterologous peptide insertion
source                  1..10
                        mol_type = protein
                        organism = synthetic construct
SEQUENCE: 30
LAGNLTKGNA                                                                        10

SEQ ID NO: 31           moltype = AA   length = 10
FEATURE                 Location/Qualifiers
REGION                  1..10
                        note = heterologous peptide insertion
source                  1..10
                        mol_type = protein
                        organism = synthetic construct
SEQUENCE: 31
LANTVKLSTA                                                                        10

SEQ ID NO: 32           moltype = AA   length = 10
FEATURE                 Location/Qualifiers
REGION                  1..10
                        note = heterologous peptide insertion
source                  1..10
                        mol_type = protein
                        organism = synthetic construct
SEQUENCE: 32
LASNTVKAIA                                                                        10

SEQ ID NO: 33           moltype = AA   length = 10
FEATURE                 Location/Qualifiers
REGION                  1..10
                        note = heterologous peptide insertion
source                  1..10
                        mol_type = protein
                        organism = synthetic construct
SEQUENCE: 33
LAASNITKAA                                                                        10

SEQ ID NO: 34           moltype = AA   length = 10
FEATURE                 Location/Qualifiers
REGION                  1..10
                        note = heterologous peptide insertion
source                  1..10
                        mol_type = protein
                        organism = synthetic construct
SEQUENCE: 34
LADNTVTRSA                                                                        10

SEQ ID NO: 35           moltype = AA   length = 10
FEATURE                 Location/Qualifiers
REGION                  1..10
                        note = heterologous peptide insertion
source                  1..10
                        mol_type = protein
                        organism = synthetic construct
SEQUENCE: 35
LANKISAKDA                                                                        10

SEQ ID NO: 36           moltype = AA   length = 10
FEATURE                 Location/Qualifiers
REGION                  1..10
                        note = heterologous peptide insertion
source                  1..10
                        mol_type = protein
                        organism = synthetic construct
SEQUENCE: 36
LANQDYTKTA                                                                        10

SEQ ID NO: 37           moltype = AA   length = 10
FEATURE                 Location/Qualifiers
REGION                  1..10
                        note = heterologous peptide insertion
```

```
source                    1..10
                          mol_type = protein
                          organism = synthetic construct
SEQUENCE: 37
LATNKIGVTS                                                                10

SEQ ID NO: 38             moltype = AA  length = 10
FEATURE                   Location/Qualifiers
REGION                    1..10
                          note = heterologous peptide insertion
source                    1..10
                          mol_type = protein
                          organism = synthetic construct
SEQUENCE: 38
LATNKIGVTA                                                                10

SEQ ID NO: 39             moltype = AA  length = 10
FEATURE                   Location/Qualifiers
REGION                    1..10
                          note = heterologous peptide insertion
source                    1..10
                          mol_type = protein
                          organism = synthetic construct
SEQUENCE: 39
LAQADTTKNA                                                                10

SEQ ID NO: 40             moltype = AA  length = 10
FEATURE                   Location/Qualifiers
REGION                    1..10
                          note = heterologous peptide insertion
source                    1..10
                          mol_type = protein
                          organism = synthetic construct
SEQUENCE: 40
LATNRTSPDA                                                                10

SEQ ID NO: 41             moltype = AA  length = 10
FEATURE                   Location/Qualifiers
REGION                    1..10
                          note = heterologous peptide insertion
source                    1..10
                          mol_type = protein
                          organism = synthetic construct
SEQUENCE: 41
LASNTTQKTA                                                                10

SEQ ID NO: 42             moltype = AA  length = 10
FEATURE                   Location/Qualifiers
REGION                    1..10
                          note = heterologous peptide insertion
source                    1..10
                          mol_type = protein
                          organism = synthetic construct
SEQUENCE: 42
LAASDSTKAA                                                                10

SEQ ID NO: 43             moltype = AA  length = 745
FEATURE                   Location/Qualifiers
REGION                    1..745
                          note = variant AAV capsid
source                    1..745
                          mol_type = protein
                          organism = synthetic construct
SEQUENCE: 43
MAADGYLPDW LEDTLSEGIR QWWKLKPGPP PPKPAERHKD DSRGLVLPGY KYLGPFNGLD          60
KGEPVNEADA AALEHDKAYD RQLDSGDNPY LKYNHADAEF QERLKEDTSF GGNLGRAVFQ         120
AKKRVLEPLG LVEEPVKTAP GKKRPVEHSP VEPDSSSGTG KAGQQPARKR LNFGQTGDAD         180
SVPDPQPLGQ PPAAPSGLGT NTMATGSGAP MADNNEGADG VGNSSGNWHC DSTWMGDRVI         240
TTSTRTWALP TYNNHLYKQI SSQSGASNDN HYFGYSTPWG YFDFNRFHCH FSPRDWQRLI         300
NNNWGFRPKR LNFKLFNIQV KEVTQNDGTT TIANNLTSTV QVFTDSEYQL PYVLGSAHQG         360
CLPPFPADVF MVPQYGYLTL NNGSQAVGRS SFYCLEYFPS QMLRTGNNFT FSYTFEDVPF         420
HSSYAHSQSL DRLMNPLIDQ YLYYLSRTNT PSGTTTQSRL QFSQAGASDI RDQSRNWLPG         480
PCYRQQRVSK TSADNNNSEY SWTGATKYHL NGRDSLVNPG PAMASHKDDE EKFFPQSGVL         540
IFGKQGSEKT NVDIEKVMIT DEEEIRTTNP VATEQYGSVS TNLQRGNLAN KIQRTDARQA         600
ATADVNTQGV LPGMVWQDRD VYLQGPIWAK IPHTDGHFHP SPLMGGFGLK HPPPQILIKN         660
TPVPANPSTT FSAAKFASFI TQYSTGQVSV EIEWELQKEN SKRWNPEIQY TSNYNKSINV         720
DFTVDTNGVY SEPRPIGTRY LTRNL                                              745

SEQ ID NO: 44             moltype = AA  length = 745
```

```
FEATURE                 Location/Qualifiers
REGION                  1..745
                        note = variant AAV capsid
source                  1..745
                        mol_type = protein
                        organism = synthetic construct
SEQUENCE: 44
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LKFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTDT PSGTTTQSRL QFSQAGASDI RDQSRNWLPG   480
PCYRQQRVSK TSADNNNSEY SWTGATKYHL NGRDSLVNPG PAMASHKDDE EKFFPQSGVL   540
IFGKQGSEKT SVDIEKVMIT DEEEIRTTNP VATEQYGSVS TNLQRGNLAN KIQRTDARQA   600
ATADVNTQGV LPGMVWQDRD VYLQGPIWAK IPHTDGHFHP SPLMGGFGLK HPPPQILIKN   660
TPVPANPSTT FSAAKFASFI TQYSTGQVSV EIEWELQKEN SKRWNPEVQY TSNYNKSVNV   720
DFTVDTNGVY SEPRPIGTRY LTRNQ                                        745

SEQ ID NO: 45           moltype = AA   length = 745
FEATURE                 Location/Qualifiers
REGION                  1..745
                        note = variant AAV capsid
source                  1..745
                        mol_type = protein
                        organism = synthetic construct
SEQUENCE: 45
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LNFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTNT PSGTTTQSRL QFSQAGASDI RDQSRNWLPG   480
PCYRQQRVSK TSADNNNSEY SWTGATKYHL NGRDSLVNPG PAMASHKDDE EKFFPQSGVL   540
IFGKQGSEKT NVDIEKVMIT DEEEIRTTNP VATEQYGSVS TNLQRGNLAN KIQRTDARQA   600
ATADVNTQGV LPGMVWQDRD VYLQGPIWAK IPHTDGHFHP SPLMGGFGLK HPPPQILIKN   660
TPVPANPSTT FSAAKFASFI TQYSTGQVSV EIEWELQKEN SKRWNPEIQY TSNYNKSVNV   720
DFTVDTNGVY SEPRPIGTRY LTRNL                                        745

SEQ ID NO: 46           moltype = AA   length = 745
FEATURE                 Location/Qualifiers
REGION                  1..745
                        note = variant AAV capsid
source                  1..745
                        mol_type = protein
                        organism = synthetic construct
SEQUENCE: 46
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LNFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTNT PSGTTTQSRL QFSQAGASDI RDQSRNWLPG   480
PCYRQQRVSK TSADNNNSEY SWTGATKYHL NGRDSLVNPG PAMASHKDDE EKFFPQSGVL   540
IFGKQGSEKT NVDIEKVMIT DEEEIRTTNP VATEQYGSVS TNLQRGNLAT NKIGVTARQA   600
ATADVNTQGV LPGMVWQDRD VYLQGPIWAK IPHTDGHFHP SPLMGGFGLK HPPPQILIKN   660
TPVPANPSTT FSAAKFASFI TQYSTGQVSV EIEWELQKEN SKRWNPEIQY TSNYNKSINV   720
DFTVDTNGVY SEPRPIGTRY LTRNL                                        745

SEQ ID NO: 47           moltype = AA   length = 745
FEATURE                 Location/Qualifiers
REGION                  1..745
                        note = variant AAV capsid
source                  1..745
                        mol_type = protein
                        organism = synthetic construct
SEQUENCE: 47
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LNFKLFNIQV KEVTQNDGTT TIANNLTSTV QVFTDSEYQL PYVLGSAHQG   360
```

```
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNLAT NKIGVTARQA  600
ATADVNTQGV LPGMVWQDRD VYLQGPIWAK IPHTDGHFHP SPLMGGFGLK HPPPQILIKN  660
TPVPANPSTT FSAAKFASFI TQYSTGQVSV EIEWELQKEN SKRWNPEIQY TSNYNKSVNV  720
DFTVDTNGVY SEPRPIGTRY LTRNL                                       745

SEQ ID NO: 48           moltype = AA  length = 745
FEATURE                 Location/Qualifiers
REGION                  1..745
                        note = variant AAV capsid
source                  1..745
                        mol_type = protein
                        organism = synthetic construct
SEQUENCE: 48
MAADGYLPDW LEDTLSEGIR QWWKLKPGPP PKPAERHKD DSRGLVLPGY KYLGPFNGLD    60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNLAN KTTNKDARQA  600
ATADVNTQGV LPGMVWQDRD VYLQGPIWAK IPHTDGHFHP SPLMGGFGLK HPPPQILIKN  660
TPVPANPSTT FSAAKFASFI TQYSTGQVSV EIEWELQKEN SKRWNPEIQY TSNYNKSINV  720
DFTVDTNGVY SEPRPIGTRY LTRNL                                       745

SEQ ID NO: 49           moltype = AA  length = 745
FEATURE                 Location/Qualifiers
REGION                  1..745
                        note = variant AAV capsid
source                  1..745
                        mol_type = protein
                        organism = synthetic construct
SEQUENCE: 49
MAADGYLPDW LEDTLSEGIR QWWKLKPGPP PKPAERHKD DSRGLVLPGY KYLGPFNGLD    60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LKFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTDT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT SVDIEKVMIT DEEEIRTTNP VATEQYGSVS TNLQRGNLAN KTTNKDARQA  600
ATADVNTQGV LPGMVWQDRD VYLQGPIWAK IPHTDGHFHP SPLMGGFGLK HPPPQILIKN  660
TPVPANPSTT FSAAKFASFI TQYSTGQVSV EIEWELQKEN SKRWNPEVQY TSNYNKSVNV  720
DFTVDTNGVY SEPRPIGTRY LTRNQ                                       745

SEQ ID NO: 50           moltype = AA  length = 745
FEATURE                 Location/Qualifiers
REGION                  1..745
                        note = variant AAV capsid
source                  1..745
                        mol_type = protein
                        organism = synthetic construct
SEQUENCE: 50
MAADGYLPDW LEDTLSEGIR QWWKLKPGPP PKPAERHKD DSRGLVLPGY KYLGPFNGLD    60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNLAN KTTNKDARQA  600
ATADVNTQGV LPGMVWQDRD VYLQGPIWAK IPHTDGHFHP SPLMGGFGLK HPPPQILIKN  660
TPVPANPSTT FSAAKFASFI TQYSTGQVSV EIEWELQKEN SKRWNPEIQY TSNYNKSVNV  720
DFTVDTNGVY SEPRPIGTRY LTRNL                                       745

SEQ ID NO: 51           moltype = AA  length = 745
FEATURE                 Location/Qualifiers
REGION                  1..745
                        note = variant AAV capsid
source                  1..745
```

```
                              mol_type = protein
                              organism = synthetic construct
SEQUENCE: 51
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LNFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTNT PSGTTTQSRL QFSQAGASDI RDQSRNWLPG   480
PCYRQQRVSK TSADNNNSEY SWTGATKYHL NGRDSLVNPG PAMASHKDDE EKFFPQSGVL   540
IFGKQGSEKT NVDIEKVMIT DEEEIRTTNP VATEQYGSVS TNLQRGNLAG NLTKGNARQA   600
ATADVNTQGV LPGMVWQDRD VYLQGPIWAK IPHTDGHFHP SPLMGGFGLK HPPPQILIKN   660
TPVPANPSTT FSAAKFASFI TQYSTGQVSV EIEWELQKEN SKRWNPEIQY TSNYNKSVNV   720
DFTVDTNGVY SEPRPIGTRY LTRNL                                        745

SEQ ID NO: 52           moltype = AA  length = 745
FEATURE                 Location/Qualifiers
REGION                  1..745
                        note = variant AAV capsid
source                  1..745
                        mol_type = protein
                        organism = synthetic construct
SEQUENCE: 52
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LNFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTNT PSGTTTQSRL QFSQAGASDI RDQSRNWLPG   480
PCYRQQRVSK TSADNNNSEY SWTGATKYHL NGRDSLVNPG PAMASHKDDE EKFFPQSGVL   540
IFGKQGSEKT NVDIEKVMIT DEEEIRTTNP VATEQYGSVS TNLQRGNLAN TVKLSTARQA   600
ATADVNTQGV LPGMVWQDRD VYLQGPIWAK IPHTDGHFHP SPLMGGFGLK HPPPQILIKN   660
TPVPANPSTT FSAAKFASFI TQYSTGQVSV EIEWELQKEN SKRWNPEIQY TSNYNKSVNV   720
DFTVDTNGVY SEPRPIGTRY LTRNL                                        745

SEQ ID NO: 53           moltype = AA  length = 745
FEATURE                 Location/Qualifiers
REGION                  1..745
                        note = variant AAV capsid
source                  1..745
                        mol_type = protein
                        organism = synthetic construct
SEQUENCE: 53
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LNFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTNT PSGTTTQSRL QFSQAGASDI RDQSRNWLPG   480
PCYRQQRVSK TSADNNNSEY SWTGATKYHL NGRDSLVNPG PAMASHKDDE EKFFPQSGVL   540
IFGKQGSEKT NVDIEKVMIT DEEEIRTTNP VATEQYGSVS TNLQRGNLAS NTVKAIARQA   600
ATADVNTQGV LPGMVWQDRD VYLQGPIWAK IPHTDGHFHP SPLMGGFGLK HPPPQILIKN   660
TPVPANPSTT FSAAKFASFI TQYSTGQVSV EIEWELQKEN SKRWNPEIQY TSNYNKSVNV   720
DFTVDTNGVY SEPRPIGTRY LTRNL                                        745

SEQ ID NO: 54           moltype = AA  length = 745
FEATURE                 Location/Qualifiers
REGION                  1..745
                        note = variant AAV capsid
source                  1..745
                        mol_type = protein
                        organism = synthetic construct
SEQUENCE: 54
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LNFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTNT PSGTTTQSRL QFSQAGASDI RDQSRNWLPG   480
PCYRQQRVSK TSADNNNSEY SWTGATKYHL NGRDSLVNPG PAMASHKDDE EKFFPQSGVL   540
IFGKQGSEKT NVDIEKVMIT DEEEIRTTNP VATEQYGSVS TNLQRGNLAA SNITKAARQA   600
```

```
ATADVNTQGV LPGMVWQDRD VYLQGPIWAK IPHTDGHFHP SPLMGGFGLK HPPPQILIKN    660
TPVPANPSTT FSAAKFASFI TQYSTGQVSV EIEWELQKEN SKRWNPEIQY TSNYNKSVNV    720
DFTVDTNGVY SEPRPIGTRY LTRNL                                         745

SEQ ID NO: 55           moltype = AA  length = 745
FEATURE                 Location/Qualifiers
REGION                  1..745
                        note = variant AAV capsid
source                  1..745
                        mol_type = protein
                        organism = synthetic construct
SEQUENCE: 55
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ    120
AKKRVLEPLG LVEEPVKTAP GKKRPVEHSP VEPDSSSGTG KAGQQPARKR LNFGQTGDAD    180
SVPDPQPLGQ PPAAPSGLGT NTMATGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI    300
NNNWGFRPKR LNFKLFNIQV KEVTQNDGTT TIANNLTSTV QVFTDSEYQL PYVLGSAHQG    360
CLPPFPADVF MVPQYGYLTL NNGSQAVGRS SFYCLEYFPS QMLRTGNNFT FSYTFEDVPF    420
HSSYAHSQSL DRLMNPLIDQ YLYYLSRTNT PSGTTTQSRL QFSQAGASDI RDQSRNWLPG    480
PCYRQQRVSK TSADNNNSEY SWTGATKYHL NGRDSLVNPG PAMASHKDDE EKFFPQSGVL    540
IFGKQGSEKT NVDIEKVMIT DEEEIRTTNP VATEQYGSVS TNLQRGNLAD NTVTRSARQA    600
ATADVNTQGV LPGMVWQDRD VYLQGPIWAK IPHTDGHFHP SPLMGGFGLK HPPPQILIKN    660
TPVPANPSTT FSAAKFASFI TQYSTGQVSV EIEWELQKEN SKRWNPEIQY TSNYNKSVNV    720
DFTVDTNGVY SEPRPIGTRY LTRNL                                         745

SEQ ID NO: 56           moltype = AA  length = 745
FEATURE                 Location/Qualifiers
REGION                  1..745
                        note = variant AAV capsid
source                  1..745
                        mol_type = protein
                        organism = synthetic construct
SEQUENCE: 56
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ    120
AKKRVLEPLG LVEEPVKTAP GKKRPVEHSP VEPDSSSGTG KAGQQPARKR LNFGQTGDAD    180
SVPDPQPLGQ PPAAPSGLGT NTMATGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI    300
NNNWGFRPKR LNFKLFNIQV KEVTQNDGTT TIANNLTSTV QVFTDSEYQL PYVLGSAHQG    360
CLPPFPADVF MVPQYGYLTL NNGSQAVGRS SFYCLEYFPS QMLRTGNNFT FSYTFEDVPF    420
HSSYAHSQSL DRLMNPLIDQ YLYYLSRTNT PSGTTTQSRL QFSQAGASDI RDQSRNWLPG    480
PCYRQQRVSK TSADNNNSEY SWTGATKYHL NGRDSLVNPG PAMASHKDDE EKFFPQSGVL    540
IFGKQGSEKT NVDIEKVMIT DEEEIRTTNP VATEQYGSVS TNLQRGNLAN KISAKDARQA    600
ATADVNTQGV LPGMVWQDRD VYLQGPIWAK IPHTDGHFHP SPLMGGFGLK HPPPQILIKN    660
TPVPANPSTT FSAAKFASFI TQYSTGQVSV EIEWELQKEN SKRWNPEIQY TSNYNKSVNV    720
DFTVDTNGVY SEPRPIGTRY LTRNL                                         745

SEQ ID NO: 57           moltype = AA  length = 745
FEATURE                 Location/Qualifiers
REGION                  1..745
                        note = variant AAV capsid
source                  1..745
                        mol_type = protein
                        organism = synthetic construct
SEQUENCE: 57
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ    120
AKKRVLEPLG LVEEPVKTAP GKKRPVEHSP VEPDSSSGTG KAGQQPARKR LNFGQTGDAD    180
SVPDPQPLGQ PPAAPSGLGT NTMATGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI    300
NNNWGFRPKR LNFKLFNIQV KEVTQNDGTT TIANNLTSTV QVFTDSEYQL PYVLGSAHQG    360
CLPPFPADVF MVPQYGYLTL NNGSQAVGRS SFYCLEYFPS QMLRTGNNFT FSYTFEDVPF    420
HSSYAHSQSL DRLMNPLIDQ YLYYLSRTNT PSGTTTQSRL QFSQAGASDI RDQSRNWLPG    480
PCYRQQRVSK TSADNNNSEY SWTGATKYHL NGRDSLVNPG PAMASHKDDE EKFFPQSGVL    540
IFGKQGSEKT NVDIEKVMIT DEEEIRTTNP VATEQYGSVS TNLQRGNLAN QDYTKTARQA    600
ATADVNTQGV LPGMVWQDRD VYLQGPIWAK IPHTDGHFHP SPLMGGFGLK HPPPQILIKN    660
TPVPANPSTT FSAAKFASFI TQYSTGQVSV EIEWELQKEN SKRWNPEIQY TSNYNKSVNV    720
DFTVDTNGVY SEPRPIGTRY LTRNL                                         745

SEQ ID NO: 58           moltype = AA  length = 745
FEATURE                 Location/Qualifiers
REGION                  1..745
                        note = variant AAV capsid
source                  1..745
                        mol_type = protein
                        organism = synthetic construct
SEQUENCE: 58
MAADGYLPDW LEDTLSEGIR QWWKLKPGPP PPKPAERHKD DSRGLVLPGY KYLGPFNGLD    60
```

```
KGEPVNEADA AALEHDKAYD RQLDSGDNPY LKYNHADAEF QERLKEDTSF GGNLGRAVFQ    120
AKKRVLEPLG LVEEPVKTAP GKKRPVEHSP VEPDSSSGTG KAGQQPARKR LNFGQTGDAD    180
SVPDPQPLGQ PPAAPSGLGT NTMATGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI    300
NNNWGFRPKR LNFKLFNIQV KEVTQNDGTT TIANNLTSTV QVFTDSEYQL PYVLGSAHQG    360
CLPPFPADVF MVPQYGYLTL NNGSQAVGRS SFYCLEYFPS QMLRTGNNFT FSYTFEDVPF    420
HSSYAHSQSL DRLMNPLIDQ YLYYLSRTNT PSGTTTQSRL QFSQAGASDI RDQSRNWLPG    480
PCYRQQRVSK TSADNNNSEY SWTGATKYHL NGRDSLVNPG PAMASHKDDE EKFFPQSGVL    540
IFGKQGSEKT NVDIEKVMIT DEEEIRTTNP VATEQYGSVS TNLQRGNLAQ ADTTKNARQA    600
ATADVNTQGV LPGMVWQDRD VYLQGPIWAK IPHTDGHFHP SPLMGGFGLK HPPPQILIKN    660
TPVPANPSTT FSAAKFASFI TQYSTGQVSV EIEWELQKEN SKRWNPEIQY TSNYNKSVNV    720
DFTVDTNGVY SEPRPIGTRY LTRNL                                         745

SEQ ID NO: 59          moltype = AA  length = 745
FEATURE                Location/Qualifiers
REGION                 1..745
                       note = variant AAV capsid
source                 1..745
                       mol_type = protein
                       organism = synthetic construct
SEQUENCE: 59
MAADGYLPDW LEDTLSEGIR QWWKLKPGPP PKPAERHKD DSRGLVLPGY KYLGPFNGLD      60
KGEPVNEADA AALEHDKAYD RQLDSGDNPY LKYNHADAEF QERLKEDTSF GGNLGRAVFQ    120
AKKRVLEPLG LVEEPVKTAP GKKRPVEHSP VEPDSSSGTG KAGQQPARKR LNFGQTGDAD    180
SVPDPQPLGQ PPAAPSGLGT NTMATGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI    300
NNNWGFRPKR LNFKLFNIQV KEVTQNDGTT TIANNLTSTV QVFTDSEYQL PYVLGSAHQG    360
CLPPFPADVF MVPQYGYLTL NNGSQAVGRS SFYCLEYFPS QMLRTGNNFT FSYTFEDVPF    420
HSSYAHSQSL DRLMNPLIDQ YLYYLSRTNT PSGTTTQSRL QFSQAGASDI RDQSRNWLPG    480
PCYRQQRVSK TSADNNNSEY SWTGATKYHL NGRDSLVNPG PAMASHKDDE EKFFPQSGVL    540
IFGKQGSEKT NVDIEKVMIT DEEEIRTTNP VATEQYGSVS TNLQRGNLAT NRTSPDARQA    600
ATADVNTQGV LPGMVWQDRD VYLQGPIWAK IPHTDGHFHP SPLMGGFGLK HPPPQILIKN    660
TPVPANPSTT FSAAKFASFI TQYSTGQVSV EIEWELQKEN SKRWNPEIQY TSNYNKSINV    720
DFTVDTNGVY SEPRPIGTRY LTRNL                                         745

SEQ ID NO: 60          moltype = AA  length = 745
FEATURE                Location/Qualifiers
REGION                 1..745
                       note = variant AAV capsid
source                 1..745
                       mol_type = protein
                       organism = synthetic construct
SEQUENCE: 60
MAADGYLPDW LEDTLSEGIR QWWKLKPGPP PKPAERHKD DSRGLVLPGY KYLGPFNGLD      60
KGEPVNEADA AALEHDKAYD RQLDSGDNPY LKYNHADAEF QERLKEDTSF GGNLGRAVFQ    120
AKKRVLEPLG LVEEPVKTAP GKKRPVEHSP VEPDSSSGTG KAGQQPARKR LNFGQTGDAD    180
SVPDPQPLGQ PPAAPSGLGT NTMATGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI    300
NNNWGFRPKR LNFKLFNIQV KEVTQNDGTT TIANNLTSTV QVFTDSEYQL PYVLGSAHQG    360
CLPPFPADVF MVPQYGYLTL NNGSQAVGRS SFYCLEYFPS QMLRTGNNFT FSYTFEDVPF    420
HSSYAHSQSL DRLMNPLIDQ YLYYLSRTNT PSGTTTQSRL QFSQAGASDI RDQSRNWLPG    480
PCYRQQRVSK TSADNNNSEY SWTGATKYHL NGRDSLVNPG PAMASHKDDE EKFFPQSGVL    540
IFGKQGSEKT NVDIEKVMIT DEEEIRTTNP VATEQYGSVS TNLQRGNLAS NTTQKTARQA    600
ATADVNTQGV LPGMVWQDRD VYLQGPIWAK IPHTDGHFHP SPLMGGFGLK HPPPQILIKN    660
TPVPANPSTT FSAAKFASFI TQYSTGQVSV EIEWELQKEN SKRWNPEIQY TSNYNKSVNV    720
DFTVDTNGVY SEPRPIGTRY LTRNL                                         745

SEQ ID NO: 61          moltype = AA  length = 745
FEATURE                Location/Qualifiers
REGION                 1..745
                       note = variant AAV capsid
source                 1..745
                       mol_type = protein
                       organism = synthetic construct
SEQUENCE: 61
MAADGYLPDW LEDTLSEGIR QWWKLKPGPP PKPAERHKD DSRGLVLPGY KYLGPFNGLD      60
KGEPVNEADA AALEHDKAYD RQLDSGDNPY LKYNHADAEF QERLKEDTSF GGNLGRAVFQ    120
AKKRVLEPLG LVEEPVKTAP GKKRPVEHSP VEPDSSSGTG KAGQQPARKR LNFGQTGDAD    180
SVPDPQPLGQ PPAAPSGLGT NTMATGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI    300
NNNWGFRPKR LNFKLFNIQV KEVTQNDGTT TIANNLTSTV QVFTDSEYQL PYVLGSAHQG    360
CLPPFPADVF MVPQYGYLTL NNGSQAVGRS SFYCLEYFPS QMLRTGNNFT FSYTFEDVPF    420
HSSYAHSQSL DRLMNPLIDQ YLYYLSRTNT PSGTTTQSRL QFSQAGASDI RDQSRNWLPG    480
PCYRQQRVSK TSADNNNSEY SWTGATKYHL NGRDSLVNPG PAMASHKDDE EKFFPQSGVL    540
IFGKQGSEKT NVDIEKVMIT DEEEIRTTNP VATEQYGSVS TNLQRGNLAA SDSTKAARQA    600
ATADVNTQGV LPGMVWQDRD VYLQGPIWAK IPHTDGHFHP SPLMGGFGLK HPPPQILIKN    660
TPVPANPSTT FSAAKFASFI TQYSTGQVSV EIEWELQKEN SKRWNPEIQY TSNYNKSVNV    720
DFTVDTNGVY SEPRPIGTRY LTRNL                                         745
```

```
SEQ ID NO: 62            moltype = AA  length = 725
FEATURE                  Location/Qualifiers
REGION                   1..725
                         note = Variant AAV capsid chimera
source                   1..725
                         mol_type = protein
                         organism = synthetic construct
SEQUENCE: 62
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPFG LVEEGAKTAP TGKRIDDHFP KRKKARTEED SKPSTSSDAE AGPSGSQQLQ   180
IPAQPASSLG ADTMSAGGGG PLGDNNQGAD GVGNASGDWH CDSTWMGDRI VTKSTRTWVL   240
PSYNNHQYRE IKSGSVDGSN ANAYFGYSTP WGYFDFNRFH SHWSPRDWQR LINNYWGFRP   300
RSLRVKIFNI QVKEVTVQDS TTTIANNLTS TVQVFTDDDY QLPYVVGNGT EGCLPAFPPQ   360
VFTLPQYGYA TLNRDNTENP TERSSFFCLE YFPSKMLRTG NNFEFTYNFE EVPFHSSFAP   420
SQNLFKLANP LVDQYLYRFV STNNTGGVQF NKNLAGRYAN TYKNWFPGPM GRTQGWNLGS   480
GVNRASVSAF TTTNRMELEG ASYQVPPQPN GMTNNLQGSN TYALENTMIF NSQPANPGTT   540
ATYLEGNMLI TSESETQPVN RVAYNVGGQM ATNNQSSTTA PTTGTYNLQE IVPGSVWMER   600
DVYLQGPIWA KIPETGAHFH PSPAMGGFGL KHPPPMMLIK NTPVPGNITS FSDVPVSSFI   660
TQYSTGQVTV EMEWELKKEN SKRWNPEIQY TNNYNDPQFV DFAPDSTGEY RTTRPIGTRY   720
LTRPL                                                              725

SEQ ID NO: 63            moltype = AA  length = 725
FEATURE                  Location/Qualifiers
REGION                   1..725
                         note = Variant AAV capsid chimera
source                   1..725
                         mol_type = protein
                         organism = synthetic construct
SEQUENCE: 63
MAADGYLPDW LEDTLSEGIR QWWKLKPGPP PPKPAERHKD DSRGLVLPGY KYLGPFNGLD    60
KGEPVNAADA AALEHDKAYD QQLKAGDNPY LRYNHADAEF QERLQEDTSF GGNLGRAVFQ   120
AKKRVLEPFG LVEEGAKTAP TGKRIDDHFP KRKKARTEED SKPSTSSDAE AGPSGSQQLQ   180
IPAQPASSLG ADTMSAGGGG PLGDNNQGAD GVGNASGDWH CDSTWMGDRI VTKSTRTWVL   240
PSYNNHQYRE IKSGSVDGSN ANAYFGYSTP WGYFDFNRFH SHWSPRDWQR LINNYWGFRP   300
RSLRVKIFNI QVKEVTVQDS TTTIANNLTS TVQVFTDDDY QLPYVVGNGT EGCLPAFPPQ   360
VFTLPQYGYA TLNRDNTENP TERSSFFCLE YFPSKMLRTG NNFEFTYNFE EVPFHSSFAP   420
SQNLFKLANP LVDQYLYRFV STNNTGGVQF NKNLAGRYAN TYKNWFPGPM GRTQGWNLGS   480
GVNRASVSAF TTTNRMELEG ASYQVPPQPN GMTNNLQGSN TYALENTMIF NSQPANPGTT   540
ATYLEGNMLI TSESETQPVN RVAYNVGGQM ATNNQSSTTA PTTGTYNLQE IVPGSVWMER   600
DVYLQGPIWA KIPETGAHFH PSPAMGGFGL KHPPPMMLIK NTPVPGNITS FSDVPVSSFI   660
TQYSTGQVTV EMEWELKKEN SKRWNPEIQY TNNYNDPQFV DFAPDSTGEY RTTRPIGTRY   720
LTRPL                                                              725

SEQ ID NO: 64            moltype = AA  length = 3685
FEATURE                  Location/Qualifiers
source                   1..3685
                         mol_type = protein
                         organism = Homo sapiens
SEQUENCE: 64
MLWWEEVEDC YEREDVQKKT FTKWVNAQFS KFGKQHIENL FSDLQDGRRL LDLLEGLTGQ    60
KLPKEKGSTR VHALNNVNKA LRVLQNNNVD LVNIGSTDIV DGNHKLTLGL IWNIILHWQV   120
KNVMKNIMAG LQQTNSEKIL LSWVRQSTRN YPQVNVINFT TSWSDGLALN ALIHSHRPDL   180
FDWNSVVCQQ SATQRLEHAF NIARYQLGIE KLLDPEDVDT TYPDKKSILM YITSLFQVLP   240
QQVSIEAIQE VEMLPRPPKV TKEEHFQLHH QMHYSQQITV SLAQGYERTS SPKPRFKSYA   300
YTQAAYVTTS DPTRSPFPSQ HLEAPEDKSF GSSLMESEVN LDRYQTALEE VLSWLLSAED   360
TLQAQGEISN DVEVVKDQFH THEGYMMDLT AHQGRVGNIL QLGSKLIGTG KLSEDEETEV   420
QEQMNLLNSR WECLRVASME KQSNLHRVLM DLQNQKLKEL NDWLTKTEER TRKMEEEPLG   480
PDLEDLKRQV QQHKVLQEDL EQEQVRVNSL THMVVVVDES SGDHATAALE EQLKVLGDRW   540
ANICRWTEDR WVLLQDILLK WQRLTEEQCL FSAWLSEKED AVNKIHTTGF KDQNEMLSSL   600
QKLAVLKADL EKKKQSMGKL YSLKQDLLST LKNKSVTQKT EAWLDNFARC WDNLVQKLEK   660
STAQISQAVT TTQPSLTQTT VMETVTTVTT REQILVKHAQ EELPPPPPQK KRQITVDSEI   720
RKRLDVDITE LHSWITRSEA VLQSPEFAIF RKEGNFSDLK EKVNAIEREK AEKFRKLQDA   780
SRSAQALVEQ MVNEGVNADS IKQASEQLNS RWIEFCQLLS ERLNWLEYQN NIIAFYNQLQ   840
QLEQMTTTAE NWLKIQPTTP SEPTAIKSQL KICKDEVNRL SGLQPQIERL KIQSIALKEK   900
GQGPMFLDAD FVAFTNHFKQ VFSDVQAREK ELQTIFDTLP PMRYQETMSA IRTWVQQSET   960
KLSIPQLSVT DYEIMEQRLG ELQALQSSLQ EQQSGLYYLS TTVKEMSKKA PSEISRKYQS  1020
EPEEIEGRWK KLSSQLVEHC QKLEEQMNKL RKIQNHIQTL KKWMAEVDVF LKEEWPALGD  1080
SEILKKQLKQ CRLLVSDIQT IQPSLNSVNE GGQKIKNEAE PEFASRLETE LKELNTQWDH  1140
MCQQVYARKE ALKGGLEKTV SLQKDLSEMH EWMTQAEEEY LERDFEYKTP DELQKAVEEM  1200
KRAKEEAQQK EAKVKLLTES VNSVIAQAPP VAQEALKKEL ETLTTNYQWL CTRLNGKCKT  1260
LEEVWACWHE LLSYLEKANK WLNEVEFKLK TTENIPGGAE EISEVLDSLE NLMRHSEDNP  1320
NQIRILAQTL TDGGVMDELI NEELETFNSR WRELHEEAVR RQKLLEQSIQ SAQETEKSLH  1380
LIQESLTFID KQLAAYIADK VDAAQMPQEA QKIQSDLTSH EISLEEMKKH NQGKEAAQRV  1440
LSQIDVAQKK LQDVSMKFRL FQKPANFEQR LQESKMILDE VKMHLPALET KSVEQEVVQS  1500
QLNHCVNLYK SLSEVKSEVE MVIKTGRQIV QKKQTENPKE LDERVTALKL HYNELGAKVT  1560
ERKQQLEKCL KLSRKMRKEM NVLTEWLAAT DMELTKRSAV EGMPSNLDSE VAWGKATQKE  1620
IEKQKVHLKS ITEVGEALKT VLGKKETLVE DKLSLLNSNW IAVTSRAEEW LNLLLEYQKH  1680
METFDQNVDH ITKWIIQADT LLDESEKKKP QQKEDVLKRL KAELNDIRPK VDSTRDQAAN  1740
```

```
LMANRGDHCR KLVEPQISEL NHRFAAISHR IKTGKASIPL KELEQFNSDI QKLLEPLEAE  1800
IQQGVNLKEE DFNKDMNEDN EGTVKELLQR GDNLQQRITD ERKREEIKIK QQLLQTKHNA  1860
LKDLRSQRRK KALEISHQWY QYKRQADDLL KCLDDIEKKL ASLPEPRDER KIKEIDRELQ  1920
KKKEELNAVR RQAEGLSEDG AAMAVEPTQI QLSKRWREIE SKFAQFRRLN FAQIHTVREE  1980
TMMVMTEDMP LEISYVPSTY LTEITHVSQA LLEVEQLLNA PDLCAKDFED LFKQEESLKN  2040
IKDSLQQSSG RIDIIHSKKT AALQSATPVE RVKLQEALSQ LDFQWEKVNK MYKDRQGRFD  2100
RSVEKWRRFH YDIKIFNQWL TEAEQFLRKT QIPENWEHAK YKWYLKELQD GIGQRQTVVR  2160
TLNATGEEII QQSSKTDASI LQEKLGSLNL RWQEVCKQLS DRKKRLEEQK NILSEFQRDL  2220
NEFVLWLEEA DNIASIPLEP GKEQQLKEKL EQVKLLVEEL PLRQGILKQL NETGGPVLVS  2280
APISPEEQDK LENKLKQTNL QWIKVSRALP EKQGEIEAQI KDLGQLEKKL EDLEEQLNHL  2340
LLWLSPIRNQ LEIYNQPNQE GPFDVQETEI AVQAKQPDVE EILSKGQHLY KEKPATQPVK  2400
RKLEDLSSEW KAVNRLLQEL RAKQPDLAPG LTTIGASPTQ TVTLVTQPVV TKETAISKLE  2460
MPSSLMLEVP ALADFNRAWT ELTDWLSLLD QVIKSQRVMV GDLEDINEMI IKQKATMQDL  2520
EQRRPQLEEL ITAAQNLKNK TSNQEARTII TDRIERIQNQ WDEVQEHLQN RRQQLNEMLK  2580
DSTQWLEAKE EAEQVLGQAR AKLESWKEGP YTVDAIQKKI TETKQLAKDL RQWQTNVDVA  2640
NDLALKLLRD YSADDTRKVH MITENINASW RSIHKRVSER EAALEETHRL LQQFPLDLEK  2700
FLAWLTEAET TANVLQDATR KERLLEDSKG VKELMKQWQD LQGEIEAHTD VYHNLDENSQ  2760
KILRSLEGSD DAVLLQRRLD NMNFKWSELR KKSLNIRSHL EASSDQWKRL HLSLQELLVW  2820
LQLKDDELSR QAPIGGDFPA VQKQNDVHRA FKRELKTKEP VIMSTLETVR IFLTEQPLEG  2880
LEKLYQEPRE LPPEERAQNV TRLLRKQAEE VNTEWEKLNL HSADWQRKID ETLERLQELQ  2940
EATDELDLKL RQAEVIKGSW QPVGDLLIDS LQDHLEKVKA LRGEIAPLKE NVSHVNDLAR  3000
QLTTLGIQLS PYNLSTLEDL NTRWKLLQVA VEDRVRQLHK AHRDFGPASQ HFLSTSVQGP  3060
WERAISPNKV PYYINHETQT TCWDHPKMTE LYQSLADLNN VRFSAYRTAM KLRRLQKALC  3120
LDLLSLSAAC DALDQHNLKQ NDQPMDILQI INCLTTIYDR LEQEHNNLVN VPLCVDMCLN  3180
WLLNVYDTGR TGRIRVLSFK TGIISLCKAH LEDKYRYLFK QVASSTGFCD QRRLGLLLHD  3240
SIQIPRQLGE VASFGGSNIE PSVRSCFQFA NNKPEIEAAL FLDWMRLEPQ SMVWLPVLHR  3300
VAAAETAKHQ AKCNICKECP IIGFRYRSLK HFNYDICQSC FFSGRVAKGH KMHYPMVEYC  3360
TPTTSGEDVR DFAKVLKNKF RTKRYFAKHP RMGYLPVQTV LEGDNMETPV TLINFWPVDS  3420
APASSPQLSH DDTHSRIEHY ASRLAEMENS NGSYLNDSIS PNESIDDEHL LIQHYCQSLN  3480
QDSPLSQPRS PAQILISLES EERGELERIL ADLEEENRNL QAEYDRLKQQ HEHKGLSPLP  3540
SPPEMMPTSP QSPRDAELIA EAKLLRQHKG RLEARMQILE DHNKQLESQL HRLRQLLEQP  3600
QAEAKVNGTT VSSPSTSLQR SDSSQPMLLR VVGSQTSDSM GEEDLLSPPQ DTSTGLEEVM  3660
EQLNNSFPSS RGRNTPGKPM REDTM                                      3685

SEQ ID NO: 65          moltype = DNA   length = 19841
FEATURE                Location/Qualifiers
source                 1..19841
                       mol_type = other DNA
                       organism = Homo sapiens
SEQUENCE: 65
tttcctactt gaagcctgac gtagtaaaga tcggggagg  gttagacaga tacagtggtc   60
cccaaccatt ttggcaccag ggactggtct tatgGaagac agttttttca cagactgttg  120
ggggatggt tttgggatga aaccgttctg cctctgatca tcaggtgtta gattctaata  180
aggagcgcac acctagatcc ctcgcatgca tagttcatgg tggggttcgc actcttacga  240
ggattgaatg gtgcgctgct ccggtaggag gctgggctca ggctgtaatg cctgctcgcc  300
caccactcac ctcctgctgc atggcctggt tcctaacagg ccacggacca ctactgttcc  360
atggcccgga ggttgaggac cccagataca aggacaattc tgtgcaagc aggactgtcc  420
cctcgccaaa gatgggacat cgaggctcct tggagcaccc tgtggccacc ttgcagcagc  480
ctctgtttcc ccatgtttcc atgacctggt gtccatctgt cttccccagt ttgggagctt  540
ctctccgagg aggacctggg cctggtgtgg cacctgctgt gtgagcgggg ccatgtccaa  600
cggcctttct tggggacttt gggtcgggag aagttctgcc tgggttttac tgccttctcc  660
caaccccaca ctgtctcccc tggcagcggt tgatcgacaa gaccaaggtg acatatctga  720
agtggctgcc tgagtcggag agccgtttcc tggcatcaca cgccagtggc cacctgtacc  780
tgtacaacgt cagccacccc tgcgcctcgg ccccgcccca gtacagcctg ctgaagcagg  840
gcgagggctt ctctgtctat gctgccaaga gcaaggcacc ccgcaaccgt ctggccaagt  900
gggcggtggg tgaggggccc ctcaacgagt tcgccttctc gcccgatggc cggcacctgg  960
cctgtgtgag ccaggatggc tgcctgcgcg tcttccactt cgactccatg ctcctgcgtg 1020
ggctcatgaa gagctacttt gggggcctgc tgtgtgtgtg ctggagccct gacggccgct 1080
acgtggtgac gggtggcgaa gatgacctgg tcaccgtgtg gtccttcacc gagggccgca 1140
tggtggctcg aggccatggc cacaagtcct gggtcaacgc tgtggccttt gaccccacta 1200
ccacaagggc agaggaggcg gcgacagcag ccggtgctga tggggagcgg agcggcgaag 1260
aggaggagga ggagcccgag gctgcgggca caggctcggc cggggcgcc  ccgctctctc 1320
cactgcccaa ggctggctcc attacttacc gctttggctc ggcgggccag gacacgcagt 1380
tctgcctgtg ggacctcact gaagacgtgc tctacccgca cccccccctg ccccccccag 1440
gcaccctccc tggcacacct ggcaccacgc caccggccgc cagcagctcg aggggtggcg 1500
agcctggccc aggcccctg cctcgctcgc tgtcccgctc aacagtctc ccgcacccag 1560
ctggcggggg caaggcgggc ggcccgggtg tggcggcaga gctggcacac ccattcagca 1620
ttggccgctt cgccacgctc acactgcagg agcggcggga ccgggggca gagaaggagc 1680
acaagcgcta ccacagcgct ggcaacatca gccgggggtg cagtggcggc agtggcagtg 1740
gtggggagaa gccagcggc cctgttcccc gcagccgcct ggaccccgcc aaggtgctgg 1800
gcactgcgct gtcccgcgc atccacgagg tgccctgct ggagcccctt gtgtgcaaga 1860
agatcgccca ggagcggctc acagtcctcc tgttcctgga ggactgcatc atcactgcct 1920
gccaggaggg cctcatctgc acctgggccc ggccgggcaa ggcggtgagt ggcccccacg 1980
cagcctgccg gggacctggg acaggccttt gtgggaagga ggcaggccattg agagagagg 2040
ggctttgttg ctgtcacagc ctctggctcc gtggggtgag gggaagccag ggaaatctta 2100
gtgtctcagt acaagacctc tcagatcctt agagtgaggg ggtctagccc taggcagcag 2160
gcagcagaaa gaggggtggg tgtgagagcc agctaggaat tggggcatcc aaggctggcc 2220
gtctgaaggg cagcagatgg gccccacatg gccaggtctt actgcctgtc actgaaccca 2280
gaatctattt ctgttgaaca tctgtttttt aaatcgtgaa acttttttga gtacttcagg 2340
```

```
ccaaaactag gggcgagctc aagcctgtgg gcatggctgc cagcctgggt ctgggactca   2400
ggatctgagc ctcctgctga aggcacaggc tgggaatccc aggcctgggt tccagtccca   2460
ctccctctgt gacccggac aagtcactgc cccctctgac ctccaactca tcacctctta   2520
gaacagagcc tgtaggatgg gcagtgggtg gatgtgcttg cctcctgggt gggctgtggc   2580
gttggaagg tcatagtagg cgaatcaggc ctggcatctt gtaagttcgg agctcgtctt   2640
gggtgtctca gcttcttagg gcttggactc agttgcccag ggtcctggag gccgtggctt   2700
ggttcctcag atcctcagtt ttggaatcgt agagtcctga gtcccctagaa cttgagagca   2760
cagtctgagt gactcagagg caagagtggt gggatttggg gagtctggtt gagtcctaaa   2820
agagaccct ctgtctccgt agttcacaga cgaggagacc gaggcccaga cagggggaagg   2880
aagttggccc aggtcaccca gcaagtcagt ggtagaggta ggactgtccc tgagttcttt   2940
ccccagcacc tcagggtccc tccaagtta gaagggagct ccagtttccc cctcccctcc   3000
caccctacc cttaccccat ggtctcactc aggatccgcc aaggactttg attattgcgt   3060
gaaagtgctg actgccagga caggaagcta gctaagatgc aagttcccag cctagagcag   3120
tggcctctgg ggggtctagg gcggacccaa gggcaaggcc agggtggcag cagcttggg   3180
gactctgggc tggctccctc cccttgacac tggctgaagc ccaggtggtc tctaacccct   3240
cccatctctc cctctcatct tccccagggc atctcctccc aaccaggcaa ctccccgagt   3300
ggcacagtgg tgtgaagcca tggatatcgg gccccccaa ccccatgccc ccagcctcct   3360
agccataacc ctccctgctg acctcacaga tcaacgtatt aacaagacta accatgatgg   3420
atggactgct ccagtccccc cacctgcaca aaatttgggg gccccccaga ctggcccgga   3480
cacgggcgat gtaatagccc ttgtggcctc agccttgtcc cccacccact gccaagtaca   3540
atgacctctt cctctgaaac atcagtgtta ccctcatccc tgtccccagc atgtgactgg   3600
tcactcctgg ggagagactc cccgcccctg ccacaagtgc ccaggtctg cagtgtgccc   3660
ctcagttgag tgggcagggc cgggggtggt ccagccctcg cccggccccc acccagctg   3720
cccttgctat tgtctgtgct tttgaagagt gttaaattat ggaagcccct caggttcctc   3780
cctgtcccgc aggacctctt atttatacta aagttccctg ttttctcagc gggtctgtcc   3840
ccttcggagg agatgatgta gaggacctgt gtgtgtactc tgtggtttcta ggcagtccga   3900
tttccccaga ggaggagtgc aggcctgctc ccagcccagc gcctcccacc cctttcata   3960
gcaggaaaag ccggagccca gggagggaac ggacctgcga gtcacacaac tggtgaccca   4020
caccagcggc tggagcagga cccctcttggg gagaagagca tcctgcccgc agccagggcc   4080
cctcatcaaa gtcctcggtg ttttttaaat tatcagaact gccaggacc acgtttccca   4140
ggccctgccc agctgggact cctcggtcct tgcctcctag ttttctcaggc ctggccctct   4200
caaggcccag gcaccccagg ccggttggag gccccgactt ccactctgga gaaccgtcca   4260
ccctggaaag aagagctcag attcctcttg gctctcggag ccgcagggag tgtgtcttcc   4320
cgcgccaccc tccaccccc gaaatgtttc tgtttctaat ccagcctgg gcagaaatgt   4380
ggctccccgg ccaggggcca aggagctatt ttggggtctc gtttgcccag ggagggcttg   4440
gctccaccac tttcctcccc cagccttgg gcagcaggtc acccctgttc aggctctgag   4500
ggtgccccct cctggtcctg tcctcaccac cccttcccca cctcctggga aaaaaaaaa   4560
aaaaaaaaaa aaaagctggt ataaagcaga gagcctgagg gctaaattta actgtccgag   4620
tcggaatcca tctctgagtc acccaagaag ctgccctggc ctcccgtccc cttcccaggc   4680
ctcaaccccc ttctcccacc cagccccaac ccccagcccc cacccctag ccccagttc   4740
tggagcttgt cgggagcaag ggggtggttg ctactgggtc actcagcctc aattggccct   4800
gtttcagcaa tgggcaggtt cttcttgaaa ttcatcacac ctgtggcttc ctctgtgctc   4860
tacctttta ttgggtgac agtgtgacag ctgagattct ccatgcattc ccctactct   4920
agcactgaag ggttctgaag ggccctgaa ggagggagct tgggggggctg gcttgtgagg   4980
ggttaaggct gggaggcggg aggggggctg gaccaagggg tggggagaag gggaggaggc   5040
ctcggccggc cgcagagaga agtggccaga gaggcccagg ggacagccag ggacaggcag   5100
acatgcagcc agggctccag ggcctgcaca gggctgcca ggcctgtga caggaggacc   5160
ccgagccccc ggcccgggga ggggccatgg tgctgcctgt ccaacatgtc agccgaggtg   5220
cggctgaggc ggctccagca gctggtgttg gaccccgggct tcctggggct ggagcccctg   5280
ctcgaccttc tcctgggcgt ccaccaggag ctgggcgcct ccgaactggc ccaggacaag   5340
tacgtgccg acttcttgca gtgggtgagg tgcctaccct cgggggctcct gcagatgggg   5400
tgggggtggg gcaggagaca ggtctggca cagaggcctg gctgttgggg gggcaggatg   5460
gcaggatggg catggggaga tcctcccatc ctggggctca gagtgtgac ctgggccctg   5520
gggcaacatt tctctgtcct atgccaccac tctggagggg cagagtaagg tcagcagagg   5580
ctagggtggc tgtgactcag agccatggct taggagtcac agcaggctag gctgccaaca   5640
gcctcccatg gcctctctgc accccgcctc agggtcaggg tcagggtcat gctgggagct   5700
ccctctccta ggaccctccc cccaaaagtg ggctctatgg ccctctcccc tggtttcctg   5760
tggcctgggg caagccagga gggccagcat ggggcagctg ccaggggcgc agccgacagg   5820
caggtgttcg gcgccagcct ctccagctgc cccaacaggt gcccaggcac tggagggcg   5880
gtgactcacg cgggccctgt gggagaacca gctttgcaga caggcgccac cagtgcccc   5940
tcctctgcga tccaggaggg acaacttggg gttcttctgg gtgtgtctcc ttcttttgta   6000
ggttctgcac ccaccccac cccagcccc aaagtctcgg ttcctatgag ccgtgtgggt   6060
cagccaccat tcccgccacc ccgggtccct gcgtcctttta gttctcctgg cccagggcct   6120
ccaacctccc agctgtccca caaaaccccct tcttgcaagg gctttccagg gcctggggcc   6180
agggctggaa ggaggatgct tccgcttctg ccagctgcct tgtctgccca cctcctcccc   6240
aagcccagga ctcgggctca ctggtcactg gtttctttca ttcccagcac cctgcccctc   6300
tggccctcat atgtctggcc ctcagtgact ggtgtttggt ttttgcctg tgtgtaacaa   6360
actgtgtgtg acacttgttt cctgtttctc cgccttcccc tgcttcctct tgtgtccatc   6420
tctttctgac caggcctgg ttcctttccc tcctcctccc atttcacaga tgggaaggtg   6480
gaggccaaga agggccaggc cattcagcct ctggaaaaac cttctcccaa cctcccacag   6540
ccctaatga ctctcctggc ctccctttag tagaggatga agttgggttg gcagggtaaa   6600
ctgagaccgt gtgggtagg ggtctggcgc tcccggagg agcactcctt ttgtggccg   6660
agctgcatct cgcggcccct cccctgccag gcctggggcg ggggagggg ccagggttcc   6720
tgctgcctta aaagggctca atgtcttggc tgttcctccc ctcagccctg   6780
gctggttcgt ccctgctggc ccactctccc ggaaccccc ggaaccctc tctttcctcc   6840
agaacccact gtctcctctc cttccctccc ctcccatacc catccctc tccatcctgc   6900
ctccacttct tccaccccg ggagtccagg cctcctgtc cccacagtcc ctgagccaca   6960
agcctccacc ccagctggtc ccccacccag gctgcccagt ttaacattcc tagtcatagg   7020
accttgactt ctgagaggcc tgattgtcat ctgtaaataa ggggtaggac taaagcactc   7080
```

```
ctcctggagg actgagagat gggctggacc ggagcacttg agtctgggat atgtgaccat   7140
gctaccttg  tctccctgtc ctgttccttc ccccagcccc aaatccaggg ttttccaaag   7200
tgtggttcaa gaaccacctg catctgaatc tagaggtact ggatacaacc ccacgtctgg   7260
gccgttaccc aggacattct acatgagaac gtggggggtgg ggccctggct gcacctgaac  7320
tgtcacctgg agtcagggtg gaaggtggaa gaactggtc  ttatttcctt ctcccttgt   7380
tctttagggt ctgtccttct gcagactccg ttaccccacc ctaaccatcc tgcacaccct   7440
tggagccctc tgggccaatg ccctgtcccg caaagggctt ctcaggcatc tcacctctat   7500
gggagggcat ttttggcccc cagaaccta  cacggtgttt atgtggggaa gcccctggga   7560
agcagacagt cctagggtga agctgagagg cagagagaag gggagacaga cagagggtgg   7620
ggctttcccc cttgtctcca gtgccctttc tggtgaccct cggttcttt ccccaccac    7680
ccccccagcg gagcccatcg tggtgaggct taaggaggtc cgactgcaga ggacgacttt   7740
cgagattctg aaggtgatcg gacgcggggc gttcagcgag gtaagccgaa ccgggcggga   7800
gcctgacttg actcgtggtg ggcggggcat aggggttggg gcggggcctt agaaattgat   7860
gaatgaccga gccttagaac ctagggctgg gctggaggcg gggcttggga ccaatgggcg   7920
tggtgtggca ggtggggcgg ggccacggct gggtgcagaa gcgggtggag ttgggtctgg   7980
gcgagccctt ttgttttccc gccgtctcca ctctgtctca ctatctcgac ctcaggtagc   8040
ggtagtgaag atgaagcaga cgggccaggt gtatgccatg aagatcatga acaagtggga   8100
catgctgaag aggggcgagg tgaggggctg ggcggacgtg ggggcttttg aggatccgcg   8160
ccccgtctcc ggctgcagct cctccggtg  ccctgcaggt gtcgtgcttc cgtgaggaga   8220
gggacgtgtt ggtgaatggg gaccggcggt ggatcacgca gctgcacttc gccttccagg   8280
atgagaacta cctggtgagc tccggccgg  ggtgactagg aagagggaca agagcccgtg   8340
ctgtcactgg acgaggaggt ggggagagga agctctagga ttggggggtgc tgcccggaaa  8400
cgtctgtggg aaagtctgtg tgcggtaaga gggtgtgtca ggtggatgag gggccttccc   8460
tatctgagac ggggatggtg tccttcactg cccgtttctg gggtgatctg ggggactctt   8520
ataaagatgt ctctgttgcg gggggtctct tacctggaat gggataggtc ttcaggaatt   8580
ctaacgggac cactgcctag ggaaggagtg tctgggacct attctctgga tgttgggtgg   8640
cctctgggtt ctctttccca gaacatctca gggggagtga atctgcccag tgacatccca   8700
ggaaagtttt tttgtttgtg ttttttttg  aggggcgggg gcggggccg  caggtggtct   8760
ctgatttggc ccggcagatc tctatggtta tctctgggct ggggctgcag gtctctgccc   8820
aaggatgggg tgtctctggg aggggttgtc ccagccatcc gtgatggatc agggcctcag   8880
gggactacca accacccatg acgaacccct tctcagtacc tggtcatgga gtattacgtg   8940
ggcggggacc tgctgacact gctgagcaag tttggggagc ggattccggc cgagatggcg   9000
cgcttctacc tggcggagat tgtcatggcc atagactcgg tgcaccggct tggctacgtg   9060
cacaggtggg tgcagcatgg ccgagggggat agcaagcttg ttccctggcc gggttcttgg   9120
aaggtcagag cccagagagg ccagggcctg gagaggacc  ttcttggttg gggcccaccg   9180
gggggtgcct gggagtaggg gtcagaactg tagaagaccc acaggggcgg aacccgagga   9240
agtggggtcc caggtggcac tgcccggagg ggcggagcct ggtgggacca cagaagggag   9300
gttcatttat cccaccttc  tcttttcctc cgtgcaggga catcaaaccc gacaacatcc   9360
tgctgaccg  ctgtggccac atccgcctgg ccgacttcgg ctcttgcctc aagctgcgg    9420
cagatggaac ggtgagccag tgccctggcc acagagcaac tggggctgct gatgagggat   9480
ggaaggcaca gagtgtggga gcgggactgg atttggaggg gaaaagaggt ggtgtgaccc   9540
aggcttaagt gtgcatctgt gtggcggagt attagaccag gcagagggag gggctaagca   9600
tttggggagt ggttggaagg agggcccaga gctggtgggc ccagaggggt gggcccaagc   9660
ctcgctctgc tccttttggt ccaggtgcgg tcgctggtgg ctgtgggcac cccagactac   9720
ctgtccccg  agatcctgca ggctgtgggc ggtgggcctg ggacaggcag ctacgggccc   9780
gagtgtgact ggtgggcgct gggtgtattc gcctatgaaa tgttctatgg gcagacgccc   9840
ttctacgcgg attccacggc ggagacctat ggcaagatcg tccactacaa ggtgagcacg   9900
gccgcaggga gacctggcct ctcccggtag gcgctcccag gctatcgcct cctctccctc   9960
tgagcaggag cacctctctc tgccgctggt ggacgaaggg gtccctgagg aggctcgaga  10020
cttcattcag cggttgctgt gtcccccgga gacacggctg ggccggggtg gagcaggcga  10080
cttccgaca  catcccttct tctttggcct cgactgggat ggtctccggg acagcgtgcg  10140
ccccttaca  ccggatttcg aaggtgccac cgacacatgc aacttcgact tggtggagga  10200
cgggctcact gccatggtga gcgggggcgg ggtaggtacc tgtggccct  gctcggctgc  10260
gggaacctcc ccatgctccc tccataaagt tggagtaagg acagtgccta ccttctgggg  10320
tcctgaatca ctcattcccc agagcacctg ctctgtgcca atctactact gaggacccag  10380
cagtgaccta gacttacagt ccagtggggg aacacagagc agtcttcaga cagtaaggcc  10440
ccagagtgat cagggctgag acaatggagt gcagggggtg ggggactcct gactcagcaa  10500
ggaaggtcct ggagggctt  ctggagtggg gagctatctg agctgagact tggagggatg  10560
agaagcagga gaggactcct cctccccttag gccgtctctc ttcaccgtgt aacaagctgt  10620
catgcatgc  ttgctcggct ctgggtgccc ttttgctgaa caatactggg gatccagcac  10680
ggaccagatg agctctggtc cctgccctca tccagttgca gtctagagaa ttagagaatt  10740
atggagagtg tggcaggtgc cctgaaggga agcaacagga tacaagaaaa aatgatgggg  10800
ccaggcacgg tggctcacgc ctgtaacccc agcaatttgg caggccgaag tgggtggatt  10860
gcttggaccc aggagttcga gaccagcctg ggcaagttcg tgagaccccc gtctctacaa  10920
aaatgtttta aaaattggtt gggcgtggtg gcgcatgcct gtatactcag ctactagggt  10980
ggccgacgtg ggcttgagcc caggaggtca aggctgcagt gagctgtgat tgtgccactg  11040
cactccagcc tgggcaacgg agagagactc tgtctcaaaa ataagataaa ctgaaattaa  11100
aaaataggct gggctggccg ggcgtggtgg ctcacgcctg taatctcagc actttgggag  11160
gccgaggcgg gtggatcacg aggtcaggag atcgagacca tcttggctaa cacggtgaaa  11220
ccccatctct cctaaaaata caaaaaatta gccaggcgtg gtgccggggcg cctgtagtcc  11280
cagctactca ggaggctgag gcaggagaat ggcgtgaacc cgggaggcag agtttgcagt  11340
gagccgagat cgtgccactg cactccagcc tgggcgacag agcgagactc tgtctcaaa   11400
aaaaaaaaa  aaaaaaaaa  aaataggctg gaccgcggcc gggcgctgtg gctcatgcct  11460
gtaatcccag cactttggga gtccaaggca gaggtggcat gatgaatcag gttttgagac  11520
taggctggcc aacacggtga aaccccgtct ctactaaaaa tacaagaaaa ttagctgggt  11580
gtggtctcgg gtgcctgtaa ttccagttac tggggaagct gaggcaggag aattgcttga  11640
acctgggagg cagagtttgc agtgagccaa gatcatgcca ctacactcca gtctgggtga  11700
cagagtgaga ctctgtctca aaaaaaaaaa aaaaaaaag  ggttgggcaa ggtggttcac  11760
gcctgtaatc ccagaacttt gggaggctga ggcaggcaga tcactggaag tcaggagttc  11820
```

```
aagaccagcc tggccaacat ggtgaaaccc tgtgtctact aaaaatacaa aatttagcca   11880
ggcttggtgg cgtatgcctg taatgccagc tactcaggag gctgaggcag gagaatcgct   11940
tgattgaacc tgggaggcag agtttgcagt gggctgggt tgtgccactg cactctaggc    12000
tgggagacag caagactcca tctaaaaaaa aaaaacagaa ctgggctggg cacagtggct   12060
tatatttgta atcccagcac tttgggaggc tgaggttgga ggactgcttg agcccagagt   12120
ttgggactac aacagctgag gtaggcggat cacttgaggt cagaagatgg agaccagcct   12180
ggccagcgtg gcgaaacccc gtctctacca aaaatataaa aaattagcca ggcgtggtag   12240
agggcgcctg taatctcagc tactcaggac gctgaggcag gagaatcgcc tgaacctggg   12300
aggcggaggt tgcagtgagc tgagattgca ccactgcact ccagcctggg taacagaacg   12360
agactccgta tcaaagaaaa agaaaaaaaga aaaaatgctg gaggggccac tttagataag   12420
ccctgagttg gggctggttt ggggggaaca tgtaagccaa gatcaaaaag cagtgagggg   12480
cccgccctga cgactgctgc tcacatctgt gtgtcttgcg caggagacac tgtcggacat   12540
tcgggaaggt gcgccgctag gggtccacct gccttttgtg ggctactcct actcctgcat   12600
ggccctcagg taagcactgc cctggacggc ctccaggccc cacgaggctg cttgagcttc   12660
ctgggtcctg ctccttggca gccaatgag ttgcaggatc agtcttggaa ccttactgtt     12720
ttgggcccaa agactcctaa gaggccagag ttggaggacc ttaaattttc agatctatgt   12780
acttcaaaat gttagattga attttaaaac ctcagagtca cagactgggc ttcccagaat   12840
cttgtaacca ttaacttta cgtctgtagt acacagagcc acaggacttc agaacttgga    12900
aaatatgaag tttagacttt tacaatcagt tgtaaaagaa tgcaaattct ttgaatcagc   12960
catataacaa taaggccatt taaaagtatt aatttaggcg ggccgcggtg gctcacgcct   13020
gtaatcctag cactttggga ggccaaggca ggtggatcat gaggtcagga gatcgagacc   13080
atcctggcta acacggtgaa accccgtctc tactaaaaat acaaaaaaat tagccgggca   13140
tggtggcggg cgcttgcggt cccagctact gggaggcgca ggcaggagaa tggcatgaac   13200
ccgggaggcg gagcttgcag tgagccgaga tcatgccact gcactccagc ctgggcgaca   13260
gagcaagact ccgtctcaaa aaaaaaaaa aaaagtatt tatttaggcc gggtgtggtg     13320
gctcacgcct gtaattccag tgctttggga ggatgaggtg ggtggatcac ctgaggtcag   13380
gagttcgaga ccagcctgac caacgtggag aaaacctcatc tctactaaaa aacaaaaatta  13440
gccaggcgtg gtggcatata cctgtaatcc cagctactca ggaggctgag gcaggagaat   13500
cagaacccag gaggggggagg ttgtggtgag ctgagatcgt gccattgcat tccagcctgg   13560
gcaacaagag tgaaacttca tctcaaaaaa aaaaaaaaaa aagtactaat ttacaggctg   13620
ggcatggtgg ctcacgcttg gaatcccagc actttgggag gctgaagtgg acggattgct   13680
tcagcccagg agttcaagac cagcctgagc aacataatga gaccctgtct ctacaaaaaa   13740
ttgaaaaaat cgtgccaggc atggtggtct gtgcctgcag tcctagctac tcaggagtct   13800
gaagtaggca aatcacttga gcctggagtt tgaggcttca gtgagccatg atagattcca   13860
gcctaggcaa caaagtgaga cctggtctca acaaaagtat taattacaca aataatgcat   13920
tgcttatcac aagtaaatta gaaaatacag ataaggaaaa ggaagttgat atctcgtgag   13980
ctcaccagat ggcagtggtc cctggctcac acgtgtactg acacatgttt aaatagtgga   14040
gaacaggtgt tttttttggtt tgtttttttc cccttcctca tgctactttg tctaagagaa   14100
cagttggttt tctagtcagc ttttattact ggacaacatt acacatacta taccttactg   14160
ttaatgaact ccagcttgat tctgaaccgc tgcggggcct gaacggtggg tcaggattga   14220
acccatcctc tattagaacc caggcgcatg tccaggatag ctaggtcctg agccgtgttc   14280
ccacaggagg gactgctggg ttggagggga cagccacttc ataccccagg gaggagctgt   14340
ccccttccca cagctgagtg gggtgtgctg acctcaagtt ggcatcttgg ggtcccatgc   14400
ccagtcttag gaccacatct gtggaggtgg ccagagccaa gcagtctccc catcaggtcg   14460
gcctccctgt cctgaggccc tgagaagagg ggtctgcagc ggtcacatgt caagggagga   14520
gatgagctga ccctagaaca tggggtctg gacccccaagt ccctgcagaa ggtttagaaa   14580
gagcagctcc caggggccca aggccaggag aggggcaggg cttttcctaa gcagaggagg   14640
ggctattggc ctacctggga ctctgttctc ttcgctctgc tgctcccctt cctcaaatca   14700
ggaggtcttg gaagcagctg cccctaccca caggccagaa gttctggttc tccaccagag   14760
aatcagcatt ctgtctccct ccccactccc tcctcctctc cccagggaca gtgaggtccc   14820
aggcccacca cccatggaac tggaggccga gcagctgctt gagccacacg tgcaagcgcc   14880
cagcctggag ccctcggtgt ccccacagga tgaaacagta agttggtgga ggggagggg   14940
tccgtcaggg acaattggga gagaaaaggt gagggcttcc cggtggcgt gcactgtaga   15000
gccctctagg gacttcctga acagaagcag acagaaacca cggagagacg aggttacttc   15060
agacatggga cggtctctgt agttacagtg gggcattaag taagggtgtg tgtgttgctg   15120
gggatctgag aagtcgatct ttgagctgag cgctggtgaa ggagaaacaa gccatggaag   15180
gaaaggtgcc aagtggtcag gcgagagcct ccagggcaaa ggcctttggg aggtgggaat   15240
cctgatttgt tcctgaaagg tagtttggct gaatcattcc tgagaaggct ggagaggcca   15300
gcaggaaaca aaacccagca aggccttttg tcgtgagggc attagggagc tggagggatt   15360
ttgagcagca gagggacata ggttgtgtta gtgtttgac accagccctc tggtccctgt   15420
gtagatttag aggaccagac tcagggatgg ggctgaggga ggtagggaag ggaggggct   15480
tggatcattg caggagctat ggggattcca gaaatgttga ggggacggag gagtagggga   15540
taaacaagga ttcctagcct ggaaccagtg cccaagtcct gagtcttcca ggagccacag   15600
gcagccttaa gcctggtccc catacacagg ctgaagtggc agttccagcg gctgtcctg    15660
cggcagaggc tgaggccgag gtgacgctgc gggagctcca ggaagccctg gaggaggagg   15720
tgctcacccg gcagagcctg agccgggaga tggaggccat ccgcacggac aaccagaact   15780
tcgccaggtc gggatcgggg ccggggccgg ggccgggatg cgggccggtg caacccttg    15840
gcatcccctc tcgtccggcc cggacggact caccgtcctc acctccccac agtcaactac   15900
gcgaggcaga ggctcggaac cgggacctag aggcacacgt ccggcagttg caggagcgga   15960
tggagtttgct gcaggcagag ggagccacac gtgagtccct catgtgtccc cttcccgga    16020
ggaccggag gaggtgggcc gtctgctccg cggggcgtgt atagacacct ggaggaggga    16080
agggacccac gctggggcac gccgcgccac cgccctcctt cgcccctcca cgcgcctat    16140
gcctcttct tctccttcca gctgtcacgg gggtcccag tccccgggcc acggatccac     16200
cttcccatgt aagaccctc tctttcccct gcctcagaac tgtgccatct tctgcagatc   16260
ccctcctgg ctcctggtct cccgtccaga atataggct cacccctacgt ctttgagact    16320
ttagagggca gaagcctttt attcagcccc agatctcct ccgttcaggc ctcaccagat    16380
tcctccgggg atccctctag ataacctccc caacctgat tccctcgct gtctctcgcc    16440
ccaccgctga gggctgggct gggctccgat cgggtccacct gtcccttctc tctccagcta   16500
gatggccccc cggccgtggc tgtgggccag tgccgctgg tggggccagg ccccatgcac    16560
```

-continued

```
cgccgccacc tgctgctccc tgccagggta cgtccggctg cccacgcccc cctccgccgt   16620
cgcgccccgc gctccacccg ccccttgcca cccgcttagc tgcgcatttg cggggctggg   16680
cccacggcag gagggcggat cttcgggcag ccaatcaaca caggccgcta ggaagcagcc   16740
aatgacgagt tcgacgggga ttcgaggcgt gcgagtggac taacaacagc tgtaggctgt   16800
tggggcgggg gcggggcgca gggaagagtg cgggcccacc tatggggcta ggcggggcga   16860
gtcccaggag ccaatcagag gcccatgccg ggtgttgacc tcgccctctc ccccgcaggtc   16920
cctaggcctg gcctatcgga ggcgctttcc ctgctcctgt tcgccgttgt tctgtctcgt   16980
gccgccgccc tgggctgcat tgggttggtg gcccacgccg ccaactcac cgcagtctgg    17040
cgccgcccga gagccgcccg cgctccctga accctagaac tgtcttcgac tccggggcgg   17100
cgttggaaga ctgagtgccc ggggcacggc acagaagccg cgcccaccgc ctgccagttc   17160
acaaccgctc cgagcgtggg tctccgccca gctccagtcc tgtgatccgg gcccgcccc    17220
tagcggccgg ggagggaggg gccgggtccg cggccggcga acggggctcg aagggtcctt   17280
gtagccggga atgctgctgc tgctgctgct gctgctgctg ctgctgctgc tgctgctgct   17340
gctgctgctg ctgtgggggat cacagaccat ttctttcttt cggccaggct gaggccctga   17400
cgtggatggg caaactgcag gcctgggaag gcagcaagcc gggccgtccg tgttccatcc   17460
tccacgcacc cccacctatc gttggttcgc aaagtgcaaa gctttcttgt gcatgacgcc   17520
ctgctctggg gagcgtctgg cgcgatctct gcctgcttac tcgggaaatt tgcttttgcc   17580
aaaccgcgtt tttcgggggat cccgcgcccc cctcctcact tgcgctgctc tcggagcccc   17640
agccggctcc gcccgcttcg gcggtttgga tatttattga cctcgtcctc cgactcgctg   17700
acaggctaca ggaccccccaa caaccccaat ccacgttttg gatgcactga dccccgaca   17760
ttcctcggta tttattgtct gtccccacct aggaccccca cccccgaccc tcgcgaataa   17820
aaggccctcc atctgcccaa agctctggac tccacagttg tcgcggtttg cgttgtgggc   17880
cggaggctcc gcagcgggcc aatccggagg cgtgtggagg cggccgaagg tctgggagga   17940
gctagcggga tgcgaagcgg ccgaatcagg gttgggggag gaaaagccac ggggcggggc   18000
tttgcgtcc ggcaataggg agggcgagcg ggccacccgg aggcaccgcc cccgcccagc    18060
tgtggcccag ctgtgccacc gagcgtcgag aagaggggc tgggctggca gcgcgcgcgg    18120
ccatcctcct tccactgcgc ctgcgcacgc cacgcgcatc cgctcctggg acgcaagctc   18180
gagaaaagtt gctgcaaact ttctagcccg ttccccgccc ctcctccggg ccagacccgc   18240
cccccctgcg gagccgggaa ttccgagggg cggagcgcag gccgagatgg ggaatgtggg   18300
ggcctgcaga ggacctggga gacggaggcg tgcagaagct cagtctccgg gcggaggctt   18360
cgcgccctta gtcctcctgg acggccgtt accttctgcg ttgtcccgat ggggaaactg    18420
aggccctgag ccagaagcac acgctggggg gaggcagaaa gcgcggccag aggcggaggg   18480
aaaacaaagg gagaatcaca gacagacggg aggggggacgg acacacacaa ggggacagag   18540
acccgagtgg agagctggat ctcgccttcc cggcgtgggg cgccagggtcg gccagaaaga   18600
agatcgagaa gagcggggag tggggggcgaa aaggggggac aggtaggggga aggggcgtagg  18660
gaaagcccga gggaggaaga gagggaggga ggaacttccc aaagttgcaa aacatggcta   18720
ccttgcctgc ggagccgagc gcggggccgg cggctggggg ggaggcggtg gcggcggcg    18780
cggcgaccga agaggaggag gaggaagcgc gccagctctt gcagactttg caggcggccg   18840
agggtgaggc ggcggcggcg ccggggccg gggcgggcgc agcggctgcg ggagctgagg    18900
gcccgggatc cccgggcgtc cccgggtcgc ccccgaggc cgcttccgaa ccgcccacgg    18960
gcctccgctt ctcgcccgag caggtggcgt cgtctgcga ggcgctgctc caggcgggcc    19020
acgccggccg cttgagccgc ttcctgggcg cactgccccc ggccgagcgc ctacgtggca   19080
gcgaccggt gttgcgcgcg cggggcctgg tggccttcca ggaggcggtga tacgccgagc    19140
tctaccggct actcgagagc cgccccttcc ccgccgccca ccacgccttc ctgcaggacc   19200
tctacctgcg cgcgcgctac catgaggccg agcgggcccg cggccgcgcg cttggccag    19260
tggacaagta tcgactgcgc aagaagttcc cgctgcccaa gaccatctgg gacggcgagg   19320
agacagtcta ctgcttcaag gagcgctccc gcgcagcgct caaggcctgc taccgcggca   19380
accgctaccc cacgccggac gagaagcgcc gcctggccac actcaccggc ctgtcgctca   19440
cgcaggtcag caactggttc aagaaccggc gacagcgcga ccgaccgggg gccggaggcg   19500
gcgcgccctg caagaggtga ggggcctcgg gcggcgcaag tccagctctc ccggggacat   19560
ccgtccacc agccctcttc cccgtgccc actgctgggg aggtgcctca                19620
gacatctccc gggaccagct cacaatctca ggcgcccgcg gggcgcgggg actaagtgtg   19680
gacgggacag gcaccgccc gggccctctc ccgcacgcg tctcctcttc cagcggctcc    19740
attccgagct cctccccaaa tcccatcggt gttggggaat cacactgcgg ggggcactag   19800
agggactgag gaaaaaggac agggcctgtg gccactccac t                       19841

SEQ ID NO: 66        moltype = AA  length = 842
FEATURE              Location/Qualifiers
source               1..842
                     mol_type = protein
                     organism = Homo sapiens
SEQUENCE: 66
MSRPLSDQEK RKQISVRGLA GVENVTELKK NFNRHLHFTL VKDRNVATPR DYYFALAHTV      60
RDHLVGRWIR TQQHYYEKDP KRIYYLSLEF YMGRTLQNTM VNLALENACD EATYQLGLDM    120
EELEEIEEDA GLGNGGLGRL AACFLDSMAT LGLAAYGYGI RYEFGIFNQK ISGGWQMEEA    180
DDWLRYGNPW EKARPEFTLP VHFYGHVEHT SQGAKWVDTQ VVLAMPYDTP VPGYRNNVVN    240
TMRLWSAKAP NDFNLKDFNV GGYIQAVLDR NLAENISRVL YPNDNFFEGK ELRLKQEYFV    300
VAATLQDIIR RFKSSKFGCR DPVRTNFDAF PDKVAIQLND THPSLAIPEL MRILVDLERM    360
DWDKAWDVTV RTCAYTNHTV LPEALERWPV HLLETLLPRH LQIIYEINQR FLNRVAAAFP    420
GDVDRLRRMS LVEEGAVKRI NMAHLCIAGS HAVNGVARIH SEILKKTIFK DFYELEPHKF    480
QNKTNGITPR RWLVLCNPGL AEVIAERIGE DFISDLDQLR KLLSFVDDEA FIRDVAKVKQ    540
ENKLKFAAYL EREYKVHINP NSLFDIQVKR IHEYKRQLLN CLHVITLYNR IKREPNKFFV    600
PRTVMIGGKA APGYHMAKMI IRLVTAIGDV VNHDPAVGDR LRVIFLENYR VSLAEKVIPA    660
ADLSEQISTA GTEASGTGNM KFMLNGALTI GTMDGANVEM AEEAGEENFF IFGMRVEDVD    720
KLDQRGYNAQ EYYDRIPELR QVIEQLSSGF FSPKQPDLFK DIVNMLMHHD RFKVFADYED    780
YIKCQEKVSA LYKNPREWTR MVIRNIATSG KFSSDRTIAQ YAREIWGVEP SRQRLPAPDE    840
AI                                                                   842

SEQ ID NO: 67        moltype = AA  length = 429
```

```
FEATURE                 Location/Qualifiers
source                  1..429
                        mol_type = protein
                        organism = Homo sapiens
SEQUENCE: 67
MQLRNPELHL GCALALRFLA LVSWDIPGAR ALDNGLARTP TMGWLHWERF MCNLDCQEEP    60
DSCISEKLFM EMAELMVSEG WKDAGYEYLC IDDCWMAPQR DSEGRLQADP QRFPHGIRQL   120
ANYVHSKGLK LGIYADVGNK TCAGFPGSFG YYDIDAQTFA DWGVDLLKFD GCYCDSLENL   180
ADGYKHMSLA LNRTGRSIVY SCEWPLYMWP FQKPNYTEIR QYCNHWRNFA DIDDSWKSIK   240
SILDWTSFNQ ERIVDVAGPG GWNDPDMLVI GNFGLSWNQQ VTQMALWAIM AAPLFMSNDL   300
RHISPQAKAL LQDKDVIAIN QDPLGKQGYQ LRQGDNFEVW ERPLSGLAWA VAMINRQEIG   360
GPRSYTIAVA SLGKGVACNP ACFITQLLPV KRKLGFYEWT SRLRSHINPT GTVLLQLENT   420
MQMSLKDLL                                                          429

SEQ ID NO: 68           moltype = AA  length = 952
FEATURE                 Location/Qualifiers
source                  1..952
                        mol_type = protein
                        organism = Homo sapiens
SEQUENCE: 68
MGVRHPPCSH RLLAVCALVS LATAALLGHI LLHDFLLVPR ELSGSSPVLE ETHPAHQQGA    60
SRPGPRDAQA HPGRPRAVPT QCDVPPNSRF DCAPDKAITQ EQCEARGCCY IPAKQGLQGA   120
QMGQPWCFFP PSYPSYKLEN LSSSEMGYTA TLTRTTPTFF PKDILTLRLD VMMETENRLH   180
FTIKDPANRR YEVPLETPHV HSRAPSPLYS VEFSEEPFGV IVRRQLDGRV LLNTTVAPLF   240
FADQFLQLST SLPSQYITGL AEHLSPLMLS TSWTRITLWN RDLAPTPGAN LYGSHPFYLA   300
LEDGGSAHGV FLLNSNAMDV VLQPSPALSW RSTGGILDVY IFLGPEPKSV VQQYLDVVGY   360
PFMPPYWGLG FHLCRWGYSS TAITRQVVEN MTRAHFPLDV QWNDLDYMDS RRDFTFNKDG   420
FRDFPAMVQE LHQGGRRYMM IVDPAISSSG PAGSYRPYDE GLRRGVFITN ETGQPLIGKV   480
WPGSTAFPDF TNPTALAWWE DMVAEFHDQV PFDGMWIDMN EPSNFIRGSE DGCPNNELEN   540
PPYVPGVVGG TLQAATICAS SHQFLSTHYN LHNLYGLTEA IASHRALVKA RGTRPFVISR   600
STFAGHGRYA GHWTGDVWSS WEQLASSVPE ILQFNLLGVP LVGADVCGFL GNTSEELCVR   660
WTQLGAFYPF MRNHNSLLSL PQEPYSFSEP AQQAMRKALT LRYALLPHLY TLFHQAHVAG   720
ETVARPLFLE FPKDSSTWTV DHQLLWGEAL LITPVLQAGK AEVTGYFPLG TWYDLQTVPV   780
EALGSLPPPP AAPREPAIHS EGQWVTLPAP LDTINVHLRA GYIIPLQGPG LTTTESRQQP   840
MALAVALTKG GEARGELFWD DGESLEVLER GAYTQVIFLA RNNTIVNELV RVTSEGAGLQ   900
LQKVTVLGVA TAPQQVLSNG VPVSNFTYSP DTKVLDICVS LLMGEQFLVS WC           952

SEQ ID NO: 69           moltype = AA  length = 210
FEATURE                 Location/Qualifiers
source                  1..210
                        mol_type = protein
                        organism = Homo sapiens
SEQUENCE: 69
MWTLGRRAVA GLLASPSPAQ AQTLTRVPRP AELAPLCGRR GLRTDIDATC TPRRASSNQR    60
GLNQIWNVKK QSVYLMNLRK SGTLGHPGSL DETTYERLAE ETLDSLAEFF EDLADKPYTF   120
EDYDVSFGSG VLTVKLGGDL GTYVINKQTP NKQIWLSSPS SGPKRYDWTG KNWVYSHDGV   180
SLHELLAAEL TKALKTKLDL SSLAYSGKDA                                   210
```